(12) United States Patent
Zhao et al.

(10) Patent No.: US 11,530,218 B2
(45) Date of Patent: Dec. 20, 2022

(54) SPIRO COMPOUNDS AS INHIBITORS OF KRAS

(71) Applicant: Incyte Corporation, Wilmington, DE (US)

(72) Inventors: Le Zhao, Wilmington, DE (US); Xiaozhao Wang, Mt. Laurel, NJ (US); Wenyu Zhu, Wilmington, DE (US); Haolin Yin, Wilmington, DE (US); Liangxing Wu, Wilmington, DE (US); Wenqing Yao, Wilmington, DE (US)

(73) Assignee: INCYTE CORPORATION, Wilmington, DE (US)

( * ) Notice: Subject to any disclaimer, the term of this patent is extended or adjusted under 35 U.S.C. 154(b) by 0 days.

(21) Appl. No.: 17/153,065

(22) Filed: Jan. 20, 2021

(65) Prior Publication Data
US 2021/0230162 A1 Jul. 29, 2021

Related U.S. Application Data

(60) Provisional application No. 62/963,467, filed on Jan. 20, 2020.

(51) Int. Cl.
*C07D 471/20* (2006.01)
*C07D 471/22* (2006.01)
*C07D 491/20* (2006.01)
*C07D 498/20* (2006.01)

(52) U.S. Cl.
CPC ......... *C07D 471/20* (2013.01); *C07D 471/22* (2013.01); *C07D 491/20* (2013.01); *C07D 498/20* (2013.01)

(58) Field of Classification Search
CPC .. C07D 471/20; C07D 498/20; C07D 471/22; C07D 491/20; A61K 31/499; A61K 31/4747
USPC ................ 544/71, 230, 231; 546/15, 17, 18; 514/250, 278
See application file for complete search history.

(56) References Cited

U.S. PATENT DOCUMENTS

| | | | |
|---|---|---|---|
| 7,592,453 B2 | 9/2009 | Kajino et al. |
| 7,897,609 B2 | 3/2011 | Niwas et al. |
| 7,943,770 B2 | 5/2011 | Kajino et al. |
| 7,973,163 B2 | 7/2011 | Kajino et al. |
| 8,034,802 B2 | 10/2011 | Averett |
| 8,143,270 B2 | 3/2012 | Kshirsagar et al. |
| 8,158,794 B2 | 4/2012 | Kshirsagar et al. |
| 8,207,187 B2 | 6/2012 | Beck et al. |
| 8,513,250 B2 | 8/2013 | Escaich et al. |
| 8,557,984 B2 | 10/2013 | Bouillot et al. |
| 8,563,565 B2 | 10/2013 | Norimine et al. |
| 8,637,670 B2 | 1/2014 | Kumar et al. |
| 8,658,666 B2 | 2/2014 | Rice et al. |
| 8,846,710 B2 | 9/2014 | Kshirsagar et al. |
| 8,895,581 B2 | 11/2014 | McConnell et al. |
| 9,062,046 B2 | 6/2015 | Kumar et al. |
| 9,169,246 B2 | 10/2015 | Benazet et al. |
| 9,550,776 B2 | 1/2017 | Norimine et al. |
| 9,573,947 B2 | 2/2017 | Ozaki |
| 9,694,006 B2 | 7/2017 | Beck et al. |
| 9,771,327 B2 | 9/2017 | Zawistoski et al. |
| 9,873,694 B2 | 1/2018 | Lipford et al. |
| 10,039,753 B2 | 8/2018 | Coffman et al. |
| 10,493,071 B2 | 12/2019 | Beck et al. |
| 10,544,138 B2 | 1/2020 | Gray et al. |
| 11,053,240 B2 | 7/2021 | Li et al. |
| 2005/0054590 A1 | 3/2005 | Averett |
| 2011/0230476 A1 | 9/2011 | Niu et al. |
| 2012/0065187 A1 | 3/2012 | Borchardt et al. |
| 2012/0108627 A1 | 5/2012 | Kumar et al. |
| 2012/0232074 A1 | 9/2012 | Bouillot et al. |
| 2014/0243286 A1 | 8/2014 | Arnold et al. |
| 2016/0264570 A1 | 9/2016 | McKew et al. |
| 2017/0197945 A1 | 7/2017 | Li et al. |
| 2017/0217960 A1 | 8/2017 | Ferguson |
| 2017/0294489 A1 | 10/2017 | Lim et al. |
| 2019/0177338 A1 | 6/2019 | Kettle et al. |
| 2021/0269434 A1 | 9/2021 | Wang et al. |
| 2021/0308123 A1 | 10/2021 | Zhang et al. |
| 2021/0317118 A1 | 10/2021 | Zhang et al. |
| 2021/0355121 A1 | 11/2021 | Zhu et al. |
| 2021/0355141 A1 | 11/2021 | Hoang et al. |
| 2022/0064188 A1 | 3/2022 | Carlsen et al. |

FOREIGN PATENT DOCUMENTS

| | | |
|---|---|---|
| CN | 102399218 A | 4/2012 |
| CN | 103012397 B | 3/2017 |
| CN | 108003153 A | 5/2018 |
| EP | 1740584 B1 | 3/2008 |

(Continued)

OTHER PUBLICATIONS

International Search Report corresponding to International Patent Application No. PCT/US2021/014187 dated Mar. 24, 2021, 4 pages.

(Continued)

*Primary Examiner* — Jeffrey H Murray

(74) *Attorney, Agent, or Firm* — Lathrop GPM LLP; Brian C. Trinque; Nicole Sassu

(57) ABSTRACT

Disclosed are spirocyclic compounds of Formula I, methods of using the compounds for inhibiting KRAS activity and treating cancer, and pharmaceutical compositions comprising such compounds. The compounds are useful in treating, preventing or ameliorating diseases or disorders associated with KRAS activity such as cancer.

42 Claims, No Drawings

(56) References Cited

FOREIGN PATENT DOCUMENTS

| EP | 2573073 B1 | 10/2014 |
|---|---|---|
| EP | 1945211 B1 | 10/2015 |
| EP | 2769980 B1 | 3/2016 |
| EP | 2760841 B1 | 8/2016 |
| EP | 2982674 B1 | 10/2017 |
| IN | 2012MU02281 A | 6/2012 |
| WO | WO 2005105802 A1 | 11/2005 |
| WO | WO 2007054693 A1 | 5/2007 |
| WO | WO 2008056151 A1 | 5/2008 |
| WO | WO 2009/123967 A1 | 10/2009 |
| WO | WO 2010030785 A2 | 3/2010 |
| WO | WO 2010049366 A1 | 5/2010 |
| WO | WO 2010135571 A1 | 11/2010 |
| WO | WO 2011031896 A2 | 3/2011 |
| WO | WO 2012/011642 A1 | 1/2012 |
| WO | WO 2013051639 A1 | 10/2012 |
| WO | WO 2012154731 A1 | 11/2012 |
| WO | WO 2013045400 A1 | 4/2013 |
| WO | WO 2014163146 A1 | 9/2014 |
| WO | 2016168540 A1 | 10/2016 |
| WO | WO 2016199943 A1 | 12/2016 |
| WO | WO 2017058805 A1 | 4/2017 |
| WO | WO 2017/092413 A1 | 8/2017 |
| WO | WO 2018119183 A2 | 6/2018 |
| WO | WO 2018217651 A1 | 11/2018 |
| WO | 2019201283 A1 | 10/2019 |
| WO | WO 2019209896 A1 | 10/2019 |
| WO | WO 2019213516 A1 | 11/2019 |
| WO | WO 2020037091 A | 2/2020 |
| WO | WO 2020037092 A | 2/2020 |

OTHER PUBLICATIONS

Korzeniecki, Claudia et al.: "Targeting KRAS mutant cancers by preventing signaling transduction in the MAPK pathway", European Journal of Medicinal Chemistry, Elsevier, Amsterdam, NL, vol. 211, Nov. 17, 2020.

Zhu Jian et al: "Structure-based discovery of selective BRPFI bromodomain inhibitors", European Journal of Medicinal Chemistry, Elsevier, Amsterdam, NL, vol. 155, Jun. 2, 2018 (Jun. 2, 2018), pp. 337-352.

SPIRO COMPOUNDS AS INHIBITORS OF KRAS

RELATED APPLICATIONS

This application claims priority to U.S. Provisional Application No. 62/963,467 filed on Jan. 20, 2020, the entire content of which is hereby incorporated by reference in its entirety.

FIELD OF THE INVENTION

The disclosure provides compounds as well as their compositions and methods of use. The compounds modulate KRAS activity and are useful in the treatment of various diseases including cancer.

BACKGROUND OF THE INVENTION

Ras proteins are part of the family of small GTPases that are activated by growth factors and various extracellular stimuli. The Ras family regulates intracellular signaling pathways responsible for growth, migration, survival and differentiation of cells. Activation of RAS proteins at the cell membrane results in the binding of key effectors and initiation of a cascade of intracellular signaling pathways within the cell, including the RAF and PI3K kinase pathways. Somatic mutations in RAS may result in uncontrolled cell growth and malignant transformation while the activation of RAS proteins is tightly regulated in normal cells (Simanshu, D. et al. Cell 170.1 (2017):17-33).

The Ras family is comprised of three members: KRAS, NRAS and HRAS. RAS mutant cancers account for about 25% of human cancers. KRAS is the most frequently mutated isoform accounting for 85% of all RAS mutations whereas NRAS and HRAS are found mutated in 12% and 3% of all Ras mutant cancers respectively (Simanshu, D. et al. Cell 170.1 (2017):17-33). KRAS mutations are prevalent amongst the top three most deadly cancer types: pancreatic (97%), colorectal (44%), and lung (30%) (Cox, A. D. et al. Nat Rev Drug Discov (2014) 13:828-51). The majority of RAS mutations occur at amino acid residue 12, 13, and 61. The frequency of specific mutations varies between RAS gene isoforms and while G12 and Q61 mutations are predominant in KRAS and NRAS respectively, G12, G13 and Q61 mutations are most frequent in HRAS. Furthermore, the spectrum of mutations in a RAS isoform differs between cancer types. For example, KRAS G12D mutations predominate in pancreatic cancers (51%), followed by colorectal adenocarcinomas (45%) and lung cancers (17%) while KRAS G12 V mutations are associated with pancreatic cancers (30%), followed by colorectal adenocarcinomas (27%) and lung adenocarcinomas (23%) (Cox, A. D. et al. Nat Rev Drug Discov (2014) 13:828-51). In contrast, KRAS G12C mutations predominate in non-small cell lung cancer (NSCLC) comprising 11-16% of lung adenocarcinomas, and 2-5% of pancreatic and colorectal adenocarcinomas (Cox, A. D. et al. Nat. Rev. Drug Discov. (2014) 13:828-51). Genomic studies across hundreds of cancer cell lines have demonstrated that cancer cells harboring KRAS mutations are highly dependent on KRAS function for cell growth and survival (McDonald, R. et al. Cell 170 (2017): 577-592). The role of mutant KRAS as an oncogenic driver is further supported by extensive in vivo experimental evidence showing mutant KRAS is required for early tumour onset and maintenance in animal models (Cox, A. D. et al. Nat Rev Drug Discov (2014) 13:828-51).

Taken together, these findings suggest that KRAS mutations play a critical role in human cancers; development of inhibitors targeting mutant KRAS may therefore be useful in the clinical treatment of diseases that are characterized by a KRAS mutation.

SUMMARY

The present disclosure provides, inter alia, a compound of Formula I:

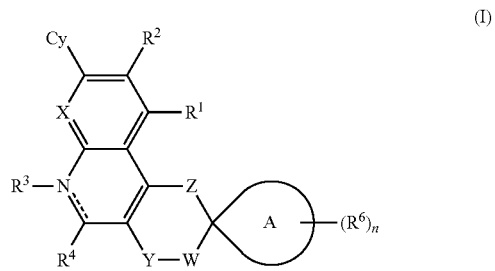

(I)

or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier or excipient.

The present disclosure further provides methods of inhibiting KRAS activity, which comprises administering to an individual a compound of the disclosure, or a pharmaceutically acceptable salt thereof. The present disclosure also provides uses of the compounds described herein in the manufacture of a medicament for use in therapy. The present disclosure also provides the compounds described herein for use in therapy.

The present disclosure further provides methods of treating a disease or disorder in a patient comprising administering to the patient a therapeutically effective amount of a compound of the disclosure, or a pharmaceutically acceptable salt thereof.

DETAILED DESCRIPTION

Compounds

In an aspect, provided herein is a compound of Formula I:

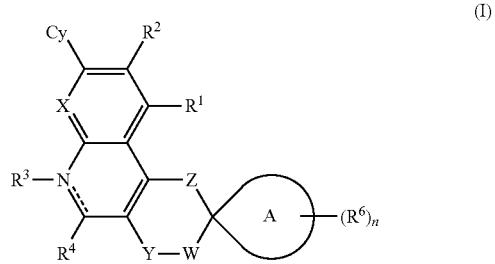

(I)

or a pharmaceutically acceptable salt thereof,
wherein:
⇌ represents a single bond or a double bond;
X is N or $CR^7$;
Y is O, $NR^{5N}$, C=O, or $C(R^5)_2$;

W is C=O, or C(R$^8$)$_2$;

Z is O, NR$^{9N}$, C(R$^9$)$_2$, or a bond;

R$^1$ is selected from H, D, C$_{1-6}$ alkyl, C$_{2-6}$ alkenyl, C$_{2-6}$ alkynyl, C$_{1-6}$ haloalkyl, C$_{3-6}$ cycloalkyl, phenyl, 5-6 membered heteroaryl, 4-7 membered heterocycloalkyl, halo, CN, OR$^{a1}$, SR$^{a1}$, C(O)R$^{1b}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{d1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, S(O)$_2$NR$^{c1}$R$^{d1}$, and BR$^{h1}$R$^{i1}$; wherein said C$_{1-6}$ alkyl, C$_{2-6}$ alkenyl, C$_{2-6}$ alkynyl, C$_{3-6}$ cycloalkyl, phenyl, 5-6 membered heteroaryl, and 4-7 membered heterocycloalkyl, are each optionally substituted with 1, 2, 3, or 4 substituents independently selected from R$^g$;

R$^2$ is selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{d2}$, NR$^{c2}$C(O)OR$^{a2}$, NR$^{c2}$C(O)NR$^{c2}$R$^{d2}$, C(=NR$^{e2}$)R$^{b2}$, C(=NOR$^{a2}$)R$^{b2}$, C(=NR$^{e2}$)NR$^{c2}$R$^{d2}$, NR$^2$C(=NR$^{e2}$)NR$^{c2}$R$^{d2}$, NR$^{c2}$C(=NR$^{e2}$)R$^{b2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, S(O)$_2$NR$^{c2}$R$^{d2}$, and BR$^{h2}$R$^{i2}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{20}$;

Cy is selected from C$_{3-10}$ cycloalkyl, 4-10 membered heterocycloalkyl, C$_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the C$_{3-10}$ cycloalkyl, 4-10 membered heterocycloalkyl, C$_{6-10}$ aryl and 5-10 membered heteroaryl are each optionally substituted with 1, 2, 3 or 4 substituents independently selected from R$^{10}$;

when R$^3$N≕CR$^4$ is a single bond, then R$^4$ is selected from =O and =S; and

R$^3$ is selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, and 5-10 membered heteroaryl-C$_{1-3}$ alkylene; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{30}$;

when R$^3$N≕CR$^4$ is a double bond, then R$^3$ is absent; and

R$^4$ is selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NOR$^{a3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$C(=NR$^{e3}$)R$^{b3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, S(O)$_2$NR$^{c3}$R$^{d3}$, and BR$^{h3}$R$^{i3}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{30}$;

R$^{5N}$ is selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, and 5-10 membered heteroaryl-C$_{1-3}$ alkylene; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{50}$;

each R$^5$ and R$^8$ are independently selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, NO$_2$, OR$^{a5}$, SR$^{a5}$, C(O)R$^{b5}$, C(O)NR$^{c5}$R$^{d5}$, (O)OR$^{a5}$, OC(O)R$^{b5}$, OC(O)NR$^{c5}$R$^{d5}$, NR$^{c5}$R$^{5d}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NOR$^{a5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$C(=NR$^{e5}$)R$^{b5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, S(O)$_2$ NR$^{c5}$R$^{d5}$, and BR$^{h5}$R$^{i5}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{50}$;

ring A is selected from C$_{3-10}$ cycloalkyl and 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group;

n is 0, 1, 2, 3, or 4;

each R$^6$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOR^{a6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{6}S(O)_2R^{b6}$, $NR^{6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $BR^{h6}R^{i6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{60}$;

$R^7$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a7}$, $SR^{a7}$, $C(O)R^{b7}$, $C(O)NR^{c7}R^{d7}$, $(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NOR^{a7})R^{b7}$, $C(=NR^{e7})NR^{c7}R^{d7}$, $NR^{c7}C(=NR^{e7})NR^{c7}R^{d7}$, $NR^{c7}C(=NR^{e7})R^{b7}$, $NR^{c7}S(O)R^{b7}$, $NR^{c7}S(O)_2R^{b7}$, $NR^{7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, and $BR^{h7}R^{i7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{70}$;

$R^{9N}$ is selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^9$ is independently selected from selected from H, D, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, $OR^{a9}$, $SR^{a9}$, $C(O)R^{b9}$, $C(O)NR^{c9}R^{d9}$, $(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$, and $BR^{h9}R^{i9}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a10}$, $SR^{a10}$, $C(O)R^{b10}$, $C(O)NR^{c10}R^{d10}$, $C(O)OR^{a10}(O)R^{b10}$, $OC(O)NR^{c10}R^{d10}$, $NR^{c10}R^{d10}$, $NR^{c10}$, $C(O)R^{b10}$, $NR^{c10}$, $C(O)OR^{a10}$, $NR^{c10}$, $C(O)NR^{c10}R^{d10}C(=NR^{e10})R^{b10}$, $C(=NOR^{a10})R^{b10}$, $C(=NR^{e10})NR^{c10}R^{d10}$, $NR^{c10}C(=NR^{e10})NR^{c10}R^{d10}$, $NR^{c10}C(=NR^{e10})R^{b10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, $S(O)_2NR^{c10}R^{d10}$, and $BR^{h10}R^{i10}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{11}C(O)R^{b11}$, $NR^{c11}C(O)OR^{a11}$, $NR^{c11}C(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, and $BR^{h11}R^{i11}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, and $BR^{h12}R^{i12}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a20}$, $SR^{a20}$, $C(O)R^{b20}$, $C(O)NR^{c20}R^{d20}$, $(O)OR^{a2}$, $OC(O)R^{b20}$, $OC(O)NR^{c20}R^{d20}$, $NR^{c20}R^{d20}$, $NR^{c20}$, $C(O)R^{b20}$, $NR^{c20}$, $C(O)OR^{a2}$, $NR^{c20}$, $C(O)NR^{c2}R^{d20}$, $NR^{c20}S(O)R^{b20}$, $NR^{c20}S(O)_2R^{b20}$, $NR^{c20}S(O)_2NR^{c20}R^{d20}$, $S(O)R^{b20}$, $S(O)NR^{c20}R^{d20}$, $S(O)_2R^{b20}$, $S(O)_2NR^{c20}R^{d20}$, and $BR^{h20}R^{i20}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, and $BR^{h21}R^{i21}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a22}$, $SR^{a22}$, $C(O)R^{b22}$, $C(O)NR^{c22}R^{d22}$, $C(O)OR^{a22}$, $OC(O)R^{b22}$, $OC(O)NR^{c22}R^{d22}$, $NR^{c22}R^{d22}$, $NR^{c22}C(O)R^{b22}$, $NR^{c22}C(O)OR^{a22}$, $NR^{c22}C(O)NR^{c22}R^{d22}$, $NR^{c22}S(O)R^{b22}$, $NR^{c22}S(O)_2R^{b22}$, $NR^{c22}S(O)_2NR^{c22}R^{d22}$, $S(O)R^{b22}$, $S(O)NR^{c22}R^{d22}$, $S(O)_2R^{b22}$, $S(O)_2NR^{c22}R^{d22}$, and $BR^{h22}R^{i22}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a30}$, $SR^{a30}$, $C(O)R^{b30}$, $C(O)NR^{c30}R^{d30}$, $C(O)OR^{a30}$, $OC(O)R^{b30}$, $OC(O)NR^{c30}R^{d30}$, $NR^{c30}R^{d30}$, $NR^{c30}C(O)R^{b30}$, $NR^{c30}C(O)OR^{a30}$, $NR^{c30}C(O)NR^{c30}R^{d30}$, $C(=NR^{e30})R^{b30}$, $C(=NOR^{a30})R^{b30}$, $C(=NR^{e30})NR^{c30}R^{d30}$, $NR^{c30}C(=NR^{e30})NR^{c30}R^{d30}$, $NR^{c30}C(=NR^{e30})R^{b30}$, $NR^{c30}S(O)R^{b30}$, $NR^{c30}S(O)_2R^{b30}$, $NR^{c30}S(O)_2NR^{c30}R^{d30}$, $S(O)R^{b30}$, $S(O)NR^{c30}R^{d30}$, $S(O)_2R^{b30}$, $S(O)_2NR^{c30}R^{d30}$, and $BR^{h30}R^{i30}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{31}$;

each $R^{31}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a31}$, $SR^{a31}$, $C(O)R^{b31}$, $C(O)NR^{c31}R^{d31}$, $C(O)OR^{a31}OC(O)R^{b31}$, $OC(O)NR^{c31}R^{d31}$, $NR^{c31}R^{d31}$, $NR^{c31}C(O)R^{b31}$, $NR^{c1}C(O)OR^{a31}$, $NR^{c1}C(O)NR^{c1}R^{d31}$, $NR^{c1}S(O)R^{b31}$, $NR^{31}S(O)_2R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, and $BR^{h31}R^{i31}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{32}$;

each $R^{32}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a32}$, $SR^{a32}$, $C(O)R^{b32}$, $C(O)NR^{c32}R^{d32}$, $C(O)OR^{a32}$, $OC(O)R^{b32}$, $OC(O)NR^{c32}R^{d32}$, $NR^{c32}R^{d32}$, $NR^{c32}C(O)R^{d32}$, $NR^{c2}C(O)OR^{a32}$, $NR^{c32}C(O)NR^{c32}R^{d32}$, $NR^{c2}S(O)R^{b32}$, $NR^{c32}S(O)_2R^{b32}$, $NR^{32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, and $BR^{h32}R^{i32}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a50}$, $SR^{a50}$, $C(O)R^{b50}$, $C(O)NR^{c50}R^{d50}$, $C(O)OR^{a50}$, $OC(O)R^{b50}$, $OC(O)NR^{c50}R^{d50}$, $NR^{c50}R^{d50}$, $NR^{c50}C(O)R^{b50}$, $NR^{c50}C(O)OR^{a50}$, $NR^{c50}C(O)NR^{d50}R^{d50}$, $NR^{c50}$, $S(O)R^{b50}$, $NR^{c50}S(O)_2R^{b50}$, $NR^{c50}S(O)_2NR^{c50}R^{d50}$, $S(O)R^{b50}$, $S(O)NR^{c5}R^{d50}$, $S(O)_2R^{b50}$, $S(O)_2NR^{c50}R^{d50}$, and $BR^{h50}R^{i50}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{51}$;

each $R^{51}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a51}$, $SR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{51}C(O)R^{b51}$, $NR^{c51}C(O)OR^{a51}$, $NR^{51}C(O)NR^{c51}R^{d51}$, $NR^{51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, and $BR^{h51}R^{i51}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene, are each optionally substituted with 1, 2, 3, or 4 substituents independently selected from $R^{52}$;

each $R^{52}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, OR$^{a52}$, SR$^{a52}$, C(O)R$^{b52}$, C(O)NR$^{c52}$R$^{d52}$, C(O)OR$^{a52}$, OC(O)R$^{b52}$, OC(O)NR$^{c52}$R$^{d52}$, NR$^{c52}$R$^{d52}$, NR$^{c52}$C(O)R$^{d52}$, NR$^{c52}$C(O)OR$^{a52}$, NR$^{c2}$C(O)NR$^{c52}$R$^{d52}$, NR$^{52}$S(O)R$^{b52}$, NR$^{c52}$S(O)$_2$R$^{b52}$, NR$^{c52}$S(O)$_2$NR$^{c52}$R$^{d52}$, S(O)R$^{b52}$, S(O)NR$^{c52}$R$^{d52}$, S(O)$_2$R$^{b52}$, S(O)$_2$NR$^{c52}$R$^{d52}$, and BR$^{h52}$R$^{i52}$; wherein said C$_{1-6}$ alkyl, C$_{2-6}$ alkenyl, C$_{2-6}$ alkynyl, C$_{3-6}$ cycloalkyl, phenyl, 5-6 membered heteroaryl, and 4-7 membered heterocycloalkyl, are each optionally substituted with 1, 2, 3, or 4 substituents independently selected from R$^g$;

each R$^{60}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, OR$^{a60}$, SR$^{a60}$, C(O)R$^{b60}$, C(O)NR$^{c60}$R$^{d60}$(O)OR$^{a60}$C(O)R$^{b60}$C(O)NR$^{c60}$R$^{d60}$, NR$^{c60}$R$^{d60}$, NR$^{c60}$C(O)R$^{b60}$, NR$^{c60}$C(O)OR$^{a60}$, NR$^{c60}$C(O)NR$^{c60}$R$^{d60}$, NR$^{c60}$S(O)R$^{d60}$, NR$^{c60}$S(O)$_2$R$^{b60}$, NR$^{c60}$S(O)$_2$NR$^{c60}$R$^{d60}$, S(O)R$^{b60}$, S(O)NR$^{c60}$R$^{d60}$S(O)$_2$R$^{b60}$, S(O)$_2$NR$^{c60}$R$^{d60}$, and BR$^{h60}$R$^{i60}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^g$;

each R$^{70}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, NO$_2$, OR$^{a70}$, SR$^{a70}$, C(O)R$^{b70}$, C(O)NR$^{c70}$R$^{d70}$, C(O)OR$^{a70}$C(O)R$^{b70}$C(O)NR$^{c70}$R$^{d70}$, NR$^{c70}$R$^{d70}$, NR$^{c70}$C(O)R$^{b70}$, NR$^{c70}$C(O)OR$^{a70}$, NR$^{c70}$C(O)NR$^{c70}$R$^{d70}$, NR$^{c70}$S(O)R$^{b70}$, NR$^{c70}$S(O)$_2$R$^{b70}$, NR$^{c70}$S(O)$_2$NR$^{c70}$R$^{d70}$, S(O)R$^{b70}$, S(O)NR$^{c70}$R$^{d70}$, S(O)$_2$R$^{b70}$, S(O)$_2$NR$^{c70}$R$^{d70}$, and BR$^{h70}$R$^{i70}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{71}$;

each R$^{71}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, OR$^{a71}$, SR$^{a71}$, C(O)R$^{b71}$, C(O)NR$^{c71}$R$^{d71}$, C(O)OR$^{a71}$, OC(O)R$^{b71}$, OC(O)NR$^{c71}$R$^{d71}$, NR$^{c71}$R$^{d71}$, NR$^{c71}$, C(O)R$^{b71}$, NR$^{c71}$, C(O)OR$^{a71}$, NR$^{c71}$C(O)NR$^{c71}$R$^{d71}$, NR$^{71}$S(O)R$^{b71}$, NR$^{c71}$S(O)$_2$R$^{b71}$, NR$^{c71}$S(O)$_2$NR$^{c71}$R$^{d71}$, S(O)R$^{b71}$, S(O)NR$^{c71}$R$^{d71}$, S(O)$_2$R$^{b71}$, S(O)$_2$NR$^{c71}$R$^{d71}$, and BR$^{h71}$R$^{i71}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{72}$;

each R$^{72}$ is independently selected from C$_{1-6}$ alkyl, C$_{2-6}$ alkenyl, C$_{2-6}$ alkynyl, C$_{1-6}$ haloalkyl, C$_{3-6}$ cycloalkyl, phenyl, 5-6 membered heteroaryl, 4-7 membered heterocycloalkyl, halo, D, CN, OR$^{a72}$, SR$^{a72}$, C(O)R$^{b72}$, C(O)NR$^{c72}$R$^{d72}$, C(O)OR$^{a72}$, OC(O)R$^{b72}$, OC(O)NR$^{c72}$R$^{d72}$, NR$^{c72}$R$^{d72}$, NR$^{c72}$C(O)R$^{b72}$, NR$^{c72}$C(O)OR$^{a72}$, NR$^{c72}$C(O)NR$^{c72}$R$^{d72}$, NR$^{c72}$S(O)R$^{b72}$, NR$^{c72}$S(O)$_2$R$^{b72}$, NR$^{c72}$S(O)$_2$NR$^{c72}$R$^{d72}$, S(O)R$^{b72}$, S(O)NR$^{c72}$R$^{d72}$, S(O)$_2$R$^{b72}$, S(O)$_2$NR$^{c72}$R$^{d72}$, and BR$^{h72}$R$^{i72}$; wherein said C$_{1-6}$ alkyl, C$_{2-6}$ alkenyl, C$_{2-6}$ alkynyl, C$_{3-6}$ cycloalkyl, phenyl, 5-6 membered heteroaryl, and 4-7 membered heterocycloalkyl, are each optionally substituted with 1, 2, 3, or 4 substituents independently selected from R$^g$;

each R$^{a1}$, R$^{b1}$, R$^{c1}$, and R$^{d1}$ is independently selected from H, C$_{1-6}$ alkyl, C$_{2-6}$ alkenyl, C$_{2-6}$ alkynyl, C$_{1-6}$ haloalkyl, C$_{3-6}$ cycloalkyl, phenyl, 5-6 membered heteroaryl, and 4-7 membered heterocycloalkyl; wherein said C$_{1-6}$ alkyl, C$_{2-6}$ alkenyl, C$_{2-6}$ alkynyl, C$_{3-6}$ cycloalkyl, phenyl, 5-6 membered heteroaryl, and 4-7 membered heterocycloalkyl, are each optionally substituted with 1, 2, 3, or 4 substituents independently selected from R$^g$;

or any R$^{c1}$ and R$^{b1}$ attached to the same N atom, together with the N atom to which they are attached, form a 4-, 5-, 6- or 7-membered heterocycloalkyl group optionally substituted with 1, 2 or 3 substituents independently selected from R$^g$;

each R$^{h1}$ and R$^{i1}$ is independently selected from OH, C$_{1-6}$ alkoxy, and C$_{1-6}$ haloalkoxy; or any R$^{h1}$ and R$^{i1}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each R$^{a2}$, R$^{b2}$, R$^{c2}$ and R$^{d2}$ is independently selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl and 5-10 membered heteroaryl; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl and 5-10 membered heteroaryl, are each optionally substituted with 1, 2, 3, or 4 substituents independently selected from R$^{20}$;

or any R$^{c2}$ and R$^{d2}$ attached to the same N atom, together with the N atom to which they are attached, form a 4-, 5-, 6- or 7-membered heterocycloalkyl group optionally substituted with 1, 2, 3, or 4 substituents independently selected from R$^{20}$;

each R$^{e2}$ is independently selected from H, CN, C$_{1-6}$ alkyl, C$_{2-6}$ alkenyl, C$_{2-6}$ alkynyl, C$_{1-6}$ haloalkyl, C$_{1-6}$ alkylthio, C$_{1-6}$ alkylsulfonyl, C$_{1-6}$ alkylcarbonyl, C$_{1-6}$ alkylaminosulfonyl, carbamyl, C$_{1-6}$ alkylcarbamyl, di(C$_{1-6}$ alkyl)carbamyl, aminosulfonyl, C$_{1-6}$ alkylaminosulfonyl and di(C$_{1-6}$ alkyl)aminosulfonyl;

each R$^{h2}$ and R$^{i2}$ is independently selected from OH, C$_{1-6}$ alkoxy, and C$_{1-6}$ haloalkoxy; or any R$^{h2}$ and R$^{i2}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene, are each optionally substituted with 1, 2, 3, or 4 substituents independently selected from $R^{30}$;

or any $R^{c3}$ and $R^{d3}$ attached to the same N atom, together with the N atom to which they are attached, form a 4-, 5-, 6- or 7-membered heterocycloalkyl group optionally substituted with 1, 2, 3, or 4 substituents independently selected from $R^{30}$;

each $R^{e3}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h3}$ and $R^{i3}$ is independently selected from OH, $C_{1-6}$ alkoxy, and $C_{1-6}$ haloalkoxy; or any $R^{h3}$ and $R^{i3}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a5}$, $R^{b5}$, $R^{c5}$ and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{50}$;

or any $R^{c5}$ and $R^{d5}$ attached to the same N atom, together with the N atom to which they are attached, form a 4-, 5-, 6- or 7-membered heterocycloalkyl group optionally substituted with 1, 2, 3, or 4 substituents independently selected from $R^5$;

each $R^{e5}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h5}$ and $R^{i5}$ is independently selected from OH, $C_{1-6}$ alkoxy, and $C_{1-6}$ haloalkoxy; or any $R^{h5}$ and $R^{i5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a6}$, $R^{b6}$, $R^{c6}$ and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2, 3, or 4 substituents independently selected from $R^{60}$;

each $R^{e6}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h6}$ and $R^{i6}$ is independently selected from OH, $C_{1-6}$ alkoxy, and $C_{1-6}$ haloalkoxy; or any $R^{h6}$ and $R^{i6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a7}$, $R^{b7}$, $R^{c7}$ and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{70}$;

or any $R^{c7}$ and $R^{d7}$ attached to the same N atom, together with the N atom to which they are attached, form a 4-, 5-, 6- or 7-membered heterocycloalkyl group optionally substituted with 1, 2, 3, or 4 substituents independently selected from $R^{70}$;

each $R^{e70}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h7}$ and $R^{i7}$ is independently selected from OH, $C_{1-6}$ alkoxy, and $C_{1-6}$ haloalkoxy; or any $R^{h7}$ and $R^{i7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a9}$, $R^{b9}$, $R^{c9}$, and $R^{d9}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

or any $R^{c9}$ and $R^{d9}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{h9}$ and $R^{i9}$ is independently selected from OH, $C_{1-6}$ alkoxy, and $C_{1-6}$ haloalkoxy; or any $R^{h9}$ and $R^{i9}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c10}$ and $R^{d10}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{e10}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h10}$ and $R^{i10}$ is independently selected from OH, $C_{1-6}$ alkoxy, and $C_{1-6}$ haloalkoxy; or any $R^{h10}$ and $R^{i10}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a11}$, $R^{b11}$, $R^{c11}$ and $R^{d11}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c11}$ and $R^{d11}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{h11}$ and $R^{i11}$ is independently selected from OH, $C_{1-6}$ alkoxy, and $C_{1-6}$ haloalkoxy; or any $R^{h11}$ and $R^{i11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a12}$, $R^{b12}$, $R^{c12}$ and $R^{d12}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h12}$ and $R^{i12}$ is independently selected from OH, $C_{1-6}$ alkoxy, and $C_{1-6}$ haloalkoxy; or any $R^{h12}$ and $R^{i12}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{21}$;

or any $R^{c20}$ and $R^{d20}$ attached to the same N atom, together with the N atom to which they are attached, form a 4-, 5-, 6- or 7-membered heterocycloalkyl group optionally substituted with 1, 2, 3, or 4 substituents independently selected from $R^{21}$;

each $R^{h20}$ and $R^{i20}$ is independently selected from OH, $C_{1-6}$ alkoxy, and $C_{1-6}$ haloalkoxy; or any $R^{h20}$ and $R^{i20}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a21}$, $R^{b21}$, $R^{c21}$ and $R^{d21}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

or any $R^{c21}$ and $R^{d21}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{h21}$ and $R^{i21}$ is independently selected from OH, $C_{1-6}$ alkoxy, and $C_{1-6}$ haloalkoxy; or any $R^{h21}$ and $R^{i21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a22}$, $R^{b22}$, $R^{c22}$ and $R^{d22}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h22}$ and $R^{i22}$ is independently selected from OH, $C_{1-6}$ alkoxy, and $C_{1-6}$ haloalkoxy; or any $R^{h22}$ and $R^{i22}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a30}$, $R^{b30}$, $R^{c30}$ and $R^{d30}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{31}$;

or any $R^{c30}$ and $R^{d30}$ attached to the same N atom, together with the N atom to which they are attached, form a 4-, 5-, 6- or 7-membered heterocycloalkyl group optionally substituted with 1, 2, 3, or 4 substituents independently selected from $R^{31}$;

each $R^{e30}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h30}$ and $R^{i30}$ is independently selected from OH, $C_{1-6}$ alkoxy, and $C_{1-6}$ haloalkoxy; or any $R^{h30}$ and $R^{i30}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a31}$, $R^{b31}$, $R^{c31}$ and $R^{d31}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{32}$;

or any $R^{c31}$ and $R^{d31}$ attached to the same N atom, together with the N atom to which they are attached, form a 4-, 5-, 6- or 7-membered heterocycloalkyl group optionally substituted with 1, 2 or 3 substituents independently selected from $R^{32}$;

each $R^{h31}$ and $R^{i31}$ is independently selected from OH, $C_{1-6}$ alkoxy, and $C_{1-6}$ haloalkoxy; or any $R^{h31}$ and $R^{i31}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a32}$, $R^{b32}$, $R^{c32}$ and $R^{d32}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h32}$ and $R^{i32}$ is independently selected from OH, $C_{1-6}$ alkoxy, and $C_{1-6}$ haloalkoxy; or any $R^{h32}$ and $R^{i32}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a50}$, $R^{b50}$, $R^{c50}$ and $R^{d50}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{51}$;

or any $R^{c50}$ and $R^{d50}$ attached to the same N atom, together with the N atom to which they are attached, form a 4-, 5-, 6- or 7-membered heterocycloalkyl group optionally substituted with 1, 2 or 3 substituents independently selected from $R^{51}$;

each $R^{h50}$ and $R^{i50}$ is independently selected from OH, $C_{1-6}$ alkoxy, and $C_{1-6}$ haloalkoxy; or any $R^{h50}$ and $R^{i50}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a51}$, $R^{b51}$, $R^{c51}$ and $R^{d51}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{52}$;

or any $R^{c51}$ and $R^{d51}$ attached to the same N atom, together with the N atom to which they are attached, form a 4-, 5-, 6- or 7-membered heterocycloalkyl group optionally substituted with 1, 2 or 3 substituents independently selected from $R^{52}$;

each $R^{h51}$ and $R^{i51}$ is independently selected from OH, $C_{1-6}$ alkoxy, and $C_{1-6}$ haloalkoxy; or any $R^{h51}$ and $R^{i51}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a52}$, $R^{b52}$, $R^{c52}$ and $R^{d52}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h52}$ and $R^{i52}$ is independently selected from OH, $C_{1-6}$ alkoxy, and $C_{1-6}$ haloalkoxy; or any $R^{h52}$ and $R^{i52}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a60}$, $R^{b60}$, $R^{c60}$ and $R^{d60}$, is independently selected from H, $C_{1-6}$ alkyl, $C_{2-6}$ alkenyl, $C_{2-6}$ alkynyl, $C_{1-6}$ haloalkyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^g$;

or any $R^{c60}$ and $R^{d60}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{h60}$ and $R^{i60}$ is independently selected from OH, $C_{1-6}$ alkoxy, and $C_{1-6}$ haloalkoxy; or any $R^{h60}$ and $R^{i60}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a70}$, $R^{b70}$, R and $R^{d70}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{71}$; or any $R^{c70}$ and $R^{d70}$ attached to the same N atom, together with the N atom to which they are attached, form a 4-, 5-, 6- or 7-membered heterocycloalkyl group optionally substituted with 1, 2, 3, or 4 substituents independently selected from $R^{71}$;

each $R^{h70}$ and $R^{i70}$ is independently selected from OH, $C_{1-6}$ alkoxy, and $C_{1-6}$ haloalkoxy; or any $R^{h70}$ and $R^{i70}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a71}$, $R^{b71}$, $R^{c71}$ and $R^{d71}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{72}$;

or any $R^{c71}$ and $R^{d71}$ attached to the same N atom, together with the N atom to which they are attached, form a 4-, 5-, 6- or 7-membered heterocycloalkyl group optionally substituted with 1, 2 or 3 substituents independently selected from $R^{72}$;

each $R^{h71}$ and $R^{i71}$ is independently selected from OH, $C_{1-6}$ alkoxy, and $C_{1-6}$ haloalkoxy; or any $R^{h71}$ and $R^{i71}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a72}$, $R^{b72}$, $R^{c72}$ and $R^{d72}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h72}$ and $R^{i72}$ is independently selected from OH, $C_{1-6}$ alkoxy, and $C_{1-6}$ haloalkoxy; or any $R^{h72}$ and $R^{i72}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^g$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$alkyl)aminocarbonylamino.

In an embodiment of a compound of Formula I, or a pharmaceutically acceptable salt thereof, represents a single bond or a double bond;

X is N or $CR^7$;

Y is O, $NR^{5N}$, C=O, or $C(R^5)_2$;

W is C=O, or $C(R^8)_2$;

Z is O, $NR^{9N}$, $C(R^9)_2$, or a bond;

$R^1$ is selected from H, D, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, $OR^{a1}$, $SR^{a1}$, $C(O)R1^b$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{d1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$;

$R^2$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{d2}$, $NR^{c2}C(O)OR^{a2}$, $NR^{c2}C(O)NR^{c2}R^{d2}$, $NR^{c2}S(O)_2R^{b2}$, $NR^2S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{20}$;

Cy is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R_{10}$;

when $R^3N=CR^4$ is a single bond, then $R^4$ is selected from =O and =S; and $R^3$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{30}$;

when $R^3N=CR^4$ is a double bond, then $R^3$ is absent; and $R^4$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c1}S(O)_2NR^{c3}R^{d3}$, $S(O)_2R^{b3}$, and $S(O)_2NR^{c3}R^{d3}$; wherein said $C_{1-6}$ alkyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{30}$;

$R^{5N}$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{50}$;

each $R^5$ and $R^8$ are independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)_2R^{b5}$, $NR^{c5}S(O)_2NR^{c5}R^{d5}$, $S(O)_2R^{b5}$, and $S(O)_2NR^{c5}R^{d5}$;

ring A is selected from $C_{3-10}$ cycloalkyl and 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group;

n is 0, 1, or 2;

each $R^6$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)_2R^{b6}$, $NR^{c6}S(O)_2NR^{c6}R^{d6}$, $S(O)_2R^{b6}$, and $S(O)_2NR^{c6}R^{d6}$;

$R^7$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a7}$, $SR^{a7}$, $C(O)R^{b7}$, $C(O)NR^{c7}R^{d7}$, $(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$ $NR^7S(O)_2R^{b7}$, $NR^7S(O)_2NR^{c7}R^{d7}$, $S(O)_2R^{b7}$, and $S(O)_2 NR^{c7}R^{d7}$;

$R^{9N}$ is selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl;

each $R^9$ is independently selected from selected from H, D, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, $OR^{a9}$, $SR^{a9}$, $C(O)R^{b9}$, $C(O)NR^{c9}R^{d9}$, $(O)OR^{a9}$, $C(O)OR^{b9}$, $OC(O)NR^{c9}R^{d9}$, $NR^{c9}R^{d9}$, $NR^9C(O)R^{b9}$, $NR^9C(O)OR^{a9}$, $NR^9C(O)NR^{c9}R^{d9}$, $NR^9S(O)_2R^{b9}$, $NR^{c9}S(O)_2NR^{c9}R^{d9}$, $S(O)_2R^{b9}$, and $S(O)_2NR^{c9}R^{d9}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a10}$, $SR^{a10}$, $C(O)R^{b10}$, $C(O)NR^{c10}R^{d10}$, $C(O)OR^{a10}(O)R^{b10}$, $OC(O)NR^{c10}R^{d10}$, $NR^{c10}R^{d10}$, $NR^{c10}$, $C(O)R^{b10}$, $NR^{c10}C(O)OR^{a10}$, $NR^{c10}C(O)NR^{c10}R^{d10}$ $NR^{c1}S(O)_2R^{b10}$, $NR^{c10}S(O)_2NR^{c10}R^{d10}$, $S(O)R^{b10}$, and $S(O)_2NR^{c10}R^{d10}$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a20}$, $SR^{a20}$, $C(O)R^{b20}$, $C(O)NR^{c20}R^{d20}$, $C(O)OR^{a20}$, $OC(O)R^{b20}$, $OC(O)NR^{c20}R^{d20}$, $NR^{c20}R^{d20}$, $NR^{c20}C(O)R^{b20}$, $NR^{c20}C(O)OR^{a20}$, $NR^{c20}C(O)NR^{c20}R^{d20}$, $NR^{c20}S(O)_2R^{b20}$, $NR^{c20}S(O)_2NR^{c20}R^{d20}$, $S(O)_2R^{b20}$, and $S(O)_2NR^{c20}R^{d20}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{a21}R^{b21}$, $NR^{c21}C(O)R^{b21}$, $NR^{c21}C(O)OR^{a21}$, $NR^{c21}C(O)NR^{c21}R^{d21}$, $NR^{c21}S(O)_2R^{b21}$, $NR^{c21}S(O)_2NR^{c21}R^{d21}$, $S(O)_2R^{b21}$, and $S(O)_2 NR^{c21}R^{d21}$;

each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a30}$, $SR^{a30}$, $C(O)R^{b30}$, $C(O)NR^{c30}R^{d30}$, $C(O)OR^{a3}$, $OC(O)R^{b30}$, $OC(O)NR^{c30}R^{d30}$, $NR^{c30}R^{d30}$, $NR^{c30}C(O)R^{b30}$, $NR^{c30}C(O)OR^{a30}$, $NR^{c30}C(O)NR^{c30}R^{d30}$, $NR^{c30}S(O)_2R^{b30}$, $NR^{c30}S(O)_2NR^{c30}R^{d30}$ $S(O)_2R^{b30}$, and $S(O)_2NR^{c30}R^{d30}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{31}$;

each $R^{31}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)OR^{a31}$, $NR^{c31}C(O)NR^{c1}R^{d31}$, $NR^{c31}S(O)_2R^{b31}$, $NR^{c31}S(O)_2NR^{c31}R^{d31}$, $S(O)_2R^{b31}$, and $S(O)_2NR^{c31}R^{d31}$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a50}$, $SR^{a50}$, $C(O)R^{b50}$, $C(O)NR^{c50}R^{d50}$, $C(O)OR^{a50}$, $OC(O)R^{b50}$, $OC(O)NR^{c50}R^{d50}$, $NR^{c50}R^{d50}$, $NR^{c50}C(O)R^{b50}$, $NR^{c50}C(O)OR^{a50}$, $NR^{c50}C(O)NR^{c50}R^{d50}$, $NR^{c50}S(O)_2R^{b50}$, $NR^{c50}S(O)_2NR^{c50}R^{d50}$, $S(O)_2R^{b50}$, and $S(O)_2NR^{c50}R^{d50}$;

each $R^{a1}$, $R^{b1}$, $R^{c1}$, and $R^{d1}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl;

or any $R^{c1}$ and $R^{d1}$ attached to the same N atom, together with the N atom to which they are attached, form a 4-, 5-, 6- or 7-membered heterocycloalkyl group;

each $R^{a2}$, $R^{b2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{20}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3, or 4 substituents independently selected from $R^{20}$;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene, are each optionally substituted with 1, 2, 3, or 4 substituents independently selected from $R^{30}$;

or any $R^{c3}$ and $R^{d3}$ attached to the same N atom, together with the N atom to which they are attached, form a 4-, 5-, 6- or 7-membered heterocycloalkyl group optionally substituted with 1, 2, 3, or 4 substituents independently selected from $R^{30}$;

each $R^{a5}$, $R^{b5}$, $R^{c5}$ and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c5}$ and $R^{d5}$ attached to the same N atom, together with the N atom to which they are attached, form a 4-, 5-, 6- or 7-membered heterocycloalkyl group;

each $R^{a6}$, $R^{b6}$, $R^{c6}$ and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c6}$ and $R^{d6}$ attached to the same N atom, together with the N atom to which they are attached, form a 4-, 5-, 6- or 7-membered heterocycloalkyl group;

each $R^{a7}$, $R^{b7}$, $R^{c7}$ and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c7}$ and $R^{d7}$ attached to the same N atom, together with the N atom to which they are attached, form a 4-, 5-, 6- or 7-membered heterocycloalkyl group;

each $R^{a9}$, $R^{b9}$, $R^{c9}$, and $R^{d9}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl;

or any $R^{c9}$ and $R^{d9}$ attached to the same N atom, together with the N atom to which they are attached, form a 4-, 5-, 6- or 7-membered heterocycloalkyl group;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c10}$ and $R^{d10}$ attached to the same N atom, together with the N atom to which they are attached, form a 4-, 5-, 6- or 7-membered heterocycloalkyl group;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{21}$;

or any $R^{c20}$ and $R^{d20}$ attached to the same N atom, together with the N atom to which they are attached, form a 4-, 5-, 6- or 7-membered heterocycloalkyl group optionally substituted with 1, 2, 3, or 4 substituents independently selected from $R^{21}$;

each $R^{a21}$, $R^{b21}$, $R^{c21}$ and $R^{d21}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c21}$ and $R^{d21}$ attached to the same N atom, together with the N atom to which they are attached, form a 4-, 5-, 6- or 7-membered heterocycloalkyl group;

each $R^{a30}$, $R^{b30}$, $R^{c30}$ and $R^{d30}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{31}$;

or any $R^{c30}$ and $R^{d30}$ attached to the same N atom, together with the N atom to which they are attached, form a 4-, 5-, 6- or 7-membered heterocycloalkyl group optionally substituted with 1, 2, 3, or 4 substituents independently selected from $R^{31}$;

each $R^{a31}$, $R^{b31}$, $R^{c31}$ and $R^{d31}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c31}$ and $R^{d31}$ attached to the same N atom, together with the N atom to which they are attached, form a 4-, 5-, 6- or 7-membered heterocycloalkyl group; and each $R^{a50}$, $R^{b50}$, $R^{c50}$ and $R^{d50}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl;

or any $R^{c10}$ and $R^{d50}$ attached to the same N atom, together with the N atom to which they are attached, form a 4-, 5-, 6- or 7-membered heterocycloalkyl group.

In yet another embodiment, the compound of Formula I is a compound of Formula II:

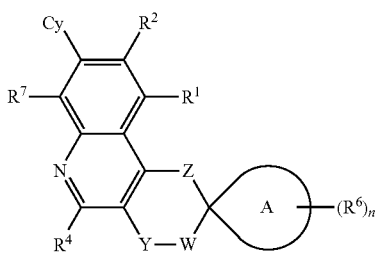

(II)

or a pharmaceutically acceptable salt thereof, wherein:

Y is $NR^{5N}$, or C=O;

W is C=O, or $C(R^8)_2$;

Z is O, $NR^{9N}$, or a bond;

$R^1$ is selected from H, D, $C_{1-6}$ alkyl, halo, and CN;

$R^2$ is selected from H, $C_{1-6}$ alkyl, $C_{1-6}$ haloalkyl, halo, D, CN, $OR^{a2}$, and $NR^{c2}R^{d2}$; wherein said $C_{1-6}$ alkyl, is optionally substituted with 1, 2, or 3 substituents independently selected from $R^{20}$;

Cy is selected from $C_{6-10}$ aryl and 5-10 membered heteroaryl; wherein the 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, or 3 substituents independently selected from $R^{10}$;

$R^4$ is selected from H, $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a3}$, and $NR^{c3}R^{d3}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, or 3 substituents independently selected from $R^{30}$;

$R^{5N}$ is selected from H, $C_{1-6}$ alkyl, and $C_{1-6}$ haloalkyl; wherein said $C_{1-6}$ alkyl is optionally substituted with 1, 2, or 3 substituents independently selected from $R^{50}$;

$R^8$ is selected from H, $C_{1-6}$ alkyl, $C_{1-6}$ haloalkyl, halo, D, CN, $OR^{a5}$, and $NR^{c5}R^{d5}$;

ring A is selected from $C_{3-10}$ cycloalkyl and 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group;

n is 0, 1, or 2;

each $R^6$ is independently selected from $C_{1-6}$ alkyl, $C_{1-6}$ haloalkyl, halo, D, CN, $OR^{a6}$, $C(O)R^{b6}$, $C(O)NR^{c6}R^{d6}$, $C(O)OR^{a6}$, $NR^{c6}R^{d6}$, and $NR^{c6}C(O)R^{b6}$;

$R^7$ is selected from H, $C_{1-6}$ alkyl, $C_{1-6}$ haloalkyl, halo, D, CN, $OR^{a7}$, and $NR^{c7}R^{d7}$;

$R^{9N}$ is selected from H, $C_{1-6}$ alkyl, and $C_{1-6}$ haloalkyl;

each $R^{10}$ is independently selected from $C_{1-6}$ alkyl, $C_{1-6}$ haloalkyl, halo, D, CN, $OR^{a10}$, and $NR^{c10}R^{d10}$;

each $R^{20}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a20}$, and $NR^{c20}R^{d20}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, or 3 substituents independently selected from $R^{21}$;

each $R^{21}$ is independently selected from $C_{1-6}$ alkyl, $C_{1-6}$ haloalkyl halo, D, CN, $OR^{a21}$ and $NR^{c21}R^{c21}$;

each $R^{30}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a30}$ and, $NR^{c30}R^{d30}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, or 3 substituents independently selected from $R^{31}$;

each $R^{31}$ is independently selected from $C_{1-6}$ alkyl, $C_{1-6}$ haloalkyl, halo, D, CN, $OR^{a31}$, and $NR^{c31}R^{d31}$;

each $R^{50}$ is independently selected from $C_{1-6}$ alkyl, $C_{1-6}$ haloalkyl, halo, D, CN, $OR^{a50}$, $C(O)R^{b50}$, $C(O)NR^{c50}R^{d50}$, $C(O)OR^{a50}$, $NR^{c50}R^{d50}$, and $NR^{c50}C(O)R^{b50}$;

each $R^{a2}$, $R^{c2}$ and $R^{d2}$ is independently selected from H, $C_{1-6}$ alkyl, and $C_{1-6}$ haloalkyl; wherein said $C_{1-6}$ alkyl, is optionally substituted with 1, 2, or 3 substituents independently selected from $R^{20}$;

each $R^{a3}$, $R^{c3}$ and $R^{d3}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, or 3 substituents independently selected from $R^{30}$;

or any $R^{c3}$ and $R^{d3}$ attached to the same N atom, together with the N atom to which they are attached, form a 4-, 5-, or 6-membered heterocycloalkyl group optionally substituted with 1, 2, or 3 substituents independently selected from $R^{30}$;

each $R^{a5}$, $R^{c5}$ and $R^{d5}$ is independently selected from H, $C_{1-6}$ alkyl, and $C_{1-6}$ haloalkyl;

each $R^{a6}$, $R^{b6}$, $R^{c6}$ and $R^{d6}$ is independently selected from H, $C_{1-6}$ alkyl, $C_{2-6}$ alkenyl, $C_{2-6}$ alkynyl, and $C_{1-6}$ haloalkyl;

each $R^{a7}$, $R^{b7}$, $R^{c7}$ and $R^{d7}$ is independently selected from H, $C_{1-6}$ alkyl, and $C_{1-6}$ haloalkyl;

each $R^{a10}$, $R^{c10}$ and $R^{d10}$ is independently selected from H, $C_{1-6}$ alkyl, and $C_{1-6}$ haloalkyl;

each $R^{a20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, or 3 substituents independently selected from $R^{21}$;

or any $R^{c20}$ and $R^{d20}$ attached to the same N atom, together with the N atom to which they are attached, form a 4-, 5-, or 6-membered heterocycloalkyl group optionally substituted with 1, 2, or 3 substituents independently selected from $R^{21}$;

each $R^{a21}$, $R^{c21}$ and $R^{d21}$, is independently selected from H, $C_{1-6}$ alkyl, and $C_{1-6}$ haloalkyl;

each $R^{a30}$, $R^{c30}$ and $R^{d30}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, or 3 substituents independently selected from $R^{31}$;

or any $R^{c30}$ and $R^{d30}$ attached to the same N atom, together with the N atom to which they are attached, form a 4-, 5-, or 6-membered heterocycloalkyl group optionally substituted with 1, 2, or 3 substituents independently selected from $R^{31}$;

each $R^{a31}$, $R^{c31}$ and $R^{d31}$, is independently selected from H, $C_{1-6}$ alkyl, and $C_{1-6}$ haloalkyl; and each $R^{a50}$, $R^{b50}$, $R^{c50}$ and $R^{d50}$, is independently selected from H, $C_{1-6}$ alkyl, and $C_{1-6}$ haloalkyl.

In an embodiment of a compound of Formula II, or a pharmaceutically acceptable salt thereof, Y is $NR^{5N}$, or C=O;

W is C=O, or $C(R^8)_2$;

Z is O, $NR^{9N}$, or a bond;

$R^1$ is selected from H, D, $C_{1-3}$ alkyl, and halo;

$R^2$ is selected from H, $C_{1-6}$ alkyl, $C_{1-6}$ haloalkyl, halo, D, and CN; wherein said $C_{1-6}$ alkyl, is optionally substituted with 1 or 2 substituents independently selected from $R^{20}$;

Cy is selected from $C_{6-10}$ aryl and 5-10 membered heteroaryl; wherein the 5-10 membered heteroaryl each has at least one ring-forming carbon atom and 1, 2, or 3 ring-forming heteroatoms independently selected from N and O; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, or 3 substituents independently selected from $R^{10}$;

$R^4$ is selected from H, $C_{1-6}$ alkyl, $C_{1-6}$ haloalkyl, $C_{3-6}$ cycloalkyl, 4-6 membered heterocycloalkyl, phenyl, 5-6 membered heteroaryl, halo, D, CN, $OR^{a3}$, and $NR^{c3}R^{d3}$; wherein said $C_{1-6}$ alkyl, $C_{3-6}$ cycloalkyl, 4-6 membered heterocycloalkyl, phenyl, and 5-6 membered heteroaryl, are each optionally substituted with 1, 2, or 3 substituents independently selected from $R^{30}$;

$R^{5N}$ is selected from H, $C_{1-6}$ alkyl, and $C_{1-6}$ haloalkyl; wherein said $C_{1-6}$ alkyl is optionally substituted with 1, 2, or 3 substituents independently selected from $R^{50}$;

$R^8$ is selected from H, $C_{1-6}$ alkyl, $C_{1-6}$ haloalkyl, halo, D, and CN;

ring A is selected from $C_{3-6}$ cycloalkyl and 4-6 membered heterocycloalkyl; wherein the 4-14 membered heterocycloalkyl has at least one ring-forming carbon atom and 1 or 2 ring-forming heteroatoms independently selected from N and O; wherein a ring-forming carbon atom of 4-6 membered heterocycloalkyl is optionally substituted by oxo to form a carbonyl group;

n is 0, 1, or 2;

each $R^6$ is independently selected from $C_{1-6}$ alkyl, $C_{1-6}$ haloalkyl, halo, D, CN, $OR^a$, $C(O)R^b$, and $NR^{c6}R^{d6}$;

$R^7$ is selected from H, $C_{1-6}$ alkyl, $C_{1-6}$ haloalkyl, halo, D, and CN;

$R^{9N}$ is selected from H, $C_{1-6}$ alkyl, and $C_{1-6}$ haloalkyl;

each $R^{10}$ is independently selected from $C_{1-6}$ alkyl, $C_{1-6}$ haloalkyl, halo, D, CN, $OR^{a21}$, and $NR^{c10}R^{d10}$;

each $R^{20}$ is independently selected from $C_{1-6}$ alkyl, $C_{1-6}$ haloalkyl, phenyl, 5-6 membered heteroaryl, halo, D, CN, $OR^{a20}$, and $NR^{c20}R^{d20}$; wherein said $C_{1-6}$ alkyl, phenyl, and 5-6 membered heteroaryl, are each optionally substituted with 1 or 2 substituents independently selected from $R^{21}$;

each $R^{21}$ is independently selected from $C_{1-6}$ alkyl, $C_{1-6}$ haloalkyl halo, D, CN, $OR^{a21}$ and $NR^{c21}R^{d21}$;

each $R^{30}$ is independently selected from $C_{1-6}$ alkyl, $C_{1-6}$ haloalkyl, $C_{3-6}$ cycloalkyl, 4-6 membered heterocycloalkyl, phenyl, 5-6 membered heteroaryl, halo, D, CN, $OR^{a30}$ and, $NR^{c30}R^{d30}$; wherein said $C_{1-6}$ alkyl, $C_{3-6}$ cycloalkyl, 4-6 membered heterocycloalkyl, phenyl, and 5-6 membered heteroaryl, are each optionally substituted with 1 or 2 substituents independently selected from $R^{31}$;

each $R^{31}$ is independently selected from $C_{1-6}$ alkyl, $C_{1-6}$ haloalkyl, halo, D, CN, $OR^{a31}$, and $NR^{c31}R^{d31}$;

each $R^{50}$ is independently selected from $C_{1-6}$ alkyl, $C_{1-6}$ haloalkyl, halo, D, CN, $OR^{a50}$, $C(O)NR^{c50}R^{d50}$, $NR^{c50}R^{d50}$, and $NR^{c50}$, $C(O)R^{b50}$;

each $R^{a3}$, $R^{c3}$ and $R^{d3}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, or 3 substituents independently selected from $R^{30}$;

or any $R^{c3}$ and $R^{d3}$ attached to the same N atom, together with the N atom to which they are attached, form a 4-, 5-, or 6-membered heterocycloalkyl group optionally substituted with 1, 2, or 3 substituents independently selected from $R^{30}$;

each $R^{a6}$, $R^{b6}$, $R^{c6}$ and $R^{d6}$ is independently selected from H, $C_{1-6}$ alkyl, $C_{2-6}$ alkenyl, $C_{2-6}$ alkynyl, and $C_{1-6}$ haloalkyl;

each $R^{a10}$, $R^{c10}$ and $R^{d10}$ is independently selected from H, $C_{1-6}$ alkyl, and $C_{1-6}$ haloalkyl;

each $R^{a20}$, $R^{c20}$ and $R^{d20}$ is independently selected from H, $C_{1-6}$ alkyl, $C_{1-6}$ haloalkyl, phenyl and 5-6 membered heteroaryl; wherein said $C_{1-6}$ alkyl, phenyl and 5-6 membered heteroaryl, are each optionally substituted with 1 or 2 substituents independently selected from $R^{21}$;

each $R^{a21}$, $R^{c21}$ and $R^{d21}$, is independently selected from H, $C_{1-6}$ alkyl, and $C_{1-6}$ haloalkyl;

each $R^{a30}$, $R^{c30}$ and $R^{d30}$ is independently selected from H, $C_{1-6}$ alkyl, $C_{1-6}$ haloalkyl, $C_{3-6}$ cycloalkyl, 4-6 membered heterocycloalkyl, phenyl and 5-6 membered heteroaryl; wherein said $C_{1-6}$ alkyl, $C_{3-6}$ cycloalkyl, 4-6 membered heterocycloalkyl, phenyl and 5-6 membered heteroaryl, are each optionally substituted with 1 or 2 substituents independently selected from $R^{31}$;

or any $R^{c30}$ and $R^{d30}$ attached to the same N atom, together with the N atom to which they are attached, form a 4-, 5-, or 6-membered heterocycloalkyl group optionally substituted with 1 or 2 substituents independently selected from $R^{31}$;

each $R^{a31}$, $R^{c31}$ and $R^{d31}$, is independently selected from H, $C_{1-6}$ alkyl, and $C_{1-6}$ haloalkyl; and each $R^{a50}$, $R^{c50}$ and $R^{d50}$, is independently selected from H, $C_{1-6}$ alkyl, and $C_{1-6}$ haloalkyl.

In another embodiment of Formula II,

Y is NH, N($C_{1-6}$ alkyl), or C=O; wherein said alkyl is optionally substituted with 1 or 2 substituents independently selected from halo, OH, C(O)NH$_2$, and CN;

W is C=O, or C($R^8$)$_2$;

Z is O, $NR^{9N}$, or a bond;

$R^1$ is H or halo;

$R^2$ is H, halo, or $C_{1-6}$ alkyl; wherein said $C_{1-6}$ alkyl, is optionally substituted with 1 or 2 substituents independently selected from $C_{1-6}$ alkyl, $C_{1-6}$ haloalkyl, phenyl, 5-6 membered heteroaryl, halo, D, CN, OH, and O($C_{1-6}$ alkyl); wherein phenyl is optionally substituted with 1 or 2 substituents independently selected from halo and CN;

Cy is $C_{6-10}$ aryl or 5-10 membered heteroaryl; both of which are optionally substituted with 1, 2, 3 or 4 substituents independently selected from $C_{1-6}$ alkyl, halo, OH, and O($C_{1-6}$ alkyl);

$R^4$ is selected from H, $C_{1-6}$ alkyl, O($C_{1-6}$ alkyl), $C_{3-6}$ cycloalkyl, and 4-6 membered heterocycloalkyl, wherein said alkyl, cycloalkyl, and heterocycloalkyl are each optionally substituted one or two times with 4-10 membered heterocycloalkyl which is optionally substituted with $C_{1-6}$ alkyl, NH$_2$, or N($C_{1-6}$ alkyl)$_2$;

each $R^5$ and $R^6$ are independently selected from H, $C_{1-6}$ alkyl, $C_{1-6}$ haloalkyl, halo, D, and CN;

ring A is 4-7 membered heterocycloalkyl;

n is 0, 1, or 2;

each $R^6$ is independently selected from $C_{1-6}$ alkyl, $C_{2-6}$ alkenyl, $C_{2-6}$ alkynyl, $C_{1-6}$ haloalkyl, halo, D, CN, OH, O($C_{1-6}$ alkyl), NH$_2$, N($C_{1-6}$ alkyl)$_2$, C(O)H, C(O)$C_{1-6}$ alkyl, and C(O)$C_{2-6}$ alkenyl;

$R^7$ is selected from H, $C_{1-6}$ alkyl, $C_{1-6}$ haloalkyl, halo, D, CN, OH, and O($C_{1-6}$ alkyl); and $R^{9N}$ is selected from H, $C_{1-6}$ alkyl, $C_{2-6}$ alkenyl, $C_{2-6}$ alkynyl, and $C_{1-6}$ haloalkyl.

In another aspect, provided herein is a compound of Formula I:

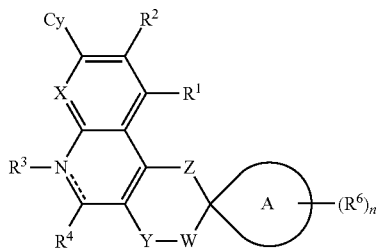

(I)

or a pharmaceutically acceptable salt thereof, wherein:

═ represents a single bond or a double bond;

X is N or $CR^7$;

Y is O, $NR^{5N}$, C=O, or C($R^5$)$_2$;

W is C=O, or C($R^8$)$_2$;

Z is O, $NR^{9N}$, O($R^9$)$_2$, or a bond;

$R^1$ and $R^2$ are each independently selected from H, D, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, $OR^a$, $SR^a$, C(O)$R^b$, C(O)$NR^cR^d$, (O)$OR^a$, OC(O)$R^b$, OC(O)$NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, S(O)$R^b$, S(O)$NR^cR^d$, S(O)$_2R^b$, S(O)$_2NR^cR^d$, and $BR^hR^i$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

Cy is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

when $R^3N\!\!=\!\!CR^4$ is a single bond, then $R^4$ is selected from =O and =S;

$R^3$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{30}$;

when $R^3N\!\!=\!\!CR^4$ is a double bond, then $R^3$ is absent;

$R^4$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, NO$_2$, $OR^{a3}$, $SR^{a3}$, C(O)$R^{b3}$, C(O)$NR^{c3}R^{d3}$, C(O)$OR^{a3}$, OC(O)$R^{b3}$, OC(O)$NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, C(=$NR^{e3}$)$R^{b3}$, C(=NO$R^{a3}$)$R^{b3}$, C(=$NR^{e3}$)$NR^{c3}R^{d3}$, $NR^{c3}C(=NR^{e3})NR^{c3}R^{d3}$, $NR^{c3}C(=NR^{e3})R^{b3}$, $NR^{c3}S(O)R^{b3}$, $NR^{c3}S(O)_2R^{b3}$, $NR^{33}S(O)_2NR^{c3}R^{d3}$, S(O)$R^{b3}$, S(O)$NR^{c3}R^{d3}$, S(O)$_2R^{b3}$, S(O)$_2NR^{c3}R^{d3}$, and $BR^{h3}R^{i3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{30}$;

$R^{5N}$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{50}$;

each $R^5$ and $R^8$ are independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a5}$, $SR^{a5}$, $C(O)R^{b5}$, $C(O)NR^{c5}R^{d5}$, $(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NOR^{a5})R^{b5}$, $C(=NR^{e5})NR^{c5}R^{d5}$, $NR^{c5}C(=NR^{e5})NR^{c5}R^{d5}$, $NR^{c5}C(=NR^{e4})R^{b5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $BR^{h5}R^{i5}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{50}$;

ring A is $C_{3-14}$ cycloalkyl or 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group;

n is 0, 1, 2, 3, or 4;

each $R^6$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOR^{a6})R^{b6}$, $C(=NR^{e6})NR^{c6}R^{d6}$, $NR^{c6}C(=NR^{e6})NR^{c6}R^{d6}$, $NRO6C(=NR^{e6})R^{b6}$, $NR^{c6}S(O)R^{b6}$, $NR^6S(O)_2R^{b6}$, $NR^6S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $BR^{h6}R^{i6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{60}$;

$R^7$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a7}$, $SR^{a7}$, $C(O)R^{b7}$, $C(O)NR^{c7}R^{d7}$, $(O)OR^{a7}$, $C(O)R^{b7}$, $OC(O)NR^{c7}R^{d7}$, $NR^{c7}R^{d7}$, $NR^7C(O)R^{b7}$, $NR^7C(O)OR^{a7}$, $NR^{c7}C(O)NR^{c7}R^{d7}$, $C(=NR^{e7})R^{b7}$, $C(=NOR^{a7})R^{b7}$, $C(=NR^{e7})NR^{c7}R^{d7}$, $NR^{c7}C(=NR^{e7})NR^{c7}R^{d7}$, $NR^{c7}C(=NR^{e7})R^{b7}$, $NR^{c7}S(O)R^{b7}$, $NR^7S(O)_2R^{b7}$, $NR^7S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, and $BR^{h7}R^{i7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{70}$;

$R^{9N}$ is selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^9$ is independently selected from selected from H, D, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, $OR^{a9}$, $SR^{a9}$, $C(O)R^{b9}$, $C(O)NR^{c9}R^{d9}$, $(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$, and $BR^{h9}R^{i9}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a10}$, $SR^{a10}$, $C(O)R^{b10}$, $C(O)NR^{c10}R^{d10}$, $C(O)OR^{a10}$, $CO(O)R^{b10}$, $OC(O)NR^{c10}R^{d10}$, $NR^{c10}R^{d10}$, $NR^{c10}$, $C(O)R^{b10}$, $NR^{c10}C(O)OR^{a10}$, $NR^{c10}C(O)NR^{c10}R^{d10}$, $C(=NR^{e10})R^{b10}$, $C(=NOR^{a10})R^{b10}$, $C(=NR^{e10})NR^{c10}R^{d10}$, $NR^{c10}C(=NR^{e10})NR^{c10}R^{d10}$, $NR^{c10}C(=NR^{e10})R^{b10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, $S(O)_2NR^{c10}R^{d10}$, and $BR^{h10}R^{i10}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, and $BR^{h11}R^{i11}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, and $BR^{h12}R^{i12}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a30}$, $SR^{a30}$, $C(O)R^{b30}$, $C(O)NR^{c30}R^{d30}$, $C(O)OR^{a30}C(O)R^{b30}C(O)NR^{c30}R^{d3}$, $NR^{c3}R^{d3}$, $NR^{c30}C(O)R^{b30}$, $NR^{c30}C(O)OR^{a30}$, $NR^{c30}C(O)NR^{c30}R^{d30}$, $C(=NR^{e30})R^{b30}$, $C(=NOR^{a30})R^{b30}$, $C(=NR^{e30})NR^{c30}R^{d30}$, $NR^{c30}C(=NR^{e30})NR^{c30}R^{d30}$, $NR^{c30}C(=NR^{e30})R^{b30}$, $NR^{c30}S(O)R^{b30}$, $NR^{c30}S(O)_2R^{b30}$, $NR^{30}S(O)_2NR^{c30}R^{d30}$, $S(O)R^{b30}$, $S(O)NR^{c30}R^{d30}$, $S(O)_2R^{b30}$, $S(O)_2NR^{c30}R^{d30}$, and $BR^{h30}R^{i30}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{31}$;

each $R^{31}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)OR^{a31}$, $NR^{b31}C(O)NR^{c1}R^{d31}$, $NR^{c1}S(O)R^{b31}$, $NR^{c31}S(O)_2R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, and $BR^{h31}R^{i31}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{32}$;

each $R^{32}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a32}$, $SR^{a32}$, $C(O)R^{b32}$, $C(O)NR^{c32}R^{d32}(O)OR^{a32}$, $OC(O)R^{b32}$, $OC(O)NR^{c32}R^{d32}$, $NR^{c32}R^{d32}$, $NR^{c32}C(O)R^{b32}$, $NR^{c32}C(O)OR^{a32}$, $NR^{c32}C(O)NR^{c32}R^{d32}$, $NR^{c32}S(O)R^{b32}$, $NR^{c32}S(O)_2R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, and $BR^{h32}R^{i32}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a50}$, $SR^{a50}$, $C(O)R^{b50}$, $C(O)NR^{c50}R^{d50}$ $(O)OR^{a50}$, $OC(O)R^{b50}$, $OC(O)NR^{c5}R^{d5}$, $NR^{c5}R^{d5}$, $NR^{c50}C(O)R^{b50}$, $NR^{c50}C(O)OR^{a50}$, $NR^{c5}C(O)NR^{c50}R^{d50}$, $NR^{c50}S(O)R^{b50}$, $NR^{c50}S(O)_2R^{b50}$, $NR^{c50}S(O)_2NR^{c50}R^{d50}$, $S(O)R^{b50}$, $S(O)NR^{c5}R^{d50}$, $S(O)_2R^{b50}$, $S(O)_2NR^{c50}R^{d50}$, and $BR^{h50}R^{i50}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{51}$;

each $R^{51}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a51}$, $SR^{a51}$, $C(O)R^{b51}$, $C(O)NR^{c51}R^{d51}$, $C(O)OR^{a510}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{51}C(O)NR^{c51}R^{d51}$, $NR^{c51}S(O)R^{b51}$, $NR^{51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, and $BR^{h51}R^{i51}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene, are each optionally substituted with 1, 2, 3, or 4 substituents independently selected from $R^{52}$;

each $R^{52}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a52}$, $SR^{a52}$, $C(O)R^{b52}$, $C(O)NR^{c52}R^{d52}$, $(O)OR^{a52}$, $C(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)R^{b52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, and $BR^{h52}R^{i52}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{60}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a60}$, $SR^{a60}$, $C(O)R^{b60}$, $C(O)NR^{c60}R^{d60}$, $(O)OR^{a60}$, $OC(O)R^{b60}$, $OC(O)NR^{c60}R^{d60}$, $NR^{c60}R^{d60}$, $NR^{c60}C(O)R^{b60}$, $NR^{c60}C(O)OR^{a60}$, $NR^{c60}C(O)NR^{c60}R^{d60}$, $NR^{60}S(O)R^{b60}$, $NR^{c60}S(O)_2R^{b60}$, $NR^{c60}S(O)_2NR^{c60}R^{d60}$, $S(O)R^{b60}$, $S(O)NR^{c60}R^{d60}$, $S(O)_2R^{b60}$, $S(O)_2NR^{c60}R^{d60}$, and $BR^{h60}R^{i60}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^g$;

each $R^{70}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a70}$, $SR^{a70}$, $C(O)R^{b70}$, $C(O)NR^{c70}R^{d70}$, $C(O)OR^{a70}C(O)R^{b70}C(O)NR^{c70}R^{d70}$, $NR^{c70}R^{d70}$, $NR^{c70}C(O)R^{b70}$, $NR^{c70}C(O)OR^{a70}$, $NR^{c7}C(O)NR^{c70}R^{d70}$, $NR^{c70}S(O)R^{b70}$, $NR^{70}S(O)_2R^{b70}$, $NR^{c70}S(O)_2NR^{c70}R^{d70}$, $S(O)R^{b70}$, $S(O)NR^{c70}R^{d70}$, $S(O)_2R^{b70}$, $S(O)_2NR^{c70}R^{d70}$, and $BR^{h70}R^{i70}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{71}$;

each $R^{71}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a71}$, $SR^{a71}$, $C(O)R^{b71}$, $C(O)NR^{c71}R^{d71}$, $C(O)OR^{a71}$, $OC(O)R^{b71}$, $OC(O)NR^{c71}R^{d71}$, $NR^{c71}R^{d71}$, $NR^{c71}C(O)R^{b71}$, $NR^{c71}C(O)OR^{a71}$, $NR^{c71}C(O)NR^{c71}R^{d71}$, $NR^{71}S(O)R^{b71}$, $NR^{71}S(O)_2R^{b71}$, $NR^{c71}S(O)_2NR^{c71}R^{d71}$, $S(O)R^{b71}$, $S(O)NR^{c71}R^{d71}$, $S(O)_2R^{b71}$, $S(O)_2NR^{c71}R^{d71}$, and $BR^{h71}R^{i71}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{72}$;

each $R^{72}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a72}$, $SR^{a72}$, $C(O)R^{b72}$, $C(O)NR^{c72}R^{d72}$, $C(O)OR^{a72}$, $OC(O)R^{b72}$, $OC(O)NR^{c72}R^{d72}$, $NR^{c72}R^{d72}$, $NR^{c72}C(O)R^{b72}$, $NR^{c72}C(O)OR^{a72}$, $NR^{c72}C(O)NR^{c72}R^{d72}$, $NR^{c72}S(O)R^{b72}$, $NR^{c72}S(O)_2R^{b72}$, $NR^{c72}S(O)_2NR^{c72}R^{d72}$, $S(O)R^{b72}$, $S(O)NR^{c72}R^{d72}$, $S(O)_2R^{b72}$, $S(O)_2NR^{c72}R^{d72}$, and $BR^{h72}R^{i72}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^a$, $R^b$, $R^c$, and $R^d$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

or any $R^c$ and $R^d$ attached to the same N atom, together with the N atom to which they are attached, form a 4-, 5-, 6- or 7-membered heterocycloalkyl group optionally substituted with 1, 2 or 3 substituents independently selected from $R^g$;

each $R^h$ and $R^i$ is independently selected from OH, $C_{1-6}$ alkoxy, and $C_{1-6}$ haloalkoxy; or any $R^h$ and $R^i$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene, are each optionally substituted with 1, 2, 3, or 4 substituents independently selected from $R^{30}$;

or any $R^{c3}$ and $R^{d3}$ attached to the same N atom, together with the N atom to which they are attached, form a 4-, 5-, 6- or 7-membered heterocycloalkyl group optionally substituted with 1, 2, 3, or 4 substituents independently selected from $R^{30}$;

each $R^{e3}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h3}$ and $R^{i3}$ is independently selected from OH, $C_{1-6}$ alkoxy, and $C_{1-6}$ haloalkoxy; or any $R^{h3}$ and $R^{i3}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a5}$, $R^{5b}$, $R^{c5}$ and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{50}$;

or any $R^{c5}$ and $R^{d5}$ attached to the same N atom, together with the N atom to which they are attached, form a 4-, 5-, 6- or 7-membered heterocycloalkyl group optionally substituted with 1, 2, 3, or 4 substituents independently selected from $R^{50}$;

each $R^{e5}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h5}$ and $R^{i5}$ is independently selected from OH, $C_{1-6}$ alkoxy, and $C_{1-6}$ haloalkoxy; or any $R^{h5}$ and $R^{i5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a6}$, $R^{b6}$, $R^{c6}$ and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2, 3, or 4 substituents independently selected from $R^{60}$;

each $R^{e6}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h6}$ and $R^{i6}$ is independently selected from OH, $C_{1-6}$ alkoxy, and $C_{1-6}$ haloalkoxy; or any $R^{h6}$ and $R^{i6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a7}$, $R^{b7}$, $R^{c7}$ and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{70}$;

or any $R^{c7}$ and $R^{d7}$ attached to the same N atom, together with the N atom to which they are attached, form a 4-, 5-, 6- or 7-membered heterocycloalkyl group optionally substituted with 1, 2, 3, or 4 substituents independently selected from $R^{70}$;

each $R^{e70}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h7}$ and $R^{i7}$ is independently selected from OH, $C_{1-6}$ alkoxy, and $C_{1-6}$ haloalkoxy; or any $R^{h7}$ and $R^{i7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a9}$, $R^{b9}$, $R^{c9}$, and $R^{d9}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

or any $R^{c9}$ and $R^{d9}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{h9}$ and $R^{i9}$ is independently selected from OH, $C_{1-6}$ alkoxy, and $C_{1-6}$ haloalkoxy; or any $R^{h9}$ and $R^{i9}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$; or any $R^{c10}$ and $R^{d10}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{e10}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h10}$ and $R^{i10}$ is independently selected from OH, $C_{1-6}$ alkoxy, and $C_{1-6}$ haloalkoxy; or any $R^{h10}$ and $R^{i10}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a11}$, $R^{b11}$, $R^{c11}$ and $R^{d11}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$; or any $R^{c11}$ and $R^{d11}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{h11}$ and $R^{i11}$ is independently selected from OH, $C_{1-6}$ alkoxy, and $C_{1-6}$ haloalkoxy; or any $R^{h11}$ and $R^{i11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a12}$, $R^{b12}$, $R^{c12}$ and $R^{d12}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h12}$ and $R^{i12}$ is independently selected from OH, $C_{1-6}$ alkoxy, and $C_{1-6}$ haloalkoxy; or any $R^{h12}$ and $R^{i12}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a30}$, $R^{b30}$, $R^{c30}$ and $R^{d30}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{31}$;

or any $R^{c30}$ and $R^{d30}$ attached to the same N atom, together with the N atom to which they are attached, form a 4-, 5-, 6- or 7-membered heterocycloalkyl group optionally substituted with 1, 2, 3, or 4 substituents independently selected from $R^{31}$; each $R^{e30}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h30}$ and $R^{i30}$ is independently selected from OH, $C_{1-6}$ alkoxy, and $C_{1-6}$ haloalkoxy; or any $R^{h30}$ and $R^{i30}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a31}$, $R^{b31}$, $R^{c31}$ and $R^{d31}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{32}$;

or any $R^{c31}$ and $R^{d31}$ attached to the same N atom, together with the N atom to which they are attached, form a 4-, 5-, 6- or 7-membered heterocycloalkyl group optionally substituted with 1, 2 or 3 substituents independently selected from $R^{32}$;

each $R^{h31}$ and $R^{i31}$ is independently selected from OH, $C_{1-6}$ alkoxy, and $C_{1-6}$ haloalkoxy; or any $R^{h31}$ and $R^{i31}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a32}$, $R^{b32}$, $R^{c32}$ and $R^{d32}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h32}$ and $R^{i32}$ is independently selected from OH, $C_{1-6}$ alkoxy, and $C_{1-6}$ haloalkoxy; or any $R^{h32}$ and $R^{i32}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a50}$, $R^{b50}$, $R^{c50}$ and $R^{b50}$, is independently selected from H, $C_{1-6}$ alkyl, $C_{2-6}$ alkenyl, $C_{2-6}$ alkynyl, $C_{1-6}$ haloalkyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{51}$;

or any $R^{c50}$ and $R^{d50}$ attached to the same N atom, together with the N atom to which they are attached, form a 4-, 5-, 6- or 7-membered heterocycloalkyl group optionally substituted with 1, 2 or 3 substituents independently selected from $R^{51}$;

each $R^{h50}$ and $R^{i50}$ is independently selected from OH, $C_{1-6}$ alkoxy, and $C_{1-6}$ haloalkoxy; or any $R^{h50}$ and $R^{i50}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a51}$, $R^{b51}$, $R^{c51}$ and $R^{d51}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{52}$;

or any $R^{c51}$ and $R^{d51}$ attached to the same N atom, together with the N atom to which they are attached, form a 4-, 5-, 6- or 7-membered heterocycloalkyl group optionally substituted with 1, 2 or 3 substituents independently selected from $R^{52}$;

each $R^{h51}$ and $R^{i51}$ is independently selected from OH, $C_{1-6}$ alkoxy, and $C_{1-6}$ haloalkoxy; or any $R^{h51}$ and $R^{i51}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a52}$, $R^{b52}$, $R^{c52}$ and $R^{d52}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h52}$ and $R^{i52}$ is independently selected from OH, $C_{1-6}$ alkoxy, and $C_{1-6}$ haloalkoxy; or any $R^{h52}$ and $R^{i32}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a60}$, $R^{b60}$, $R^{c60}$ and $R^{d60}$, is independently selected from H, $C_{1-6}$ alkyl, $C_{2-6}$ alkenyl, $C_{2-6}$ alkynyl, $C_{1-6}$ haloalkyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^g$;

or any $R^{c60}$ and $R^{d60}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{h60}$ and $R^{i60}$ is independently selected from OH, $C_{1-6}$ alkoxy, and $C_{1-6}$ haloalkoxy; or any $R^{h60}$ and $R^{i60}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a70}$, $R^{b70}$, $R^{c70}$ and $R^{d70}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{71}$;

or any $R^{c70}$ and $R^{d70}$ attached to the same N atom, together with the N atom to which they are attached, form a 4-, 5-, 6- or 7-membered heterocycloalkyl group optionally substituted with 1, 2, 3, or 4 substituents independently selected from $R^{71}$;

each $R^{h70}$ and $R^{i70}$ is independently selected from OH, $C_{1-6}$ alkoxy, and $C_{1-6}$ haloalkoxy; or any $R^{h70}$ and $R^{i70}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a71}$, $R^{b71}$, $R^{c71}$ and $R^{d71}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{72}$;

or any $R^{c71}$ and $R^{d71}$ attached to the same N atom, together with the N atom to which they are attached, form a 4-, 5-, 6- or 7-membered heterocycloalkyl group optionally substituted with 1, 2 or 3 substituents independently selected from $R^{72}$;

each $R^{h}71$ and $R^{i71}$ is independently selected from OH, $C_{1-6}$ alkoxy, and $C_{1-6}$ haloalkoxy; or any $R^{h71}$ and $R^{i71}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a72}$, $R^{b72}$, $R^{c72}$ and $R^{d72}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h72}$ and $R^{i72}$ is independently selected from OH, $C_{1-6}$ alkoxy, and $C_{1-6}$ haloalkoxy; or any $R^{h72}$ and $R^{i7}2$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^g$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$alkyl)aminocarbonylamino.

In an embodiment of Formula I, X is $CR^7$. In another embodiment, X is N.

In an embodiment, Y is O. In another embodiment, Y is $C(R^5)_2$. In yet another embodiment, Y is C=O. In still another embodiment, Y is $NR^{5N}$.

In an embodiment, W is C=O. In another embodiment, W is $C(R^8)_2$.

In an embodiment, Z is $C(R^9)_2$. In another embodiment, Z is O. In yet another embodiment, Z is $NR^{9N}$. In still another embodiment Z is a bond. ═

In an embodiment, ═ represents a double bond, and $R^3$ is absent. In another embodiment, ═ represents a single bond. In yet another embodiment, ═ represents a single bond, and $R^4$ is ═O. In still another embodiment, ═ represents a single bond, and $R^4$ is ═S.

In another embodiment of Formula I,

═ represents a double bond;

X is $CR^7$ or N;

Y is $NR^{5N}$ or C=O;

W is C=O, or $C(R^8)_2$;

Z is O, $NR^{9N}$, or a bond;

$R^1$ and $R^2$ are each independently selected from H, $C_{1-6}$ alkyl, $C_{1-6}$ haloalkyl, halo, and CN;

Cy is $C_{6-10}$ aryl or 5-10 membered heteroaryl, both of which are optionally substituted with 1, 2, 3 or 4 substituents independently selected from $R^{10}$;

$R^3$ absent;

$R^4$ is selected from H, $C_{1-6}$ alkyl, and $OR^{a3}$, wherein alkyl is optionally substituted one or two times with $R^{30}$;

$R^{5N}$ is H or $C_{1-6}$ alkyl;

$R^5$ and $R^8$ are each independently selected from H, $C_{1-6}$ alkyl, $C_{1-6}$ haloalkyl, halo, D, and CN;

ring A is 4-7 membered heterocycloalkyl;

n is 1 or 2;

R is selected from $C_{1-6}$ alkyl, halo, D, CN, $C(O)R^b$, $C(O)OR^a$, and $OC(O)R^b$;

$R^7$ is selected from H, $C_{1-6}$ alkyl, $C_{1-6}$ haloalkyl, halo, D, and CN;
$R^{9N}$ is H or $C_{1-6}$ alkyl;
each $R^{10}$ is independently selected from $C_{1-6}$ alkyl, halo, and $OR^{a10}$;
each $R^{30}$ is 4-10 membered heterocycloalkyl optionally substituted with 1, 2, 3, or 4 substituents independently selected from $R^{31}$;
each $R^{31}$ is independently selected from $C_{1-6}$ alkyl, $C_{2-6}$ alkenyl, $C_{2-6}$ alkynyl, $C_{1-6}$ haloalkyl, halo, D, and CN;
$R^{a3}$ is $C_{1-6}$ alkyl optionally substituted one or two times with $R^{30}$;
each $R^aB$ and $R^bB$ is independently selected from H, $C_{1-6}$ alkyl, and $C_{2-6}$ alkenyl; and
$R^{a10}$ is H or $C_{1-6}$ alkyl.
In another embodiment of Formula I,
= represents a double bond;
X is $CR^7$;
Y is $NR^{5N}$ or C=O;
W is C=O, or $C(R^8)_2$;
Z is O, $NR^{9N}$, or a bond;
$R^1$ and $R^2$ are each independently H or halo;
Cy is $C_{6-10}$ aryl or 5-10 membered heteroaryl, both of which are optionally substituted with 1, 2, 3 or 4 substituents independently selected from $R^{10}$;
$R^3$ is absent;
$R^4$ is selected from H, $C_{1-6}$ alkyl, and $OR^{a3}$, wherein alkyl is optionally substituted one or two times with $R^{30}$;
$R^{5N}$ is H or $C_{1-6}$ alkyl;
each $R^5$ and $R^8$ are H;
ring A is 4-6 membered heterocycloalkyl;
n is 1;
$R^6$ is $C(O)R^{b6}$;
$R^7$ is halo;
$R^{9N}$ is H;
each $R^{10}$ is independently selected from $C_{1-6}$ alkyl, halo, and $OR^{a10}$;
each $R^{30}$ is 4-10 membered heterocycloalkyl optionally substituted with 1, 2, 3, or 4 substituents independently selected from $R^{31}$;
each $R^{31}$ is $C_{1-6}$ alkyl;
$R^{a3}$ is $C_{1-6}$ alkyl optionally substituted one or two times with $R^{30}$;
each $R^{b6}$ is $C_{2-6}$ alkenyl; and
$R^{a10}$ is H or $C_{1-6}$ alkyl.
In an embodiment, the compound of Formula I is a compound of Formula Ia:

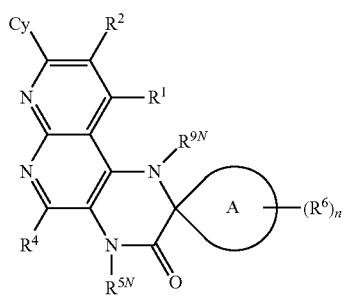

(Ia)

or a pharmaceutically acceptable salt thereof.

In another embodiment, the compound of Formula I is a compound of Formula Ib:

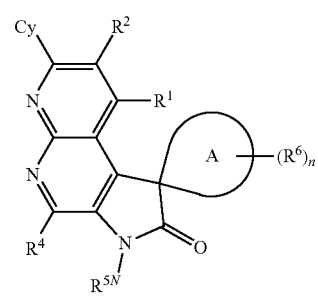

(Ib)

or a pharmaceutically acceptable salt thereof.
In yet another embodiment, the compound of Formula I is a compound of Formula Ic:

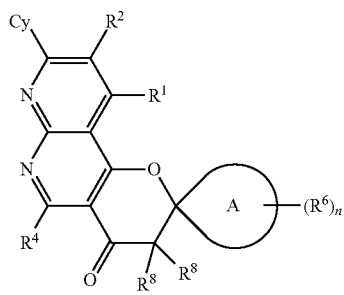

(Ic)

or a pharmaceutically acceptable salt thereof.
In an embodiment, the compound of Formula I is a compound of Formula II':

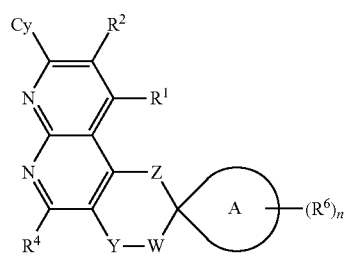

(II')

or a pharmaceutically acceptable salt thereof.
In an embodiment of Formula II',
X is N or $CR^7$;
Y is $NR^{5N}$, or C=O;
W is C=O, or $C(R^8)_2$;
Z is O, $NR^{9N}$, $O(R^9)_2$, or a bond;
$R^1$ and $R^2$ are each independently selected from H, D, $C_{1-6}$ alkyl, $C_{2-6}$ alkenyl, $C_{2-6}$ alkynyl, $C_{1-6}$ haloalkyl, halo, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $NR^cS(O)_2R^b$, $NR^cS(O)_2NR^cR^d$, $S(O)_2R^b$, and $S(O)_2NR^cR^d$, wherein said $C_{1-6}$ alkyl, $C_{2-6}$ alkenyl, and $C_{2-6}$ alkynyl, are each optionally substituted with 1, 2, 3, or 4 substituents independently selected from $R^g$;

Cy is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^4$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $C(O)R^{b3}$, $OC(O)NR^{c3}R^{d3}$, $NR^{c3}R^{d3}$, $NR^{3c}C(O)R^{b3}$, $NR^{3c}C(O)OR^{a3}$, $NR^{c3}C(O)NR^{c3}R^{d3}$, $NR^{c3}S(O)_2R^{b3}$, $NR^{c1}S(O)_2NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{30}$;

$R^{5N}$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{0-10}$ aryl, and 5-10 membered heteroaryl, are each optionally substituted with 1, 2, 3, or 4 substituents independently selected from $R^{50}$;

each $R^5$ and $R^8$ are independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a5}$, $SR^{a5}$, $C(O)R^b$, $C(O)NR^{c5}R^{d5}$, $(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c4}S(O)_2R^{b5}$, $NR^{c5}S(O)_2NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{50}$;

ring A is $C_{3-14}$ cycloalkyl or 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group;

n is 0, 1, 2, 3, or 4;

each $R^6$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^6C(O)NR^{c6}R^{d6}$, $NR^{c6}S(O)_2R^{b6}$, $NR^{c6}S(O)_2NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{60}$;

$R^7$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a7}$, $SR^{a7}$, $C(O)R^{b7}$, $C(O)NR^{c7}R^{d7}$, $(O)OR^{a7}$, $OC(O)R^{b7}$, $OC(O)NR^{c7}R^{d7}$, $NR^{c7}R^{d7}$, $NR^{c7}C(O)R^{b7}$, $NR^7C(O)OR^{a7}$, $NR^7C(O)NR^{c7}R^{d7}$, $NR^7S(O)_2R^{b7}$, $NR^7S(O)_2NR^{c7}R^{d7}$, $S(O)_2R^{b7}$, and $S(O)_2NR^{c7}R^{d7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{70}$;

$R^{9N}$ is selected from H, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl, are each optionally substituted with 1, 2, 3, or 4 substituents independently selected from $R^g$;

each $R^9$ is independently selected from selected from H, D, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, $OR^{a9}$, $SR^{a9}$, $C(O)R^{b9}$, $C(O)NR^{c9}R^{d9}$, $(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)_2R^{b9}$, $NR^{c9}S(O)_2NR^{c9}R^{d9}$, $S(O)_2R^{b9}$, and $S(O)_2NR^{c9}R^{d9}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a10}$, $SR^{a10}$, $C(O)R^{b10}$, $C(O)NR^{c1}R^{d10}$, $C(O)OR^{a10}$ $(O)R^{b10}$, $OC(O)NR^{c10}R^{d10}$, $NR^{c10}R^{d10}$, $NR^{c10}C(O)R^{b10}$, $NR^{c10}C(O)OR^{a10}$, $NR^{c10}$, $C(O)NR^{c10}R^{d10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, and $S(O)_2NR^{c10}R^{d10}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)_2R^{b11}$, $NR^{c11}S(O)_2NR^{c11}R^{d11}$, $S(O)_2R^{b11}$, and $S(O)_2NR^{c11}R^{d11}$;

each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a30}$, $SR^{a30}$, $C(O)R^{b30}$, $C(O)NR^{c30}R^{d30}$, $C(O)OR^{a30}$, $OC(O)R^{b30}$, $OC(O)NR^{c30}R^{d30}$, $NR^{c30}R^{d30}$, $NR^{c30}C(O)R^{b30}$, $NR^{c30}C(O)OR^{a30}$, $NR^{c30}C(O)NR^{c30}R^{b30}$, $NR^{c30}(O)_2R^{b30}$, $NR^{c30}S(O)_2NR^{c30}R^{d30}$; $S(O)_2R^{b30}$, and $S(O)_2NR^{c30}R^{d30}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{31}$;

each $R^{31}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c1}C(O)R^{b31}$, $NR^{c1}C(O)OR^{a31}$, $NR^{c31}C(O)NR^{c31}R^{d31}$, $NR^{c31}S(O)_2R^{b31}$, $NR^{c31}S(O)_2NR^{c31}R^{d31}$, $S(O)_2R^{b31}$, and $S(O)_2NR^{c1}R^{d31}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{32}$;

each $R^{32}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a32}$, $SR^{a32}$, $C(O)R^{b32}$, $C(O)NR^{c32}R^{d32}$, $C(O)OR^{a32}$, $OC(O)R^{b32}$, $OC(O)NR^{c32}R^{d32}$, $NR^{c32}R^{d32}$, $NR^{c32}C(O)R^{d32}$, $NR^{c2}C(O)OR^{a32}$, $NR^{c32}C(O)NR^{c32}R^{d32}$, $NR^{c32}S(O)_2R^{b32}$, $NR^{c32}S(O)_2NR^{c32}R^{d32}$, $S(O)_2R^{b32}$, and $S(O)_2NR^{c32}R^{d32}$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a50}$, $SR^{a50}$, $C(O)R^{b50}$, $C(O)NR^{c50}R^{d50}$, $C(O)OR^{a50}$, $OC(O)R^{b50}$, $OC(O)NR^{c50}R^{d50}$, $NR^{c50}R^{d50}$, $NR^{c50}C(O)R^{b50}$, $NR^{c50}C(O)OR^{a50}$, $NR^{c50}C(O)NR^{c50}R^{d50}$, $NR^{c50}S(O)_2R^{b50}$, $NR^{c50}S(O)_2NR^{c50}R^{d5}$, $S(O)_2R^{b50}$, and $S(O)_2NR^{c50}R^{d50}$;

each $R^{60}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a60}$, $SR^{a60}$, $C(O)R^{b60}$, $C(O)NR^{c60}R^{d60}$, $C(O)OR^{a60}$, $OC(O)R^{b60}$, $OC(O)NR^{c60}R^{d60}$, $NR^{c60}R^{d60}$, $NR^{c60}C(O)R^{b60}$, $NR^{c60}C(O)OR^{a60}$, $NR^{c60}C(O)NR^{c60}R^{d60}$; $NR^{c60}S(O)_2R^{b60}$, $NR^{c60}S(O)_2NR^{c60}R^{d60}$, $S(O)_2R^{b60}$, and $S(O)_2NR^{c60}R^{d60}$;

each $R^{70}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a70}$, $SR^{a70}$, $C(O)R^{b70}$, $C(O)NR^{c70}R^{d70}$, $C(O)OR^{a70}$, $OC(O)R^{b70}$; $OC(O)NR^{c70}R^{d70}$, $NR^{c70}R^{d70}$, $NR^{c70}C(O)R^{b70}$, $NR^{c70}C(O)OR^{a7}$, $NR^{c7}C(O)NR^{c70}R^{d70}$, $NR^{c70}S(O)_2R^{b70}$, $NR^{c70}S(O)_2NR^{c70}R^{d70}$, $S(O)_2R^{b70}$, and $S(O)_2NR^{c70}R^{d70}$;

each $R^a$, $R^b$, $R^c$, and $R^d$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

or any $R^c$ and $R^d$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene, are each optionally substituted with 1, 2, 3, or 4 substituents independently selected from $R^{30}$;

or any $R^{c3}$ and $R^{d3}$ attached to the same N atom, together with the N atom to which they are attached, form a 4-, 5-, 6- or 7-membered heterocycloalkyl group optionally substituted with 1, 2, 3, or 4 substituents independently selected from $R^{30}$;

each $R^{a5}$, $R^{b5}$, $R^{c5}$ and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{50}$;

or any $R^{c5}$ and $R^{d5}$ attached to the same N atom, together with the N atom to which they are attached, form a 4-, 5-, 6- or 7-membered heterocycloalkyl group optionally substituted with 1, 2, 3, or 4 substituents independently selected from $R^{50}$;

each $R^{a6}$, $R^{b6}$, $R^{c6}$ and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2, 3, or 4 substituents independently selected from $R^{60}$;

each $R^{a7}$, $R^{b7}$, $R^{c7}$ and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{70}$;

or any $R^{c7}$ and $R^{d7}$ attached to the same N atom, together with the N atom to which they are attached, form a 4-, 5-, 6- or 7-membered heterocycloalkyl group optionally substituted with 1, 2, 3, or 4 substituents independently selected from $R^{70}$;

each $R^{a9}$, $R^{b9}$, $R^{c9}$, and $R^{d9}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl;

or any $R^{c9}$ and $R^{d9}$ attached to the same N atom, together with the N atom to which they are attached, form a 4-, 5-, 6- or 7-membered heterocycloalkyl group;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c10}$ and $R^{d10}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{a11}$, $R^{b11}$, $R^{c11}$ and $R^{d11}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c11}$ and $R^{d11}$ attached to the same N atom, together with the N atom to which they are attached, form a 4-, 5-, 6- or 7-membered heterocycloalkyl group;

each $R^{a30}$, $R^{b30}$, $R^{c30}$ and $R^{d30}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{31}$;

or any $R^{c30}$ and $R^{d30}$ attached to the same N atom, together with the N atom to which they are attached, form a 4-, 5-, 6- or 7-membered heterocycloalkyl group optionally substituted with 1, 2, 3, or 4 substituents independently selected from $R^{31}$;

each $R^{a31}$, $R^{b31}$, $R^{c31}$ and $R^{d31}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{32}$;

or any $R^{c1}$ and $R^{d3}1$ attached to the same N atom, together with the N atom to which they are attached, form a 4-, 5-, 6- or 7-membered heterocycloalkyl group optionally substituted with 1, 2 or 3 substituents independently selected from $R^{32}$;

each $R^{a32}$, $R^{b32}$, $R^{c32}$ and $R^{d32}$, is independently selected from H, $C_{1-6}$ alkyl, $C_{2-6}$ alkenyl, $C_{2-6}$ alkynyl and $C_{1-6}$ haloalkyl;

each $R^{a50}$, $R^{b50}$, $R^{c50}$ and $R^{d50}$, is independently selected from H, $C_{1-6}$ alkyl, $C_{2-6}$ alkenyl, $C_{2-6}$ alkynyl, $C_{1-6}$ haloalkyl, $C_{1-6}$ haloalkyl, $C_{3-10}$ cycloalkyl, 4-10 membered heterocycloalkyl, $C_{6-10}$ aryl, and 5-10 membered heteroaryl;

or any $R^{c50}$ and $R^{d50}$ attached to the same N atom, together with the N atom to which they are attached, form a 4-, 5-, 6- or 7-membered heterocycloalkyl group;

each $R^{a60}$, $R^{b60}$, $R^{c60}$ and $R^{d60}$, is independently selected from H, $C_{1-6}$ alkyl, $C_{2-6}$ alkenyl, $C_{2-6}$ alkynyl, $C_{1-6}$ haloalkyl, $C_{1-6}$ haloalkyl, $C_{3-10}$ cycloalkyl, 4-10 membered heterocycloalkyl, $C_{6-10}$ aryl, and 5-10 membered heteroaryl;

or any $R^{c60}$ and $R^{d60}$ attached to the same N atom, together with the N atom to which they are attached, form a 4-, 5-, 6- or 7-membered heterocycloalkyl group;

each $R^{a70}$, $R^{b70}$, $R^{c70}$ and $R^{d70}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c70}$ and $R^{d7}$ attached to the same N atom, together with the N atom to which they are attached, form a 4-, 5-, 6- or 7-membered heterocycloalkyl group; and each $R^g$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$alkyl)aminocarbonylamino.

In an embodiment, the compound of Formula I is a compound of Formula II:

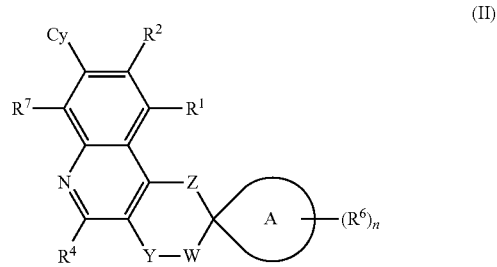

(II)

or a pharmaceutically acceptable salt thereof.

In an embodiment of Formulas I and II,

Y is $NR^{5N}$, or C=O;

W is C=O, or $C(R^8)_2$;

Z is O, $NR^{9N}$, or a bond;

$R^1$ and $R^2$ are each independently selected from H, D, $C_{1-6}$ alkyl, $C_{1-6}$ haloalkyl, halo, CN, $OR^a$, and $NR^c R^d$;

Cy is $C_{6-10}$ aryl or 5-10 membered heteroaryl; wherein the 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

$R^4$ is selected from H, $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, and $S(O)_2R^{b3}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{30}$;

$R^{5N}$ is selected from H, $C_{1-6}$ alkyl, $C_{2-6}$ alkenyl, $C_{2-6}$ alkynyl, and $C_{1-6}$ haloalkyl;

each $R^5$ and $R^8$ are independently selected from H, $C_{1-6}$ alkyl, $C_{1-6}$ haloalkyl, halo, D, CN, $OR^{a5}$, and $NR^{c5}R^{d5}$;

ring A is $C_{3-6}$ cycloalkyl or 4-7 membered heterocycloalkyl; wherein the 4-7 membered heterocycloalkyl has at least one ring-forming carbon atom and 1, 2, 3, or 4 ring-forming heteroatoms independently selected from N, O, and S; wherein a ring-forming carbon atom of 4-6 membered heterocycloalkyl is optionally substituted by oxo to form a carbonyl group;

n is 0, 1, or 2;

each $R^6$ is independently selected from $C_{1-6}$ alkyl, $C_{2-6}$ alkenyl, $C_{2-6}$ alkynyl, $C_{1-6}$ haloalkyl, halo, D, CN, $OR^a$, $C(O)R^b$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, and $S(O)_2R^{b6}$; $R^7$ is selected from H, $C_{1-6}$ alkyl, $C_{1-6}$ haloalkyl, halo, D, CN, $OR^{a7}$, and $NR^{c7}R^{d7}$;

$R^{9N}$ is selected from H, $C_{1-6}$ alkyl, $C_{2-6}$ alkenyl, $C_{2-6}$ alkynyl, and $C_{1-6}$ haloalkyl;

each $R^{10}$ is independently selected from $C_{1-6}$ alkyl, $C_{2-6}$ alkenyl, $C_{2-6}$ alkynyl, $C_{1-6}$ haloalkyl, halo, D, CN, $OR^{a10}$, and $NR^{c10}R^{d10}$;

each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a30}$, $C(O)R^{b30}$, $C(O)NR^{c30}R^{d30}$, $C(O)OR^{a30}$, $OC(O)R^{b30}$, $OC(O)NR^{c30}R^{d30}$, $NR^{c30}R^{d30}$, $NR^{c30}$, $C(O)R^{b30}$, and $S(O)_2R^{b30}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{3-10}$ aryl, and 5-10 membered heteroaryl, are each optionally substituted with 1, 2, 3, or 4 substituents independently selected from $R^{31}$;

each $R^{31}$ is independently selected from $C_{1-6}$ alkyl, $C_{2-6}$ alkenyl, $C_{2-6}$ alkynyl, $C_{1-6}$ haloalkyl, halo, D, CN, $OR^{a31}$, and $NR^{c31}R^{d31}$;

each $R^a$, $R^c$, and $R^d$ is independently selected from H, $C_{1-6}$ alkyl, $C_{2-6}$ alkenyl, $C_{2-6}$ alkynyl, and $C_{1-6}$ haloalkyl;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ aryl, and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{3-10}$ aryl, and 5-10 membered heteroaryl, are each optionally substituted with 1, 2, 3, or 4 substituents independently selected from $R^{30}$;

or any $R^{c3}$ and $R^{d3}$ attached to the same N atom, together with the N atom to which they are attached, form a 4-, 5-, 6- or 7-membered heterocycloalkyl group optionally substituted with 1, 2, 3, or 4 substituents independently selected from $R^{30}$;

each $R^{a5}$, $R^{c5}$ and $R^{d5}$ is independently selected from H, $C_{1-6}$ alkyl, $C_{2-6}$ alkenyl, $C_{2-6}$ alkynyl, and $C_{1-6}$ haloalkyl;

each $R^{a6}$, $R^{b6}$, $R^{c6}$ and $R^{d6}$ is independently selected from H, $C_{1-6}$ alkyl, $C_{2-6}$ alkenyl, $C_{2-6}$ alkynyl, and $C_{1-6}$ haloalkyl;

each $R^{a7}$, $R^{b7}$ and $R^{d7}$ is independently selected from H, $C_{1-6}$ alkyl, $C_{2-6}$ alkenyl, $C_{2-6}$ alkynyl, and $C_{1-6}$ haloalkyl;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, and $C_{1-6}$ haloalkyl;

each $R^{a11}$, $R^{b11}$, $R^{c11}$ and $R^{d11}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

each $R^{a30}$, $R^{b30}$, $R^{c30}$ and $R^{d30}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{31}$;

or any $R^{c30}$ and $R^{d30}$ attached to the same N atom, together with the N atom to which they are attached, form a 4-, 5-, 6- or 7-membered heterocycloalkyl group optionally substituted with 1, 2, 3, or 4 substituents independently selected from $R^{31}$; and each $R^{a31}$, $R^{c31}$ and $R^{d31}$, is independently selected from H, $C_{1-6}$ alkyl, $C_{2-6}$ alkenyl, $C_{2-6}$ alkynyl, and $C_{1-6}$ haloalkyl.

In an embodiment, the compound of Formula I or II is a compound of Formula IIa:

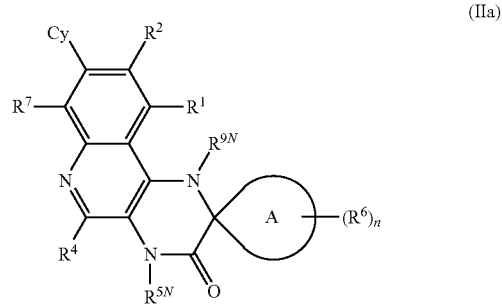

(IIa)

or a pharmaceutically acceptable salt thereof.

In an embodiment of Formula IIa, $R^1$ and $R^2$ are each independently H or halo;

Cy is $C_{6-10}$ aryl or 5-10 membered heteroaryl, both of which are optionally substituted one, two, or three times with $R^{10}$;

$R^4$ is selected from H, $C_{1-6}$ alkyl, and $OR^{a3}$, wherein alkyl is optionally substituted one or two times with $R^{30}$;

$R^{5N}$ is H or $C_{1-6}$ alkyl;

ring A is 4-6 membered heterocycloalkyl;

n is 1;

$R^1$ is $C(O)R^{b6}$;

$R^7$ is halo;

$R^{9N}$ is H;

each $R^{10}$ is independently selected from $C_{1-6}$ alkyl, halo, and $OR^{a10}$;

each $R^{30}$ is 4-6 membered heterocycloalkyl optionally substituted one or two times with $R^{31}$;

each $R^{31}$ is $C_{1-6}$ alkyl;

$R^{a3}$ is $C_{1-6}$ alkyl optionally substituted one or two times with $R^{30}$;

each $R^b$s is $C_{2-6}$ alkenyl; and $R^{a10}$ is H or $C_{1-6}$ alkyl.

In another embodiment, the compound of Formula I or II is a compound of Formula IIb:

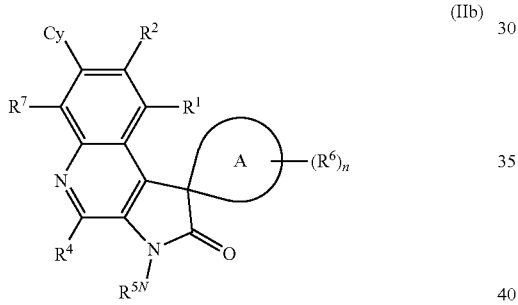

(IIb)

or a pharmaceutically acceptable salt thereof.

In an embodiment of Formula IIb, $R^1$ and $R^2$ are each independently H or halo;

Cy is $C_{3-10}$ aryl or 5-10 membered heteroaryl, both of which are optionally substituted one, two, or three times with $R^{10}$;

$R^4$ is selected from H, $C_{1-6}$ alkyl, and $OR^{a3}$, wherein alkyl is optionally substituted one or two times with $R^{30}$;

$R^{5N}$ is H or $C_{1-6}$ alkyl;

each $R^5$ and $R^8$ are H;

ring A is 4-6 membered heterocycloalkyl;

n is 1;

$R^6$ is $C(O)R^{b6}$;

$R^7$ is halo;

each $R^{10}$ is independently selected from $C_{1-6}$ alkyl, halo, and $OR^{a10}$;

each $R^{30}$ is 4-6 membered heterocycloalkyl optionally substituted one or two times with $R^{31}$;

each $R^{31}$ is $C_{1-6}$ alkyl;

$R^{a3}$ is $C_{1-6}$ alkyl optionally substituted one or two times with $R^{30}$;

each $R^{b6}$ is $C_{2-6}$ alkenyl; and $R^{a10}$ is H or $C_{1-6}$ alkyl.

In yet another embodiment, the compound of Formula I or II is a compound of Formula IIc:

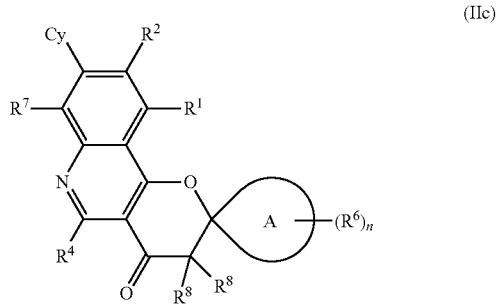

(IIc)

or a pharmaceutically acceptable salt thereof.

In an embodiment of Formula IIc, $R^1$ and $R^2$ are each independently H or halo;

Cy is selected from $C_{6-10}$ aryl and 5-10 membered heteroaryl both of which are optionally substituted with one, two, or three $R^{10}$;

$R^4$ is selected from H, $C_{1-6}$ alkyl, and $OR^{a3}$, wherein alkyl is optionally substituted one or two times with $R^{30}$;

ring A is 4-6 membered heterocycloalkyl;

n is 1;

$R^6$ is $C(O)R^{b6}$;

$R^7$ is halo;

both $R^8$ are H;

each $R^{10}$ is independently selected from $C_{1-6}$ alkyl, halo, and $OR^{a10}$;

each $R^{30}$ is 4-6 membered heterocycloalkyl optionally substituted one or two times with $R^{31}$;

each $R^{31}$ is $C_{1-6}$ alkyl;

$R^{a3}$ is $C_{1-6}$ alkyl optionally substituted one or two times with $R^{30}$;

each $R^{b6}$ is $C_{2-6}$ alkenyl; and $R^{a10}$ is H or $C_{1-6}$ alkyl.

In an embodiment of any of the Formulae disclosed herein, $R^1$ is selected from H, D, $C_{1-6}$ alkyl, $C_{2-6}$ alkenyl, $C_{2-6}$ alkynyl, $C_{1-6}$ haloalkyl, halo, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $NR^cS(O)_2R^b$, $S(O)_2R^b$, and $S(O)_2NR^cR^d$; wherein said $C_{1-6}$ alkyl, $C_{2-6}$ alkenyl, and $C_{2-6}$ alkynyl, are each optionally substituted with 1 or 2 substituents independently selected from $R^g$.

In another embodiment, $R^1$ is selected from H, D, $C_{1-6}$ alkyl, $C_{2-6}$ alkenyl, $C_{2-6}$ alkynyl, $C_{1-6}$ haloalkyl, halo, CN, $OR^a$, $SR^a$, $C(O)R^b$, $C(O)NR^cR^d$, (O)$OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $NR^cS(O)_2R^b$, $S(O)_2R^b$, and $S(O)_2NR^cR^d$.

In an embodiment of any of the Formulae disclosed herein, $R^1$ is selected from H, D, $C_{1-6}$ alkyl, $C_{2-6}$ alkenyl, $C_{2-6}$ alkynyl, $C_{1-6}$ haloalkyl, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{d1}$, $NR^{c1}C(O)OR^{a1}$, $NR^{c1}C(O)NR^{c1}R^{d1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl, are each optionally substituted with 1 or 2 substituents independently selected from $R^g$.

In another embodiment, $R^1$ is selected from H, D, $C_{1-6}$ alkyl, $C_{2-6}$ alkenyl, $C_{2-6}$ alkynyl, $C_{1-6}$ haloalkyl, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{d1}$, $NR^{c1}C(O)OR^{a1}$, $NR^{c1}C(O)NR^{c1}R^{d1}$, $NR^{c1}S(O)_2R^{b1}$, $S(O)_2R^{b1}$, and $S(O)_2NR^{c1}R^{d1}$.

In yet another embodiment, $R^1$ is selected from H, D, $C_{1-6}$ alkyl, $C_{2-6}$ alkenyl, $C_{2-6}$ alkynyl, $C_{1-6}$ haloalkyl, halo, and CN. In still another embodiment, $R^1$ is selected from H, D, and $C_{1-3}$ alkyl. In another embodiment, $R^1$ is H.

In an embodiment, $R^2$ is selected from H, D, $C_{1-6}$ alkyl, $C_{2-6}$ alkenyl, $C_{2-6}$ alkynyl, $C_{1-6}$ haloalkyl, halo, CN, $OR^a$, $SR^a$, $C(O)R^b$, $C(O)NR^cR^d$, $(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $NR^cS(O)_2R^b$, $S(O)_2R^b$, and $S(O)_2NR^cR^d$; wherein said $C_{1-6}$ alkyl, $C_{2-6}$ alkenyl, and $C_{2-6}$ alkynyl, are each optionally substituted with 1 or 2 substituents independently selected from $R^g$.

In another embodiment, $R^2$ is selected from H, D, $C_{1-6}$ alkyl, $C_{2-6}$ alkenyl, $C_{2-6}$ alkynyl, $C_{1-6}$ haloalkyl, halo, CN, $OR^a$, $SR^a$, $C(O)R^b$, $C(O)NR^cR^d$, $(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $NR^cS(O)_2R^b$, $S(O)_2R^b$, and $S(O)_2NR^cR^d$.

In an embodiment, $R^2$ is selected from H, D, $C_{1-6}$ alkyl, $C_{2-6}$ alkenyl, $C_{2-6}$ alkynyl, $C_{1-6}$ haloalkyl, halo, CN, $OR^{a2}$, $SR^{a2}$, $C(O)R^{b2}$, $C(O)NR^{c2}R^{d2}$, $(O)OR^{a2}$, $OC(O)R^{b2}$, $OC(O)NR^{c2}R^{d2}$, $NR^{c2}R^{d2}$, $NR^{c2}C(O)R^{d2}$, $NR^{c2}C(O)OR^{a2}$, $NR^{c2}C(O)NR^{c2}R^{d2}$, $NR^2S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl, are each optionally substituted with 1 or 2 substituents independently selected from $R^{20}$.

In another embodiment, $R^2$ is selected from H, D, $C_{1-6}$ alkyl, $C_{2-6}$ alkenyl, $C_{2-6}$ alkynyl, $C_{1-6}$ haloalkyl, halo, CN, $OR^{a2}$, $SR^{a2}$, $C(O)R^{b2}$, $C(O)NR^{c2}R^{d2}$, $(O)OR^{a2}$, $OC(O)R^{b2}$, $OC(O)NR^{c2}R^{d2}$, $NR^{c2}R^{d2}$, $NR^{c2}C(O)R^{d2}$, $NR^{c2}C(O)OR^{a2}$, $NR^{c2}C(O)NR^{c2}R^{d2}$, $NR^2S(O)_2R^{b2}$, $S(O)_2R^{b2}$, and $S(O)_2NR^{c2}R^{d2}$.

In yet another embodiment, $R^2$ is selected from H, D, $C_{1-6}$ alkyl, $C_{1-6}$ haloalkyl, halo, and CN. In another embodiment, $R^2$ is selected from $C_{1-6}$ alkyl and halo. In still another embodiment, $R^2$ is halo. In another embodiment, $R^2$ is chloro.

In an embodiment, Cy is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, or 3 substituents independently selected from $R^{10}$.

In another embodiment, Cy is selected from $C_{6-10}$ aryl and 5-10 membered heteroaryl; wherein the 5-10 membered heteroaryl each has at least one ring-forming carbon atom and 1, 2, or 3 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 6-10 membered heteroaryl are each optionally substituted with 1, 2, or 3 substituents independently selected from $R^{10}$.

In yet another embodiment, Cy is selected from phenyl, naphthalenyl and indazolyl; wherein the phenyl, naphthalenyl and indazolyl are each optionally substituted with 1, 2, or 3 substituents independently selected from $R^{10}$. In an embodiment, each $R^{10}$ is independently selected from $C_{1-6}$ alkyl, halo, $OR^{a10}$. In another embodiment, $R^{a10}$ is H or $C_{1-6}$ alkyl.

In an embodiment, Cy is selected from 2-fluoro-6-hydroxyphenyl, 2-chloro-5-hydroxy-phenyl, 5-methyl-1H-indazol-4-yl, 3-methyl-1H-indazol-4-yl, and 2-fluoro-6-methoxyphenyl.

In another embodiment, Cy is 2-fluoro-6-hydroxyphenyl. In yet another embodiment, Cy is 2-chloro-5-hydroxy-phenyl. In still another embodiment, Cy is 5-methyl-1H-indazol-4-yl.

In another embodiment, Cy is 3-methyl-1H-indazol-4-yl. In yet another embodiment, Cy is 2-fluoro-6-methoxyphenyl.

In an embodiment, $R^3N=CR^4$ is a single bond, and $R^4$ is $=O$. In another embodiment, $R^3N=CR^4$ is a single bond, and $R^4$ is $=S$. In yet another embodiment, $R^3N=CR^4$ is a double bond, and $R^3$ is absent.

In an embodiment, $R^3$ is selected from H, $C_{1-6}$ alkyl, $C_{1-6}$ haloalkyl, $C_{3-10}$ cycloalkyl, 4-10 membered heterocycloalkyl, $C_{6-10}$ aryl, and 5-10 membered heteroaryl, wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, or 3 substituents independently selected from $R^{30}$.

In another embodiment, $R^3$ is selected from H, $C_{1-6}$ alkyl, $C_{1-6}$ haloalkyl, $C_{3-10}$ cycloalkyl, 4-10 membered heterocycloalkyl, $C_{6-10}$ aryl, and 5-10 membered heteroaryl.

In an embodiment, $R^4$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^3C(O)NR^{c3}R^{d3}$, $NR^3S(O)_2R^{b3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{30}$.

In another embodiment, $R^4$ is selected from H, $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, and $S(O)_2R^{b3}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{30}$.

In yet another embodiment, $R^4$ is selected from H, $C_{1-6}$ alkyl, $C_{1-6}$ haloalkyl, 4-10 membered heterocycloalkyl, $C_{6-10}$ aryl, 5-10 membered heteroaryl, halo, D, CN, $OR^{a3}$, and $NR^{c3}R^{d3}$; wherein said $C_{1-6}$ alkyl, 4-10 membered heterocycloalkyl, $C_{6-10}$ aryl, and 5-10 membered heteroaryl, are each optionally substituted with 1, 2, or 3 substituents independently selected from $R^{30}$.

In still another embodiment, $R^4$ is selected from H, 4-10 membered heterocycloalkyl, $C_{6-10}$ aryl, and $OR^{a3}$; wherein said 4-10 membered heterocycloalkyl, and $C_{6-10}$ aryl, are each optionally substituted with 1 or 2 substituents independently selected from $R^3$.

In another embodiment, $R^4$ is selected from H, 4-6 membered heterocycloalkyl, and $OR^{a3}$; wherein said 4-6 membered heterocycloalkyl is optionally substituted with 1 or 2 substituents independently selected from $R^{30}$.

In an embodiment, $R^4$ is selected from H, 1-(methyl-pyrrolidin-2-yl)methoxy, and N-(ethoxy)piperidine. In another embodiment, $R^4$ is H. In yet another embodiment, $R^4$ is 1-(methyl-pyrrolidin-2-yl)methoxy. In still another embodiment, $R^4$ is N-(ethoxy)piperidine. In another embodiment, $R^4$ is 3-(dimethylamino)-azetidin-1-yl.

In an embodiment, $R^{5N}$ is selected from H, $C_{1-6}$ alkyl, $C_{2-6}$ alkenyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{2-6}$ alkenyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{50}$.

In another embodiment, $R^{5N}$ is selected from H, $C_{1-6}$ alkyl, $C_{2-6}$ alkenyl, $C_{1-6}$ haloalkyl, $C_{3-10}$ cycloalkyl, 4-10 membered heterocycloalkyl, $C_{6-10}$ aryl, and 5-10 membered heteroaryl. In yet another embodiment, $R^{5N}$ is selected from H, $C_{1-6}$ alkyl, $C_{2-6}$ alkenyl, and $C_{1-6}$ haloalkyl.

In still another embodiment, $R^{5N}$ is H. In another embodiment, $R^{5N}$ is methyl. In an embodiment, each $R^5$ and $R^8$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)_2R^{b5}$, $NR^{c5}S(O)_2NR^{c3}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{1-6}$ aryl, and 5-10 membered heteroaryl, are each optionally substituted with 1, 2, 3, or 4 substituents independently selected from $R^5$.

In another embodiment, each $R^5$ and $R^8$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{5}S(O)_2R^{b5}$, $NR^{c5}S(O)_2NR^{c5}R^{d5}$, $S(O)_2R^{b5}$, and $S(O)_2NR^{c5}R^{d5}$.

In yet another embodiment, each $R^5$ and $R^8$ is independently selected from H, $C_{1-6}$ alkyl, $C_{2-6}$ alkenyl, $C_{2-6}$ alkynyl, $C_{1-6}$ haloalkyl, halo, D, CN, and $OR^a$.

In another embodiment each $R^5$ is independently selected from H and $C_{1-6}$ alkyl. In another embodiment each $R^5$ is H. In another embodiment each $R^8$ is independently selected from H and $C_{1-6}$ alkyl. In another embodiment each $R^8$ is H.

In an embodiment, ring A is $C_{3-10}$ cycloalkyl or 4-10 membered heterocycloalkyl; wherein the 4-10 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-10 membered heterocycloalkyl is optionally substituted by oxo to form a carbonyl group.

In another embodiment, ring A is $C_{3-6}$ cycloalkyl or 4-6 membered heterocycloalkyl; wherein the 4-6 membered heterocycloalkyl has at least one ring-forming carbon atom and 1 or 2 ring-forming heteroatoms independently selected from N and O.

In another embodiment, ring A is 4-10 membered heterocycloalkyl; wherein the 4-10 membered heterocycloalkyl has at least one ring-forming carbon atom and 1, 2, 3, or 4 ring-forming heteroatoms independently selected from N, O, and S. In yet another embodiment, ring A is 4-7 membered heterocycloalkyl. In another embodiment, ring A is 4-6 membered heterocycloalkyl. In yet another embodiment, ring A is piperidine. In still another embodiment, ring A is azetidine. In an embodiment, ring A is pyrrolidine.

In another embodiment, ring A is $C_{3-10}$ cycloalkyl. In another embodiment, ring A is $C_{3-6}$ cycloalkyl.

In still another embodiment, n is 1, 2, or 3. In another embodiment, n is 0, 1, or 2. In yet another embodiment, n is 0 or 1. In another embodiment, n is 1. In still another embodiment, n is 0.

In an embodiment, each $R^6$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a6}$, $SR^{a6}$, $C(O)R^{b8}$, $C(O)NR^{c6}R^{d8}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{6c}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{60}$.

In another embodiment, each $R^6$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a6}$, $SR^{a6}$, $C(O)R^{b6}$, $C(O)NR^{c6}R^{d6}$, $(O)OR^{a6}$, $OC(O)R^{b6}$, $OC(O)NR^{c6}R^{d6}$, $NR^{c6}R^{d6}$, $NR^{c6}C(O)R^{b6}$, $NR^{6c}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$.

In yet another embodiment, each $R^6$ is independently selected from $C(O)R^{b6}$, $C(O)NR^{c6}R^{d6}$, $C(O)OR^{a6}$, $OC(O)R^{b6}$, and $OC(O)NR^{c6}R^{d6}$. In another embodiment, each $R^6$ is independently selected from $C_{1-6}$ alkyl, and $C(O)R^{b6}$. In another embodiment, each $R^6$ is $C(O)R^{b6}$.

In another embodiment, each $R^6$ is independently selected from $C(O)R^{b6}$ and $NR^{c6}R^{d6}$. In another embodiment, each $R^6$ is $NR^{c6}R^{d6}$.

In an embodiment, ring A-$R^6$ is selected from 4,4-(piperidin-1-yl)prop-2-en-1-one, 3,3-(piperidin-1-yl)prop-2-en-1-one, 3,3-(azetidin-1-yl)prop-2-en-1-one, and 3,3-(pyrrolidin-1-yl)prop-2-en-1-one. In another embodiment, ring A-$R^6$ is 4,4-(piperidin-1-yl)prop-2-en-1-one.

In yet another embodiment, ring A-$R^6$ is 3,3-(piperidin-1-yl)prop-2-en-1-one. In still another embodiment, ring A-$R^6$ is 3,3-(azetidin-1-yl)prop-2-en-1-one. In another embodiment, ring A-$R^6$ is 3,3-(pyrrolidin-1-yl) prop-2-en-1-one.

In yet another embodiment, ring A-$R^6$ is selected from:

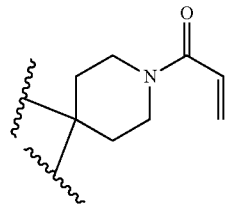

A-1

-continued

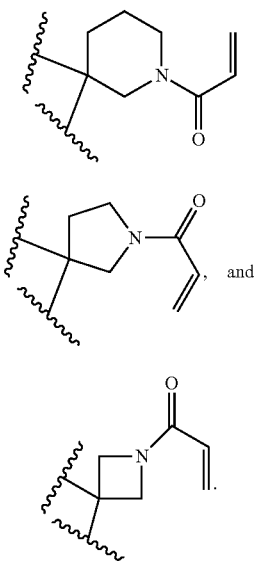

A-2

A-3, and

A-4

In an embodiment, ring A-R$^6$ is A-1. In another embodiment, ring A-R$^6$ is A-2. In yet another embodiment, ring A-R$^6$ is A-3. In still another embodiment, ring A-R$^6$ is A-4. In an embodiment, ring A-R$^6$ is selected from:

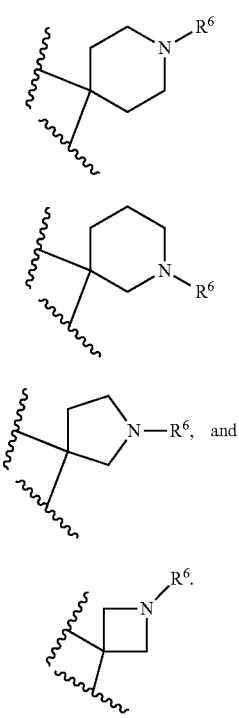

A-1a

A-2a

A-3a, and

A-4a.

In an embodiment, ring A-R$^6$ is A-1a. In another embodiment, ring A-R$^6$ is A-2a. In yet another embodiment, ring A-R$^6$ is A-3a. In still another embodiment, ring A-R$^6$ is A-4a. In an embodiment, ring A-R$^6$ is selected from A-1a, A-2a, A-3a, and A-4a; wherein R$^6$ is H.

In an embodiment, R$^7$ is selected from H, C$_{1-6}$ alkyl, C$_{2-6}$ alkenyl, C$_{2-6}$ alkynyl, C$_{1-6}$ haloalkyl, C$_{3-6}$ cycloalkyl, and 4-6 membered heterocycloalkyl, halo, D, CN, OR$^{a7}$, C(O) R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)OR$^{a7}$, NR$^{c7}$C(O) NR$^{c7}$R$^{d7}$ NR$^{c7}$S(O)$_2$R$^{b7}$, S(O)$_2$R$^{b7}$, and S(O)$_2$NR$^{c7}$R$^{d7}$; wherein said C$_{1-6}$ alkyl, C$_{2-6}$ alkenyl, C$_{2-6}$ alkynyl, C$_{3-6}$ cycloalkyl, and 4-6 membered heterocycloalkyl, are each optionally substituted with 1, 2, 3, or 4 substituents independently selected from R$^{70}$.

In another embodiment, R$^7$ is selected from H, C$_{1-6}$ alkyl, C$_{2-6}$ alkenyl, C$_{2-6}$ alkynyl, C$_{1-6}$ haloalkyl, C$_{3-6}$ cycloalkyl, and 4-6 membered heterocycloalkyl, halo, D, CN, OR$^{a7}$, C(O)R$^{b7}$, C(O)NR$^{c7}$R$^{d7}$, C(O)OR$^{a7}$, OC(O)R$^{b7}$, OC(O) NR$^{c7}$R$^{d7}$, NR$^{c7}$R$^{d7}$, NR$^{c7}$C(O)R$^{b7}$, NR$^{c7}$C(O)OR$^{a7}$, NR$^{c7}$C (O)NR$^{c7}$R$^{d7}$ NR$^7$S(O)$_2$R$^{b7}$, S(O)$_2$R$^{b7}$, and S(O)$_2$NR$^{c7}$R$^{d7}$.

In yet another embodiment, wherein R$^7$ is selected from H, D, C$_{1-6}$ alkyl, C$_{1-6}$ haloalkyl, halo, and CN. In still another embodiment, R$^7$ is halo. In another embodiment, R$^7$ is fluoro.

In an embodiment, R$^{9N}$ is selected from H, C$_{1-6}$ alkyl, C$_{2-6}$ alkenyl, C$_{2-6}$ alkynyl, and C$_{1-6}$ haloalkyl; wherein said C$_{1-6}$ alkyl, C$_{2-6}$ alkenyl, and C$_{2-6}$ alkynyl, are each optionally substituted with 1, 2, 3, or 4 substituents independently selected from R$^g$.

In another embodiment, R$^{9N}$ is selected from H, C$_{1-6}$ alkyl, C$_{2-6}$ alkenyl, C$_{2-6}$ alkynyl, and C$_{1-6}$ haloalkyl. In yet another embodiment, R$^{9N}$ is H.

In an embodiment, each R$^9$ is independently selected from H, D, C$_{1-6}$ alkyl, C$_{2-6}$ alkenyl, C$_{2-6}$ alkynyl, C$_{1-6}$ haloalkyl, C$_{3-6}$ cycloalkyl, phenyl, 5-6 membered heteroaryl, 4-7 membered heterocycloalkyl, halo, CN, OR$^{a9}$, SR$^{a9}$, C(O)R$^{b9}$, C(O)NR$^{c9}$R$^{d9}$, (O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)OR$^{a9}$, NR$^{c9}$C(O) NR$^{c9}$R$^{d9}$, NR$^{c9}$S(O)R$^{b9}$, NR$^{c9}$S(O)$_2$R$^{b9}$, NR$^{c9}$S(O)$_2$NR$^{c9}$R$^{d9}$, S(O)R$^{b9}$, S(O)NR$^{c9}$R$^{d9}$, S(O)$_2$R$^{b9}$, and S(O)$_2$NR$^{c9}$R$^{d9}$.

In another embodiment, each R$^9$ is independently selected from H, D, C$_{1-6}$ alkyl, C$_{2-6}$ alkenyl, C$_{2-6}$ alkynyl, C$_{1-6}$ haloalkyl, C$_{3-6}$ cycloalkyl, phenyl, 5-6 membered heteroaryl, 4-7 membered heterocycloalkyl, halo, CN, OR$^{a9}$, SR$^{a9}$, C(O)R$^{b9}$, C(O)NR$^{c9}$R$^{d9}$, (O)OR$^{a9}$, OC(O)R$^{b9}$, OC(O) NR$^{c9}$R$^{d9}$, NR$^{c9}$R$^{d9}$, NR$^{c9}$C(O)R$^{b9}$, NR$^{c9}$S(O)$_2$R$^{b9}$, S(O)$_2$ R$^{b9}$, and S(O)$_2$NR$^{c9}$R$^{d9}$.

In an embodiment, each R$^9$ is independently selected from H, D, C$_{1-6}$ alkyl, C$_{2-6}$ alkenyl, C$_{2-6}$ alkynyl, and C$_{1-6}$ haloalkyl. In an embodiment, each R$^9$ is independently selected from H, D, and C$_{1-6}$ alkyl. In an embodiment, each R$^9$ is H.

In an embodiment, each R$^{10}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, OR$^{a10}$, SR$^{a10}$, C(O)R$^{b10}$, C(O) NR$^{c10}$R$^{d10}$, C(O)OR$^{a10}$, C(O)R$^{b10}$, OC(O)NR$^{c10}$R$^{d10}$, NR$^{c10}$R$^{d10}$, NR$^{c10}$, C(O)R$^{b10}$, NR$^{c10}$, C(O)OR$^{a10}$, NR$^{c10}$, C(O)NR$^{c10}$R$^{d10}$, NR$^{c10}$S(O)$_2$R$^{b10}$, NR$^{c10}$S(O)$_2$NR$^{c10}$R$^{d10}$, S(O)R$^{b10}$, S(O)NR$^{c10}$R$^{d10}$, S(O)$_2$R$^{b10}$, and S(O)$_2$ NR$^{c10}$R$^{b10}$.

In another embodiment, each R$^{10}$ is independently selected from C$_{1-6}$ alkyl, C$_{2-6}$ alkenyl, C$_{2-6}$ alkynyl, C$_{1-6}$ haloalkyl, halo, D, CN, OR$^{a10}$, and NR$^{c10}$R$^{d10}$. In yet another embodiment, each R$^{10}$ is independently selected from C$_{1-6}$ alkyl, halo, and OR$^{a10}$. In still another embodiment, R$^{10}$ is methyl. In an embodiment, R$^{10}$ is methoxy. In another embodiment, R$^{10}$ is fluoro. In yet another embodiment, R$^{10}$ is chloro.

In another embodiment, each R$^{20}$ is independently selected from C$_{1-6}$ alkyl, C$_{1-6}$ haloalkyl, C$_{3-10}$ cycloalkyl, 4-10 membered heterocycloalkyl, $C_{6-10}$ aryl, 5-10 membered heteroaryl, halo, D, CN, $OR^{a20}$, and $NR^{c20}R^{d20}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, or 3 substituents independently selected from $R^{21}$.

In another embodiment, each $R^{20}$ is independently selected from $C_{1-6}$ alkyl, $C_{1-6}$ haloalkyl, phenyl, 5-6 membered heteroaryl, halo, D, CN, $OR^{a20}$, and $NR^{c20}R^{d20}$; wherein said $C_{1-6}$ alkyl, phenyl, and 5-6 membered heteroaryl, are each optionally substituted with 1 or 2 substituents independently selected from $R^{21}$.

In another embodiment, each $R^{20}$ is independently selected from phenyl and CN; wherein said phenyl is optionally substituted with 1 or 2 substituents independently selected from $R^{21}$.

In another embodiment, each $R^{21}$ is independently selected from $C_{1-6}$ alkyl, $C_{1-6}$ haloalkyl halo, D, CN, $OR^{a21}$, and $NR^{c21}R^{d21}$. In another embodiment, each $R^{21}$ is independently selected from halo and CN.

In an embodiment, each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a30}$, $SR^{a30}$, $C(O)R^{b30}$, $C(O)NR^{c30}R^{d30}$, $(O)OR^{a30}$, $C(O)R^{b30}$, $OC(O)NR^{c30}R^{d30}$, $NR^{c30}R^{d30}$, $NR^{c30}C(O)R^{b30}$, $NR^{30}C(O)OR^{a3}$, $NR^{c30}C(O)NR^{c3}R^{d30}$, $NR^{c30}S(O)_2R^{b30}$, $NR^{c30}S(O)_2NR^{c30}R^{d30}$, $S(O)_2R^{b30}$, and $S(O)_2NR^{c30}R^{d30}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{31}$.

In another embodiment, each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a30}$, $C(O)R^{b30}$, $C(O)NR^{c30}R^{d30}$, $C(O)OR^{a30}$, $OC(O)R^{b30}$, $OC(O)NR^{c30}R^{d30}$, $NR^{c30}R^{d30}$, $NR^{30}$, $C(O)R^{b30}$, and $S(O)_2R^{b30}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{31}$.

In yet another embodiment, each $R^{30}$ is 4-10 membered heterocycloalkyl optionally substituted with 1, 2, 3, or 4 substituents independently selected from $R^{31}$. In still another embodiment, each $R^{30}$ is 4-6 membered heterocycloalkyl optionally substituted with 1 or 2 substituents independently selected from $R^{31}$.

In another embodiment, each $R^{30}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a30}$ and, $NR^{c30}R^{d30}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, or 3 substituents independently selected from $R^{31}$.

In another embodiment, each $R^{30}$ is independently selected from $C_{1-6}$ alkyl, $C_{1-6}$ haloalkyl, $C_{3-6}$ cycloalkyl, 4-6 membered heterocycloalkyl, phenyl, 5-6 membered heteroaryl, halo, D, CN, $OR^{a30}$ and, $NR^{c30}R^{d30}$; wherein said $C_{1-6}$ alkyl, $C_{3-6}$ cycloalkyl, 4-6 membered heterocycloalkyl, phenyl, and 5-6 membered heteroaryl, are each optionally substituted with 1 or 2 substituents independently selected from $R^{31}$.

In another embodiment, each $R^{30}$ is independently selected from 4-6 membered heterocycloalkyl and $NR^{C30}R^{d30}$; wherein said 4-6 membered heterocycloalkyl is optionally 5 substituted with 1 or 2 substituents independently selected from $R^{31}$.

In an embodiment, each $R^{31}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{31}C(O)OR^{a31}$, $NR^{c31}C(O)NR^{c31}R^{d31}$, $NR^{c31}S(O)_2R^{b31}$, $NR^{31}S(O)_2NR^{c31}R^{d31}$, $S(O)_2R^{b31}$, and $S(O)_2NR^{c31}R^{d31}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{32}$.

In another embodiment, each $R^{31}$ is independently selected from $C_{1-6}$ alkyl, $C_{2-6}$ alkenyl, $C_{2-6}$ alkynyl, $C_{1-6}$ haloalkyl, halo, D, CN, $OR^{a31}$, and $NR^{c31}R^{d31}$. In yet another embodiment, each $R^{31}$ is independently selected from $C_{1-6}$ alkyl, $C_{2-6}$ alkenyl, $C_{2-6}$ alkynyl, $C_{1-6}$ haloalkyl, halo, D, and CN. In still another embodiment, each $R^{31}$ is $C_{1-6}$ alkyl. In another embodiment, $R^{31}$ is methyl.

In another embodiment, each $R^{50}$ is independently selected from $C_{1-6}$ alkyl, $C_{1-6}$ haloalkyl, halo, D, CN, $OR^{a50}$, $C(O)R^{b50}$, $C(O)NR^{c50}R^{d50}$, $C(O)OR^{a50}$, $NR^{c50}R^{d50}$, and $NR^{c50}C(O)R^{b50}$. In another embodiment, each $R^{50}$ is independently selected from CN, $OR^{a50}$, and $C(O)NR^{c50}R^{d50}$.

In an embodiment, each $R^a$, $R^b$, $R^c$, and $R^d$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^g$.

In another embodiment, each $R^a$, $R^c$, and $R^d$ is independently selected from H, $C_{1-6}$ alkyl, $C_{2-6}$ alkenyl, $C_{2-6}$ alkynyl, and $C_{1-6}$ haloalkyl, wherein $C_{1-6}$ alkyl, $C_{2-6}$ alkenyl, and $C_{2-6}$ alkynyl are each optionally substituted with 1, 2, 3, or 4 substituents independently selected from $R^g$. In yet another embodiment, each $R^a$, $R^c$, and $R^d$ is independently selected from H, $C_{1-6}$ alkyl, $C_{2-6}$ alkenyl, $C_{2-6}$ alkynyl, and $C_{1-6}$ haloalkyl.

In an embodiment, each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl, are each optionally substituted with 1, 2, or 3 substituents independently selected from $R^{30}$. In an embodiment, each $R^{a3}R^{b3}$, $R^{c3}$ and $R^{d3}$ is independently selected from H and $C_{1-6}$ alkyl, wherein said $C_{1-6}$ alkyl, is optionally substituted with 1 substituent selected from $R^{30}$. In an embodiment, each $R^{a3}$, $R^{b3}$, $R^{c3}$ and $R^{d3}$ is independently $C_{1-6}$ alkyl, wherein said $C_{1-6}$ alkyl, is optionally substituted with 1 substituent selected from $R^{30}$. In an embodiment, each $R^{a3}$, $R^{b3}$, $R^{c3}$ and $R^{d3}$ is independently H, In an embodiment, each $R^{a3}$, $R^{b3}$, $R^{c3}$ and $R^{d3}$ is independently $C_{1-6}$ alkyl, In an embodiment, each $R^a$, $R^b$, $R^{c6}$ and $R^{d6}$ is independently selected from H, $C_{1-6}$ alkyl, $C_{2-6}$ alkenyl, $C_{2-6}$ alkynyl, and $C_{1-6}$ haloalkyl. In an embodiment, each $R^{a6}$, $R^{b6}$, $R^{c6}$ and $R^{d6}$ is independently selected from H and $C_{2-6}$ alkenyl. In an embodiment, each $R^{a6}$, $R^{b6}$, $R^{c6}$ and $R^{d6}$ is independently H. In an embodiment, each $R^{a6}$, $R^{b6}$, $R^{c6}$ and $R^{d6}$ is independently $C_{2-6}$ alkenyl.

In an embodiment, each $R^{a10}$, $R^{b10}$, $R^{c10}$, and $R^{d10}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^{11}$.

In an embodiment, each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, and $C_{1-6}$ haloalkyl. In an embodiment, each $R^{a10}$, $R^{b10}$, $R^{c10}$ and $R^{d10}$ is independently selected from H and $C_{1-6}$ alkyl, In an embodiment, each $R^{a10}$; $R^{b10}$, $R^{c10}$ and $R^{d10}$ is independently H, In an embodiment, each $R^{a10}$, $R^{b10}$, $R^{c10}$ and $R^{d10}$ is independently $C_{1-6}$ alkyl.

In an embodiment, each $R^{a30}$, $R^{c30}$ and $R^{d30}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{1-6}$ aryl and 5-10 membered heteroaryl, are each optionally substituted with 1, 2, or 3 substituents independently selected from $R^{31}$.

In an embodiment, each $R^{a30}$, $R^{c30}$ and $R^{d30}$ is independently selected from H, $C_{1-6}$ alkyl, $C_{1-6}$ haloalkyl, $C_{3-6}$ cycloalkyl, 4-6 membered heterocycloalkyl, phenyl and 5-6 membered heteroaryl; wherein said $C_{1-6}$ alkyl, $C_{3-6}$ cycloalkyl, 4-6 membered heterocycloalkyl, phenyl and 5-6 membered heteroaryl, are each optionally substituted with 1 or 2 substituents independently selected from $R^{31}$. In an embodiment, each $R^{c30}$ and $R^{d30}$ is independently selected from H and $C_{1-6}$ alkyl.

In an embodiment, each $R^{a50}$, $R^{c50}$ and $R^{d50}$, is independently selected from H, $C_{1-6}$ alkyl, and $C_{1-6}$ haloalkyl. In an embodiment, each $R^{a50}$, $R^{c50}$ and $R^{d50}$ is independently selected from H and $C_{1-6}$ alkyl.

In an embodiment, the compound of Formula I is selected from:
1-acryloyl-9'-chloro-7'-fluoro-8'-(2-fluoro-6-hydroxyphenyl)-1',4'-dihydro-3'H-spiro-[piperidine-4,2'-pyrazino[2,3-c]quinolin]-3'-one;
1-acryloyl-9'-chloro-8'-(2-chloro-5-hydroxyphenyl)-7'-fluoro-1',4'-dihydro-3'H-spiro-[piperidine-4,2'-pyrazino[2,3-c]quinolin]-3'-one;
1-acryloyl-9'-chloro-7'-fluoro-8'-(3-methyl-1H-indazol-4-yl)-1',4'-dihydro-3'H-spiro-[piperidine-4,2'-pyrazino[2,3-c]quinolin]-3'-one;
1-acryloyl-9'-chloro-7'-fluoro-8'-(5-methyl-1H-indazol-4-yl)-1',4'-dihydro-3'H-spiro-[piperidine-4,2'-pyrazino[2,3-c]quinolin]-3'-one;
1-acryloyl-9'-chloro-7'-fluoro-8'-(2-fluoro-6-methoxyphenyl)-1',4'-dihydro-3'H-spiro-[piperidine-4,2'-pyrazino[2,3-c]quinolin]-3'-one;
1-acryloyl-9'-chloro-7'-fluoro-8'-(2-fluoro-6-hydroxyphenyl)-1',4'-dihydro-3'H-spiro-[azetidine-3,2'-pyrazino[2,3-c]quinolin]-3'-one;
1-acryloyl-9'-chloro-7'-fluoro-8'-(5-methyl-1H-indazol-4-yl)-1',4'-dihydro-3'H-spiro-[azetidine-3,2'-pyrazino[2,3-c]quinolin]-3'-one;
1'-acryloyl-9-chloro-7-fluoro-8-(2-fluoro-6-hydroxyphenyl)-1,4-dihydro-3H-spiro-[pyrazino[2,3-c]quinoline-2,3'-pyrrolidin]-3-one;
1'-acryloyl-9-chloro-7-fluoro-8-(5-methyl-1H-indazol-4-yl)-1,4-dihydro-3H-spiro-[pyrazino[2,3-c]quinoline-2,3'-pyrrolidin]-3-one;
1-acryloyl-9'-chloro-7'-fluoro-8'-(2-fluoro-6-hydroxyphenyl)-5'-((1-methylpyrrolidin-2-yl)methoxy)-1',4'-dihydro-3'H-spiro[piperidine-4,2'-pyrazino[2,3-c]quinolin]-3'-one;
1-acryloyl-9'-chloro-7'-fluoro-8'-(3-hydroxynaphthalen-1-yl)-5'-((1-methylpyrrolidin-2-yl)methoxy)-1',4'-dihydro-3'H-spiro[piperidine-4,2'-pyrazino[2,3-c]quinolin]-3'-one;
1-acryloyl-9'-chloro-7'-fluoro-8'-(2-fluoro-6-hydroxyphenyl)-5'-(2-(piperidin-1-yl)ethoxy)-1',4'-dihydro-3'H-spiro[piperidine-4,2'-pyrazino[2,3-c]quinolin]-3'-one;
1-acryloyl-8'-chloro-6'-fluoro-7'-(3-hydroxynaphthalen-1-yl)-4'-((1-methylpyrrolidin-2-yl)methoxy)spiro[piperidine-4,1'-pyrrolo[2,3-c]quinolin]-2'(3'H)-one;
1-acryloyl-8'-chloro-6'-fluoro-7'-(3-hydroxynaphthalen-1-yl)-4'-((1-methylpyrrolidin-2-yl)methoxy)spiro[pyrrolidine-3,1'-pyrrolo[2,3-c]quinolin]-2'(3'H)-one;
1-acryloyl-8'-chloro-6'-fluoro-7'-(3-hydroxynaphthalen-1-yl)-3'-methyl-4'-((1-methyl-pyrrolidin-2-yl)methoxy)spiro[piperidine-4,1'-pyrrolo[2,3-c]quinolin]-2'(3'H)-one;
1-acryloyl-9'-chloro-7'-fluoro-8'-(3-hydroxynaphthalen-1-yl)spiro[piperidine-4,2'-pyrano-[3,2-c]quinolin]-4'(3'H)-one; and
1-acryloyl-9'-chloro-7'-fluoro-8'-(2-fluoro-6-hydroxyphenyl)-5'-((1-methylpyrrolidin-2-yl)methoxy)-1',4'-dihydro-3'H-spiro[azetidine-3,2'-pyrazino[2,3-c]quinolin]-3'-one;

or a pharmaceutically acceptable salt thereof.

In another embodiment, the compound of Formula I is selected from:
4'-(3-(dimethylamino)azetidin-1-yl)-6'-fluoro-7'-(3-hydroxynaphthalen-1-yl)-8'-methylspiro[piperidine-3,1'-pyrrolo[2,3-c]quinolin]-2'(3'H)-one;
8'-chloro-7'-(7-chloro-3-hydroxynaphthalen-1-yl)-4'-(3-(dimethylamino)azetidin-1-yl)-6'-fluorospiro[piperidine-3,1'-pyrrolo[2,3-c]quinolin]-2'(3'H)-one;
8'-chloro-4'-(3-(dimethylamino)azetidin-1-yl)-6'-fluoro-7'-(3-hydroxynaphthalen-1-yl)-5-azaspiro[bicyclo[2.2.1]heptane-2,1'-pyrrolo[2,3-c]quinolin]-2'(3')-one;
3-amino-8'-chloro-4'-(3-(dimethylamino)azetidin-1-yl)-6'-fluoro-7'-(3-hydroxynaphthalen-1-yl)spiro[cyclobutane-1,1'-pyrrolo[2,3-c]quinolin]-2'(3')-one;
4-(4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)butanenitrile;
2-(4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)acetonitrile;
3-(4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)propanenitrile;
8'-(2-chlorobenzyl)-4'-(3-(dimethylamino)azetidin-1-yl)-6'-fluoro-7'-(3-hydroxynaphthalen-1-yl)spiro[piperidine-3,1'-pyrrolo[2,3-c]quinolin]-2'(3')-one;
2-((4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)methyl)benzonitrile;
4-(4'-(3-(dimethylamino)azetidin-1-yl)-6'-fluoro-7'-(3-hydroxynaphthalen-1-yl)-2',3'-dihydrospiro[piperidine-3,1'-pyrrolo[2,3-c]quinolin]-8'-yl)butanenitrile
3-(4'-(3-(dimethylamino)azetidin-1-yl)-6'-fluoro-7'-(3-hydroxynaphthalen-1-yl)-2'-oxo-2',3'-dihydrospiro[azetidine-3,1'-pyrrolo[2,3-c]quinolin]-8'-yl)propanenitrile;
4-(4'-(3-(dimethylamino)azetidin-1-yl)-6'-fluoro-7'-(3-hydroxynaphthalen-1-yl)-2'-oxo-2',3'-dihydrospiro[pyrrolidine-3,1'-pyrrolo[2,3-c]quinolin]-8'-yl)butanenitrile;

4-(4'-(3-(dimethylamino)azetidin-1-yl)-6'-fluoro-7'-(3-hydroxynaphthalen-1-yl)-2'-oxo-2',3'-dihydrospiro[morpholine-2,1'-pyrrolo[2,3-c]quinolin]-8'-yl)butanenitrile;

4-(6'-fluoro-7'-(3-hydroxynaphthalen-1-yl)-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile;

4-(6'-fluoro-7'-(3-hydroxynaphthalen-1-yl)-3'-methyl-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile;

4-(6'-fluoro-3'-(2-hydroxyethyl)-7'-(3-hydroxynaphthalen-1-yl)-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile;

4-(6'-fluoro-7'-(3-hydroxynaphthalen-1-yl)-3'-isopentyl-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile;

4-(3'-(cyanomethyl)-6'-fluoro-7'-(3-hydroxynaphthalen-1-yl)-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile; and 2-(8'-(3-cyanopropyl)-6'-fluoro-7'-(3-hydroxynaphthalen-1-yl)-4'-(((S)-1-methylpyrrolidin-2-yl)methoxy)-2'-oxospiro[piperidine-3,1'-pyrrolo[2,3-c]quinolin]-3'(2'H)-yl)acetamide;

or a pharmaceutically acceptable salt thereof.

In another aspect, provided herein is a pharmaceutical composition comprising the compound of Formula I, or a pharmaceutically acceptable salt thereof, and a pharmaceutically acceptable carrier.

In an aspect, provided herein is a method of inhibiting a KRAS protein harboring a G12C mutation, said method comprising contacting a compound of the instant disclosure with KRAS.

In another aspect, provided herein is a method of inhibiting a KRAS protein harboring a G12D mutation, said method comprising contacting a compound of the instant disclosure with KRAS.

In yet another aspect, provided herein is a method of inhibiting a KRAS protein harboring a G12V mutation, said method comprising contacting a compound of the instant disclosure with KRAS.

In an embodiment, compounds of the Formulae herein are compounds of the Formulae or pharmaceutically acceptable salts thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula I can be combined in any suitable combination.

At various places in the present specification, certain features of the compounds are disclosed in groups or in ranges. It is specifically intended that such a disclosure include each and every individual subcombination of the members of such groups and ranges. For example, the term "$C_6$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or aryene group, respectively.

The term "substituted" means that an atom or group of atoms formally replaces hydrogen as a "substituent" attached to another group. The term "substituted," unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl," refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene," employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy," employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms. The term "$C_{n-m}$ dialkoxy" refers to a linking group of formula —O—($C_{n-m}$ alkyl)-O—, the alkyl group of which has n to m carbons. Example dialkyoxy groups include —OCH$_2$CH$_2$O— and OCH$_2$CH$_2$CH$_2$—. In some embodiments, the two O atoms of a $C_{n-m}$ dialkoxy group may be attached to the same B atom to form a 5- or 6-membered heterocycloalkyl group.

The term "alkylthio," employed alone or in combination with other terms, refers to a group of formula —S-alkyl, wherein the alkyl group is as defined above.

The term "amino," employed alone or in combination with other terms, refers to a group of formula —NH$_2$, wherein the hydrogen atoms may be substituted with a substituent described herein. For example, "alkylamino" can refer to —NH(alkyl) and —N(alkyl)$_2$.

The term "carbonyl," employed alone or in combination with other terms, refers to a —C(=O)— group, which also may be written as C(O).

The term "cyano" or "nitrile" refers to a group of formula —C≡N, which also may be written as —CN.

The term "carbamyl," as used herein, refers to a —NHC(O)O— or —OC(O)NH— group, wherein the carbon atom is doubly bound to one oxygen atom, and singly bound to a nitrogen and second oxygen atom.

The term "sulfonyl" refers to a —SO$_2$— group wherein a sulfur atom is doubly bound to two oxygen atoms.

The terms "halo" or "halogen," used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1}halogen atoms, which may either be the same or different. In some embodiments, the halogen atoms are fluoro atoms. In some embodiments, the haloalkyl group has 1 to 6 or 1 to 4 carbon atoms. Example haloalkyl groups include CF$_3$, C$_2$F, CHF$_2$, CH$_2$F, CCl$_3$, CHCl$_2$, C$_2$Cl$_5$ and the like. In some embodiments, the haloalkyl group is a fluoroalkyl group.

The term "haloalkoxy," employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" or "oxy" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, isoindolyl, benzothiophenyl, benzofuranyl, benzisoxazolyl, imidazo[1,2-b]thiazolyl, purinyl, and the like. In some embodiments, the heteroaryl group is pyridone (e.g., 2-pyridone).

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups.

Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or $S(O)_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 2,5-diazobicyclo[2.2.1] heptanyl; pyrrolidinyl; hexahydropyrrolo[3,4-b]pyrrol-1(2)-yl; 1,6-dihydropyridinyl; morpholinyl; azetidinyl; piperazinyl; and 4,7-diazaspiro[2.5]octan-7-yl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term "compound" as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6*th* Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high-performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

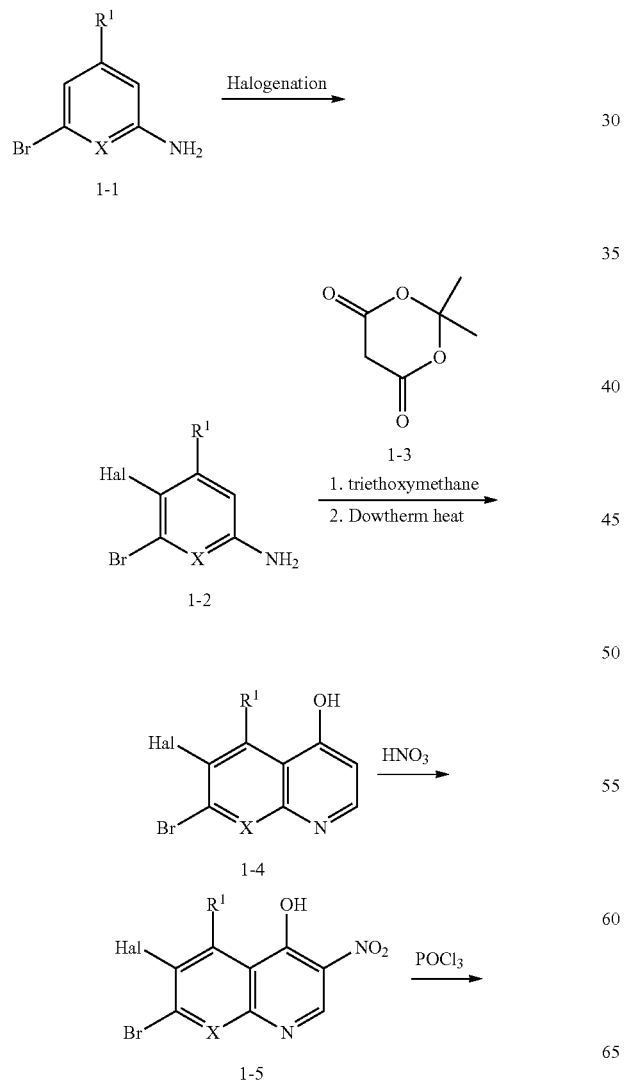

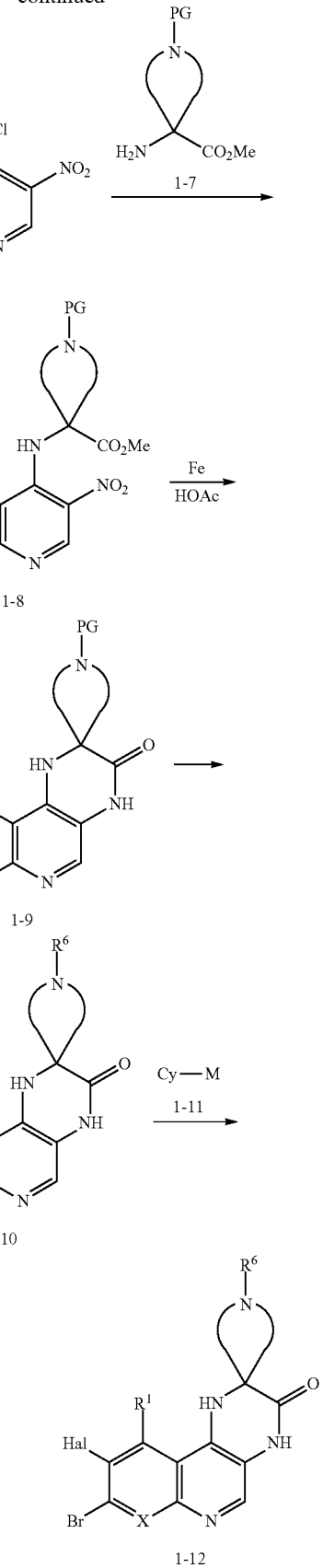

Compounds of formula 1-12 can be prepared via the synthetic route outlined in Scheme 1. Halogenation of starting material 1-1 with an appropriate reagent, such as N-chloro-succinimide (NCS), first affords intermediate 1-2 (Hal is a halide, such as F, Cl, Br, or I). Compound 1-4 can then be prepared by a condensation reaction of 1-2 with 2,2-dimethyl-1,3-dioxane-4,6-dione (1-3) and triethoxymethane, followed by decarboxylation under thermal condition. Nitration of intermediate 1-4 with nitric acid gives the nitro adduct 1-5, which upon treatment with a reagent, such as $POCl_3$, yields intermediate 1-6. A $S_NAr$ reaction of 1-6 with an amine adduct of formula 1-7 (PG is an appropriate protecting group, such as Boc) then generate compound 1-8. The nitro functionality in 1-8 is reduced under suitable conditions (such as using Fe in acetic acid), followed by a cyclization reaction, to deliver product 1-9. Removal of the protecting group (PG) in 1-9, followed by functionalization of the resulting amine adduct (e.g. reacting with acryloyl chloride), generates intermediate 1-10. The desired product 1-12 can then be prepared by a coupling reaction of compound 1-10 with an adduct of formula 1-11, in which M is a boronic acid, boronic ester or an appropriately substituted metal [e.g., M is $B(OR)_2$, $Sn(Alkyl)_3$, or Zn-Hal], under standard Suzuki Cross-Coupling conditions (Tetrahedron 2002, 58, 9633-9695) (e.g., in the presence of a palladium catalyst and a suitable base), or standard Stille cross-coupling conditions (ACS Catalysis 2015, 5, 3040-3053) (e.g., in the presence of a palladium catalyst), or standard Negishi cross-coupling conditions (ACS Catalysis 2016, 6, 1540-1552) (e.g., in the presence of a palladium catalyst). The order of the above described chemical reactions can be rearranged as appropriate to suit the preparation of different analogues.

Scheme 2

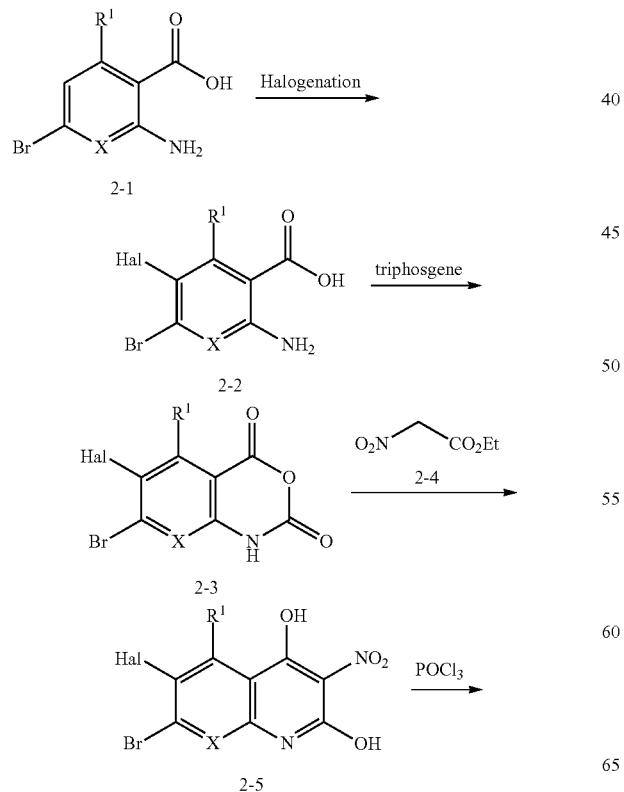

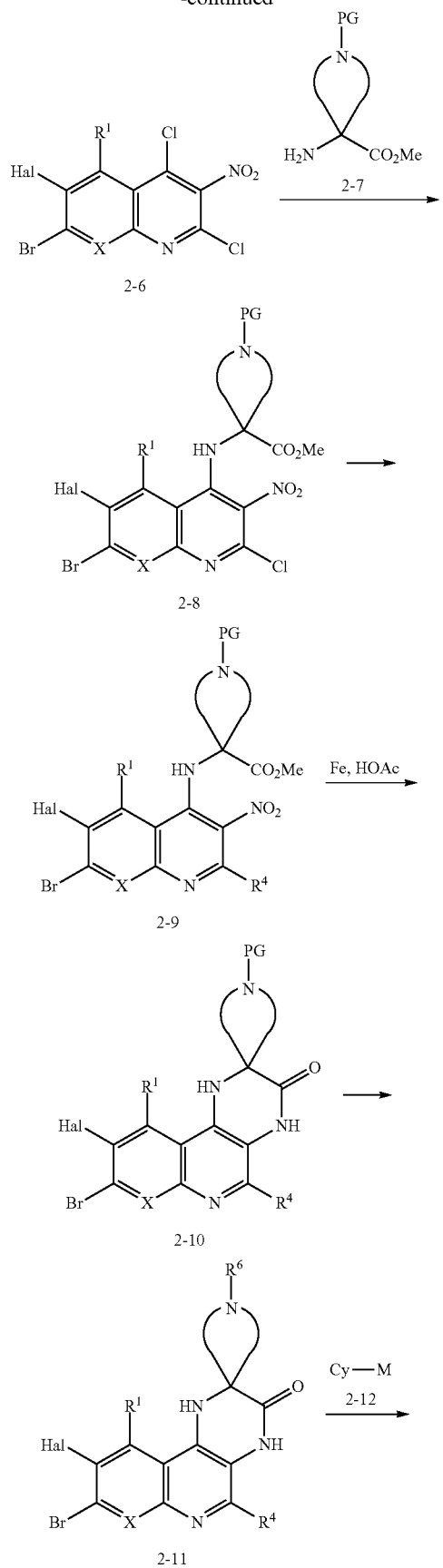

-continued

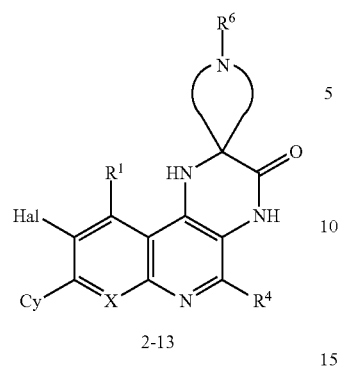

2-13

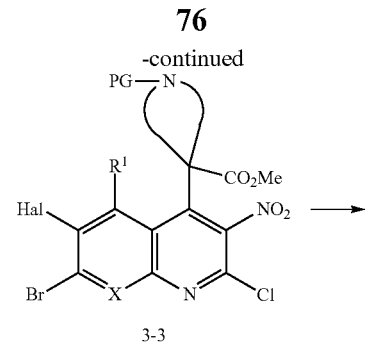

3-3

Compounds of formula 2-13 can be prepared via the synthetic route outlined in Scheme 2. Halogenation of starting material 2-1 with an appropriate reagent, such as N-chloro-succinimide (NCS), first affords intermediate 2-2 (Hal is a halide, such as F, Cl, Br, or I). Compound 2-3 can then be prepared by treatment of intermediate 2-2 with an appropriate reagent, such as triphosgene. Further condensation reaction of 2-3 with reagent 2-4 delivers nitro compound 2-5, which was treated with $POCl_3$ to yield intermediate 2-6. A $S_NAr$ reaction of 2-6 with an amine adduct of formula 2-7 (PG is an appropriate protecting group, such as Boc) then generate compound 2-8. The $R^4$ group in 2-9 can then be installed via a suitable transformation, such as a $S_NAr$ reaction or a coupling reaction. The nitro functionality in 2-9 is reduced under suitable conditions (such as using Fe in acetic acid), followed by a cyclization reaction, to deliver product 2-10. Removal of the protecting group (PG) in 2-10, followed by functionalization of the resulting amine adduct (e.g. reacting with acryloyl chloride), generates intermediate 2-11. The desired product 2-13 can then be prepared by a coupling reaction of compound 2-11 with an adduct of formula 2-12, in which M is a boronic acid, boronic ester or an appropriately substituted metal [e.g., M is $B(OR)_2$, $Sn(Alkyl)_3$, or Zn-Hal], under standard Suzuki Cross-Coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst). The order of the above described chemical reactions can be rearranged as appropriate to suit the preparation of different analogues.

Scheme 3

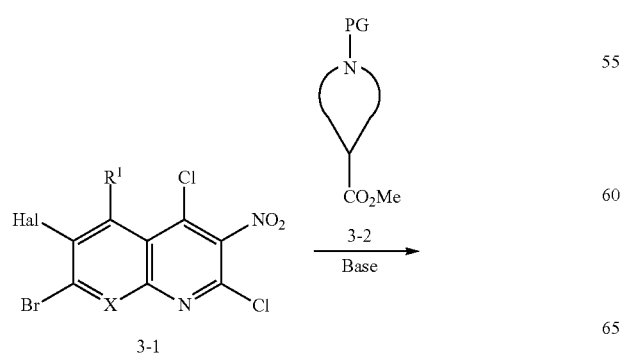

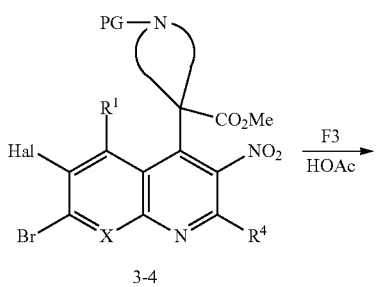

3-4

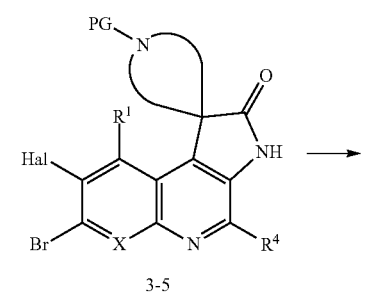

3-5

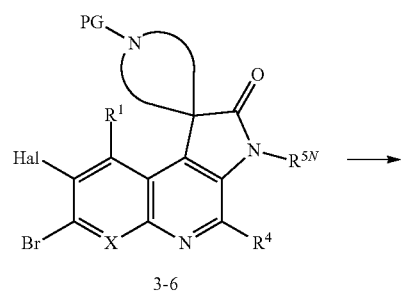

3-6

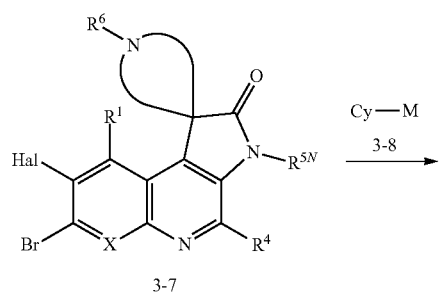

3-7

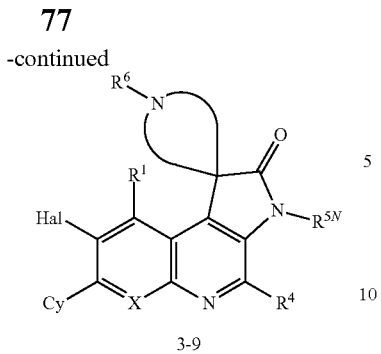

3-9

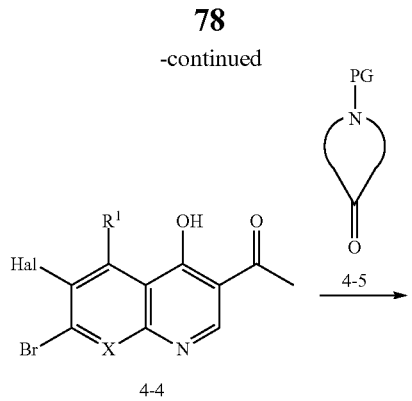

4-4

Compounds of formula 3-9 can be prepared via the synthetic route outlined in Scheme 3. A $S_NAr$ reaction of starting material 3-1 (prepared following procedures described in Scheme 2) with an adduct of formula 3-2, in the presence of an appropriate base (e.g. KHMDS), first affords compound 3-3. The $R^4$ group in 3-4 can then be installed via a suitable transformation, such as a $S_NAr$ reaction or a coupling reaction. The nitro functionality in 3-4 is reduced under suitable conditions (such as using Fe in acetic acid), followed by a cyclization reaction, to deliver product 3-5. Intermediate 3-5 can then be functionalized (e.g. an alkylation reaction) into compound 3-6. Removal of the protecting group (PG) in 3-6, followed by functionalization of the resulting amine adduct (e.g. reacting with acryloyl chloride), generates intermediate 3-7. The desired product 3-9 can then be prepared by a coupling reaction of compound 3-7 with an adduct of formula 3-8, in which M is a boronic acid, boronic ester or an appropriately substituted metal [e.g., M is B(OR)$_2$, Sn(Alkyl)$_3$, or Zn-Hal], under standard Suzuki Cross-Coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst). The order of the above described chemical reactions can be rearranged or omitted as appropriate to suit the preparation of different analogues.

Scheme 4

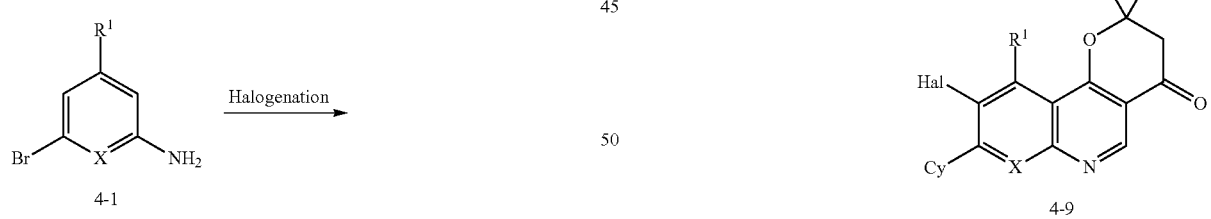

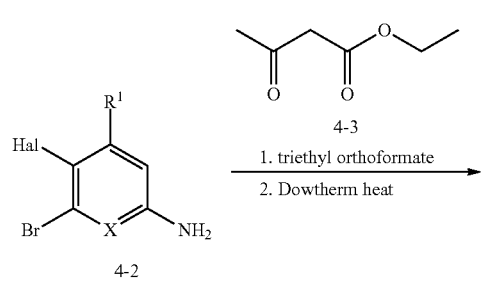

Compounds of formula 4-9 can be prepared via the synthetic route outlined in Scheme 4. Halogenation of starting material 4-1 with an appropriate reagent, such as N-chloro-succinimide (NCS), first affords intermediate 4-2 (Hal is a halide, such as F, Cl, Br, or I). Intermediate 4-4 can then be prepared by a condensation reaction of intermediate 4-2 with ethyl 3-oxobutanoate (4-3) and triethyl orthoformate, followed by decarboxylation under thermal condition. Treatment of intermediate 4-4 with ketone 4-5, in the presence of a suitable base (e.g. pyrrolidine), generates compound 4-6. Removal of the protecting group (PG) in 4-6, followed by functionalization of the resulting amine adduct (e.g. reacting with acryloyl chloride), yields intermediate 4-7. Product 4-9 can then be prepared by coupling of 4-7 with an adduct of formula 4-8, in which M is a boronic acid, boronic ester or an appropriately substituted metal [e.g., M is B(OR)$_2$, Sn(Alkyl)$_3$, or Zn-Hal], under standard Suzuki Cross-Coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a pallidum catalyst). The order of the above described chemical reactions can be rearranged as appropriate to suit the preparation of different analogues.

Scheme 5

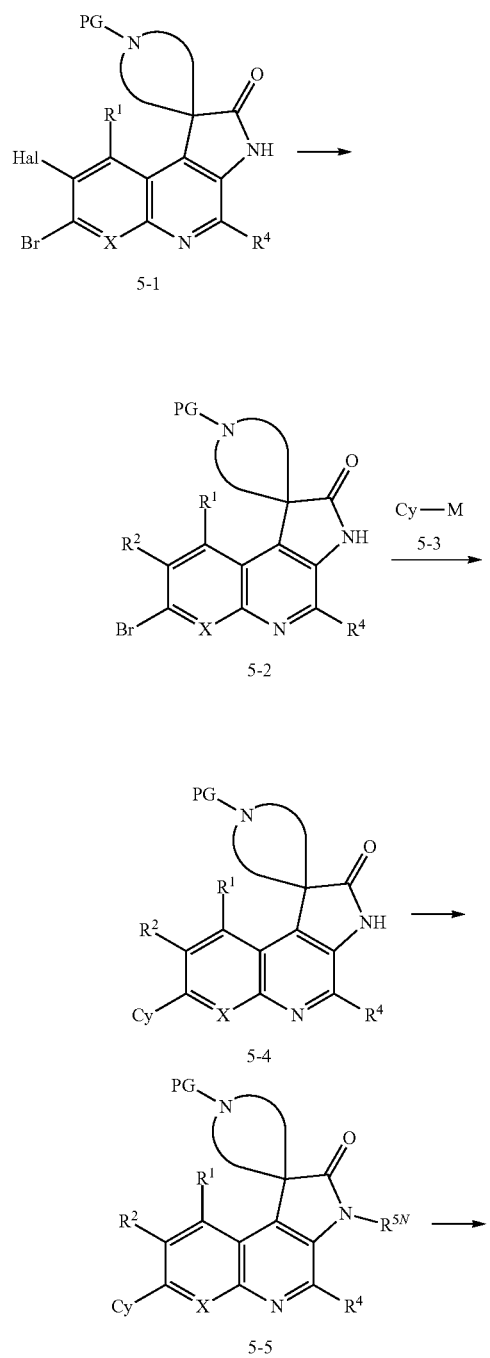

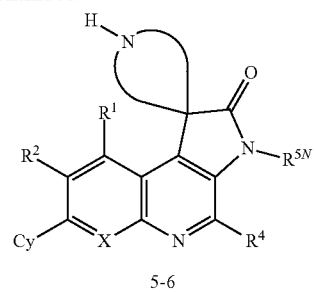

Compounds of formula 5-6 can be prepared via the synthetic route outlined in Scheme 5. Starting material 5-1 (prepared following procedures described in Scheme 3) can be functionalized (e.g. a Negishi cross-coupling reaction) into compound 5-2. Intermediate 5-4 can be prepared by a coupling reaction of compound 5-2 with an adduct of formula 5-3, in which M is a boronic acid, boronic ester or an appropriately substituted metal [e.g., M is B(OR)$_2$, Sn(Alkyl)$_3$, or Zn-Hal], under standard Suzuki Cross-Coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst). Intermediate 5-4 can then be functionalized (e.g. an alkylation reaction) into compound 5-5. The desired product 5-6 can then be prepared by removing the protecting group (PG) in 5-5. The order of the above described chemical reactions can be rearranged or omitted as appropriate to suit the preparation of different analogues.

Scheme 6

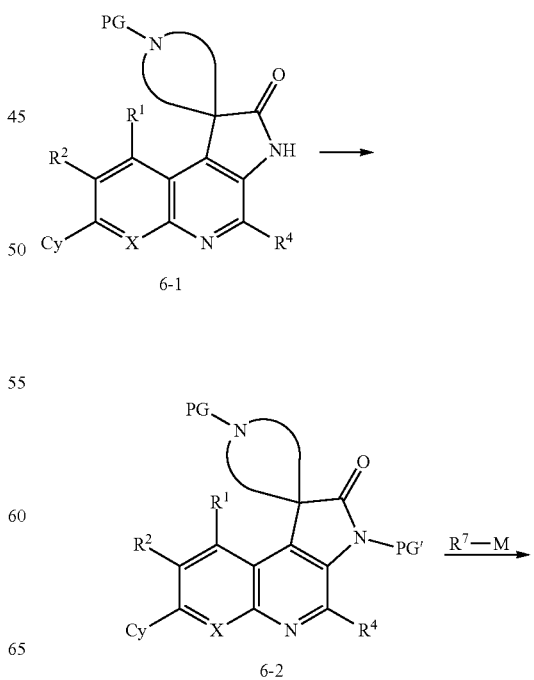

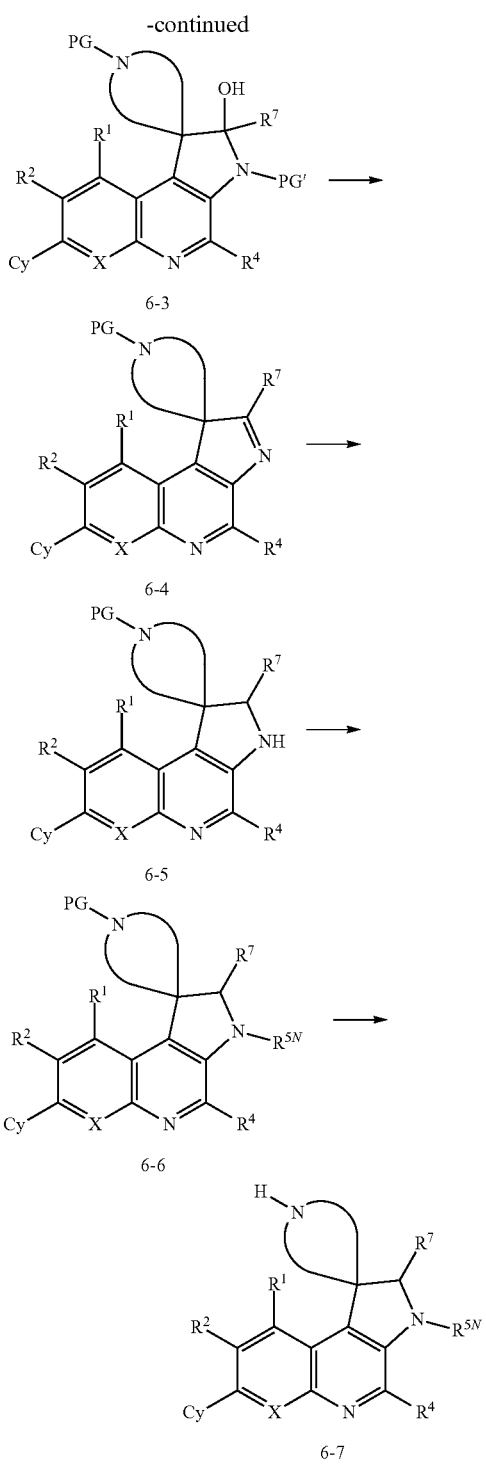

Compounds of formula 6-7 can be prepared via the synthetic route outlined in Scheme 6. The lactam functionality in the starting material 6-1 (prepared following procedures described in Scheme 5) can be protected to afford compound 6-2. The carbonyl in the protected lactam compound 6-2 can be functionalized by a nucleophilic addition reaction to give intermediate 6-3. Removal of the protecting group (PG') in 6-3, followed by an elimination reaction generates intermediate 6-4. Reduction of 6-4 under suitable conditions delivers compound 6-5. Compound 6-5 can then be functionalized (e.g. an alkylation reaction) into compound 6-6. The desired product 6-7 can then be prepared by removing the protecting group (PG) in 6-6. The order of the above described chemical reactions can be rearranged or omitted as appropriate to suit the preparation of different analogues.

KRAS Protein

The Ras family is comprised of three members; KRAS, NRAS and HRAS. RAS mutant cancers account for about 25% of human cancers. KRAS is the most frequently mutated isoform in human cancers: 85% of all RAS mutations are in KRAS, 12% in NRAS, and 3% in HRAS (Simanshu, D. et al. Cell 170.1 (2017):17-33). KRAS mutations are prevalent amongst the top three most deadly cancer types: pancreatic (97%), colorectal (44%), and lung (30%) (Cox, A. D. et al. Nat Rev Drug Discov (2014) 13:828-51). The majority of RAS mutations occur at amino acid residues/codons 12, 13, and 61; Codon 12 mutations are most frequent in KRAS. The frequency of specific mutations varied between RAS genes and G12D mutations are most predominant in KRAS whereas Q61R and G12R mutations are most frequent in NRAS and HRAS. Furthermore, the spectrum of mutations in a RAS isoform differs between cancer types. For example, KRAS G12D mutations predominate in pancreatic cancers (51%), followed by colorectal adenocarcinomas (45%) and lung cancers (17%) (Cox, A. D. et al. Nat Rev Drug Discov (2014) 13:828-51). In contrast, KRAS G12C mutations predominate in non-small cell lung cancer (NSCLC) comprising 11-16% of lung adenocarcinomas (nearly half of mutant KRAS is G12C), as well as 2-5% of pancreatic and colorectal adenocarcinomas, respectively (Cox, A. D. et al. Nat Rev Drug Discov (2014) 13:828-51). Genomic studies using shRNA knockdown thousands of genes across hundreds of cancer cell lines have demonstrated that cancer cells exhibiting KRAS mutations are highly dependent on KRAS function for cell growth (McDonald, R. et al. Cell 170 (2017): 577-592). Taken together, these findings suggested that KRAS mutations play a critical role in human cancers, therefore development of the inhibitors targeting mutant KRAS may be useful in the clinical treatment of diseases that have characterized by a KRAS mutation.

Methods of Use

The cancer types in which KRAS harboring G12C, G12V, and G12D mutations are implicated include, but are not limited to: carcinomas (e.g., pancreatic, colorectal, lung, bladder, gastric, esophageal, breast, head and neck, cervical skin, thyroid); hematopoietic malignancies (e.g., myeloproliferative neoplasms (MPN), myelodysplastic syndrome (MDS), chronic and juvenile myelomonocytic leukemia (CMML and JMML), acute myeloid leukemia (AML), acute lymphocytic leukemia (ALL) and multiple myeloma (MM)); and other neoplasms (e.g., glioblastoma and sarcomas). In addition, KRAS mutations were found in acquired resistance to anti-EGFR therapy (Knickelbein, K. et al. Genes & Cancer, (2015): 4-12). KRAS mutations were found in immunological and inflammatory disorders (Fernandez-Medarde, A. et al. Genes & Cancer, (2011): 344-358) such as Ras-associated lymphoproliferative disorder (RALD) or juvenile myelomonocytic leukemia (JMML) caused by somatic mutations of KRAS or NRAS.

Compounds of the present disclosure can inhibit the activity of KRAS. For example, compounds of the present disclosure can be used to inhibit activity of KRAS in a cell or in an individual or patient in need of inhibition of the enzyme by administering an inhibiting amount of one or more compounds of the present disclosure to the cell, individual, or patient.

In an aspect, provided herein is a method of inhibiting KRAS activity, said method comprising administering to a patient in need thereof a therapeutically effective amount of a compound of any of the formulae disclosed herein.

In another aspect, provided herein is a method of treating a KRAS-mediated disease or disorder in a subject in need thereof comprising administering to the subject a therapeutically effective amount of the compound of any of the formulae disclosed herein.

In an embodiment, the disease or disorder is an immunological or inflammatory disorder.

In another embodiment, the immunological or inflammatory disorder is Ras-associated lymphoproliferative disorder and juvenile myelomonocytic leukemia caused by somatic mutations of KRAS.

In an aspect, provided herein is a method of treating a disease or disorder associated with inhibiting a KRAS protein harboring a G12C mutation, said method comprising administering to a patient in need thereof a therapeutically effective amount of a compound of any of the formulae disclosed herein, or pharmaceutically acceptable salt thereof.

In another aspect, provided herein is a method of treating cancer in a subject in need thereof comprising administering to the subject a therapeutically effective amount of the compound of any of the formulae disclosed herein.

In an embodiment, the cancer is selected from carcinomas, hematological cancers, sarcomas, and glioblastoma.

In another embodiment, the hematological cancer is selected from myeloproliferative neoplasms, myelodysplastic syndrome, chronic and juvenile myelomonocytic leukemia, acute myeloid leukemia, acute lymphocytic leukemia, and multiple myeloma.

In yet another embodiment, the carcinoma is selected from pancreatic, colorectal, lung, bladder, gastric, esophageal, breast, head and neck, cervical, skin, and thyroid.

In still another aspect, provided herein is a method of treating a disease or disorder associated with inhibiting a KRAS protein harboring a G12C mutation, said method comprising administering to a patient in need thereof a therapeutically effective amount of the compound of any of the formulae disclosed herein, or a pharmaceutically acceptable salt thereof.

In another aspect, provided herein is a method of treating cancer in a patient in need thereof comprising administering to the patient a therapeutically effective amount of the compounds disclosed herein wherein the cancer is characterized by an interaction with a KRAS protein harboring a G12C mutation.

In another aspect, provided herein is a method for treating a disease or disorder associated with inhibition of KRAS interaction or a mutant thereof in a patient in need thereof comprising the step of administering to the patient a compound disclosed herein, or a pharmaceutically acceptable salt thereof, or a composition comprising a compound disclosed herein or a pharmaceutically acceptable salt thereof, in combination with another therapy or therapeutic agent as described herein.

In some embodiments, the compounds of the disclosure have selective inhibitory activity for KRAS over other RAS proteins. In some embodiments, the selectivity of the compounds of the disclosure for KRAS over other RAS proteins is 10-fold to 25-fold, or 25-fold to 50-fold.

As KRAS inhibitors, the compounds of the present disclosure are useful in the treatment of various diseases associated with abnormal expression or activity of KRAS. Compounds that inhibit KRAS will be useful in providing a means of preventing the growth or inducing apoptosis in tumors, particularly by inhibiting angiogenesis. It is therefore anticipated that compounds of the present disclosure will prove useful in treating or preventing proliferative disorders such as cancers. In particular, tumors with activating mutants of receptor tyrosine kinases or upregulation of receptor tyrosine kinases may be particularly sensitive to the inhibitors.

In certain embodiments, the disclosure provides a method for treating a KRAS-mediated disorder in a subject in need thereof, comprising the step of administering to said patient a compound according to the invention, or a pharmaceutically acceptable composition thereof.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET), myelodysplasia syndrome (MDS), T-cell acute lymphoblastic lymphoma (T-ALL), multiple myeloma, cutaneous T-cell lymphoma, adult T-cell leukemia, Waldenstrom's Macroglubulinemia, hairy cell lymphoma, marginal zone lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, lymphosarcoma, leiomyosarcoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, mesothelioma, pavicellular and non-pavicellular carcinoma, bronchial adenoma and pleuropulmonary blastoma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (exocrine pancreatic carcinoma, ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer, gall bladder cancer and anal cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) and urothelial carcinoma.

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors, neuro-ectodermal tumors), and spinal cord (neurofibroma, meningioma, glioma, sarcoma), neuroblastoma, Lhermitte-Duclos disease and pineal tumors.

Exemplary gynecological cancers include cancers of the breast (ductal carcinoma, lobular carcinoma, breast sarcoma, triple-negative breast cancer, HER2-positive breast cancer, inflammatory breast cancer, papillary carcinoma), uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers, tumors of the eye, tumors of the lips and mouth and squamous head and neck cancer.

The compounds of the present disclosure can also be useful in the inhibition of tumor metastases.

In addition to oncogenic neoplasms, the compounds of the invention are useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes. In some embodiments, the present disclosure provides a method for treating a patient suffering from a skeletal and chondrocyte disorder.

In some embodiments, compounds described herein can be used to treat Alzheimer's disease, HIV, or tuberculosis.

As used herein, the term "8p11 myeloproliferative syndrome" is meant to refer to myeloid/lymphoid neoplasms associated with eosinophilia and abnormalities of FGFR1.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the KRAS enzyme with a compound described herein includes the administration of a compound described herein to an individual or patient, such as a human, having KRAS, as well as, for example, introducing a compound described herein into a sample containing a cellular or purified preparation containing the KRAS protein.

As used herein, the term "individual," "subject," or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, Fla., 2009.

As used herein, the term "treating" or "treatment" refers to inhibiting a disease; for example, inhibiting a disease, condition, or disorder in an individual who is experiencing or displaying the pathology or symptomology of the disease, condition, or disorder (i.e., arresting further development of the pathology and/or symptomology) or ameliorating the disease; for example, ameliorating a disease, condition, or disorder in an individual who is experiencing or displaying the pathology or symptomology of the disease, condition, or disorder (i.e., reversing the pathology and/or symptomology) such as decreasing the severity of the disease.

The term "prevent," "preventing," or "prevention" as used herein, comprises the prevention of at least one symptom associated with or caused by the state, disease or disorder being prevented.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with compounds described herein for treatment of KRAS-associated diseases, disorders or conditions, or diseases or conditions as described herein. The agents can be combined with the present compounds in a single dosage form, or the agents can be administered simultaneously or sequentially as separate dosage forms.

Compounds described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-pRβ, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Ft2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the solid forms of the KRAS inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, compounds described herein can be used in combination with one or more inhibitors of the enzyme or protein receptors such as HPK1, SBLB, TUT4, A2A/A2B, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, compounds described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat. For treating cancer and other proliferative diseases, compounds described herein can be used in combination with targeted therapies, including JAK kinase inhibitors (Ruxolitinib, additional JAK1/2 and JAK1-selective, baricitinib or INCB39110), Pim kinase inhibitors (e.g., LGH447, INCB053914 and SGI-1776), PI3 kinase inhibitors including PI3K-delta selective and broad spectrum PI3K inhibitors (e.g., INCB50465 and INCB54707), PI3K-gamma inhibitors such as PI3K-gamma selective inhibitors, MEK inhibitors, CSF1R inhibitors (e.g., PLX3397 and LY3022855), TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as OTX015, CPI-0610, INCB54329 or INCB57643), LSD1 inhibitors (e.g., GSK2979552, INCB59872 and INCB60003), arginase inhibitors (e.g., INCB1158), indoleamine 2,3-dioxygenase inhibitors (e.g., epacadostat, NLG919 or BMS-986205), PARP inhibitors (e.g., olaparib or rucaparib), and inhibitors of BTK such as ibrutinib.

In addition, for treating cancer and other proliferative diseases, compounds described herein can be used in combination with targeted therapies such as, e.g., c-MET inhibitors (e.g., capmatinib), an anti-CD19 antibody (e.g., tafasitamab), an ALK2 inhibitor (e.g., INCB00928); or combinations thereof.

For treating cancer and other proliferative diseases, compounds described herein can be used in combination with chemotherapeutic agents, agonists or antagonists of nuclear receptors, or other anti-proliferative agents. Compounds described herein can also be used in combination with a medical therapy such as surgery or radiotherapy, e.g., gamma-radiation, neutron beam radiotherapy, electron beam radiotherapy, proton therapy, brachytherapy, and systemic radioactive isotopes.

Examples of suitable chemotherapeutic agents include any of: abarelix, abiraterone, afatinib, aflibercept, aldesleukin, alemtuzumab, alitretinoin, allopurinol, altretamine, amidox, amsacrine, anastrozole, aphidicolon, arsenic trioxide, asparaginase, axitinib, azacitidine, bevacizumab, bexarotene, baricitinib, bendamustine, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, didox, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lonafarnib, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, niraparib, nofetumomab, oserelin, oxaliplatin, paclitaxel, pamidronate, panitumumab, panobinostat, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, rucaparib, ruxolitinib, sorafenib, streptozocin, sunitinib, sunitinib maleate, tamoxifen, tegafur, temozolomide, teniposide, testolactone, tezacitabine, thalidomide, thioguanine, thiotepa, tipifarnib, topotecan, toremifene, tositumomab, trastuzumab, tretinoin, triapine, trimidox, triptorelin, uracil mustard, valrubicin, vandetanib, vinblastine, vincristine, vindesine, vinorelbine, vorinostat, veliparib, talazoparib, and zoledronate.

In some embodiments, compounds described herein can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is a small molecule PD-L1 inhibitor. In some embodiments, the small molecule PD-L1 inhibitor has an IC50 less than 1 µM, less than 100 nM, less than 10 nM or less than 1 nM in a PD-L1 assay described in US Patent Publication Nos. US 20170107216, US 20170145025, US 20170174671, US20170174679, US20170320875, US20170342060, US20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is MGA012 (retifanlimab), nivolumab, pembrolizumab (also known as MK-3475), pidilizumab, SHR-1210, PDR001, ipilumimab orAMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is nivolumab. In some embodiments, the anti-PD-1 monoclonal antibody is MGA012 (retifanlimab). In some embodiments, the anti-PD1 antibody is SHR-1210. Other anti-cancer agent(s) include antibody therapeutics such as 4-1BB (e.g. urelumab, utomilumab.

In some embodiments, the compounds of the disclosure can be used in combination with INCB086550.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MED11873.

In some embodiments, the inhibitor of an immune checkpoint molecule is an agonist of OX40, e.g., OX40 agonist antibody or OX40L fusion protein. In some embodiments, the anti-OX40 antibody is MED10562, MOXR-0916, PF-04518600, GSK3174998, or BMS-986178. In some embodiments, the OX40L fusion protein is MED16383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

In some embodiments, the compounds described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6-diamino-purine dioxolane); and Iodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with compounds described herein for the treatment of cancer include chemotherapeutic agents, targeted cancer therapies, immunotherapies or radiation therapy. Compounds described herein may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds described herein. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Ak. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with KRAS inhibitors. These include onartumzumab, tivantnib, and INC-280. Agents against Ab (or Bcr-Abl) include imatinib, dasatinib, nilotinib, and ponatinib and those against Alk (or EML4-ALK) include crizotinib.

Angiogenesis inhibitors may be efficacious in some tumors in combination with KRAS inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with KRAS inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds described herein. In some embodiments, the JAK inhibitor is selective for JAK over JAK2 and JAK3.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane@).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds described herein include steroids including 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

The compounds of the present disclosure can be used in combination with bone marrow transplant for the treatment of a variety of tumors of hematopoietic origin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

As provided throughout, the additional compounds, inhibitors, agents, etc. can be combined with the present compound in a single or continuous dosage form, or they can be administered simultaneously or sequentially as separate dosage forms.

Formulation, Dosage Forms and Administration

When employed as pharmaceuticals, the compounds of the present disclosure can be administered in the form of pharmaceutical compositions. Thus, the present disclosure provides a composition comprising a compound of Formula I, II, or any of the formulas as described herein, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208K4M (e.g., Methocel K4 M Premier™) and/or hydroxypropyl methylcellulose 2208K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 g/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods Another aspect of the present invention relates to labeled compounds of the disclosure (radio-labeled, fluorescent-labeled, etc.) that would be useful not only in imaging techniques but also in assays, both in vitro and in vivo, for localizing and quantitating KRAS protein in tissue samples, including human, and for identifying KRAS ligands by inhibition binding of a labeled compound. Substitution of one or more of the atoms of the compounds of the present disclosure can also be useful in generating differentiated ADME (Adsorption, Distribution, Metabolism and Excretion). Accordingly, the present invention includes KRAS binding assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula I or II can be optionally substituted with deuterium atoms, such as $-CD_3$ being substituted for $-CH_3$). In some embodiments, alkyl groups in Formula I or II can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radiolabeled compounds will depend on the specific application of that radio-labeled compound. For example, for in vitro adenosine receptor labeling and competition assays, compounds that incorporate $^{3}H$, $^{14}C$, $^{82}Br$, $^{125}I$, $^{131}I$ or $^{35}S$ can be useful. For radio-imaging applications $^{11}C$ $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments, the radionuclide is selected from $^{3}H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the invention can be used in a screening assay to identify and/or evaluate compounds. For example, a newly synthesized or identified compound (i.e., test compound) which is labeled can be evaluated for its ability to bind a KRAS protein by monitoring its concentration variation when contacting with the KRAS, through tracking of the labeling. For example, a test compound (labeled) can be evaluated for its ability to reduce binding of another compound which is known to bind to a KRAS protein (i.e., standard compound). Accordingly, the ability of a test compound to compete with the standard compound for binding to the KRAS protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, e.g., in the treatment or prevention of diseases or disorders associated with the activity of KRAS, such as cancer or infections, which include one or more containers containing a pharmaceutical composition comprising a therapeutically effective amount of a compound of Formula I, II, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of KRAS according to at least one assay described herein.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check.

The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 µm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 µm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute."

The following abbreviations may be used herein: AcOH (acetic acid); $Ac_2O$ (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N,N'-diisopropyl azidodicarboxylate); DIEA (N,N-diisopropylethylamine); DIPEA or DIEA (N, N-diisopropylethylamine); DIBAL (diisobutylaluminium hydride); DMF (N, N-dimethylformamide); Et (ethyl); EtOAc (ethyl acetate); FCC (flash column chromatography); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); IPA (isopropyl alcohol); J (coupling constant); LCMS (liquid chromatography-mass spectrometry); LDA (lithium diisopropylamide); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); mmol (millimole(s)); N (normal); NCS (N-chlorosuccinimide); nM (nanomolar); NMP (N-methylpyrrolidinone); NMR (nuclear magnetic resonance spectroscopy); OTf (trifluoromethanesulfonate); Ph (phenyl); pM (picomolar); RP-HPLC (reverse phase high performance liquid chromatography); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); µg (microgram(s)); µL (microliter(s)); µM (micromolar); wt % (weight percent). Brine is saturated aqueous sodium chloride. In vacuo is under vacuum.

Example 1. 1-Acryloyl-9'-chloro-7'-fluoro-8'-(2-fluoro-6-hydroxyphenyl)-1',4'-dihydro-3'H-spiro[piperidine-4,2'-pyrazino[2,3-c]quinolin]-3'-one

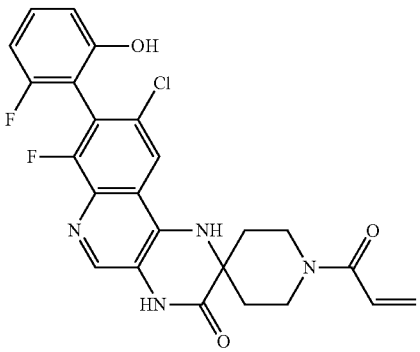 [SMILES: C=CC(=O)N1CCC2(CC1)Nc1c(cnc3c(F)c(-c4c(O)cccc4F)c(Cl)cc13)NC2=O]

Step 1. 3-Bromo-4-chloro-2-fluoroaniline

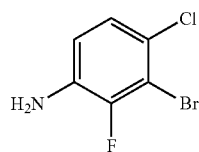

To a solution of 3-bromo-2-fluoroaniline (46.8 g, 246 mmol) in DMF (246 ml) was added NCS (34.5 g, 259 mmol) portionwise, and the resultant mixture stirred at room temperature overnight. The mixture was poured onto ice-water (400 mL) and extracted with ethyl acetate. The organic layer was washed with water (2×), brine, dried over $Na_2SO_4$, filtered and concentrated. The crude was purified with silica gel column (0-30% ethyl acetate in hexanes) to give the desired product as brown oil which solidified on standing (38 g, 69%). LC-MS calculated for $C_6H_5BrClFN$ $(M+H)^+$: m/z=223.9, 225.9; found 223.9, 225.9.

Step 2. 7-Bromo-6-chloro-8-fluoroquinolin-4(IH)-one

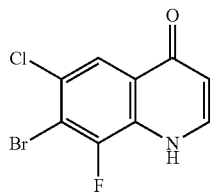 [SMILES: O=c1cc[nH]c2c(F)c(Br)c(Cl)cc12]

The mixture of 3-bromo-4-chloro-2-fluoroaniline (1.3 g, 5.79 mmol), 5-(methoxymethylene)-2,2-dimethyl-1,3-dioxane-4,6-dione (1.186 g, 6.37 mmol) and 2-propanol (12 ml) was heated at 90° C. for 2 h. The mixture was cooled to room temperature, and the solid formed in the mixture was collected by filtration, and washed with IPA (20 mL) and diethyl ether (20 mL) to give a colorless solid. The solid and DOWTHERM (25 mL) was heated at 220° C.-vigorous evolution of gas. The orange solution was stirred at 220° C. for 40 min then cooled to room temperature. To the mixture was added heptane (25 mL), and the mixture was filtered, with the solid collected, washed with heptane and ethyl ether and dried under vacuum to give the desired product as a tan solid (2.1 g, 96%). LC-MS calculated for $C_9H_5BrClFNO$ $(M+H)^+$: m/z=275.9, 277.9; found 275.9, 277.9.

Step 3. 7-Bromo-6-chloro-8-fluoro-3-nitroquinolin-4(1H)-one

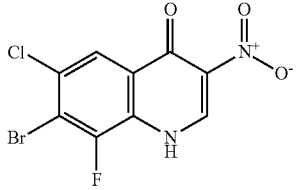

7-Bromo-6-chloro-8-fluoroquinolin-4(1H)-one (804 mg, 2.91 mmol) was added to stirred propionic acid (7.86 ml) and the mixture was heated at 125° C. with stirring. Nitric acid (260 µl, 5.82 mmol) was added dropwise, and the solution was stirred for 2 hours at 125° C. before being allowed to cool to room temperature. Water was added, and the mixture was filtered. The solid collected was washed with water and diethyl ether then dried to give the desired product as a pale solid (0.57 g, 61%). LC-MS calculated for $CH_4BrClFN_2O_3$ $(M+H)^+$: m/z=320.9, 322.9; found 320.9, 322.8.

Step 4. 7-Bromo-4,6-dichloro-8-fluoro-3-nitroquinoline

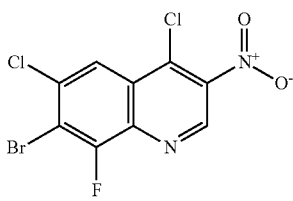 [SMILES: O=[N+]([O-])c1cnc2c(F)c(Br)c(Cl)cc2c1Cl]

$POCl_3$ (0.893 ml, 9.58 mmol) was added to 7-bromo-6-chloro-8-fluoro-3-nitroquinolin-4-ol (0.77 g, 2.395 mmol) in toluene (14 ml) at room temperature. The mixture was heated at 110° C. with stirring, at which point DMF (0.1 mL) was added and the mixture was stirred at 110° C. overnight. The solvents were removed by evaporation. Toluene (15 mL) was added and the solvents evaporated. The residue was taken up in DCM (100 mL) and poured into ice-cold sat $NaHCO_3$ (150 mL). The mixture was extracted with DCM (3×). The combined organic layers were washed with brine, dried and evaporated to give the desired product as light brown solid (0.80 g, 98%). LC-MS calculated for $C_9H_3BrCl_2FN_2O_2$ $(M+H)^+$: m/z=338.9, 340.9; found 338.9, 340.9.

Step 5. 1-(tert-Butyl)-4-methyl 4-((7-bromo-6-chloro-8-fluoro-3-nitroquinolin-4-yl)amino)-piperidine-1,4-dicarboxylate

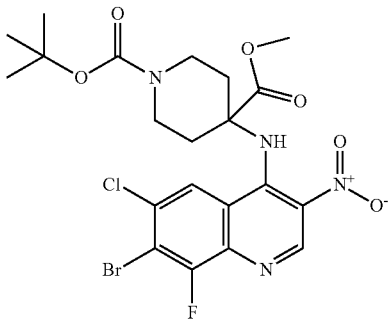 [SMILES: COC(=O)C1(Nc2c([N+](=O)[O-])cnc3c(F)c(Br)c(Cl)cc23)CCN(C(=O)OC(C)(C)C)CC1]

To a solution of 7-bromo-4,6-dichloro-8-fluoro-3-nitroquinoline (330 mg, 0.971 mmol), 1-(tert-butyl) 4-methyl 4-aminopiperidine-1,4-dicarboxylate (301 mg, 1.165 mmol) in DMF (3.24 ml) was added DIEA (424 µl, 2.427 mmol). The mixture was stirred at 40° C. for 2 hours. The reaction mixture was diluted with ethyl acetate and water. The organic layer was separated and concentrated. The residue was purified with silica gel column to give the desired product (0.32 g, 59%). LC-MS calculated for $C_{21}H_{24}BrClFN_4O_6$ (M+H)$^+$: m/z=561.1, 563.1; found 561.1, 563.1.

Step 6. tert-Butyl 8'-bromo-9'-chloro-7'-fluoro-3'-oxo-3',4'-dihydro-1'H-spiro[piperidine-4,2'-pyrazino[2,3-c]quinoline]-1-carboxylate

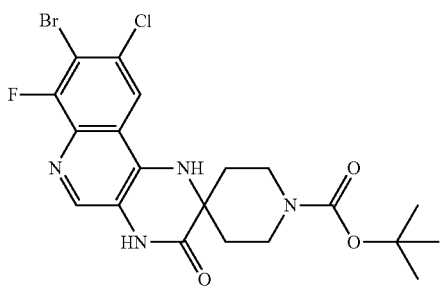 [SMILES: CC(C)(C)OC(=O)N1CCC2(CC1)Nc1c(cnc3c(F)c(Br)c(Cl)cc13)NC2=O]

To a solution of 1-(tert-butyl) 4-methyl 4-((7-bromo-6-chloro-8-fluoro-3-nitroquinolin-4-yl)amino)piperidine-1,4-dicarboxylate (320 mg, 0.570 mmol) in acetic acid (2.0 ml) was added iron (159 mg, 2.85 mmol). The resulting mixture was stirred at 80° C. for 1 h. The mixture was filtered through a pad of Celite and washed with methanol. The filtrate was concentrated and purified with silica gel column (0.19 g, 68%). LC-MS calculated for $C_{20}H_{22}BrClFN_4O_3$ (M+H)$^+$: m/z=499.1, 501.1; found 499.1, 501.1.

Step 7. 1-Acryloyl-8'-bromo-9'-chloro-7'-fluoro-1'4'-dihydro-3'H-spiro[piperidine-4,2'-pyrazino[2,3-c]quinolin]-3'-one

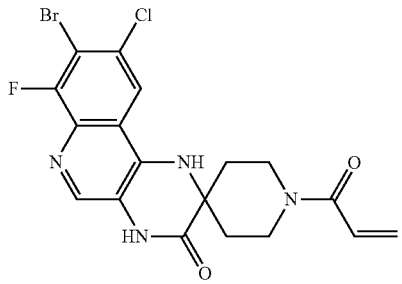 [SMILES: C=CC(=O)N1CCC2(CC1)Nc1c(cnc3c(F)c(Br)c(Cl)cc13)NC2=O]

To a reaction mixture of tert-butyl 8'-bromo-9'-chloro-7'-fluoro-3'-oxo-3',4'-dihydro-1'H-spiro[piperidine-4,2'-pyrazino[2,3-c]quinoline]-1-carboxylate (194 mg, 0.388 mmol) and DCM (1.0 mL) was added TFA (1.2 mL, 15.53 mmol). After stirring for 1 hour at room temperature, the volatiles were removed under reduced pressure. The residue was dissolved in DCM (1.0 mL) and 1.0 M acryloyl chloride in DCM (466 µl, 0.466 mmol) was added, followed by DIEA (339 µl, 1.941 mmol) at 0° C. After stirring at same temperature for 0.5 h, the reaction mixture was diluted with ethyl acetate and water. The aqueous layer was extracted with ethyl acetate once. The combined organic layers were washed with brine, dried over $Na_2SO_4$, filtered and concentrated. The crude was purified with flash chromatography to yield the desired product (125 mg, 71%). LC-MS calculated for $C_{18}H_{16}BrClFN_4O_2$ (M+H)$^+$: m/z=453.0, 455.0; found 453.0, 455.0.

Step 8. 1-Acryloyl-9'-chloro-7'-fluoro-8'-(2-fluoro-6-hydroxyphenyl)-1',4'-dihydro-3'H-spiro[piperidine-4,2'-pyrazino[2,3-c]quinolin]-3'-one A mixture of 1-acryloyl-8'-bromo-9'-chloro-7'-fluoro-1',4'-dihydro-3'H-spiro[piperidine-4,2'-pyrazino[2,3-c]quinolin]-3'-one (12 mg, 0.026 mmol), (2-fluoro-6-hydroxyphenyl)boronic acid (9.07 mg, 0.058 mmol), tetrakis (3.06 mg, 2.64 µmol) and tripotassium phosphate hydrate (13.40 mg, 0.058 mmol) in 1,4-Dioxane (1.0 mL)/Water (0.200 mL) was stirred at 80° C. for 2 h. The residue was dissolved in methanol and 1 N HCl and purified with prep-LCMS (pH 2, acetonitrile/water+TFA) to give the product as a pair of atropisomers as TFA salt. LC-MS calculated for $C_{24}H_{20}ClF_2N_4O_3$ (M+H)$^+$: m/z=485.2; found 485.2.

Example 2. 1-Acryloyl-9'-chloro-8'-(2-chloro-5-hydroxyphenyl)-7'-fluoro-1',4'-dihydro-3'H-spiro[piperidine-4,2'-pyrazino[2,3-c]quinolin]-3'-one

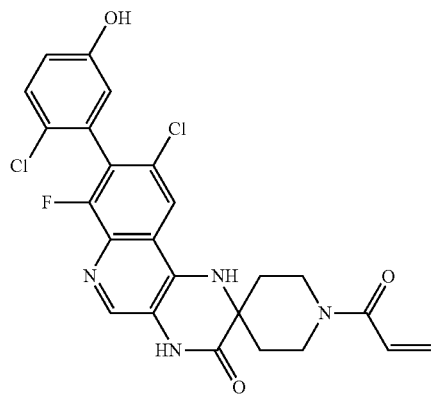 [SMILES: C=CC(=O)N1CCC2(CC1)Nc1c(cnc3c(F)c(-c4cc(O)ccc4Cl)c(Cl)cc13)NC2=O]

This compound was prepared using similar procedures as described for Example 1, with (2-chloro-5-hydroxyphenyl) boronic acid replacing (2-fluoro-6-hydroxyphenyl)boronic acid in Step 8. The reaction mixture was purified by prep-HPLC (pH=2, acetonitrile/water+TFA) to give the desired product as TFA salt. LC-MS calculated for $C_{24}H_{20}Cl_2FN_4O_3$ (M+H)$^+$: m/z=501.1; found 501.1.

Example 3. 1-Acryloyl-9'-chloro-7'-fluoro-8'-(3-methyl-1H-indazol-4-yl)-1',4'-dihydro-3'H-spiro [piperidine-4,2'-pyrazino[2,3-c]quinolin]-3'-one

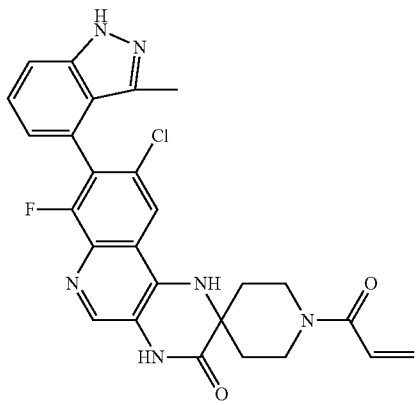 [SMILES: C=CC(=O)N1CCC2(CC1)Nc1c(cnc3c(F)c(-c4cccc5[nH]nc(C)c45)c(Cl)cc13)NC2=O]

This compound was prepared using similar procedures as described for Example 1, with (3-methyl-1H-indazol-4-yl) boronic acid replacing (2-fluoro-6-hydroxyphenyl)boronic acid in Step 8. The reaction mixture was purified by prep-HPLC (pH=2, acetonitrile/water+TFA) to give the desired product as a pair of atropisomers as TFA salt. LC-MS calculated for $C_{26}H_{23}ClFN_6O_2$ (M+H)$^+$: m/z=505.2; found 505.2.

Example 4. 1-Acryloyl-9'-chloro-7'-fluoro-8'-(5-methyl-1H-indazol-4-yl)-1',4'-dihydro-3'H-spiro [piperidine-4,2'-pyrazino[2,3-c]quinolin]-3'-one

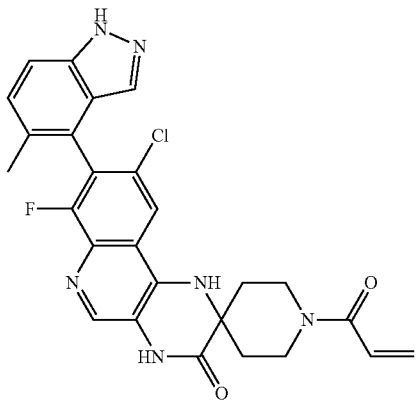 [SMILES: C=CC(=O)N1CCC2(CC1)Nc1c(cnc3c(F)c(-c4c(C)ccc5[nH]ncc45)c(Cl)cc13)NC2=O]

This compound was prepared using similar procedures as described for Example 1, with 5-methyl-4-(4,4,5,5-tetramethyl-1,3,2-dioxaborolan-2-yl)-1H-indazole replacing (2-fluoro-6-hydroxyphenyl)boronic acid in Step 8. The reaction mixture was purified by prep-HPLC (pH=2, acetonitrile/water+TFA) to give the desired product as a pair of atropisomers as TFA salt. LC-MS calculated for $C_{26}H_{23}ClFN_6O_2$ (M+H)$^+$: m/z=505.2; found 505.2.

Example 5. 1-Acryloyl-9'-chloro-7'-fluoro-8'-(2-fluoro-6-methoxyphenyl)-1',4'-dihydro-3'H-spiro [piperidine-4,2'-pyrazino[2,3-c]quinolin]-3'-one

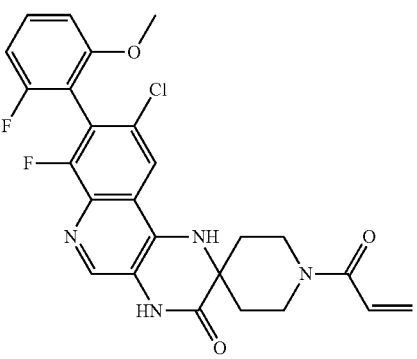 [SMILES: C=CC(=O)N1CCC2(CC1)Nc1c(cnc3c(F)c(-c4c(F)cccc4OC)c(Cl)cc13)NC2=O]

This compound was prepared using similar procedures as described for Example 1, with (2-fluoro-6-methoxyphenyl) boronic acid replacing (2-fluoro-6-hydroxyphenyl)boronic acid in Step 8. The reaction mixture was purified by prep-HPLC (pH=2, acetonitrile/water+TFA) to give the desired product as a pair of atropisomers as TFA salt. LC-MS calculated for $C_{25}H_{22}ClF_2N_4O_3$ (M+H)$^+$: m/z=499.1; found 499.1.

Example 6. 1-Acryloyl-9'-chloro-7'-fluoro-8'-(2-fluoro-6-hydroxyphenyl)-1',4'-dihydro-3'H-spiro [azetidine-3,2'-pyrazino[2,3-c]quinolin]-3'-one

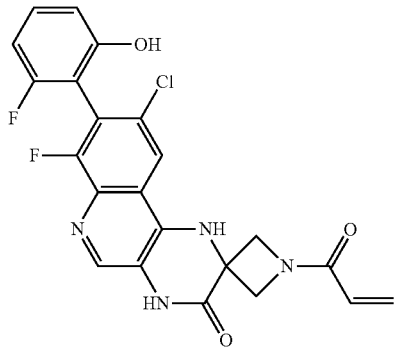 [SMILES: C=CC(=O)N1CC2(C1)Nc1c(cnc3c(F)c(-c4c(O)cccc4F)c(Cl)cc13)NC2=O]

Step 1. 1-(tert-Butyl) 3-ethyl 3-((7-bromo-6-chloro-8-fluoro-3-nitroquinolin-4-yl)amino)azetidine-1,3-dicarboxylate

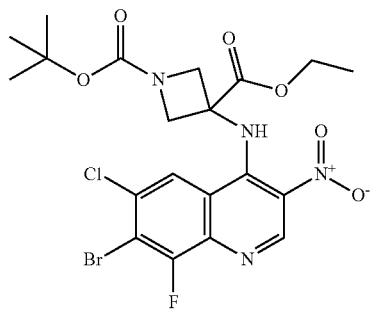 [SMILES: CCOC(=O)C1(Nc2c([N+](=O)[O-])cnc3c(F)c(Br)c(Cl)cc23)CN(C(=O)OC(C)(C)C)C1]

This compound was prepared using similar procedures as described for Example 1, with 1-(tert-butyl) 3-ethyl 3-aminoazetidine-1,3-dicarboxylate replacing 1-(tert-butyl) 4-methyl 4-aminopiperidine-1,4-dicarboxylate in Step 5. LC-MS calculated for $C_2H_{22}BrClFN_4O_6$ (M+H)$^+$: m/z=547.0, 549.0; found 547.0, 549.0.

Step 2. tert-Butyl 8'-bromo-9'-chloro-7'-fluoro-3'-oxo-3',4'-dihydro-1'H-spiro[azetidine-3,2'-pyrazino[2,3-c]quinoline]-1-carboxylate

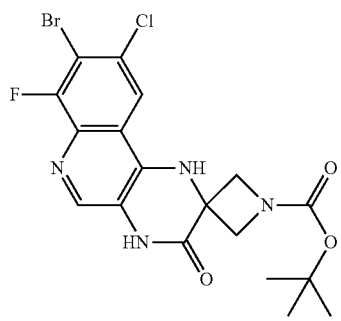 [SMILES: CC(C)(C)OC(=O)N1CC2(C1)Nc1c(cnc3c(F)c(Br)c(Cl)cc13)NC2=O]

This compound was prepared using similar procedures as described for Example 1, with tert-butyl 8'-bromo-9'-chloro-7'-fluoro-3'-oxo-3',4'-dihydro-1'H-spiro[azetidine-3,2'-pyrazino[2,3-c]quinoline]-1-carboxylate replacing tert-butyl 8'-bromo-9'-chloro-7'-fluoro-3'-oxo-3',4'-dihydro-1'H-spiro[piperidine-4,2'-pyrazino[2,3-c]quinoline]-1-carboxylate in Step 6. LC-MS calculated for $C_{18}H_{18}BrClFN_4O_3$ (M+H)$^+$: m/z=471.0, 473.0; found 471.0, 473.0.

Step 3. 1-Acryloyl-8'-bromo-9'-chloro-7'-fluoro-1'4'-dihydro-3'H-spiro[azetidine-3,2'-pyrazino[2,3-c]quinolin]-3'-one

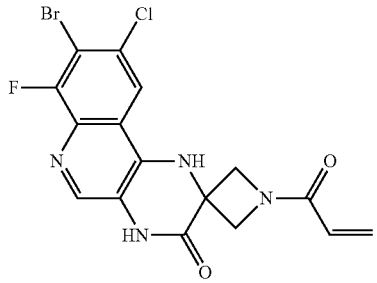 [SMILES: C=CC(=O)N1CC2(C1)Nc1c(cnc3c(F)c(Br)c(Cl)cc13)NC2=O]

This compound was prepared using similar procedures as described for Example 1, with tert-butyl 8'-bromo-9'-chloro-7'-fluoro-3'-oxo-3',4'-dihydro-1'H-spiro[azetidine-3,2'-pyrazino[2,3-c]quinoline]-1-carboxylate replacing tert-butyl 8'-bromo-9'-chloro-7'-fluoro-3'-oxo-3',4'-dihydro-1'H-spiro[piperidine-4,2'-pyrazino[2,3-c]quinoline]-1-carboxylate in Step 6. LC-MS calculated for $C_{16}H_{12}BrClFN_4O_2$ (M+H)$^+$: m/z=425.0, 427.0; found 425.0, 427.0.

Step 4. 1-Acryloyl-9'-chloro-7'-fluoro-8'-(2-fluoro-6-hydroxyphenyl)-1',4'-dihydro-3'H-spiro[azetidine-3,2'-pyrazino[2,3-c]quinolin]-3'-one A microwave vial charged with 1-acryloyl-8'-bromo-9'-chloro-7'-fluoro-1',4'-dihydro-3'H-spiro[azetidine-3,2'-pyrazino[2,3-c]quinolin]-3'-one (20 mg, 0.047 mmol), (2-fluoro-6-hydroxyphenyl)boronic acid (16.12 mg, 0.103 mmol), tetrakis (5.43 mg, 4.70 µmol) and potassium carbonate (19.48 mg, 0.141 mmol) in 1,4-dioxane (1.0 mL) and water (0.200 mL) was sealed with Teflon cap. The vial was evacuated under high vacuum and refilled with nitrogen (repeated three times). The reaction mixture was stirred at 80° C. for 2 h. The reaction solution was diluted with methanol and 1 N HCl and purified by prep-HPLC (pH=2, acetonitrile/water+TFA) to give the product as a pair of atropisomers as TFA salt. LC-MS calculated for $C_{22}H_{16}ClF_2N_4O_3$ (M+H)$^+$: m/z=457.1; found 457.2.

Example 7. 1-Acryloyl-9'-chloro-7'-fluoro-8'-(5-methyl-1H-indazol-4-yl)-1',4'-dihydro-3'H-spiro[azetidine-3,2'-pyrazino[2,3-c]quinolin]-3'-one

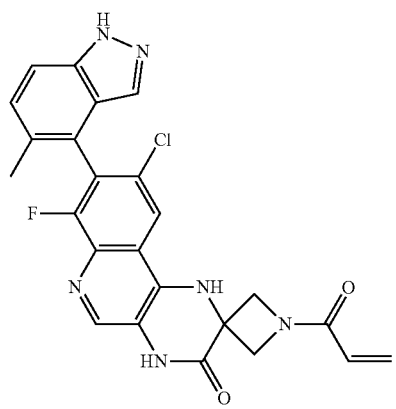 [SMILES: C=CC(=O)N1CC2(C1)Nc1c(cnc3c(F)c(-c4c(C)ccc5[nH]ncc45)c(Cl)cc13)NC2=O]

This compound was prepared using similar procedures as described for Example 6, with 5-methyl-4-(4,4,5,5-tetramethyl-1,3,2-dioxaborolan-2-yl)-1H-indazole replacing (2-fluoro-6-hydroxyphenyl)boronic acid in Step 4. The reaction mixture was purified by prep-HPLC (pH=2, acetonitrile/water+TFA) to give the desired product as a pair of atropisomers as TFA salt. LC-MS calculated for $C_{24}H_{19}ClFN_6O_2$ (M+H)$^+$: m/z=477.1; found 477.1.

Example 8. 1'-Acryloyl-9-chloro-7-fluoro-8-(2-fluoro-6-hydroxyphenyl)-1,4-dihydro-3H-spiro[pyrazino[2,3-c]quinoline-2,3'-pyrrolidin]-3-one

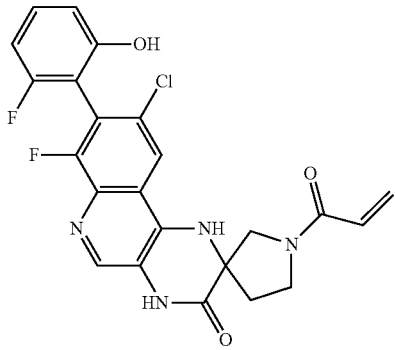 [SMILES: C=CC(=O)N1CCC2(C1)Nc1c(cnc3c(F)c(-c4c(O)cccc4F)c(Cl)cc13)NC2=O]

Step 1. 1-(tert-Butyl) 3-methyl 3-((7-bromo-6-chloro-8-fluoro-3-nitroquinolin-4-yl)amino)-pyrrolidine-1,3-dicarboxylate

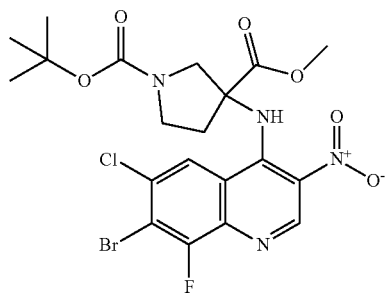 [SMILES: COC(=O)C1(Nc2c([N+](=O)[O-])cnc3c(F)c(Br)c(Cl)cc23)CCN(C(=O)OC(C)(C)C)C1]

This compound was prepared using similar procedures as described for Example 1, with 1-(tert-butyl) 3-methyl 3-aminopyrrolidine-1,3-dicarboxylate replacing 1-(tert-butyl) 4-methyl 4-aminopiperidine-1,4-dicarboxylate in Step 5. LC-MS calculated for $C_{20}H_{22}BrClFN_4O_6$ (M+H)$^+$: m/z=547.0, 549.0; found 547.0, 549.0.

Step 2. tert-Butyl 8-bromo-9-chloro-7-fluoro-3-oxo-3,4-dihydro-1H-spiro[pyrazino[2,3-c]quinoline-2,3'-pyrrolidine]-1'-carboxylate

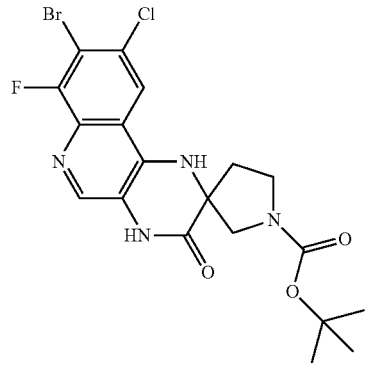 [SMILES: CC(C)(C)OC(=O)N1CCC2(C1)Nc1c(cnc3c(F)c(Br)c(Cl)cc13)NC2=O]

This compound was prepared using similar procedures as described for Example 1, with 1-(tert-butyl) 3-methyl 3-((7-bromo-6-chloro-8-fluoro-3-nitroquinolin-4-yl)amino)pyrrolidine-1,3-dicarboxylate replacing tert-butyl 8'-bromo-9'-chloro-7'-fluoro-3'-oxo-3',4'-dihydro-1'H-spiro[piperidine-4,2'-pyrazino[2,3-c]quinoline]-1-carboxylate in Step 6. LC-MS calculated for $C_{19}H_{20}BrClFN_4O_3$ (M+H)$^+$: m/z=485.0, 487.0; found 485.0, 487.0.

Step 3. 1'-Acryloyl-8-bromo-9-chloro-7-fluoro-1,4-dihydro-3H-spiro[pyrazino[2,3-c]quinoline-2,3'-pyrrolidin]-3-one

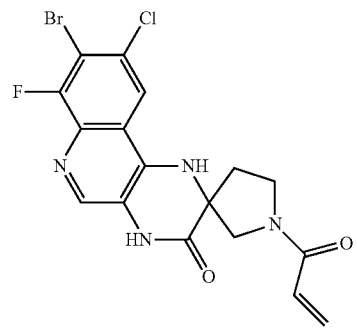 [SMILES: C=CC(=O)N1CCC2(C1)Nc1c(cnc3c(F)c(Br)c(Cl)cc13)NC2=O]

This compound was prepared using similar procedures as described for Example 1, with tert-butyl 8-bromo-9-chloro-7-fluoro-3-oxo-3,4-dihydro-1H-spiro[pyrazino[2,3-c]quinoline-2,3'-pyrrolidine]-1'-carboxylate replacing tert-butyl 8'-bromo-9'-chloro-7'-fluoro-3'-oxo-3',4'-dihydro-1'H-spiro[piperidine-4,2'-pyrazino[2,3-c]quinoline]-1-carboxylate in Step 7. LC-MS calculated for $C_{17}H_{14}BrClFN_4O_2$ (M+H)$^+$: m/z=439.0, 441.0; found 439.0, 441.0.

Step 4. 1'-Acryloyl-9-chloro-7-fluoro-8-(2-fluoro-6-hydroxyphenyl)-1,4-dihydro-3H-spiro[pyrazino[2,3-c]quinoline-2,3'-pyrrolidin]-3-one A microwave vial charged with 1'-acryloyl-8-bromo-9-chloro-7-fluoro-1,4-dihydro-3H-spiro[pyrazino[2,3-c]quinoline-2,3'-pyrrolidin]-3-one (24 mg, 0.055 mmol), (2-fluoro-6-hydroxyphenyl)boronic acid (18.72 mg, 0.120 mmol), tetrakis (6.31 mg, 5.46 µmol) and potassium carbonate (22.63 mg, 0.164 mmol) in 1,4-dioxane (1.0 mL) and water (0.200 mL) was sealed with Teflon cap. The vial was evacuated under high vacuum and refilled with nitrogen (repeated three times). The reaction mixture was stirred at 80° C. for 2 h. The reaction solution was diluted with methanol and 1 N HCl and purified by prep-HPLC (pH=2, acetonitrile/water+TFA) to give the product as a mixture of diastereomers as TFA salt. LC-MS calculated for $C_{23}H_{18}ClF_2N_4O_3$ (M+H)$^+$: m/z=471.1; found 471.2.

Example 9. 1'-Acryloyl-9-chloro-7-fluoro-8-(5-methyl-1H-indazol-4-yl)-1,4-dihydro-3H-spiro[pyrazino[2,3-c]quinoline-2,3'-pyrrolidin]-3-one

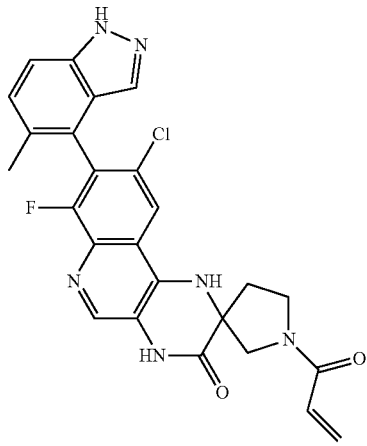 [SMILES: C=CC(=O)N1CCC2(C1)Nc1c(cnc3c(F)c(-c4c(C)ccc5[nH]ncc45)c(Cl)cc13)NC2=O]

This compound was prepared using similar procedures as described for Example 8, with 5-methyl-4-(4,4,5,5-tetramethyl-1,3,2-dioxaborolan-2-yl)-1H-indazole replacing (2-fluoro-6-hydroxyphenyl)boronic acid in Step 4. The reaction mixture was purified by prep-HPLC (pH=2, acetonitrile/water+TFA) to give the desired product as a mixture of diastereomers as TFA salt. LC-MS calculated for $C_{25}H_{21}ClFN_6O_2$ (M+H)$^+$: m/z=491.1; found 491.1.

Example 10. 1-Acryloyl-9'-chloro-7'-fluoro-8'-(2-fluoro-6-hydroxyphenyl)-5'-(((S)-1-methylpyrrolidin-2-yl)methoxy)-1',4'-dihydro-3'H-spiro[piperidine-4,2'-pyrazino[2,3-c]quinolin]-3'-one

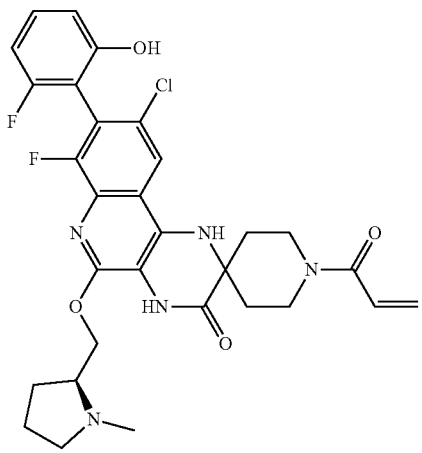 [SMILES: C=CC(=O)N1CCC2(CC1)Nc1c(c(OC[C@@H]3CCCN3C)nc3c(F)c(-c4c(O)cccc4F)c(Cl)cc13)NC2=O]

Step 1. 2-Amino-4-bromo-5-chloro-3-fluorobenzoic acid

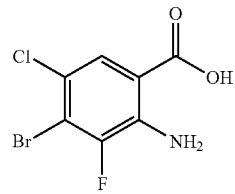 [SMILES: Nc1c(C(=O)O)cc(Cl)c(Br)c1F]

To a solution of 2-amino-4-bromo-3-fluorobenzoic acid (10.02 g, 42.8 mmol) in DMF (143 ml) was added NCS (6.29 g, 47.1 mmol) at room temperature. The mixture was heated at 70° C. for 2 h. The reaction mixture was cooled to room temperature, and diluted with water. The precipitate was collected with filtration and washed with water and ethyl acetate/hexane (1:2). The filtrate was acidified with 1 N HCl and extracted with ethyl acetate. The organic layer was concentrated. The solid was collected with filtration and washed ethyl acetate/hexane (1:2) (10.6 g, 92%). LC-MS calculated for $C_7HBrClFNO_2$ (M+H)$^+$: m/z=267.9, 269.9; found 267.9, 269.9.

Step 2. 7-Bromo-6-chloro-8-fluoro-2H-benzo[d][1,3]oxazine-2,4(1H)-dione

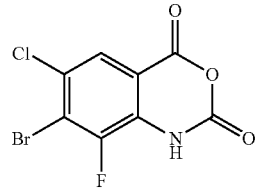 [SMILES: O=c1[nH]c2c(F)c(Br)c(Cl)cc2c(=O)o1]

To a solution of 2-amino-4-bromo-5-chloro-3-fluorobenzoic acid (9.10 g, 33.9 mmol) in THF (113 ml) was added triphosgene (3.42 g, 11.52 mmol). The resulting solution was stirred at room temperature overnight. LCMS showed completion of reaction. The most solvent was removed under reduced pressure. The reaction solution was diluted with hexanes. The resulting precipitate was collected via filtration and dried under vacuum (9.1 g, 91%). LC-MS calculated for $C_8H_3BrClFNO_3$ (M+H)$^+$: m/z=293.9, 295.9; found 294.0, 296.0.

Step 3. 7-Bromo-6-chloro-8-fluoro-4-hydroxy-3-nitroquinolin-2(1H)-one

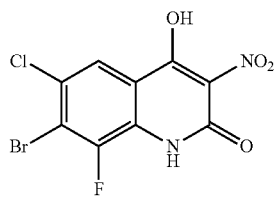 [SMILES: O=c1[nH]c2c(F)c(Br)c(Cl)cc2c(O)c1[N+](=O)[O-]]

To a solution of 7-bromo-6-chloro-8-fluoro-2H-benzo[d][1,3]oxazine-2,4(1H)-dione (9.0 g, 30.6 mmol) in DMF (153 ml) was added ethyl 2-nitroacetate (6.79 ml, 61.1 mmol) and DIEA (10.68 ml, 61.1 mmol). The resulting mixture was stirred at 95° C. for 4 h. LCMS showed the desired product and compound A was hydrolyzed back to acid. The reaction mixture was cooled to rt and diluted with ethyl acetate and water. The compound C was in aqueous layer. The aqueous layer was concentrated and resulting precipitate was collected via filtration and washed with ethyl acetate/hexanes (1:1) (4.6 g, 45%). LC-MS calculated for $C_9H_4BrClFN_2O_4$ (M+H)$^+$: m/z=336.9, 338.9; found 336.9, 338.9.

Step 4.
7-Bromo-2,4,6-trichloro-8-fluoro-3-nitroquinoline

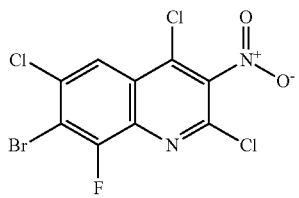 [SMILES: O=[N+]([O-])c1c(Cl)nc2c(F)c(Br)c(Cl)cc2c1Cl]

DIEA (0.558 ml, 3.19 mmol) was added to 7-bromo-6-chloro-8-fluoro-3-nitroquinoline-2,4-diol (0.539 g, 1.597 mmol) in toluene (9.2 ml) at room temperature. The mixture was cooled to 0° C., and POCl$_3$ (0.744 ml, 7.99 mmol) was added. The mixture was heated at 110° C. with stirring for 1 h. The solvents were removed by evaporation. Toluene (15 mL) was added and the solvents evaporated. The residue was taken up in DCM (100 mL) and poured into ice-cold sat NaHCO$_3$(150 mL). The mixture was extracted with DCM once. The combined organic layers were washed with brine, dried and evaporated. The crude purified with silica gel column to give the title compound.

Step 5. 1-(tert-Butyl) 4-methyl 4-((7-bromo-2,6-dichloro-8-fluoro-3-nitroquinolin-4-yl)amino)piperidine-1,4-dicarboxylate

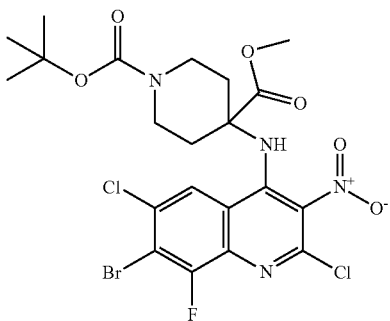 [SMILES: COC(=O)C1(Nc2c([N+](=O)[O-])c(Cl)nc3c(F)c(Br)c(Cl)cc23)CCN(C(=O)OC(C)(C)C)CC1]

To a solution of 7-bromo-2,4,6-trichloro-8-fluoro-3-nitroquinoline (1.74 g, 4.65 mmol), 1-(tert-butyl) 4-methyl 4-aminopiperidine-1,4-dicarboxylate (1.801 g, 6.97 mmol) in DMF (15 ml) was added DIEA (2.03 ml, 11.62 mmol). The mixture was stirred at 50° C. overnight. The reaction mixture was diluted with ethyl acetate and water. The organic layer was separated and concentrated. The residue was purified with silica gel column to give the desired product (1.2 g, 43%). LC-MS calculated for $C_{21}H_{23}BrCl_2FN_4O_6$ (M+H)$^+$: m/z=595.1, 597.1; found 595.1, 597.1.

Step 6. 1-(tert-Butyl) 4-methyl (S)-4-((7-bromo-6-chloro-8-fluoro-2-((1-methylpyrrolidin-2-yl)methoxy)-3-nitroquinolin-4-yl)amino)piperidine-1,4-dicarboxylate

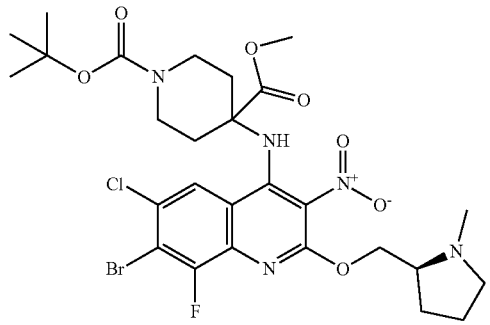 [SMILES: COC(=O)C1(Nc2c([N+](=O)[O-])c(OC[C@@H]3CCCN3C)nc3c(F)c(Br)c(Cl)cc23)CCN(C(=O)OC(C)(C)C)CC1]

To a solution of (S)-(1-methylpyrrolidin-2-yl)methanol (46.4 mg, 0.403 mmol) in THF (2 ml) was added 60% sodium hydride (20.1 mg, 0.503 mmol). The mixture was stirred at 0° C. for 0.5 h, 1-(tert-butyl) 4-methyl 4-((7-bromo-2,6-dichloro-8-fluoro-3-nitroquinolin-4-yl)amino)piperidine-1,4-dicarboxylate (120 mg, 0.201 mmol) was added to reaction vial and mixture was stirred for 1 h at rt. The reaction mixture was diluted with ethyl acetate and water. The organic layer was separated and concentrated. The crude was used in the next step without further purification. LC-MS calculated for $C_{27}H_{35}BrClFN_5O_7$ (M+H)$^+$: m/z=674.1, 676.1; found 674.1, 676.1.

Step 7. tert-Butyl (S)-8'-bromo-9'-chloro-7'-fluoro-5'-((1-methylpyrrolidin-2-yl)methoxy)-3'-oxo-3',4'-dihydro-1'H-spiro[piperidine-4,2'-pyrazino[2,3-c]quinoline]-1-carboxylate

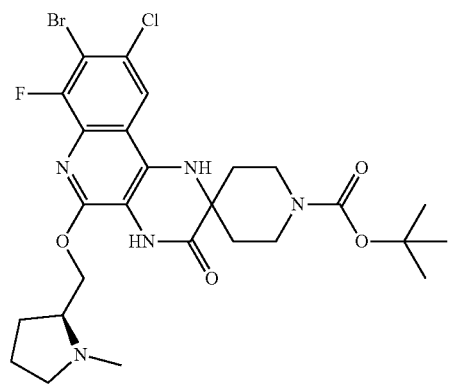 [SMILES: CN1CCC[C@H]1COc1nc2c(F)c(Br)c(Cl)cc2c2c1NC(=O)C1(CCN(C(=O)OC(C)(C)C)CC1)N2]

To a solution of 1-(tert-butyl) 4-methyl (S)-4-((7-bromo-6-chloro-8-fluoro-2-((1-methylpyrrolidin-2-yl)methoxy)-3-nitroquinolin-4-yl)amino)piperidine-1,4-dicarboxylate (136 mg, 0.201 mmol) in acetic acid (2.0 ml) was added iron (56.3 mg, 1.007 mmol). The resulting mixture was stirred at 80° C. for 1 h, the mixture was filtered through a pad of Celite and washed with methanol. The filtrate was concentrated and purified with silica gel column to yield the desired product (124 mg, 100%). LC-MS calculated for $C_{26}H_{33}BrClFNO_4$ (M+H)$^+$: m/z=612.1, 614.1; found 612.1, 614.1.

115

Step 8. (S)-1-Acryloyl-8'-bromo-9'-chloro-7'-fluoro-5'-((1-methylpyrrolidin-2-yl)methoxy)-1',4'-dihydro-3'H-spiro[piperidine-4,2'-pyrazino[2,3-c]quinolin]-3'-one

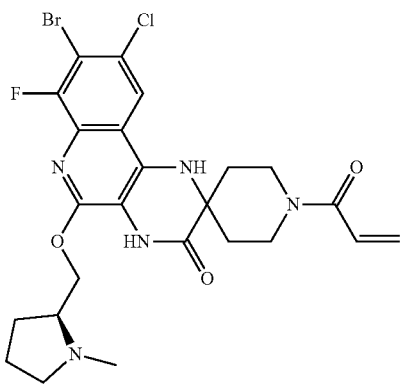 [SMILES: C=CC(=O)N1CCC2(CC1)Nc1c(c(OC[C@@H]3CCCN3C)nc3c(F)c(Br)c(Cl)cc13)NC2=O]

To a reaction mixture of tert-butyl (S)-8'-bromo-9'-chloro-7'-fluoro-5'-((1-methylpyrrolidin-2-yl)methoxy)-3'-oxo-3',4'-dihydro-1'H-spiro[piperidine-4,2'-pyrazino[2,3-c]quinoline]-1-carboxylate (124 mg, 0.202 mmol) and DCM (1.0 ml) was added TFA (623 µl, 8.09 mmol). After stirring for 1 hour at room temperature, the volatiles were removed under reduced pressure. The residue was dissolved in DCM (1.0 ml) and 1.0 M acryloyl chloride in DCM (243 µl, 0.243 mmol) was added, followed by DIEA (70.7 µl, 0.405 mmol) at 0° C. After stirring at same temperature for 0.5 h, the reaction mixture was diluted with ethyl acetate and water. The aqueous layer was extracted with ethyl acetate once. The combined organic layers were washed with brine, dried over Na$_2$SO$_4$, filtered and concentrated. The crude was purified with prep-LCMS (pH 2, acetonitrile/water+TFA) to yield the desired product (45 mg, 43%). LC-MS calculated for C$_{24}$H$_{27}$BrClFN$_5$O$_3$ (M+H)$^+$: m/z=566.1, 568.1; found 566.1, 568.1.

Step 9. 1-Acryloyl-9'-chloro-7'-fluoro-8'-(2-fluoro-6-hydroxyphenyl)-5'-(((S)-1-methylpyrrolidin-2-yl)methoxy)-1',4'-dihydro-3'H-spiro[piperidine-4,2'-pyrazino[2,3-c]quinolin]-3'-one A mixture of(S)-1-acryloyl-8'-bromo-9'-chloro-7'-fluoro-5'-((1-methylpyrrolidin-2-yl)methoxy)-1',4'-dihydro-3'H-spiro[piperidine-4,2'-pyrazino[2,3-c]quinolin]-3'-one(28 mg, 0.049 mmol), (2-fluoro-6-hydroxyphenyl)boronic acid (16.94 mg, 0.109 mmol), tetrakis (5.71 mg, 4.94 µmol) and sodium carbonate (5.24 mg, 0.049 mmol) in 1,4-dioxane (1.0 mL)/water (0.20 mL) was stirred at 80° C. for 2 h. The reaction solution was dissolved in methanol and 1 N HCl and purified with prep-LCMS (pH 2, acetonitrile/water+TFA) to give the product as a mixture of diastereomers as TFA salt. LC-MS calculated for C$_{30}$H$_{31}$ClF$_2$N$_5$O$_4$ (M+H)$^+$: m/z=598.2; found 598.2.

116

Example 11. 1-Acryloyl-9'-chloro-7'-fluoro-8'-(3-hydroxynaphthalen-1-yl)-5'-(((S)-1-methylpyrrolidin-2-yl)methoxy)-1',4'-dihydro-3'H-spiro[piperidine-4,2'-pyrazino[2,3-c]quinolin]-3'-one

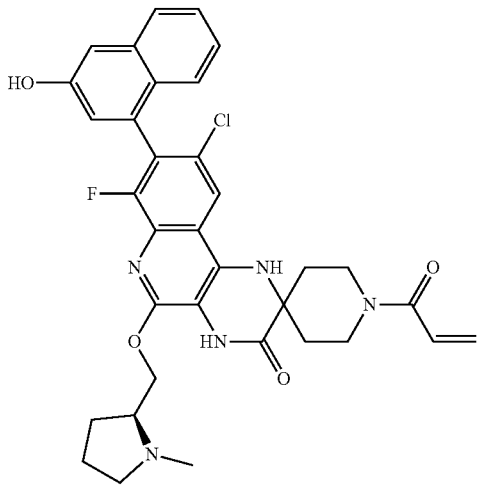 [SMILES: C=CC(=O)N1CCC2(CC1)Nc1c(c(OC[C@@H]3CCCN3C)nc3c(F)c(-c4cc(O)cc5ccccc45)c(Cl)cc13)NC2=O]

This compound was prepared using similar procedures as described for Example 10, with 4-(4,4,5,5-tetramethyl-1,3,2-dioxaborolan-2-yl)naphthalen-2-ol replacing (2-fluoro-6-hydroxyphenyl)boronic acid in Step 9. The reaction mixture was purified by prep-HPLC (pH=2, acetonitrile/water+TFA) to give the desired product as a mixture of diastereomers as TFA salt. LC-MS calculated for C$_{34}$H$_{34}$ClFN$_5$O$_4$ (M+H)$^+$: m/z=630.2; found 630.2. $^1$H NMR (500 MHz, DMSO) δ 10.30 (s, 1H), 9.99 (s, 1H), 8.52 (s, 1H), 7.81 (d, J=8.3 Hz, 1H), 7.44 (t, J=7.4 Hz, 1H), 7.29 (s, 2H), 7.25-7.15 (m, 2H), 7.07 (s, 1H), 6.87 (m, 1H), 6.16 (d, J=16.7 Hz, 1H), 5.73 (d, J=10.6 Hz, 1H), 4.90-4.82 (m, 1H), 4.70 (bs, 1H), 4.05-3.75 (m, 5H), 3.71 (m, 2H), 3.62-3.12 (m, 2H), 2.99 (d, J=4.6 Hz, 3H), 2.25-1.67 (m, 8H).

Example 12. 1-Acryloyl-9'-chloro-7'-fluoro-8'-(2-fluoro-6-hydroxyphenyl)-5'-(2-(piperidin-1-yl)ethoxy)-1',4'-dihydro-3'H-spiro[piperidine-4,2'-pyrazino[2,3-c]quinolin]-3'-one

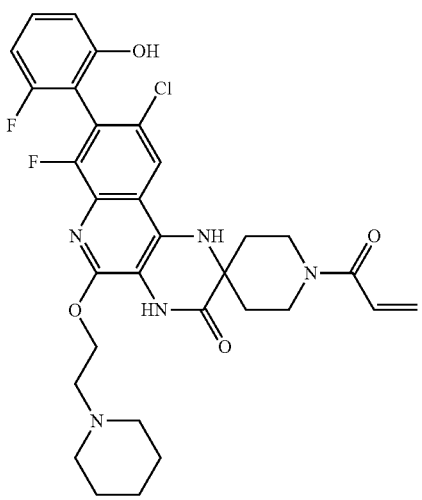 [SMILES: C=CC(=O)N1CCC2(CC1)Nc1c(c(OCCN3CCCCC3)nc3c(F)c(-c4c(O)cccc4F)c(Cl)cc13)NC2=O]

Step 1. 1-(tert-Butyl) 4-methyl 4-((7-bromo-6-chloro-8-fluoro-3-nitro-2-(2-(piperidin-1-yl)ethoxy)quinolin-4-yl)amino)piperidine-1,4-dicarboxylate

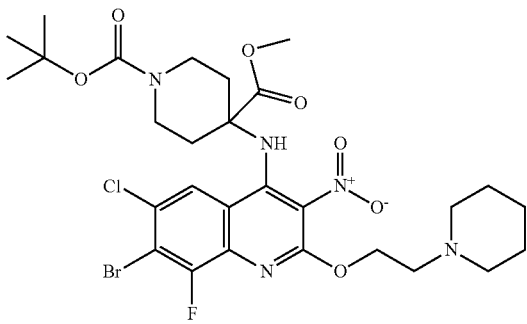 [SMILES: COC(=O)C1(Nc2c([N+](=O)[O-])c(OCCN3CCCCC3)nc3c(F)c(Br)c(Cl)cc23)CCN(C(=O)OC(C)(C)C)CC1]

This compound was prepared using similar procedures as described for Example 10, with 2-(piperidin-1-yl)ethan-1-ol replacing (S)-(1-methylpyrrolidin-2-yl)methanol in Step 6. LC-MS calculated for $C_{28}H_{37}BrClFN_5O_7$ $(M+H)^+$: m/z=688.2, 690.2; found 688.2, 690.2.

Step 2. tert-Butyl 8'-bromo-9'-chloro-7'-fluoro-3'-oxo-5'-(2-(piperidin-1-yl)ethoxy)-3',4'-dihydro-1'H-spiro[piperidine-4,2'-pyrazino[2,3-c]quinoline]-1-carboxylate

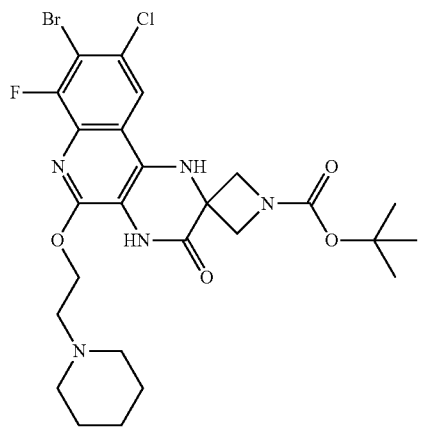 [SMILES: CC(C)(C)OC(=O)N1CC2(C1)Nc1c(c(OCCN3CCCCC3)nc3c(F)c(Br)c(Cl)cc13)NC2=O]

This compound was prepared using similar procedures as described for Example 10, with 1-(tert-butyl) 4-methyl 4-((7-bromo-6-chloro-8-fluoro-3-nitro-2-(2-(piperidin-1-yl)ethoxy)quinolin-4-yl)amino)piperidine-1,4-dicarboxylate replacing 1-(tert-butyl) 4-methyl (S)-4-((7-bromo-6-chloro-8-fluoro-2-(((1-methylpyrrolidin-2-yl)methoxy)-3-nitroquinolin-4-yl)amino)piperidine-1,4-dicarboxylate in Step 7. LC-MS calculated for $C_{27}H_{35}BrClFN_5O_4$ $(M+H)^+$: m/z=626.2, 628.1; found 626.2, 628.2.

Step 3. 1-Acryloyl-8'-bromo-9'-chloro-7'-fluoro-5'-(2-(piperidin-1-yl)ethoxy)-1',4'-dihydro-3'H-spiro[piperidine-4,2'-pyrazino[2,3-c]quinolin]-3'-one

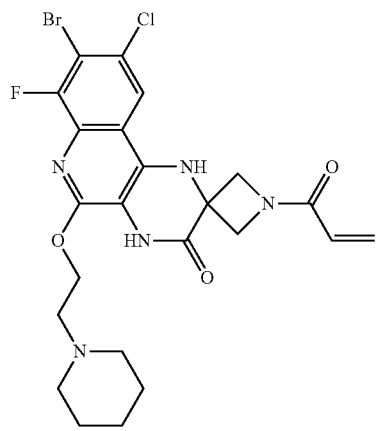 [SMILES: C=CC(=O)N1CC2(C1)Nc1c(c(OCCN3CCCCC3)nc3c(F)c(Br)c(Cl)cc13)NC2=O]

This compound was prepared using similar procedures as described for Example 10, with tert-butyl 8'-bromo-9'-chloro-7'-fluoro-3'-oxo-5'-(2-(piperidin-1-yl)ethoxy)-3',4'-dihydro-1'H-spiro[piperidine-4,2'-pyrazino[2,3-c]quinoline]-1-carboxylate replacing tert-butyl (S)-8'-bromo-9'-chloro-7'-fluoro-5'-(((1-methylpyrrolidin-2-yl)methoxy)-3'-oxo-3',4'-dihydro-1'H-spiro[piperidine-4,2'-pyrazino[2,3-c]quinoline]-1-carboxylate in Step 8. LC-MS calculated for $C_{25}H_{29}BrClFN_5O_3$ $(M+H)^+$: m/z=580.1, 582.1; found 580.1, 582.1.

Step 4. 1-Acryloyl-9'-chloro-7'-fluoro-8'-(2-fluoro-6-hydroxyphenyl)-5'-(2-(piperidin-1-yl)ethoxy)-1',4'-dihydro-3'H-spiro[piperidine-4,2'-pyrazino[2,3-c]quinolin]-3'-one This compound was prepared using similar procedures as described for Example 10, with 1-acryloyl-8'-bromo-9'-chloro-7'-fluoro-5'-(2-(piperidin-1-yl)ethoxy)-1',4'-dihydro-3'H-spiro[piperidine-4,2'-pyrazino[2,3-c]quinolin]-3'-one replacing (S)-1-acryloyl-8'-bromo-9'-chloro-7'-fluoro-5'-((1-methylpyrrolidin-2-yl)methoxy)-1',4'-dihydro-3'H-spiro[piperidine-4,2'-pyrazino[2,3-c]quinolin]-3'-one in Step 9. The reaction mixture was purified by prep-HPLC (pH=2, acetonitrile/water+TFA) to give the desired product as a mixture of diastereomers as TFA salt. LC-MS calculated for $C_{31}H_{33}ClF_2N_5O_4$ $(M+H)^+$: m/z=612.2; found 612.2.

Example 13. 1-Acryloyl-8'-chloro-6'-fluoro-7'-(3-hydroxynaphthalen-1-yl)-4'-(((S)-1-methylpyrrolidin-2-yl)methoxy)spiro[piperidine-4,1'-pyrrolo[2,3-c]quinolin]-2'(3'H)-one

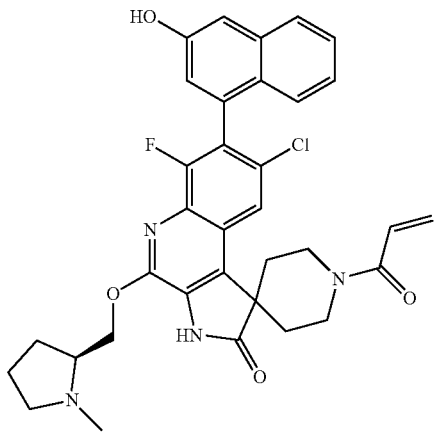 [SMILES: C=CC(=O)N1CCC2(CC1)C(=O)Nc1c(OC[C@@H]3CCCN3C)nc3c(F)c(-c4cc(O)cc5ccccc45)c(Cl)cc3c12]

Step 1. 1-(tert-Butyl) 4-methyl 4-(7-bromo-2,6-dichloro-8-fluoro-3-nitroquinolin-4-yl)piperidine-1,4-dicarboxylate 7-Bromo-2,4,6-trichloro-8-fluoro-3-nitroquinoline (Example 10, Step 4, 100 mg, 0.267 mmol) and 1-(tert-butyl) 4-methyl piperidine-1,4-dicarboxylate (130 mg, 0.534 mmol) were combined and THF (2 ml) was added. The solution was cooled to −78° C. then KHMDS (0.5 M, in toluene, 1068 µl, 0.534 mmol) was added. The mixture was stirred at −78° C. for 10 min, then quenched with saturated aqueous NH$_4$Cl, diluted with EtOAc, separated. The aqueous layer was extracted with EtOAc and the combined organic layer was washed with brine, dried over Na$_2$SO$_4$, filtered and evaporated. The residue was purified with column chromatography (0-50% ethyl acetate in hexanes) to give the desired product as a brown solid. LC-MS calculated for C$_{16}$H$_{14}$BrCl$_2$FN$_3$O$_4$ (M−Boc+H)$^+$: m/z=480.0; found 480.0.

Step 2. 1-(tert-Butyl) 4-methyl (S)-4-(7-bromo-6-chloro-8-fluoro-2-((1-methylpyrrolidin-2-yl)methoxy)-3-nitroquinolin-4-yl)piperidine-1,4-dicarboxylate (S)-(1-Methylpyrrolidin-2-yl)methanol (49.0 µl, 0.413 mmol) in THF (2 ml) was added NaH (16.52 mg, 0.413 mmol) at 0° C. After stirring at 0° C. for 30 min, 1-(tert-butyl) 4-methyl 4-(7-bromo-2,6-dichloro-8-fluoro-3-nitroquinolin-4-yl)piperidine-1,4-dicarboxylate (120 mg, 0.206 mmol) was added. The mixture was stirred at room temperature for 1 h, then quenched with saturated aqueous NH$_4$Cl, diluted with EtOAc, separated. The aqueous layer was extracted with EtOAc and the combined organic layer was washed with brine, dried over Na$_2$SO$_4$, filtered and evaporated to give the desired product as a brown solid. The residue was used without further purification. LC-MS calculated for C$_{27}$H$_{34}$BrClFN$_4$O$_7$ (M+H)$^+$: m/z=659.2; found 659.2.

Step 3. tert-Butyl(S)-7'-bromo-8'-chloro-6'-fluoro-4'-((1-methylpyrrolidin-2-yl)methoxy)-2'-oxo-2',3'-dihydrospiro[piperidine-4,1'-pyrrolo[2,3-c]quinoline]-1-carboxylate

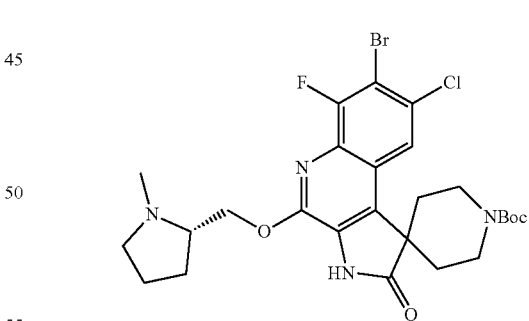

To a solution of 1-(tert-butyl) 4-methyl (S)-4-(7-bromo-6-chloro-8-fluoro-2-((1-methylpyrrolidin-2-yl)methoxy)-3-nitroquinolin-4-yl)piperidine-1,4-dicarboxylate (100 mg, 0.152 mmol) in acetic acid (2.0 ml) was added Fe (42.3 mg, 0.758 mmol). The resulting mixture was stirred at 80° C. for 1 h. The mixture was filtered through a pad of Celite and washed with methanol. The filtrate was concentrated and purified with silica gel column chromatography (0-10% MeOH in DCM) to give the desired product as a white solid. LC-MS calculated for C$_{26}$H$_{32}$BrClFN$_4$O$_4$ (M+H)$^+$: m/z=597.1; found 597.1.

Step 4. (S)-1-Acryloyl-7'-bromo-8'-chloro-6'-fluoro-4'-((1-methylpyrrolidin-2-yl)methoxy)-spiro[piperidine-4,1'-pyrrolo[2,3-c]quinolin]-2'(3'H)-one

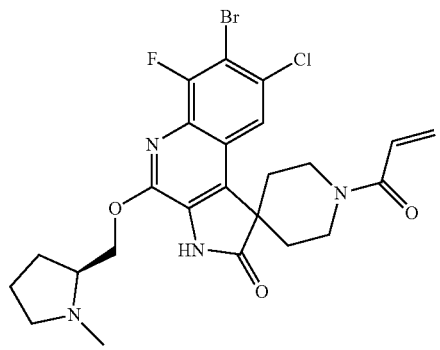 [SMILES: C=CC(=O)N1CCC2(CC1)C(=O)Nc1c(OC[C@@H]3CCCN3C)nc3c(F)c(Br)c(Cl)cc3c12]

4N HCl (1.0 mL) was added to a solution of tert-butyl (S)-7'-bromo-8'-chloro-6'-fluoro-4'-((1-methylpyrrolidin-2-yl)methoxy)-2'-oxo-2',3'-dihydrospiro[piperidine-4,1'-pyrrolo[2,3-c]quinoline]-1-carboxylate (50 mg, 0.084 mmol) in DCM/MeOH (0.5/0.5 mL) and stirred at room temperature for 30 min. The solvent was removed under vacuum. The residue was dissolved in DCM (2.0 ml) and cooled to 0° C., to this was added triethylamine (69.9 µl, 0.502 mmol) followed by acryloyl chloride (6.76 µl, 0.084 mmol) and the reaction was stirred at 0° C. for 20 min. The reaction was diluted with DCM and washed with saturated NaHCO$_3$, separated; the organic layer was dried over Na$_2$SO$_4$ and concentrated. The product was purified by silica gel column chromatography (0-10% MeOH in DCM) to give the desired product as a white solid. LC-MS calculated for C$_{24}$H$_{26}$BrClFN$_4$O$_3$ (M+H)$^+$: m/z=551.1; found 551.1.

Step 5. 1-Acryloyl-8'-chloro-6'-fluoro-7'-(3-hydroxynaphthalen-1-yl)-4'-(((S)-1-methylpyrrolidin-2-yl)methoxy)spiro[piperidine-4,1'-pyrrolo[2,3-c]quinolin]-2'(3'H)-one A mixture of (S)-1-acryloyl-7'-bromo-8'-chloro-6'-fluoro-4'-((1-methylpyrrolidin-2-yl)methoxy)spiro[piperidine-4,1'-pyrrolo[2,3-c]quinolin]-2'(3'H)-one (20 mg, 0.036 mmol), 4-(4,4,5,5-tetramethyl-1,3,2-dioxaborolan-2-yl)naphthalen-2-ol (29.4 mg, 0.109 mmol), sodium carbonate (19.21 mg, 0.181 mmol) and Pd(PPh$_3$)$_4$ (12.56 mg, 10.87 µmol) in Dioxane (0.8 ml)/Water (0.200 ml) was vacuumed and refilled with N$_2$ twice and then the reaction was stirred at 95° C. for 2 h. The reaction mixture was cooled to room temperature, quenched and acidified with TFA, filtered and purified by prep-HPLC (pH=2, acetonitrile/water+TFA) to give the desired product as a mixture of diastereomers as TFA salt. LC-MS calculated for C$_{34}$H$_{33}$ClFN$_4$O$_4$ (M+H)$^+$: m/z=615.2; found 615.2.

Example 14. 1-Acryloyl-8'-chloro-6'-fluoro-7'-(3-hydroxynaphthalen-1-yl)-4'-(((S)-1-methylpyrrolidin-2-yl)methoxy)spiro[pyrrolidine-3,1'-pyrrolo[2,3-c]quinolin]-2'(3'H)-one

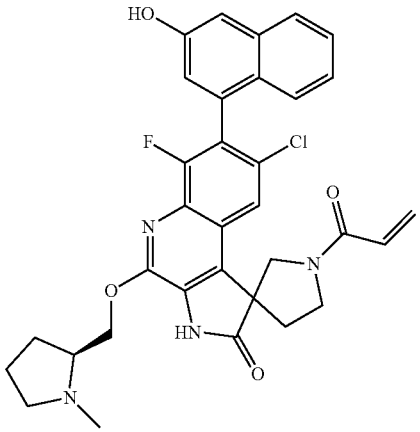 [SMILES: C=CC(=O)N1CCC2(C1)C(=O)Nc1c(OC[C@@H]3CCCN3C)nc3c(F)c(-c4cc(O)cc5ccccc45)c(Cl)cc3c12]

This compound was prepared using similar procedures as described for Example 13, with 1-(tert-butyl) 3-ethyl pyrrolidine-1,3-dicarboxylate replacing 1-(tert-butyl) 4-methyl piperidine-1,4-dicarboxylate in Step 1. The reaction mixture was purified by prep-HPLC (pH=2, acetonitrile/water+TFA) to give the product as a mixture of diastereomers as TFA salt. LC-MS calculated for C$_{33}$H$_{31}$ClFN$_4$O$_4$ (M+H)$^+$: m/z=601.2; found 601.2.

Example 15. 1-Acryloyl-8'-chloro-6'-fluoro-7'-(3-hydroxynaphthalen-1-yl)-4'-(((S)-1-methylpyrrolidin-2-yl)methoxy)spiro[piperidine-3,1'-pyrrolo[2,3-c]quinolin]-2'(3'H)-one

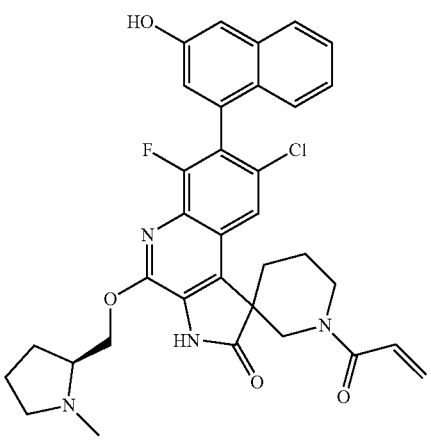 [SMILES: C=CC(=O)N1CCCC2(C1)C(=O)Nc1c(OC[C@@H]3CCCN3C)nc3c(F)c(-c4cc(O)cc5ccccc45)c(Cl)cc3c12]

This compound was prepared using similar procedures as described for Example 13, with 1-(tert-butyl) 3-methyl piperidine-1,3-dicarboxylate replacing 1-(tert-butyl) 4-methyl piperidine-1,4-dicarboxylate in Step 1. The reaction mixture was purified by prep-HPLC (pH=2, acetonitrile/water+TFA) to give the product as a mixture of diastereomers as TFA salt. LC-MS calculated for C$_{34}$H$_{33}$ClFN$_4$O$_4$ (M+H)$^+$: m/z=615.2; found 615.2.

Example 16a and Example 16b. 1-Acryloyl-8'-chloro-6'-fluoro-7'-(3-hydroxynaphthalen-1-yl)-3'-methyl-4'-(((S)-1-methylpyrrolidin-2-yl)methoxy)spiro[piperidine-4,1'-pyrrolo[2,3-c]quinolin]-2'(3'H)-one

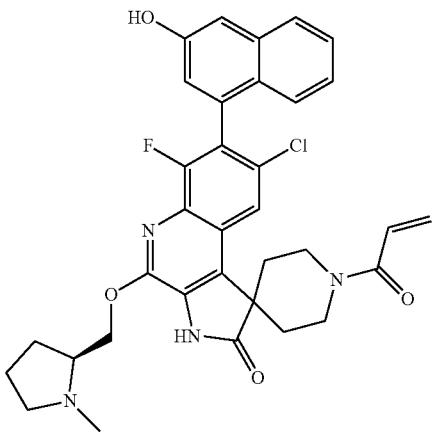 [SMILES: C=CC(=O)N1CCC2(CC1)C(=O)Nc1c(OC[C@@H]3CCCN3C)nc3c(F)c(-c4cc(O)cc5ccccc45)c(Cl)cc3c12]

Step 1. tert-Butyl(S)-7'-bromo-8'-chloro-6'-fluoro-3'-methyl-4'-((1-methylpyrrolidin-2-yl)methoxy)-2'-oxo-2',3'-dihydrospiro[piperidine-4,1'-pyrrolo[2,3-c]quinoline]-1-carboxylate

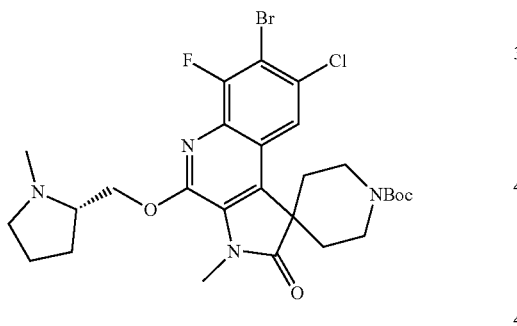

To a solution of tert-butyl (S)-7'-bromo-8'-chloro-6'-fluoro-4'-((1-methylpyrrolidin-2-yl)methoxy)-2'-oxo-2',3'-dihydrospiro[piperidine-4,1'-pyrrolo[2,3-c]quinoline]-1-carboxylate (Example 13, Step 3) (30 mg, 0.050 mmol) in DMF (1 ml) was added NaH (60% in mineral oil, 4.01 mg, 0.100 mmol) at 0° C. After stirring at 0° C. for 30 min, MeI (15.69 µl, 0.251 mmol) was added. The mixture was stirred room temperature for 1 h then quenched with water, extracted with EtOAc, separated; the organic layer was dried over Na$_2$SO$_4$ and concentrated. The product was purified by silica gel column chromatography (0-10% MeOH in DCM) to give the desired product as a white solid. LC-MS calculated for C$_{27}$H$_{34}$BrClFN$_4$O$_4$ (M+H)$^+$: m/z=611.1; found 611.1.

Step 2. 1-Acryloyl-8'-chloro-6'-fluoro-7'-(3-hydroxynaphthalen-1-yl)-3'-methyl-4'-(((S)-1-methylpyrrolidin-2-yl)methoxy)spiro[piperidine-4,1'-pyrrolo[2,3-c]quinolin]-2'(3'H)-one This compound was prepared using similar procedures as described for Example 13, with tert-butyl (S)-7'-bromo-8'-chloro-6'-fluoro-3'-methyl-4'-((1-methylpyrrolidin-2-yl)methoxy)-2'-oxo-2',3'-dihydrospiro[piperidine-4,1'-pyrrolo[2,3-c]quinoline]-1-carboxylate replacing tert-butyl (S)-7'-bromo-8'-chloro-6'-fluoro-4'-((1-methylpyrrolidin-2-yl)methoxy)-2'-oxo-2',3'-dihydrospiro[piperidine-4,1'-pyrrolo[2,3-c]quinoline]-1-carboxylate in Step 4. The reaction mixture was purified by prep-HPLC (pH=2, acetonitrile/water+TFA) to give the desired products as TFA salt.

Example 16a. Diastereomer 1. Peak 1. LC-MS calculated for C$_{35}$H$_{35}$ClFN$_4$O$_4$ (M+H)$^+$: m/z=629.2; found 629.2.

Example 16b. Diastereomer 2. Peak 2. LC-MS calculated for C$_{35}$H$_{35}$ClFN$_4$O$_4$ (M+H)$^+$: m/z=629.2; found 629.2.

Example 17. 1-Acryloyl-9'-chloro-7'-fluoro-8'-(3-hydroxynaphthalen-1-yl)spiro[piperidine-4,2'-pyrano[3,2-c]quinolin]-4'(3'H)-one

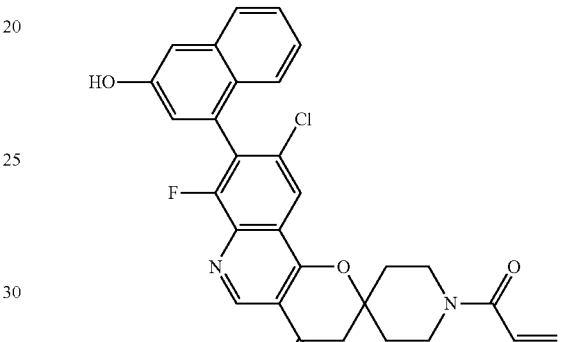

Step 1. Ethyl (Z)-2-(((3-bromo-4-chloro-2-fluorophenyl)amino)methylene)-3-oxobutanoate

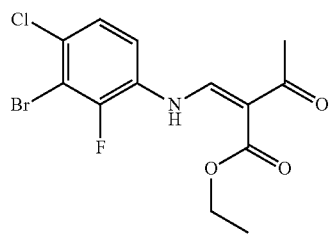 [SMILES: CCOC(=O)/C(=C\Nc1ccc(Cl)c(Br)c1F)C(C)=O]

A stirred mixture of ethyl 3-oxobutanoate (3.16 ml, 24.95 mmol), triethyl orthoformate (4.99 ml, 29.9 mmol), and 3-bromo-4-chloro-2-fluoroaniline (Example 1, Step 1) (5.60 g, 24.95 mmol) were heated at 150° C. for 16 h with a Dean Stark trap. After this time the reaction was cooled to room temperature and the resulting precipitate was suspended in 1:1 ether/hexanes, and filtered to afford the desired product (5.3 g, 58%). LC-MS calculated for C$_{13}$H$_{13}$BrClFNO$_3$ (M+H)$^+$: m/z=364.0, 366.0; found=364.0, 366.0.

Step 2. 1-(7-Bromo-6-chloro-8-fluoro-4-hydroxy-quinolin-3-yl)ethan-1-one

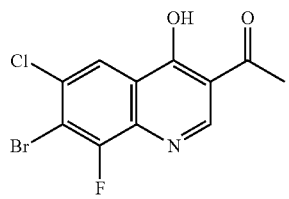 [SMILES: CC(=O)c1cnc2c(F)c(Br)c(Cl)cc2c1O]

A microwave vial charged with ethyl (Z)-2-(((3-bromo-4-chloro-2-fluorophenyl)-amino)methylene)-3-oxobutanoate (1.00 g, 2.74 mmol) and diphenyl ether (10 ml) was heated at 260° C. for 1 h. After cooling to room temperature, mixture was added heptane (25 mL), and the mixture was filtered, with the solid collected, washed with heptane and ethyl ether and dried under vacuum to give the desired product as a tan solid (0.7 g, 80%). LC-MS calculated for $CH_7BrClFNO_2$ (M+H)$^+$: m/z=318.0, 320.0; found=318.0, 320.0.

Step 3. tert-Butyl 8'-bromo-9'-chloro-7'-fluoro-4'-oxo-3',4'-dihydrospiro[piperidine-4,2'-pyrano[3,2-c]quinoline]-1-carboxylate

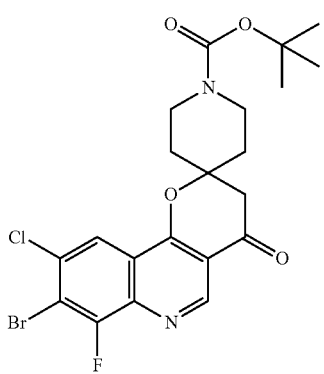 [SMILES: CC(C)(C)OC(=O)N1CCC2(CC1)CC(=O)c1cnc3c(F)c(Br)c(Cl)cc3c1O2]

To a solution of 1-(7-bromo-6-chloro-8-fluoro-4-hydroxyquinolin-3-yl)ethan-1-one (645 mg, 2.025 mmol) in MeOH (6.14 ml) was added tert-butyl 4-oxopiperidine-1-carboxylate (403 mg, 2.025 mmol) and pyrrolidine (335 μl, 4.05 mmol). The resulting mixture was heated at 80° C. overnight. The solvent was removed and the crude was purified with flash chromatography (eluting with 0-60% ethyl acetate in hexanes) to give the desired product (0.2 g, 20%). LC-MS calculated for $C_{21}H_{22}BrClFN_2O_4$ (M+H)$^+$: m/z=499.0, 501.0; found 499.1, 501.1.

Step 4. 1-Acryloyl-8'-bromo-9'-chloro-7'-fluorospiro[piperidine-4,2'-pyrano[3,2-c]quinolin]-4'(3'H)-one

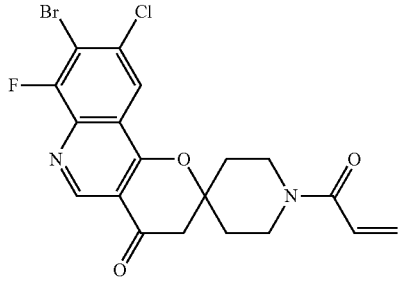 [SMILES: C=CC(=O)N1CCC2(CC1)CC(=O)c1cnc3c(F)c(Br)c(Cl)cc3c1O2]

To a solution of tert-butyl 8'-bromo-9'-chloro-7'-fluoro-4'-oxo-3',4'-dihydrospiro[piperidine-4,2'-pyrano[3,2-c]quinoline]-1-carboxylate (34 mg, 0.068 mmol) in DCM (1.0 ml) was added TFA (105 μl, 1.361 mmol). The mixture was stirred for 1 h. The solvent was removed and the residue was dissolved in DCM (1.0 ml). DIEA (29.7 μl, 0.170 mmol) was added to reaction vial, followed by 1 M acryloyl chloride (102 μl, 0.102 mmol). After stirring at 0° C. for 1 h, the solvent was removed and the residue was diluted with methanol and purified with prep-LCMS to give the desired product (25 mg, 81%). LC-MS calculated for $C_1H_{16}BrClFN_2O_3$ (M+H)$^+$: m/z=453.0, 455.0; found 453.1, 455.1.

Step 5. 1-Acryloyl-9'-chloro-7'-fluoro-8'-(3-hydroxynaphthalen-1-yl)spiro[piperidine-4,2'-pyrano[3,2-c]quinolin]-4'(3'H)-one A mixture of 1-acryloyl-8'-bromo-9'-chloro-7'-fluorospiro[piperidine-4,2'-pyrano[3,2-c]quinolin]-4'(3'H)-one (36 mg, 0.079 mmol), 4-(4,4,5,5-tetramethyl-1,3,2-dioxaborolan-2-yl)naphthalen-2-ol (47.2 mg, 0.175 mmol), tetrakis (9.17 mg, 7.93 μmol) and sodium carbonate (25.2 mg, 0.238 mmol) in 1,4-dioxane (1.0 mL)/water (0.200 mL) was stirred at 90° C. for 2 h. The residue was dissolved in methanol and 1 N HCl and purified with prep-HPLC (pH=2, acetonitrile/water+TFA) to give the desired product as a pair of atropisomers (brown solid, 28 mg, 68%). LC-MS calculated for $C_2H_{23}ClFN_2O_4$ (M+H)$^+$: m/z=517.1; found 517.1.

Example 18. 1-Acryloyl-9'-chloro-7'-fluoro-8'-(2-fluoro-6-hydroxyphenyl)-5'-(((S)-1-methylpyrrolidin-2-yl)methoxy)-1',4'-dihydro-3'H-spiro[azetidine-3,2'-pyrazino[2,3-c]quinolin]-3'-one

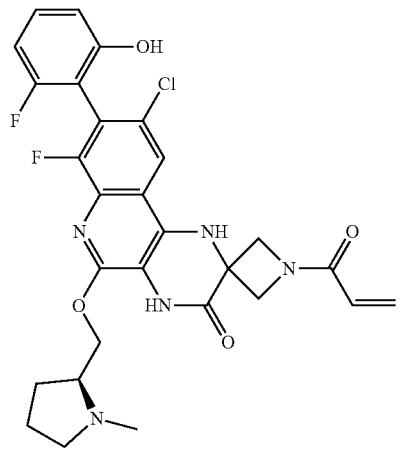 [SMILES: C=CC(=O)N1CC2(C1)Nc1c(c(OC[C@@H]3CCCN3C)nc3c(F)c(-c4c(O)cccc4F)c(Cl)cc13)NC2=O]

Step 1. 1-(tert-Butyl) 3-methyl 3-((7-bromo-2,6-dichloro-8-fluoro-3-nitroquinolin-4-yl)amino)-azetidine-1,3-dicarboxylate

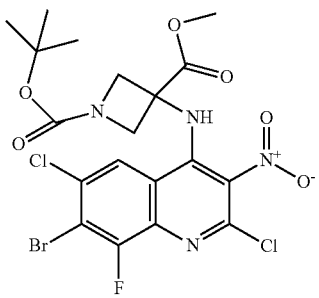 [SMILES: COC(=O)C1(Nc2c([N+](=O)[O-])c(Cl)nc3c(F)c(Br)c(Cl)cc23)CN(C(=O)OC(C)(C)C)C1]

This compound was prepared using similar procedures as described for Example 10, with 1-(tert-butyl) 3-methyl 3-aminoazetidine-1,3-dicarboxylate replacing 1-(tert-butyl) 4-methyl 4-aminopiperidine-1,4-dicarboxylate in Step 5. LC-MS calculated for $C_{19}H_{19}BrCl_2FN_4O_6$ (M+H)⁺: m/z=567.0, 569.0; found 567.0, 569.0.

Step 2. 1-(tert-Butyl) 3-methyl (S)-3-((7-bromo-6-chloro-8-fluoro-2-((1-methylpyrrolidin-2-yl)methoxy)-3-nitroquinolin-4-yl)amino)azetidine-1,3-dicarboxylate

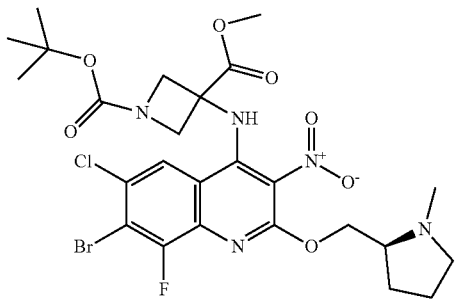 [SMILES: COC(=O)C1(Nc2c([N+](=O)[O-])c(OC[C@@H]3CCCN3C)nc3c(F)c(Br)c(Cl)cc23)CN(C(=O)OC(C)(C)C)C1]

This compound was prepared using similar procedures as described for Example 10, with 1-(tert-butyl) 3-methyl 3-((7-bromo-2,6-dichloro-8-fluoro-3-nitroquinolin-4-yl)amino)-azetidine-1,3-dicarboxylate replacing 1-(tert-butyl) 4-methyl 4-((7-bromo-2,6-dichloro-8-fluoro-3-nitroquinolin-4-yl)amino)piperidine-1,4-dicarboxylate in Step 6. LC-MS calculated for $C_{25}H_{31}BrClFN_5O_7$ (M+H)⁺: m/z=646.1, 648.1; found 646.1, 648.1.

Step 3. tert-Butyl (S)-8'-bromo-9'-chloro-7'-fluoro-5'-((1-methylpyrrolidin-2-yl)methoxy)-3'-oxo-3',4'-dihydro-1'H-spiro[azetidine-3,2'-pyrazino[2,3-c]quinoline]-1-carboxylate

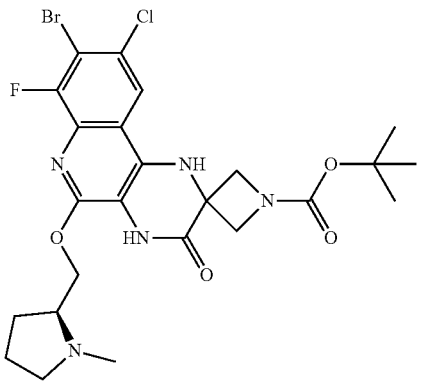 [SMILES: CN1CCC[C@H]1COc1nc2c(F)c(Br)c(Cl)cc2c2c1NC(=O)C1(CN(C(=O)OC(C)(C)C)C1)N2]

This compound was prepared using similar procedures as described for Example 10, with 1-(tert-Butyl) 3-methyl (S)-3-((7-bromo-6-chloro-8-fluoro-2-((1-methylpyrrolidin-2-yl)-methoxy)-3-nitroquinolin-4-yl)amino)azetidine-1,3-dicarboxylate replacing 1-(tert-butyl) 4-methyl (S)-4-((7-bromo-6-chloro-8-fluoro-2-((1-methylpyrrolidin-2-yl)methoxy)-3-nitroquinolin-4-yl)amino)piperidine-1,4-dicarboxylate in Step 7. LC-MS calculated for $C_{24}H_{29}BrClFN_5O_4$ (M+H)⁺: m/z=584.1, 586.1; found 584.1, 586.1.

Step 4. (S)-1-Acryloyl-8'-bromo-9'-chloro-7'-fluoro-5'-((1-methylpyrrolidin-2-yl)methoxy)-1',4'-dihydro-3'H-spiro[azetidine-3,2'-pyrazino[2,3-c]quinolin]-3'-one

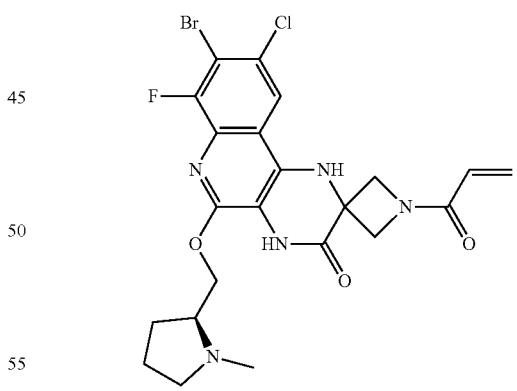

This compound was prepared using similar procedures as described for Example 10, with tert-butyl (S)-8'-bromo-9'-chloro-7'-fluoro-5'-((1-methylpyrrolidin-2-yl)methoxy)-3'-oxo-3',4'-dihydro-1'H-spiro[azetidine-3,2'-pyrazino[2,3-c]quinoline]-1-carboxylate replacing tert-butyl (S)-8'-bromo-9'-chloro-7'-fluoro-5'-((1-methylpyrrolidin-2-yl)methoxy)-3'-oxo-3',4'-dihydro-1'H-spiro[piperidine-4,2'-pyrazino[2,3-c]quinoline]-1-carboxylate in Step 8. LC-MS calculated for $C_{22}H_{23}BrClFN_5O_3$ (M+H)⁺: m/z=538.1, 540.1; found 538.1, 540.1.

Step 5. 1-Acryloyl-9'-chloro-7'-fluoro-8'-(2-fluoro-6-hydroxyphenyl)-5'-(((S)-1-methylpyrrolidin-2-yl)methoxy)-1',4'-dihydro-3'H-spiro[azetidine-3,2'-pyrazino[2,3-c]quinolin]-3'-one This compound was prepared using similar procedures as described for Example 10, with (S)-1-acryloyl-8'-bromo-9'-chloro-7'-fluoro-5'-((1-methylpyrrolidin-2-yl)methoxy)-1',4'-dihydro-3'H-spiro[azetidine-3,2'-pyrazino[2,3-c]quinolin]-3'-one replacing (S)-1-acryloyl-8'-bromo-9'-chloro-7'-fluoro-5'-((1-methylpyrrolidin-2-yl)methoxy)-1',4'-dihydro-3'H-spiro[piperidine-4,2'-pyrazino[2,3-c]quinolin]-3'-one in Step 9. The reaction mixture was purified by prep-HPLC (pH=2, acetonitrile/water+TFA) to give the product as a mixture of diastereomers as TFA salt. LC-MS calculated for $C_{28}H_{27}ClF_2N_5O_4$ $(M+H)^+$: m/z=570.2; found 570.2. $^1H$ NMR (600 MHz, DMSO) b 8.23 (s, 2H), 7.32 (m, 1H), 6.83 (d, J=8.3 Hz, 1H), 6.77 (m, 1H), 6.63 (bs, 1H), 6.38 (m, 1H), 6.18 (d, J=16.9 Hz, 1H), 5.74 (dd, J=10.3, 2.0 Hz, 1H), 4.75 (t, J=9.4 Hz, 1H), 4.50-4.45 (m, 2H), 4.33 (m, 1H), 4.25 (m, 1H), 4.12 (m, 1H), 2.96 (m, 1H), 2.68 (m, 1H), 2.36 (s, 3H), 2.18 (m, 1H), 2.02 (m, 1H), 1.68 (m, 3H).

Example 19a and Example 19b. 4'-(3-(dimethylamino)azetidin-1-yl)-6'-fluoro-7'-(3-hydroxynaphthalen-1-yl)-8'-methylspiro[piperidine-3,1'-pyrrolo[2,3-c]quinolin]-2'(3'H)-one

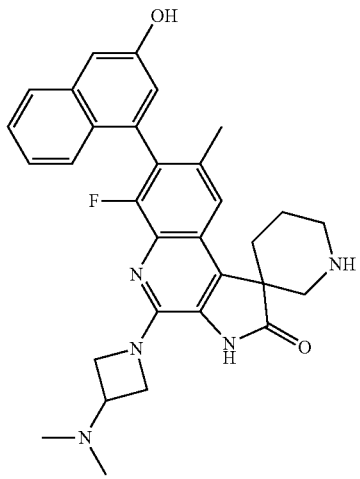 [SMILES: Cc1cc2c3c(c(N4CC(N(C)C)C4)nc2c(F)c1-c1cc(O)cc2ccccc12)NC(=O)C31CCCNC1]

Step 1. 1-(tert-Butyl) 3-methyl 3-(7-bromo-2,6-dichloro-8-fluoro-3-nitroquinolin-4-yl)piperidine-1,3-dicarboxylate

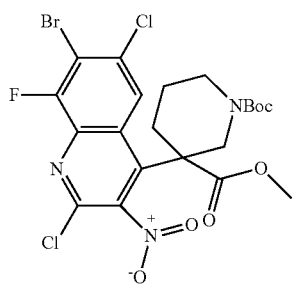

7-Bromo-2,4,6-trichloro-8-fluoro-3-nitroquinoline (Example 10, Step 4, 210 mg, 0.561 mmol) and 1-(tert-butyl) 3-methyl piperidine-1,3-dicarboxylate (273 mg, 1.122 mmol) were combined and THF (4 ml) was added. The solution was cooled to −78° C. then LiHMDS (1.0 M, in THF, 785 µl, 0.785 mmol) was added. The mixture was stirred at −78° C. for 30 min, then allowed to warm up to room temperature. After quenching with saturated aqueous NH₄Cl, the mixture was diluted with EtOAc and separated. The aqueous layer was extracted with EtOAc and the combined organic layer was washed with brine, dried over Na₂SO₄, filtered and evaporated. The residue was purified with column chromatography (DCM) to give the desired product as a solid.

Step 2. 1-(tert-butyl) 3-methyl 3-(7-bromo-6-chloro-2-(3-(dimethylamino)azetidin-1-yl)-8-fluoro-3-nitroquinolin-4-yl)piperidine-1,3-dicarboxylate

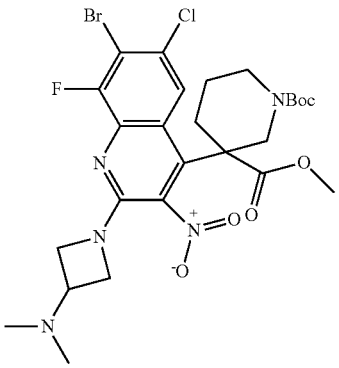

To N,N-dimethylazetidin-3-amine dihydrochloride (0.104 g, 0.600 mmol) in MeCN was added DIPEA (0.35 ml, 2.00 mmol) and the reaction was stirred for 10 min. Then 1-(tert-butyl) 3-methyl 3-(7-bromo-2,6-dichloro-8-fluoro-3-nitroquinolin-4-yl)piperidine-1,3-dicarboxylate (0.232 g, 0.400 mmol) was added. The mixture was stirred at room temperature for 30 min, then diluted with DCM. The resulting solution was washed with water, dried over Na₂SO₄, filtered and evaporated to give the desired product as a solid. The residue was used without further purification. LCMS calculated for $C_{26}H_{33}BrClFN_5O_6$ $(M+H)^+$: m/z=644.1, 646.1; found 644.1, 646.1.

Step 3. tert-butyl 7'-bromo-8'-chloro-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate

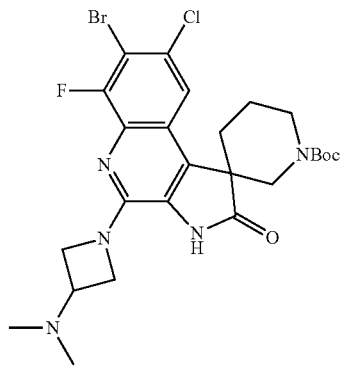 [SMILES: CN(C)C1CN(c2nc3c(F)c(Br)c(Cl)cc3c3c2NC(=O)C32CCCN(C(=O)OC(C)(C)C)C2)C1]

To a solution of 1-(tert-butyl) 3-methyl 3-(7-bromo-6-chloro-2-(3-(dimethylamino)-azetidin-1-yl)-8-fluoro-3-nitroquinolin-4-yl)piperidine-1,3-dicarboxylate (0.100 g, 0.152 mmol) in acetic acid (2.0 ml) was added Fe (0.042 g, 0.758 mmol). The resulting mixture was stirred at 80° C. for 30 min. The mixture was filtered through a pad of Celite and evaporated. The residue was quenched with saturated aqueous $NaHCO_3$, diluted with DCM and separated. The aqueous layer was extracted with DCM and the combined organic layer was washed with brine, dried over $Na_2SO_4$, filtered and evaporated. The residue was purified with column chromatography (0-20% MeOH in DCM) to give the desired product as a solid. LC-MS calculated for $C_{25}H_{31}BrClFN_5O_3$ (M+H)$^+$: m/z=582.1, 584.1; found 582.1, 584.1.

Step 4. tert-butyl 8'-chloro-4'-(3-(dimethylamino) azetidin-1-yl)-6'-fluoro-7'-(3-hydroxynaphthalen-1-yl)-2'-oxo-2',3'-dihydrospiro[piperidine-3,1'-pyrrolo[2,3-c]quinoline]-1-carboxylate

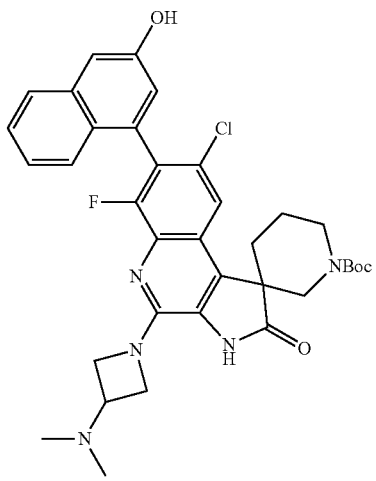 [SMILES: CN(C)C1CN(c2nc3c(F)c(-c4cc(O)cc5ccccc45)c(Cl)cc3c3c2NC(=O)C32CCCN(C(=O)OC(C)(C)C)C2)C1]

A mixture of tert-butyl 7'-bromo-8'-chloro-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate (0.050 g, 0.086 mmol), 4-(4,4,5,5-tetramethyl-1,3,2-dioxaborolan-2-yl)naphthalen-2-ol (0.028 g, 0.103 mmol), potassium phosphate (0.073 g, 0.343 mmol) and Pd(PPh$_3$)$_4$ (0.020 mg, 0.017 mmol) was evacuated under vacuum and refilled with nitrogen (repeated three times). After addition of degassed 1,4-dioxane (0.4 ml) and water (0.04 ml), the reaction mixture was stirred at 100° C. for 2 h. The reaction mixture was cooled to room temperature, filtered through a pad of silica, washed with MeCN and evaporated. The residue was purified with column chromatography (0-20% MeOH in DCM) to give the desired product. LC-MS calculated for $C_{35}H_{38}ClFN_5O_4$ (M+H)$^+$: m/z=646.3; found 646.2.

Step 5. 4'-(3-(dimethylamino)azetidin-1-yl)-6'-fluoro-7'-(3-hydroxynaphthalen-1-yl)-8'-methylspiro[piperidine-3,1'-pyrrolo[2,3-c]quinoline]-2'(3'H)-one A mixture of tert-butyl 8'-chloro-4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinoline]-1-carboxylate (0.030 g, 0.046 mmol), potassium methyltrifluoroborate (0.017 g, 0.139 mmol), cesium carbonate (0.045 g, 0.139 mmol), palladium acetate (0.002 g, 0.009 mmol) and di(1-adamantyl)-n-butylphosphine (0.007 g, 0.017 mmol) was evacuated under vacuum and refilled with nitrogen (repeated three times). After addition of degassed toluene (0.42 ml) and water (0.04 ml), the reaction mixture was stirred at 120° C. for 1 h. The reaction mixture was cooled to room temperature, filtered through a pad of silica, washed with MeCN and evaporated. To the residue, DCM (1.0 ml) and TFA (1.2 ml, 15.5 mmol) were added. After stirring for 30 min at room temperature, the volatiles were removed under reduced pressure. The residue was dissolved in MeCN, filtered and purified by prep-HPLC (pH=2, acetonitrile/water+TFA) to give the desired products as TFA salt.

Example 19a. Diastereomer 1. Peak 1. LC-MS calculated for $C_{31}H_{33}FN_5O_2$ (M+H)$^+$: m/z=526.3; found 526.3.

Example 19b. Diastereomer 2. Peak 2. LC-MS calculated for $C_{31}H_{33}FN_5O_2$ (M+H)$^+$: m/z=526.3; found 526.4.

Example 20a and Example 20b. 8'-chloro-7'-(7-chloro-3-hydroxynaphthalen-1-yl)-4'-(3-(dimethylamino)azetidin-1-yl)-6'-fluorospiro[piperidine-3,1'-pyrrolo[2,3-c]quinolin]-2'(3'H)-one

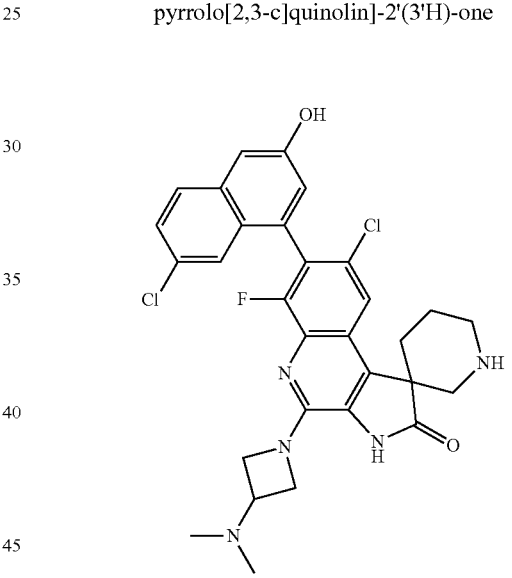

A mixture of tert-butyl 7'-bromo-8'-chloro-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate (Example 19a and 19b, Step 3, 0.050 g, 0.086 mmol), 6-chloro-4-(4,4,5,5-tetramethyl-1,3,2-dioxaborolan-2-yl)naphthalen-2-ol (0.031 g, 0.103 mmol), potassium phosphate (0.073 g, 0.343 mmol) and Pd(PPh$_3$)$_4$ (0.020 mg, 0.017 mmol) was evacuated under vacuum and refilled with nitrogen (repeated three times). After addition of degassed 1,4-dioxane (0.4 ml) and water (0.04 ml), the reaction mixture was stirred at 100° C. for 2 h. The reaction mixture was cooled to room temperature and filtered through a pad of silica, washed with MeCN and evaporated. To the residue, DCM (1.0 ml) and TFA (1.2 ml, 15.5 mmol) were added. After stirring for 30 min at room temperature, the volatiles were removed under reduced pressure. The residue was dissolved in MeCN, filtered and purified by prep-HPLC (pH=2, acetonitrile/water+TFA) to give the desired products as TFA salt.

Example 20a. Diastereomer 1. Peak 1. LC-MS calculated for $C_{30}H_{29}Cl_2FN_5O_2$ (M+H)$^+$: m/z=580.2; found 580.2.

Example 20b. Diastereomer 2. Peak 2. LC-MS calculated for $C_{30}H_{29}Cl_2FN_5O_2$ (M+H)$^+$: m/z=580.2; found 580.2.

Example 21a and Example 21b. 8'-chloro-4'-(3-(dimethylamino)azetidin-1-yl)-6'-fluoro-7'-(3-hydroxynaphthalen-1-yl)-5-azaspiro[bicyclo[2.2.1]heptane-2,1'-pyrrolo[2,3-c]quinolin]-2'(3'H)-one

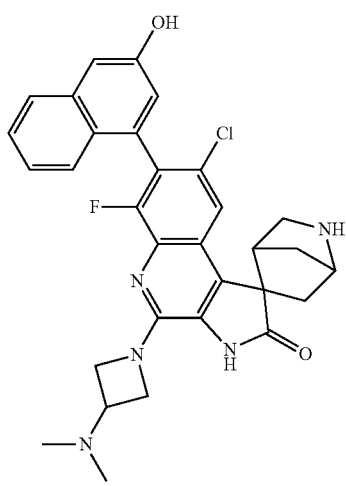 [SMILES: CN(C)C1CN(c2nc3c(F)c(-c4cc(O)cc5ccccc45)c(Cl)cc3c3c2NC(=O)C32CC3CC2CN3)C1]

Step 1. 2-(tert-butyl) 5-methyl 5-(7-bromo-2,6-dichloro-8-fluoro-3-nitroquinolin-4-yl)-2-azabicyclo[2.2.1]heptane-2,5-dicarboxylate

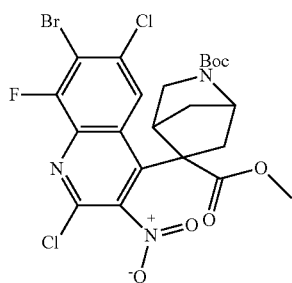

This compound was prepared using similar procedures as described for Example 19a and 19b, with 2-(tert-butyl) 5-methyl 2-azabicyclo[2.2.1]heptane-2,5-dicarboxylate replacing 1-(tert-butyl) 3-methyl piperidine-1,3-dicarboxylate in Step 1.

Step 2. 2-(tert-butyl) 5-methyl 5-(7-bromo-6-chloro-2-(3-(dimethylamino)azetidin-1-yl)-8-fluoro-3-nitroquinolin-4-yl)-2-azabicyclo[2.2.1]heptane-2,5-dicarboxylate

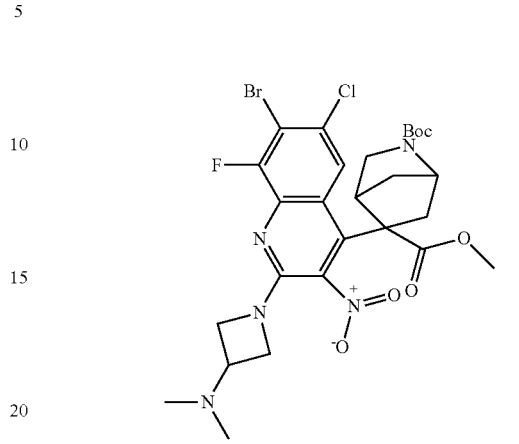

This compound was prepared using similar procedures as described for Example 19a and 19b, with 2-(tert-butyl) 5-methyl 5-(7-bromo-2,6-dichloro-8-fluoro-3-nitroquinolin-4-yl)-2-azabicyclo[2.2.1]heptane-2,5-dicarboxylate replacing 1-(tert-Butyl) 3-methyl 3-(7-bromo-2,6-dichloro-8-fluoro-3-nitroquinolin-4-yl)piperidine-1,3-dicarboxylate in Step 2. LC-MS calculated for $C_{27}H_{33}BrClFN_5O_6$ (M+H)$^+$: m/z=656.1, 658.1; found 656.1, 658.0.

Step 3. tert-butyl 7'-bromo-8'-chloro-4'-(3-(dimethylamino)azetidin-1-yl)-6'-fluoro-2'-oxo-2',3'-dihydro-5-azaspiro[bicyclo[2.2.1]heptane-2,1'-pyrrolo[2,3-c]quinoline]-5-carboxylate

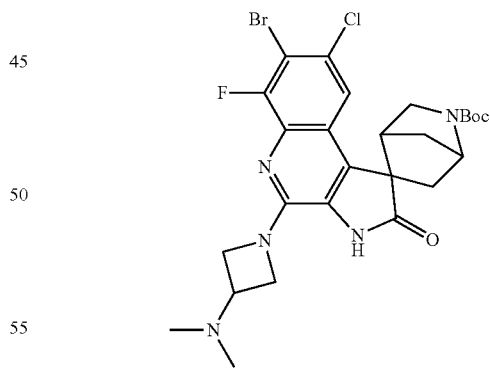

This compound was prepared using similar procedures as described for Example 19a and 19b, with 2-(tert-butyl) 5-methyl 5-(7-bromo-6-chloro-2-(3-(dimethylamino)azetidin-1-yl)-8-fluoro-3-nitroquinolin-4-yl)-2-azabicyclo[2.2.1]heptane-2,5-dicarboxylate replacing 1-(tert-butyl) 3-methyl 3-(7-bromo-6-chloro-2-(3-(dimethylamino)azetidin-1-yl)-8-fluoro-3-nitroquinolin-4-yl)piperidine-1,3-dicarboxylate in Step 3. LC-MS calculated for $C_{26}H_{31}BrClFN_5O_3$ (M+H)$^+$: m/z=594.1, 596.1; found 594.1, 596.1.

Step 4. 8'-chloro-4'-(3-(dimethylamino)azetidin-1-yl)-6'-fluoro-7'-(3-hydroxynaphthalen-1-yl)-5-azaspiro[bicyclo[2.2.1]heptane-2,1'-pyrrolo[2,3-c]quinolin]-2'(3'H)-one A mixture of tert-butyl 7'-bromo-8'-chloro-4'-(3-(dimethylamino)azetidin-1-yl)-6'-fluoro-2'-oxo-2',3'-dihydro-5-azaspiro[bicyclo[2.2.1]heptane-2,1'-pyrrolo[2,3-c]quinoline]-5-carboxylate (0.059 g, 0.099 mmol), 4-(4,4,5,5-tetramethyl-1,3,2-dioxaborolan-2-yl)naphthalen-2-ol (0.040 g, 0.149 mmol), potassium phosphate (0.084 g, 0.397 mmol) and Pd(PPh$_3$)$_4$ (0.022 mg, 0.020 mmol) was evacuated under vacuum and refilled with nitrogen (repeated three times). After addition of degassed 1,4-dioxane (0.5 ml) and water (0.05 ml), the reaction mixture was stirred at 100° C. for 2 h. The reaction mixture was cooled to room temperature, filtered through a pad of silica, washed with MeCN and evaporated. To the residue, DCM (1.0 ml) and TFA (1.2 ml, 15.5 mmol) were added. After stirring for 30 min at room temperature, the volatiles were removed under reduced pressure. The residue was dissolved in MeCN, filtered and purified by prep-HPLC (pH=2, acetonitrile/water+TFA) to give the desired products as TFA salt.

Example 21a. Diastereomer 1. Peak 1. LC-MS calculated for C$_{31}$H$_{30}$ClFN$_5$O$_2$ (M+H)$^+$: m/z=558.2; found 558.2.

Example 21b. Diastereomer 2. Peak 2. LC-MS calculated for C$_{31}$H$_{30}$ClFN$_5$O$_2$ (M+H)$^+$: m/z=558.2; found 558.2.

Example 22. 3-amino-8'-chloro-4'-(3-(dimethylamino)azetidin-1-yl)-6'-fluoro-7'-(3-hydroxynaphthalen-1-yl)spiro[cyclobutane-1,1'-pyrrolo[2,3-c]quinolin]-2'(3'H)-one

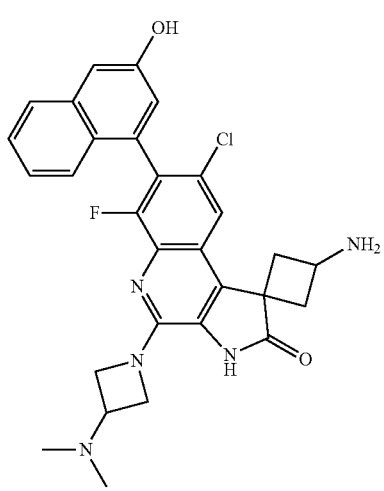 [SMILES: CN(C)C1CN(c2nc3c(F)c(-c4cc(O)cc5ccccc45)c(Cl)cc3c3c2NC(=O)C32CC(N)C2)C1]

Step 1. methyl 1-(7-bromo-2,6-dichloro-8-fluoro-3-nitroquinolin-4-yl)-3-((tert-butoxycarbonyl)amino)cyclobutane-1-carboxylate

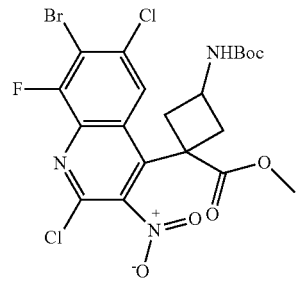

This compound was prepared using similar procedures as described for Example 19a and 19b, with methyl 3-((tert-butoxycarbonyl)amino)cyclobutane-1-carboxylate replacing 1-(tert-butyl) 3-methyl piperidine-1,3-dicarboxylate in Step 1.

Step 2. methyl 1-(7-bromo-6-chloro-2-(3-(dimethylamino)azetidin-1-yl)-8-fluoro-3-nitroquinolin-4-yl)-3-((tert-butoxycarbonyl)amino)cyclobutane-1-carboxylate

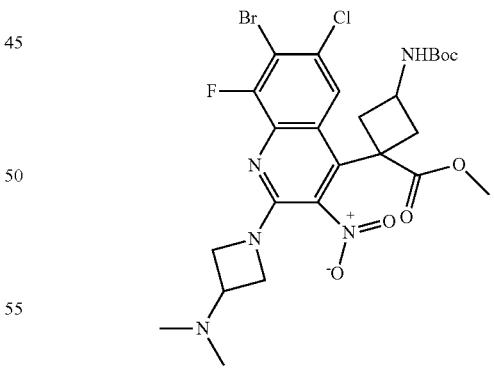

This compound was prepared using similar procedures as described for Example 19a and 19b, with methyl 1-(7-bromo-2,6-dichloro-8-fluoro-3-nitroquinolin-4-yl)-3-((tert-butoxycarbonyl)amino)cyclobutane-1-carboxylate replacing 1-(tert-Butyl) 3-methyl 3-(7-bromo-2,6-dichloro-8-fluoro-3-nitroquinolin-4-yl)piperidine-1,3-dicarboxylate in Step 2. LC-MS calculated for C$_{25}$H$_{31}$BrClFN$_5$O$_6$ (M+H)$^+$: m/z=630.1, 632.1; found 630.1, 632.1.

Step 3. tert-butyl (7'-bromo-8'-chloro-4'-(3-(dimethylamino)azetidin-1-yl)-6'-fluoro-2'-oxo-2',3'-dihydrospiro[cyclobutane-1,1'-pyrrolo[2,3-c]quinolin]-3-yl)carbamate

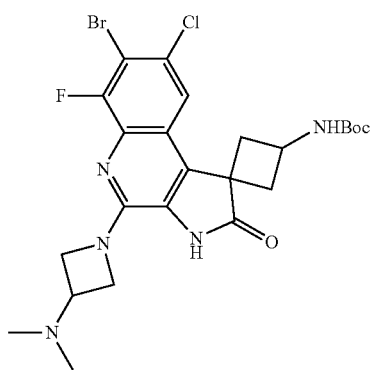 [SMILES: CN(C)C1CN(c2nc3c(F)c(Br)c(Cl)cc3c3c2NC(=O)C32CC(NC(=O)OC(C)(C)C)C2)C1]

This compound was prepared using similar procedures as described for Example 19a and 19b, with methyl 1-(7-bromo-6-chloro-2-(3-(dimethylamino)azetidin-1-yl)-8-fluoro-3-nitroquinolin-4-yl)-3-((tert-butoxycarbonyl)amino)cyclobutane-1-carboxylate replacing 1-(tert-butyl) 3-methyl 3-(7-bromo-6-chloro-2-(3-(dimethylamino)azetidin-1-yl)-8-fluoro-3-nitroquinolin-4-yl)piperidine-1,3-dicarboxylate in Step 3. LC-MS calculated for $C_{24}H_{29}BrClFN_5O_3$ $(M+H)^+$: m/z=568.1, 570.1; found 568.2, 570.3.

Step 4. 3-amino-8'-chloro-4'-(3-(dimethylamino)azetidin-1-yl)-6'-fluoro-7'-(3-hydroxynaphthalen-1-yl)spiro[cyclobutane-1,1'-pyrrolo[2,3-c]quinolin]-2'(3'H)-one This compound was prepared using similar procedures as described for Example 19a and 19b, with tert-butyl (7'-bromo-8'-chloro-4'-(3-(dimethylamino)azetidin-1-yl)-6'-fluoro-2'-oxo-2',3'-dihydrospiro[cyclobutane-1,1'-pyrrolo[2,3-c]quinolin]-3-yl)carbamate replacing tert-butyl 7'-bromo-8'-chloro-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate in Step 4. The residue was dissolved in MeCN, filtered and purified by prep-HPLC (pH=2, acetonitrile/water+TFA) to give the desired product as TFA salt. LC-MS calculated for $C_{29}H_{28}ClFN_5O_2$ $(M+H)^+$: m/z=532.2; found 532.2.

Example 23a and Example 23b. 4-(4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)butanenitrile

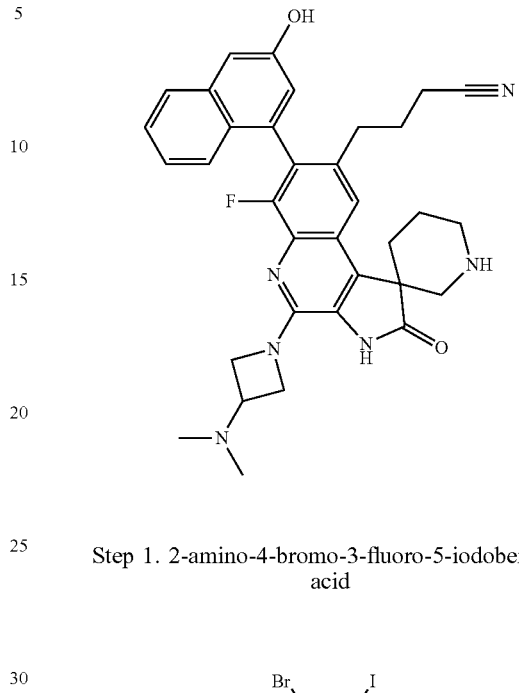

Step 1. 2-amino-4-bromo-3-fluoro-5-iodobenzoic acid

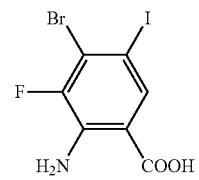

1-iodopyrrolidine-2,5-dione (21.5 g, 95.0 mmol) was added to a DMF (200 ml) solution of 2-amino-4-bromo-3-fluorobenzoic acid (20.3 g, 87.0 mmol)) and then the reaction was stirred at 80° C. for 3 h. The mixture was cooled with ice water and then water (500 mL) was added, the precipitation was filtered and washed with water, dried under reduced pressure to provide the desired product as a solid.

Step 2. 7-bromo-8-fluoro-6-iodo-2H-benzo[d][1,3]oxazine-2,4(1H)-dione

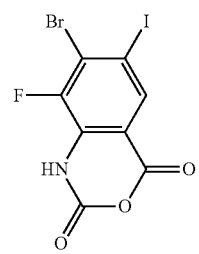

Triphosgene (11.5 g, 38.9 mmol) was added to a dioxane (200 ml) solution of 2-amino-4-bromo-3-fluoro-5-iodobenzoic acid (28.0 g, 78.0 mmol) and then the reaction was stirred at 80° C. for 2 h. The reaction mixture was cooled with ice water and then filtered. The solid was washed with ethyl acetate to provide the desired product as a solid.

Step 3.
7-bromo-8-fluoro-6-iodo-3-nitroquinoline-2,4-diol

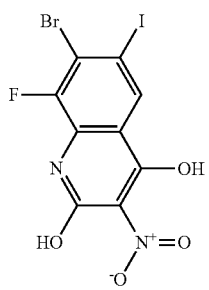

N,N-Diisopropyl ethylamine (17.1 ml, 98.0 mmol) was added to a toluene (200 ml) solution of ethyl 2-nitroacetate (10.9 ml, 98.0 mmol) and 7-bromo-8-fluoro-6-iodo-2H-benzo[d][1,3]oxazine-2,4(1H)-dione (19.0 g, 49.0 mmol) and then the reaction was stirred at 95° C. for 3 h. The reaction mixture was cooled with ice water and then filtered. The solid was washed with hexanes to provide the desired product as a solid. LC-MS calculated for $C_9H_4BrFIN_2O_4$ (M+H)$^+$: m/z=428.8, 430.8; found 429.0, 431.0.

Step 4. 7-bromo-2,4-dichloro-8-fluoro-6-iodo-3-nitroquinoline

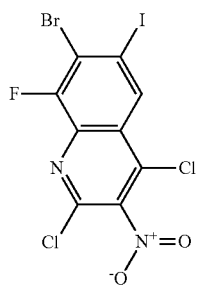

N,N-Diisopropyl ethylamine (4.9 ml, 28.0 mmol) was added to a mixture of 7-bromo-8-fluoro-6-iodo-3-nitroquinoline-2,4-diol (6.00 g, 14.0 mmol) in phosphorus oxychloride (6.5 ml, 70.0 mmol) and then the reaction was stirred at 100° C. for 2 h. The solvent was removed under reduced pressure and then azeotroped with toluene 3 times. The residue was purified with column chromatography (DCM) to give the desired product as a solid.

Step 5. 1-(tert-butyl) 3-methyl 3-(7-bromo-2-chloro-8-fluoro-6-iodo-3-nitroquinolin-4-yl)piperidine-1,3-dicarboxylate

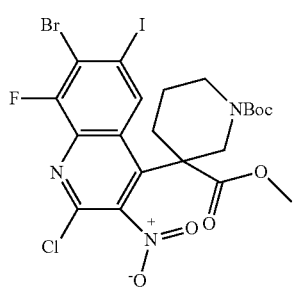

This compound was prepared using similar procedures as described for Example 19a and 19b, with 7-bromo-2,4-dichloro-8-fluoro-6-iodo-3-nitroquinoline replacing 7-Bromo-2,4,6-trichloro-8-fluoro-3-nitroquinoline in Step 1.

Step 6. 1-(tert-butyl) 3-methyl 3-(7-bromo-2-(3-(dimethylamino)azetidin-1-yl)-8-fluoro-6-iodo-3-nitroquinolin-4-yl)piperidine-1,3-dicarboxylate

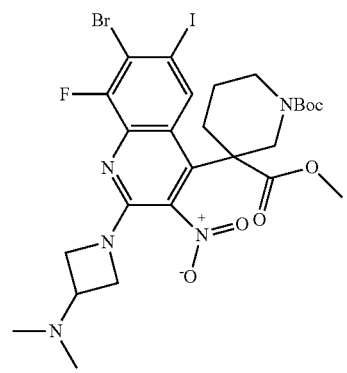

This compound was prepared using similar procedures as described for Example 19a and 19b, with 1-(tert-butyl) 3-methyl 3-(7-bromo-2-chloro-8-fluoro-6-iodo-3-nitroquinolin-4-yl)piperidine-1,3-dicarboxylate replacing 1-(tert-butyl) 3-methyl 3-(7-bromo-2,6-dichloro-8-fluoro-3-nitroquinolin-4-yl)piperidine-1,3-dicarboxylate in Step 2. LC-MS calculated for $C_{26}H_{33}BrFIN_5O_6$ (M+H)$^+$: m/z=736.1, 738.1; found 736.1, 738.0.

Step 7. tert-butyl 7'-bromo-4'-(3-(dimethylamino)azetidin-1-yl)-6'-fluoro-8'-iodo-2'-oxo-2',3'-dihydrospiro[piperidine-3,1'-pyrrolo[2,3-c]quinoline]-1-carboxylate

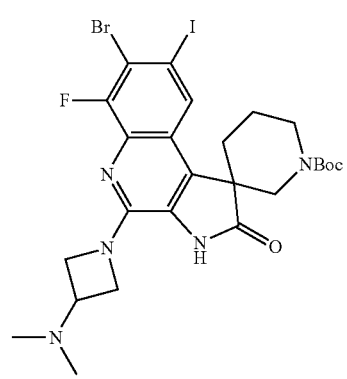 [SMILES: CN(C)C1CN(c2nc3c(F)c(Br)c(I)cc3c3c2NC(=O)C32CCCN(C(=O)OC(C)(C)C)C2)C1]

This compound was prepared using similar procedures as described for Example 19a and 19b, with 1-(tert-butyl) 3-methyl 3-(7-bromo-2-(3-(dimethylamino)azetidin-1-yl)-8-fluoro-6-iodo-3-nitroquinolin-4-yl)piperidine-1,3-dicarboxylate replacing 1-(tert-butyl) 3-methyl 3-(7-bromo-6-chloro-2-(3-(dimethylamino)azetidin-1-yl)-8-fluoro-3-nitroquinolin-4-yl)piperidine-1,3-dicarboxylate in Step 3. LC-MS calculated for $C_{25}H_{31}BrFIN_5O_3$ (M+H)$^+$: m/z=674.1, 676.1; found 674.1, 676.0.

Step 8. tert-butyl 7'-bromo-8'-(3-cyanopropyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate

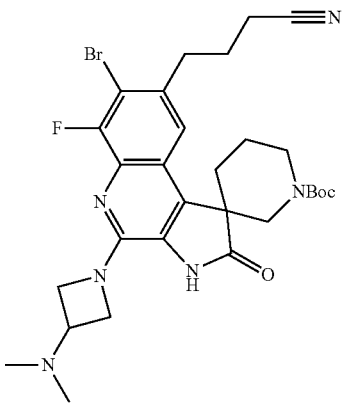 [SMILES: CN(C)C1CN(c2nc3c(F)c(Br)c(CCCC#N)cc3c3c2NC(=O)C32CCCN(C(=O)OC(C)(C)C)C2)C1]

A mixture of tert-butyl 7'-bromo-4'-(3-(dimethylamino)azetidin-1-yl)-6'-fluoro-8'-iodo-2'-oxo-2',3'-dihydrospiro[piperidine-3,1'-pyrrolo[2,3-c]quinoline]-1-carboxylate (0.133 g, 0.197 mmol) and bis(triphenylphosphine)palladium dichloride (0.014 g, 0.020 mmol) was evacuated under vacuum and refilled with nitrogen (repeated three times). After addition of a 0.5 M THF solution of (3-cyanopropyl) zinc bromide (2.0 ml, 0.986 mmol), the reaction mixture was stirred at 50° C. for 30 min. After cooling to room temperature, the mixture was quenched with saturated aqueous NH$_4$Cl, diluted with EtOAc and separated. The aqueous layer was extracted with EtOAc and the combined organic layer was washed with brine, dried over Na$_2$SO$_4$, filtered and evaporated. The residue was purified with column chromatography (0-20% MeOH in DCM) to give the desired product. LC-MS calculated for C$_{29}$H$_{37}$BrFN$_6$O$_3$ (M+H)$^+$: m/z=615.2, 617.2; found 615.2, 617.2.

Step 9. 4-(4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)butanenitrile This compound was prepared using similar procedures as described for Example 21a and 21b, with tert-butyl 7'-bromo-8'-(3-cyanopropyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate replacing tert-butyl 7'-bromo-8'-chloro-4'-(3-(dimethylamino)azetidin-1-yl)-6'-fluoro-2'-oxo-2',3'-dihydro-5-azaspiro[bicyclo[2.2.1]heptane-2,1'-pyrrolo[2,3-c]quinoline]-5-carboxylate in Step 4. The residue was dissolved in MeCN, filtered and purified by prep-HPLC (pH=2, acetonitrile/water+TFA) to give the desired product as TFA salt.

Example 23a. Diastereomer 1. Peak 1. LC-MS calculated for C$_{34}$H$_{36}$FN$_6$O$_2$ (M+H)$^+$: m/z=579.3; found 579.3.

Example 23b. Diastereomer 2. Peak 2. LC-MS calculated for C$_{34}$H$_{36}$FN$_6$O$_2$ (M+H)$^+$: m/z=579.3; found 579.3.

Example 24a and Example 24b. 2-(4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)acetonitrile

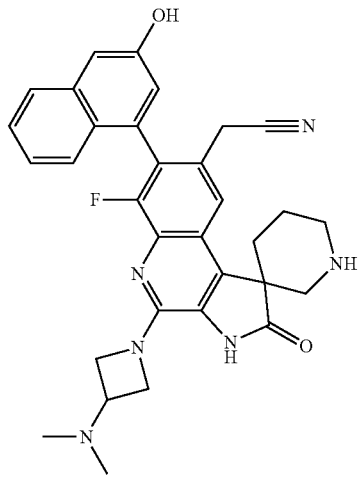 [SMILES: CN(C)C1CN(c2nc3c(F)c(-c4cc(O)cc5ccccc45)c(CC#N)cc3c3c2NC(=O)C32CCCNC2)C1]

Step 1. tert-butyl 7'-bromo-8'-(cyanomethyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate

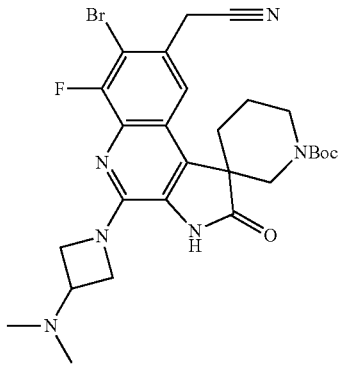 [SMILES: CN(C)C1CN(c2nc3c(F)c(Br)c(CC#N)cc3c3c2NC(=O)C32CCCN(C(=O)OC(C)(C)C)C2)C1]

A mixture of tert-butyl 7'-bromo-4'-(3-(dimethylamino)azetidin-1-yl)-6'-fluoro-8'-iodo-2'-oxo-2',3'-dihydrospiro[piperidine-3,1'-pyrrolo[2,3-c]quinoline]-1-carboxylate (Example 23a and 23b, Step 7, 0.100 g, 0.148 mmol), 4-(4,4,5,5-tetramethyl-1,3,2-dioxaborolan-2-yl)isoxazole (0.032 g, 0.163 mmol), potassium phosphate (0.126 g, 0.593 mmol) and Pd(PPh$_3$)$_4$ (0.017 mg, 0.015 mmol) was evacuated under vacuum and refilled with nitrogen (repeated three times). After addition of degassed 1,4-dioxane (0.7 ml) and water (0.07 ml), the reaction mixture was stirred at 100° C. for 2 h. After cooling to room temperature, the mixture was added water, diluted with DCM and separated. The aqueous layer was extracted with DCM and the combined organic layer was washed with water, dried over Na$_2$SO$_4$, filtered and evaporated. The residue was purified with column chromatography (0-20% MeOH in DCM) to give the desired product. LC-MS calculated for C$_{27}$H$_{33}$BrFN$_6$O$_3$ (M+H)$^+$: m/z=587.2, 589.2; found 587.1, 589.2.

Step 2. 2-(4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)acetonitrile This compound was prepared using similar procedures as described for Example 21a and 21b, with tert-butyl 7'-bromo-8'-(cyanomethyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate replacing tert-butyl 7'-bromo-8'-chloro-4'-(3-(dimethylamino)azetidin-1-yl)-6'-fluoro-2'-oxo-2',3'-dihydro-5-azaspiro[bicyclo[2.2.1]heptane-2,1'-pyrrolo[2,3-c]quinoline]-5-carboxylate in Step 4. The residue was dissolved in MeCN, filtered and purified by prep-HPLC (pH=2, acetonitrile/water+TFA) to give the desired products as TFA salt.

Example 24a. Diastereomer 1. Peak 1. LC-MS calculated for $C_{32}H_{32}FN_6O_2$ (M+H)$^+$: m/z=551.3; found 551.3.

Example 24b. Diastereomer 2. Peak 2. LC-MS calculated for $C_{32}H_{32}FN_6O_2$ (M+H)$^+$: m/z=551.3; found 551.3.

Example 25a and Example 25b. 3-(4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)propanenitrile

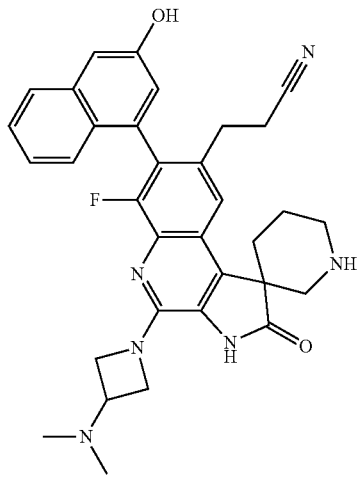 [SMILES: CN(C)C1CN(c2nc3c(F)c(-c4cc(O)cc5ccccc45)c(CCC#N)cc3c3c2NC(=O)C32CCCNC2)C1]

Step 1. tert-butyl (E)-7'-bromo-8'-(2-cyanovinyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate

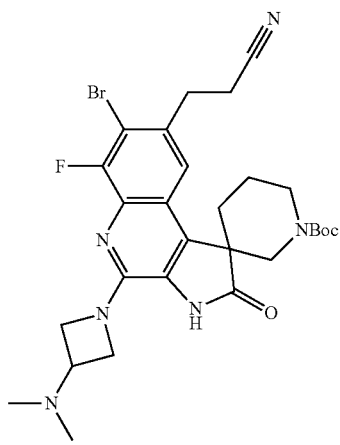 [SMILES: CN(C)C1CN(c2nc3c(F)c(Br)c(CCC#N)cc3c3c2NC(=O)C32CCCN(C(=O)OC(C)(C)C)C2)C1]

A mixture of tert-butyl 7'-bromo-4'-(3-(dimethylamino)azetidin-1-yl)-6'-fluoro-8'-iodo-2'-oxo-2',3'-dihydrospiro[piperidine-3,1'-pyrrolo[2,3-c]quinoline]-1-carboxylate (Example 23a and 23b, Step 7, 0.150 g, 0.222 mmol), palladium acetate (0.005 g, 0.022 mmol), tri-o-tolylphosphane (0.014 g, 0.044 mmol) was evacuated under vacuum and refilled with nitrogen (repeated three times). After addition of degassed DMF (1.1 ml), triethylamine (0.046 ml, 0.334 mmol) and acrylonitrile (0.029 ml, 0.445 mmol), the reaction mixture was stirred at 80° C. for 3 h. After cooling to room temperature, the mixture was added water, diluted with DCM and separated. The aqueous layer was extracted with DCM and the combined organic layer was washed with water, dried over $Na_2SO_4$, filtered and evaporated. The residue was purified with column chromatography (0-20% MeOH in DCM) to give the desired product. LC-MS calculated for $C_{28}H_{33}BrFN_6O_3$ (M+H)$^+$: m/z=599.2, 601.2; found 599.1, 601.2.

Step 2. tert-butyl (E)-8'-(2-cyanovinyl)-4'-(3-(dimethylamino)azetidin-1-yl)-6'-fluoro-7'-(3-(methoxymethoxy)naphthalen-1-yl)-2'-oxo-2',3'-dihydrospiro[piperidine-3,1'-pyrrolo[2,3-c]quinoline]-1-carboxylate

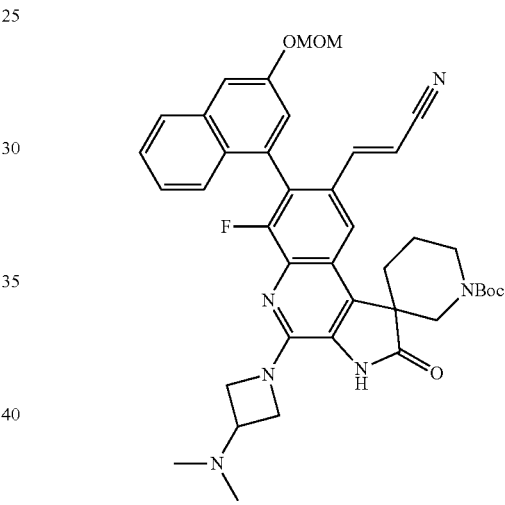

A mixture of tert-butyl (E)-7'-bromo-8'-(2-cyanovinyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate (0.120 g, 0.200 mmol), 2-(3-(methoxymethoxy)naphthalen-1-yl)-4,4,5,5-tetramethyl-1,3,2-dioxaborolane (0.079 g, 0.250 mmol), potassium phosphate (0.170 g, 0.800 mmol) and Pd(PPh$_3$)$_4$ (0.035 g, 0.030 mmol) was evacuated under vacuum and refilled with nitrogen (repeated three times). After addition of degassed 1,4-dioxane (0.9 ml) and water (0.09 ml), the reaction mixture was stirred at 100° C. for 2 h. The reaction mixture was cooled to room temperature, filtered through a pad of silica, washed with MeCN and evaporated. The residue was purified with column chromatography (0-20% MeOH in DCM) to give the desired product. LC-MS calculated for $C_{40}H_{44}FN_6O_5$ (M+H)$^+$: m/z=707.3; found 707.3.

Step 3. 3-(4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)propanenitrile To an anhydrous THF solution of tert-butyl (E)-8'-(2-cyanovinyl)-4'-(3-(dimethylamino)azetidin-1-yl)-6'-fluoro- 7'-(3-(methoxymethoxy)naphthalen-1-yl)-2'-oxo-2',3'-dihydrospiro[piperidine-3,1'-pyrrolo[2,3-c]quinoline]-1-carboxylate (0.100 g, 0.141 mmol) cooled to 0° C. was added 1.0 M THF solution of lithium triethylborohydride (0.85 ml, 0.850 mmol). After stirring for 30 min, the reaction was quenched with saturated aqueous NH₄Cl, diluted with EtOAc and separated. The aqueous layer was extracted with EtOAc and the combined organic layer was washed with brine, dried over Na₂SO₄, filtered and evaporated. To the residue, DCM (1.0 ml) and TFA (1.2 ml, 15.5 mmol) were added. After stirring for 30 min at room temperature, water (0.2 ml) was added and the reaction stirred for another 10 min. Then the volatiles were removed under reduced pressure. The residue was dissolved in MeCN, filtered and purified by prep-HPLC (pH=2, acetonitrile/water+TFA) to give the desired products as TFA salt.

Example 25a. Diastereomer 1. Peak 1. LC-MS calculated for $C_{33}H_{34}FN_6O_2$ (M+H)⁺: m/z=565.3; found 565.3.

Example 25b. Diastereomer 2. Peak 2. LC-MS calculated for $C_{33}H_{34}FN_6O_2$ (M+H)⁺: m/z=565.3; found 565.3.

Example 26a and Example 26b. 8'-(2-chlorobenzyl)-4'-(3-(dimethylamino)azetidin-1-yl)-6'-fluoro-7'-(3-hydroxynaphthalen-1-yl)spiro[piperidine-3,1'-pyrrolo[2,3-c]quinolin]-2'(3'H)-one

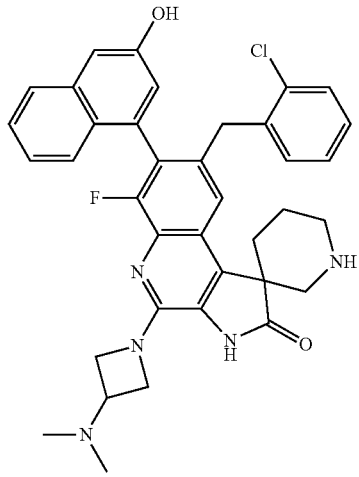 [SMILES: CN(C)C1CN(c2nc3c(F)c(-c4cc(O)cc5ccccc45)c(Cc4ccccc4Cl)cc3c3c2NC(=O)C32CCCNC2)C1]

Step 1. tert-butyl 7'-bromo-8'-(2-chlorobenzyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate

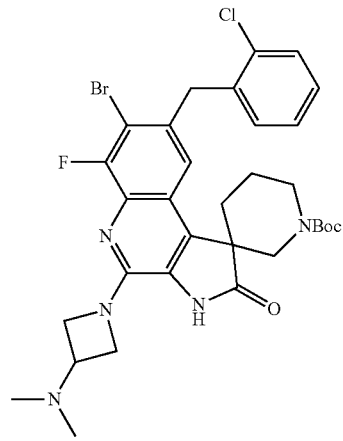 [SMILES: CN(C)C1CN(c2nc3c(F)c(Br)c(Cc4ccccc4Cl)cc3c3c2NC(=O)C32CCCN(C(=O)OC(C)(C)C)C2)C1]

This compound was prepared using similar procedures as described for Example 23a and 23b, with (2-chlorobenzyl)zinc chloride replacing (3-cyanopropyl)zinc bromide in Step 8. LC-MS calculated for $C_{32}H_{37}BrClFN_5O_3$ (M+H)⁺: m/z=672.2, 674.2; found 672.2, 674.2.

Step 2. 8'-(2-chlorobenzyl)-4'-(3-(dimethylamino)azetidin-1-yl)-6'-fluoro-7'-(3-hydroxynaphthalen-1-yl)spiro[piperidine-3,1'-pyrrolo[2,3-c]quinolin]-2'(3'H)-one This compound was prepared using similar procedures as described for Example 21a and 21b, with tert-butyl 7'-bromo-8'-(2-chlorobenzyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate replacing tert-butyl 7'-bromo-8'-chloro-4'-(3-(dimethylamino)azetidin-1-yl)-6'-fluoro-2'-oxo-2',3'-dihydro-5-azaspiro[bicyclo[2.2.1]heptane-2,1'-pyrrolo[2,3-c]quinoline]-5-carboxylate in Step 4. The residue was dissolved in MeCN, filtered and purified by prep-HPLC (pH=2, acetonitrile/water+TFA) to give the desired products as TFA salt.

Example 26a. Diastereomer 1. Peak 1. LC-MS calculated for $C_{37}H_{36}ClFN_5O_2$ (M+H)⁺: m/z=636.3; found 636.3.

Example 26b. Diastereomer 2. Peak 2. LC-MS calculated for $C_{37}H_{36}ClFN_5O_2$ (M+H)⁺: m/z=636.3; found 636.3.

Example 27a and Example 27b. 2-((4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)methyl)benzonitrile

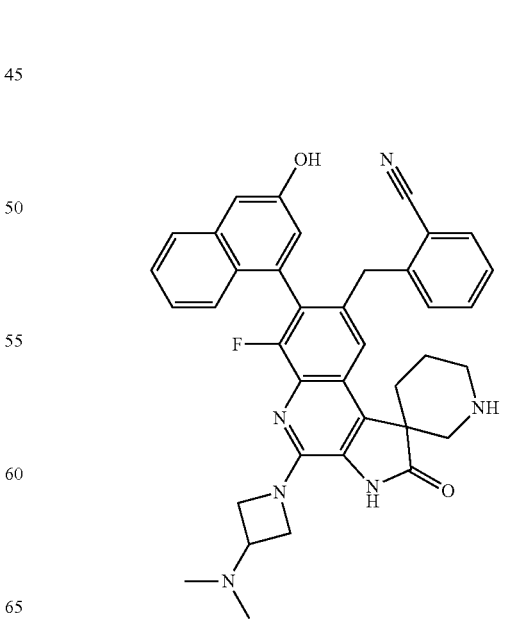

Step 1. tert-butyl 7'-bromo-8'-(2-cyanobenzyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate

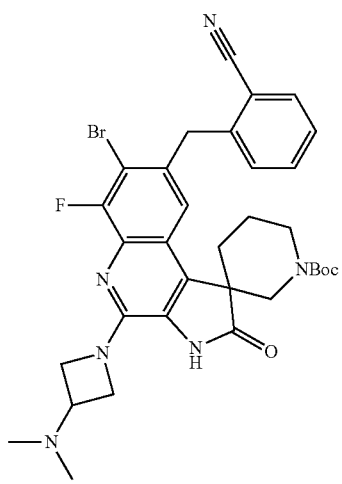 [SMILES: CN(C)C1CN(c2nc3c(F)c(Br)c(Cc4ccccc4C#N)cc3c3c2NC(=O)C32CCCN(C(=O)OC(C)(C)C)C2)C1]

This compound was prepared using similar procedures as described for Example 23a and 23b, with (2-cyanobenzyl)zinc bromide replacing (3-cyanopropyl)zinc bromide in Step 8. LC-MS calculated for $C_{33}H_{37}BrFN_6O_3$ (M+H)$^+$: m/z=663.2, 665.2; found 663.2, 665.2.

Step 2. 2-((4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)methyl)benzonitrile This compound was prepared using similar procedures as described for Example 21a and 21b, with tert-butyl 7'-bromo-8'-(2-cyanobenzyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate replacing tert-butyl 7'-bromo-8'-chloro-4'-(3-(dimethylamino)azetidin-1-yl)-6'-fluoro-2'-oxo-2',3'-dihydro-5-azaspiro[bicyclo[2.2.1]heptane-2,1'-pyrrolo[2,3-c]quinoline]-5-carboxylate in Step 4. The residue was dissolved in MeCN, filtered and purified by prep-HPLC (pH=2, acetonitrile/water+TFA) to give the desired products as TFA salt.

Example 27a. Diastereomer 1. Peak 1. LC-MS calculated for $C_{38}H_{36}FN_6O_2$ (M+H)$^+$: m/z=627.3; found 627.1.

Example 27b. Diastereomer 2. Peak 2. LC-MS calculated for $C_{38}H_{36}FN_6O_2$ (M+H)$^+$: m/z=627.3; found 627.1.

Example 28a and Example 28b. 4-(4'-(3-(dimethylamino)azetidin-1-yl)-6'-fluoro-7'-(3-hydroxynaphthalen-1-yl)-2',3'-dihydrospiro[piperidine-3,1'-pyrrolo[2,3-c]quinolin]-8'-yl)butanenitrile

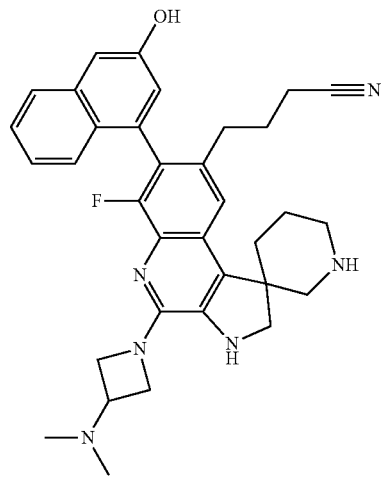 [SMILES: CN(C)C1CN(c2nc3c(F)c(-c4cc(O)cc5ccccc45)c(CCCC#N)cc3c3c2NCC32CCCNC2)C1]

Step 1. tert-butyl 8'-(3-cyanopropyl)-4'-(3-(dimethylamino)azetidin-1-yl)-6'-fluoro-7'-(3-(methoxymethoxy)naphthalen-1-yl)-2'-oxo-2',3'-dihydrospiro[piperidine-3,1'-pyrrolo[2,3-c]quinoline]-1-carboxylate

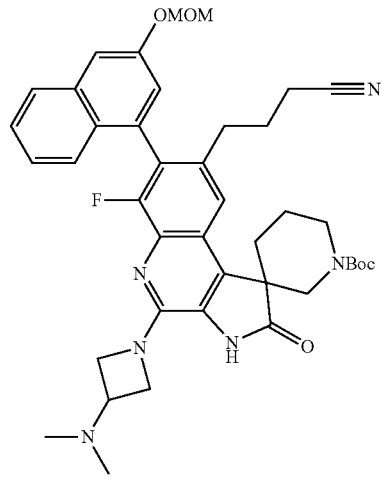

A mixture of tert-butyl 7'-bromo-8'-(3-cyanopropyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate (Example 23a and 23b, Step 8, 0.310 g, 0.504 mmol), 2-(3-(methoxymethoxy)naphthalen-1-yl)-4,4,5,5-tetramethyl-1,3,2-dioxaborolane (0198 g, 0.630 mmol), potassium phosphate (0.428 g, 2.01 mmol) and Pd(PPh$_3$)$_4$ (0.087 g, 0.076 mmol) was evacuated under vacuum and refilled with nitrogen (repeated three times). After addition of degassed 1,4-dioxane (2.3 ml) and water (0.23 ml), the reaction mixture was stirred at 100° C. for 2 h. The reaction mixture was cooled to room temperature, filtered through a pad of silica, washed with MeCN and evaporated. The residue was purified with column chromatography (0-20% MeOH in DCM) to give the desired product. LC-MS calculated for $C_{41}H_{48}FN_6O_5$ (M+H)$^+$: m/z=723.4; found 723.3.

Step 2. di-tert-butyl 8'-(3-cyanopropyl)-4'-(3-(dimethylamino)azetidin-1-yl)-6'-fluoro-7'-(3-(methoxymethoxy)naphthalen-1-yl)-2'-oxospiro[piperidine-3,1'-pyrrolo[2,3-c]quinoline]-1,3'(2'H)-dicarboxylate

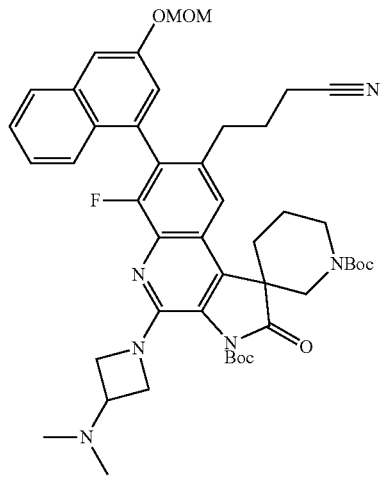

To a THF solution of tert-butyl 8'-(3-cyanopropyl)-4'-(3-(dimethylamino)azetidin-1-yl)-6'-fluoro-7'-(3-(methoxymethoxy)naphthalen-1-yl)-2'-oxo-2',3'-dihydrospiro[piperidine-3,1'-pyrrolo[2,3-c]quinoline]-1-carboxylate (0.270 g, 0.374 mmol) was added di-tert-butyl carbonate (0.13 ml, 0.560 mmol), triethylamine (0.15 ml, 1.12 mmol) and N,N-dimethylpyridin-4-amine (0.005 g, 0.037 mmol). The reaction was stirred for 1 h, diluted with EtOAc, washed with water, dried over $Na_2SO_4$, filtered and evaporated. The resulting yellow solids were used without further purification for the next step. LC-MS calculated for $C_{46}H_{56}FN_6O_7$ (M+H)$^+$: m/z=823.4; found 823.3.

Step 3. di-tert-butyl 8'-(3-cyanopropyl)-4'-(3-(dimethylamino)azetidin-1-yl)-6'-fluoro-2'-hydroxy-7'-(3-(methoxymethoxy)naphthalen-1-yl)spiro[piperidine-3,1'-pyrrolo[2,3-c]quinoline]-1,3'(2'H)-dicarboxylate

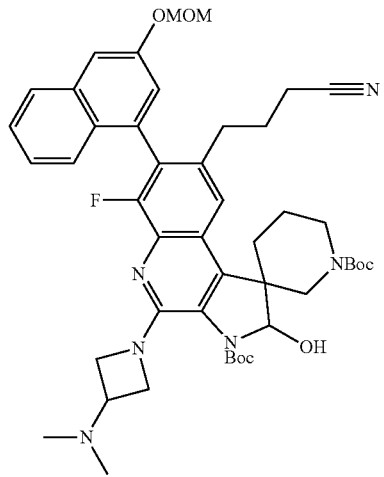

To a MeOH solution containing di-tert-butyl 8'-(3-cyanopropyl)-4'-(3-(dimethylamino)azetidin-1-yl)-6'-fluoro-7'-(3-(methoxymethoxy)naphthalen-1-yl)-2'-oxospiro[piperidine-3,1'-pyrrolo[2,3-c]quinoline]-1,3'(2'H)-dicarboxylate (0.080 g, 0.097 mmol) cooled to 0° C. was added sodium borohydride (0.018 g, 0.486 mmol) in batches. After stirring for 15 min, the reaction was quenched with saturated aqueous $NH_4Cl$, diluted with EtOAc and separated. The aqueous layer was extracted with EtOAc and the combined organic layer was washed with brine, dried over $Na_2SO_4$, filtered and evaporated. The residue was purified with column chromatography (0-20% MeOH in DCM) to give the desired product. LC-MS calculated for $C_{46}H_{58}FN_6O_7$ (M+H)$^+$: m/z=825.4; found 825.6.

Step 4. 4-(4'-(3-(dimethylamino)azetidin-1-yl)-6'-fluoro-7'-(3-hydroxynaphthalen-1-yl)-2',3'-dihydrospiro[piperidine-3,1'-pyrrolo[2,3-c]quinolin]-8'-yl)butanenitrile To a 1,4-dioxane solution containing di-tert-butyl 8'-(3-cyanopropyl)-4'-(3-(dimethylamino)azetidin-1-yl)-6'-fluoro-2'-hydroxy-7'-(3-(methoxymethoxy)naphthalen-1-yl) spiro[piperidine-3,1'-pyrrolo[2,3-c]quinoline]-1,3'(2'H)-dicarboxylate (0.060 g, 0.073 mmol) was added potassium phosphate (0.077 g, 0.365 mmol). After stirring at 100° C. for 16 h, the mixture was filtered through a pad of Celite, dried over $Na_2SO_4$, and evaporated. The residue was dissolved in anhydrous THF, cooled to 0° C. and added a 1.0 M THF solution of lithium triethylborohydride (0.37 ml, 0.365 mmol). After stirring for 30 min, the reaction was quenched with saturated aqueous $NH_4Cl$, diluted with EtOAc and separated. The aqueous layer was extracted with EtOAc and the combined organic layer was washed with brine, dried over $Na_2SO_4$, filtered and evaporated. To the residue, DCM (1.0 ml) and TFA (1.2 ml, 15.5 mmol) were added. After stirring for 30 min at room temperature, water (0.2 ml) was added and the reaction stirred for another 10 min. Then the volatiles were removed under reduced pressure. The residue was dissolved in MeCN, filtered and purified by prep-HPLC (pH=2, acetonitrile/water+TFA) to give the desired products as TFA salt.

Example 28a. Diastereomer 1. Peak 1. LC-MS calculated for $C_{34}H_{38}FN_6O$ (M+H)$^+$: m/z=565.3; found 565.4.

Example 28b. Diastereomer 2. Peak 2. LC-MS calculated for $C_{34}H_{38}FN_6O$ (M+H)$^+$: m/z=565.3; found 565.4. $^1$H NMR (500 MHz, DMSO) b 9.25 (br), 8.60 (br), 7.79 (d, 1H, J=8.3 Hz), 7.72 (s, 1H), 7.44-7.39 (m, 1H), 7.24 (d, 1H, J=2.2 Hz), 7.20-7.13 (m, 2H), 7.03 (d, 1H, J=2.4 Hz), 4.50-4.27 (m, 5H), 3.95-3.50 (m, 4H), 3.37 (m, 2H), 2.83 (s, 6H), 2.66-2.55 (m, 2H), 2.26 (t, 2H, J=7.2 Hz), 1.92 (m, 4H), 1.54 (m, 2H).

Example 29. 3-(4'-(3-(dimethylamino)azetidin-1-yl)-6'-fluoro-7'-(3-hydroxynaphthalen-1-yl)-2'-oxo-2',3'-dihydrospiro[azetidine-3,1'-pyrrolo[2,3-c]quinolin]-8'-yl)propanenitrile

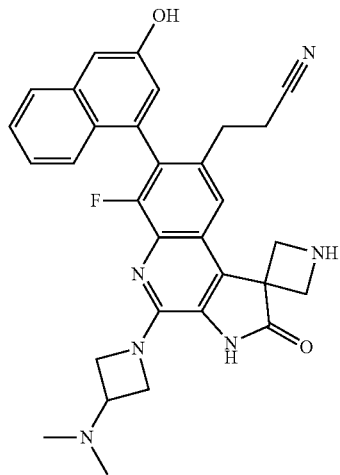 [SMILES: CN(C)C1CN(c2nc3c(F)c(-c4cc(O)cc5ccccc45)c(CCC#N)cc3c3c2NC(=O)C32CNC2)C1]

Step 1. 1-(tert-butyl) 3-methyl 3-(7-bromo-2-chloro-8-fluoro-6-iodo-3-nitroquinolin-4-yl)azetidine-1,3-dicarboxylate

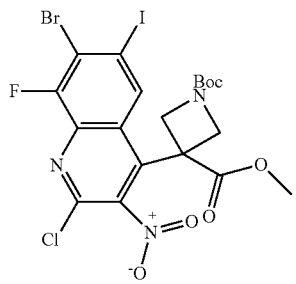

This compound was prepared using similar procedures as described for Example 23a and 23b, with 1-(tert-butyl) 3-methyl azetidine-1,3-dicarboxylate replacing 1-(tert-butyl) 3-methyl piperidine-1,3-dicarboxylate in Step 5.

Step 2. 1-(tert-butyl) 3-methyl 3-(7-bromo-2-(3-(dimethylamino)azetidin-1-yl)-8-fluoro-6-iodo-3-nitroquinolin-4-yl)azetidine-1,3-dicarboxylate

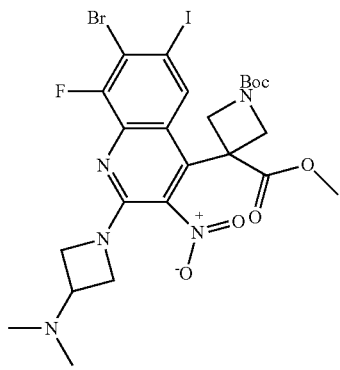

This compound was prepared using similar procedures as described for Example 23a and 23b, with 1-(tert-butyl) 3-methyl 3-(7-bromo-2-chloro-8-fluoro-6-iodo-3-nitroquinolin-4-yl)azetidine-1,3-dicarboxylate replacing 1-(tert-butyl) 3-methyl 3-(7-bromo-2-chloro-8-fluoro-6-iodo-3-nitroquinolin-4-yl)piperidine-1,3-dicarboxylate in Step 6. LC-MS calculated for $C_{24}H_{29}BrFIN_5O_6$ $(M+H)^+$: m/z=708.0, 710.0; found 708.0, 710.0.

Step 3. tert-butyl 7'-bromo-4'-(3-(dimethylamino)azetidin-1-yl)-6'-fluoro-8'-iodo-2'-oxo-2',3'-dihydrospiro[azetidine-3,1'-pyrrolo[2,3-c]quinoline]-1-carboxylate

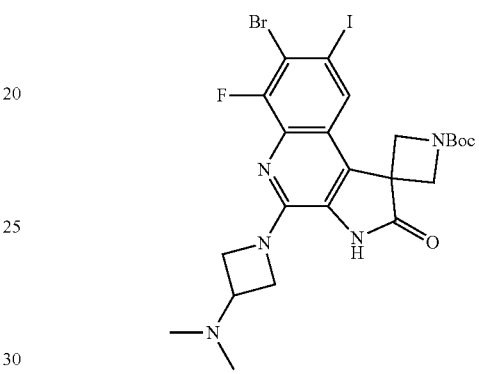

This compound was prepared using similar procedures as described for Example 23a and 23b, with 1-(tert-butyl) 3-methyl 3-(7-bromo-2-(3-(dimethylamino)azetidin-1-yl)-8-fluoro-6-iodo-3-nitroquinolin-4-yl)azetidine-1,3-dicarboxylate replacing 1-(tert-butyl) 3-methyl 3-(7-bromo-2-(3-(dimethylamino)azetidin-1-yl)-8-fluoro-6-iodo-3-nitroquinolin-4-yl)piperidine-1,3-dicarboxylate in Step 7. LC-MS calculated for $C_{23}H_{27}BrFIN_5O_3$ $(M+H)^+$: m/z=646.0, 648.0; found 646.0, 648.0.

Step 4. tert-butyl (E)-7'-bromo-8'-(2-cyanovinyl)-4'-(3-(dimethylamino)azetidin-1-yl)-6'-fluoro-2'-oxo-2',3'-dihydrospiro[azetidine-3,1'-pyrrolo[2,3-c]quinoline]-1-carboxylate

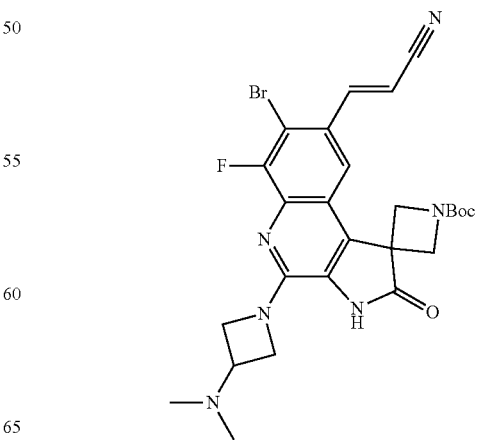

This compound was prepared using similar procedures as described for Example 25a and 25b, with tert-butyl 7'-bromo-4'-(3-(dimethylamino)azetidin-1-yl)-6'-fluoro-8'-iodo-2'-oxo-2',3'-dihydrospiro[azetidine-3,1'-pyrrolo[2,3-c]quinoline]-1-carboxylate replacing tert-butyl 7'-bromo-4'-(3-(dimethylamino)azetidin-1-yl)-6'-fluoro-8'-iodo-2'-oxo-2',3'-dihydrospiro[piperidine-3,1'-pyrrolo[2,3-c]quinoline]-1-carboxylate in Step 1. LC-MS calculated for $C_{26}H_{29}BrFN_6O_3$ (M+H)$^+$: m/z=571.1, 573.1; found 571.1, 573.1.

Step 5. tert-butyl (E)-8'-(2-cyanovinyl)-4'-(3-(dimethylamino)azetidin-1-yl)-6'-fluoro-7'-(3-(methoxymethoxy)naphthalen-1-yl)-2'-oxo-2',3'-dihydrospiro[azetidine-3,1'-pyrrolo[2,3-c]quinoline]-1-carboxylate

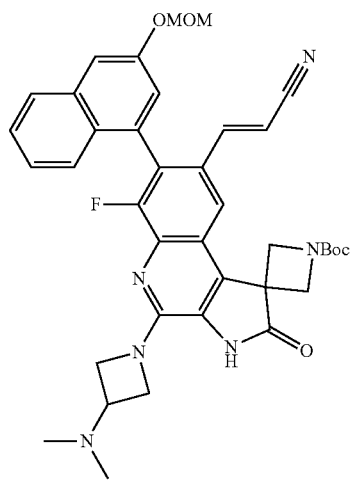

This compound was prepared using similar procedures as described for Example 25a and 25b, with tert-butyl (E)-7'-bromo-8'-(2-cyanovinyl)-4'-(3-(dimethylamino)azetidin-1-yl)-6'-fluoro-2'-oxo-2',3'-dihydrospiro[azetidine-3,1'-pyrrolo[2,3-c]quinoline]-1-carboxylate replacing tert-butyl (E)-7'-bromo-8'-(2-cyanovinyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate in Step 2. LC-MS calculated for $C_{38}H_{40}FN_6O_5$ (M+H)$^+$: m/z=679.3; found 679.3.

Step 6. 3-(4'-(3-(dimethylamino)azetidin-1-yl)-6'-fluoro-7'-(3-hydroxynaphthalen-1-yl)-2'-oxo-2',3'-dihydrospiro[azetidine-3,1'-pyrrolo[2,3-c]quinolin]-8'-yl)propanenitrile This compound was prepared using similar procedures as described for Example 25a and 25b, with tert-butyl (E)-8'-(2-cyanovinyl)-4'-(3-(dimethylamino)azetidin-1-yl)-6'-fluoro-7'-(3-(methoxymethoxy)naphthalen-1-yl)-2'-oxo-2',3'-dihydrospiro[azetidine-3,1'-pyrrolo[2,3-c]quinoline]-1-carboxylate replacing tert-butyl (E)-8'-(2-cyanovinyl)-4'-(3-(dimethylamino)azetidin-1-yl)-6'-fluoro-7'-(3-(methoxymethoxy)naphthalen-1-yl)-2'-oxo-2',3'-dihydrospiro[piperidine-3,1'-pyrrolo[2,3-c]quinoline]-1-carboxylate in Step 3. The reaction mixture was purified by prep-HPLC (pH=2, acetonitrile/water+TFA) to give the desired products as TFA salt. LC-MS calculated for $C_{31}H_{30}FN_6O_2$ (M+H)$^+$: m/z=537.2; found 537.3.

Example 30a and Example 30b. 4-(4'-(3-(dimethylamino)azetidin-1-yl)-6'-fluoro-7'-(3-hydroxynaphthalen-1-yl)-2'-oxo-2',3'-dihydrospiro[pyrrolidine-3,1'-pyrrolo[2,3-c]quinolin]-8'-yl)butanenitrile

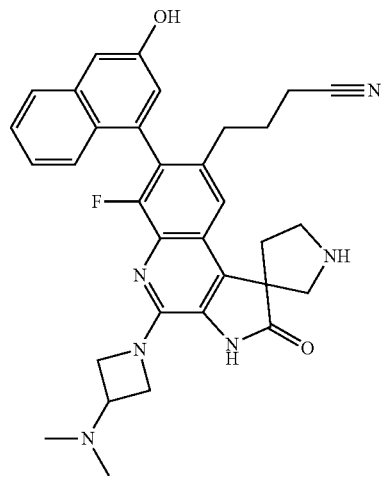 [SMILES: CN(C)C1CN(c2nc3c(F)c(-c4cc(O)cc5ccccc45)c(CCCC#N)cc3c3c2NC(=O)C32CCNC2)C1]

Step 1. 1-(tert-butyl) 3-methyl 3-(7-bromo-2-chloro-8-fluoro-6-iodo-3-nitroquinolin-4-yl)pyrrolidine-1,3-dicarboxylate

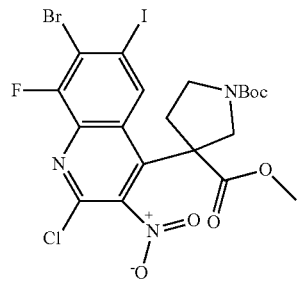

This compound was prepared using similar procedures as described for Example 23a and 23b, with 1-(tert-butyl) 3-methyl pyrrolidine-1,3-dicarboxylate replacing 1-(tert-butyl) 3-methyl piperidine-1,3-dicarboxylate in Step 5.

Step 2. 1-(tert-butyl) 3-methyl 3-(7-bromo-2-(3-(dimethylamino)azetidin-1-yl)-8-fluoro-6-iodo-3-nitroquinolin-4-yl)pyrrolidine-1,3-dicarboxylate

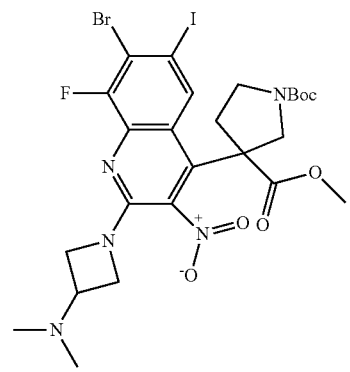

This compound was prepared using similar procedures as described for Example 23a and 23b, with 1-(tert-butyl) 3-methyl 3-(7-bromo-2-chloro-8-fluoro-6-iodo-3-nitroquinolin-4-yl)pyrrolidine-1,3-dicarboxylate replacing 1-(tert-butyl) 3-methyl 3-(7-bromo-2-chloro-8-fluoro-6-iodo-3-nitroquinolin-4-yl)piperidine-1,3-dicarboxylate in Step 6. LC-MS calculated for $C_{25}H_{31}BrFIN_5O_6$ (M+H)$^+$: m/z=722.0, 724.0; found 722.0, 724.0.

Step 3. tert-butyl 7'-bromo-4'-(3-(dimethylamino) azetidin-1-yl)-6'-fluoro-8'-iodo-2'-oxo-2',3'-dihydrospiro[pyrrolidine-3,1'-pyrrolo[2,3-c]quinoline]-1-carboxylate

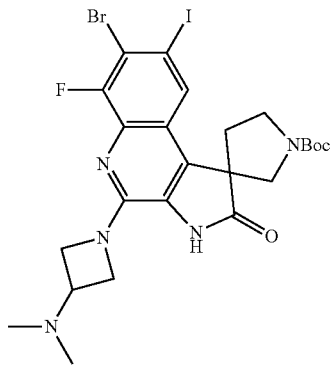 [SMILES: CN(C)C1CN(c2nc3c(F)c(Br)c(I)cc3c3c2NC(=O)C32CCN(C(=O)OC(C)(C)C)C2)C1]

This compound was prepared using similar procedures as described for Example 23a and 23b, with 1-(tert-butyl) 3-methyl 3-(7-bromo-2-(3-(dimethylamino)azetidin-1-yl)-8-fluoro-6-iodo-3-nitroquinolin-4-yl)pyrrolidine-1,3-dicarboxylate replacing 1-(tert-butyl) 3-methyl 3-(7-bromo-2-(3-(dimethylamino)azetidin-1-yl)-8-fluoro-6-iodo-3-nitroquinolin-4-yl)piperidine-1,3-dicarboxylate in Step 7. LC-MS calculated for $C_{24}H_{29}BrFIN_5O_3$ (M+H)$^+$: m/z=660.0, 662.0; found 660.0, 662.1.

Step 4. tert-butyl 7'-bromo-8'-(3-cyanopropyl)-4'-(3-(dimethylamino)azetidin-1-yl)-6'-fluoro-2'-oxo-2',3'-dihydrospiro[pyrrolidine-3,1'-pyrrolo[2,3-c]quinoline]-1-carboxylate

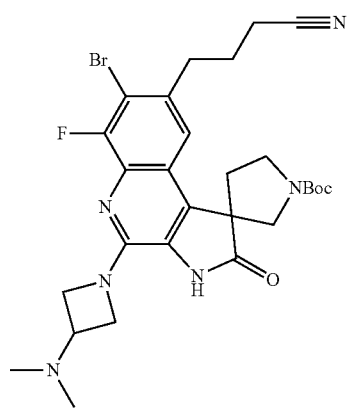 [SMILES: CN(C)C1CN(c2nc3c(F)c(Br)c(CCCC#N)cc3c3c2NC(=O)C32CCN(C(=O)OC(C)(C)C)C2)C1]

This compound was prepared using similar procedures as described for Example 23a and 23b, with tert-butyl 7'-bromo-4'-(3-(dimethylamino)azetidin-1-yl)-6'-fluoro-8'-iodo-2'-oxo-2',3'-dihydrospiro[pyrrolidine-3,1'-pyrrolo[2,3-c]quinoline]-1-carboxylate replacing tert-butyl 7'-bromo-4'-(3-(dimethylamino)azetidin-1-yl)-6'-fluoro-8'-iodo-2'-oxo-2',3'-dihydrospiro[piperidine-3,1'-pyrrolo[2,3-c]quinoline]-1-carboxylate in Step 8. LC-MS calculated for $C_{28}H_{35}BrFN_6O_3$ (M+H)$^+$: m/z=601.2, 603.2; found 601.2, 603.2.

Step 5. 4-(4'-(3-(dimethylamino)azetidin-1-yl)-6'-fluoro-7'-(3-hydroxynaphthalen-1-yl)-2'-oxo-2',3'-dihydrospiro[pyrrolidine-3,1'-pyrrolo[2,3-c]quinolin]-8'-yl)butanenitrile This compound was prepared using similar procedures as described for Example 23a and 23b, with tert-butyl 7'-bromo-8'-(3-cyanopropyl)-4'-(3-(dimethylamino)azetidin-1-yl)-6'-fluoro-2'-oxo-2',3'-dihydrospiro[pyrrolidine-3,1'-pyrrolo[2,3-c]quinoline]-1-carboxylate replacing tert-butyl 7'-bromo-8'-(3-cyanopropyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate in Step 9. The reaction mixture was purified by prep-HPLC (pH=2, acetonitrile/water+TFA) to give the desired products as TFA salt.

Example 30a. Diastereomer 1. Peak 1. LC-MS calculated for $C_{33}H_{34}FN_6O_2$ (M+H)$^+$: m/z=565.3; found 565.4.

Example 30b. Diastereomer 2. Peak 2. LC-MS calculated for $C_{33}H_{34}FN_6O_2$ (M+H)$^+$: m/z=565.3; found 565.4.

Example 31a and Example 31b. 4-(4'-(3-(dimethylamino)azetidin-1-yl)-6'-fluoro-7'-(3-hydroxynaphthalen-1-yl)-2'-oxo-2',3'-dihydrospiro[morpholine-2,1'-pyrrolo[2,3-c]quinolin]-8'-yl)butanenitrile

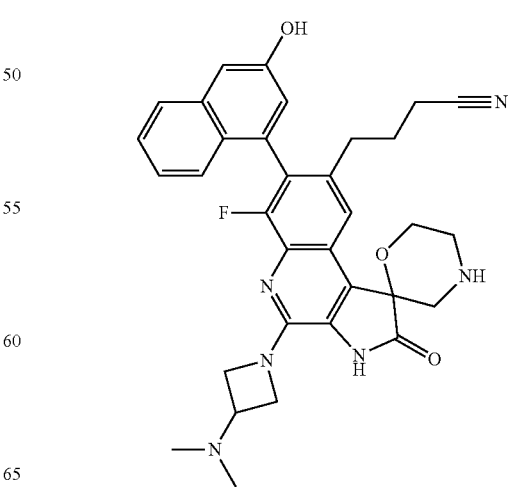

Step 1. 4-(tert-butyl) 2-methyl 2-(7-bromo-2-chloro-8-fluoro-6-iodo-3-nitroquinolin-4-yl)morpholine-2,4-dicarboxylate

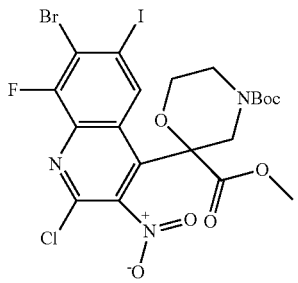

This compound was prepared using similar procedures as described for Example 23a and 23b, with 4-(tert-butyl) 2-methyl morpholine-2,4-dicarboxylate replacing 1-(tert-butyl) 3-methyl piperidine-1,3-dicarboxylate in Step 5.

Step 2. 4-(tert-butyl) 2-methyl 2-(7-bromo-2-(3-(dimethylamino)azetidin-1-yl)-8-fluoro-6-iodo-3-nitroquinolin-4-yl)morpholine-2,4-dicarboxylate

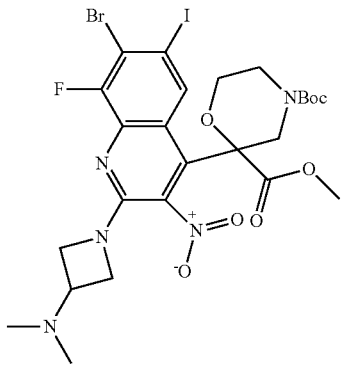

This compound was prepared using similar procedures as described for Example 23a and 23b, with 4-(tert-butyl) 2-methyl 2-(7-bromo-2-chloro-8-fluoro-6-iodo-3-nitroquinolin-4-yl)morpholine-2,4-dicarboxylate replacing 1-(tert-butyl) 3-methyl 3-(7-bromo-2-chloro-8-fluoro-6-iodo-3-nitroquinolin-4-yl)piperidine-1,3-dicarboxylate in Step 6. LC-MS calculated for $C_{25}H_{31}BrFIN_5O_7$ $(M+H)^+$: m/z=738.0, 740.0; found 738.0, 740.0.

Step 3. tert-butyl 7'-bromo-4'-(3-(dimethylamino)azetidin-1-yl)-6'-fluoro-8'-iodo-2'-oxo-2',3'-dihydrospiro[morpholine-2,1'-pyrrolo[2,3-c]quinoline]-4-carboxylate

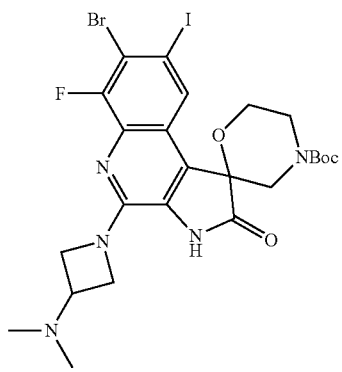 [SMILES: CN(C)C1CN(c2nc3c(F)c(Br)c(I)cc3c3c2NC(=O)C32CN(C(=O)OC(C)(C)C)CCO2)C1]

This compound was prepared using similar procedures as described for Example 23a and 23b, with 4-(tert-butyl) 2-methyl 2-(7-bromo-2-(3-(dimethylamino)azetidin-1-yl)-8-fluoro-6-iodo-3-nitroquinolin-4-yl)morpholine-2,4-dicarboxylate replacing 1-(tert-butyl) 3-methyl 3-(7-bromo-2-(3-(dimethylamino)azetidin-1-yl)-8-fluoro-6-iodo-3-nitroquinolin-4-yl)piperidine-1,3-dicarboxylate in Step 7. LC-MS calculated for $C_{24}H_{29}BrFIN_5O_4$ $(M+H)^+$: m/z=676.0, 678.0; found 676.0, 678.0.

Step 4. tert-butyl 7'-bromo-8'-(3-cyanopropyl)-4'-(3-(dimethylamino)azetidin-1-yl)-6'-fluoro-2'-oxo-2',3'-dihydrospiro[morpholine-2,1'-pyrrolo[2,3-c]quinoline]-4-carboxylate

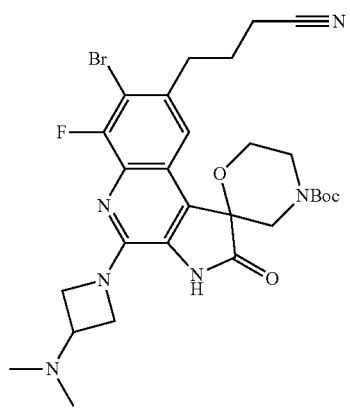 [SMILES: CN(C)C1CN(c2nc3c(F)c(Br)c(CCCC#N)cc3c3c2NC(=O)C32CN(C(=O)OC(C)(C)C)CCO2)C1]

This compound was prepared using similar procedures as described for Example 23a and 23b, with tert-butyl 7'-bromo-4'-(3-(dimethylamino)azetidin-1-yl)-6'-fluoro-8'-iodo-2'-oxo-2',3'-dihydrospiro[morpholine-2,1'-pyrrolo[2,3-c]quinoline]-4-carboxylate replacing tert-butyl 7'-bromo-4'-(3-(dimethylamino)azetidin-1-yl)-6'-fluoro-8'-iodo-2'-oxo-2',3'-dihydrospiro[piperidine-3,1'-pyrrolo[2,3-c]quinoline]-1-carboxylate in Step 8. LC-MS calculated for $C_{28}H_{35}BrFN_6O_4$ $(M+H)^+$: m/z=617.2, 619.2; found 617.2, 619.2.

Step 5. 4-(4'-(3-(dimethylamino)azetidin-1-yl)-6'-fluoro-7'-(3-hydroxynaphthalen-1-yl)-2'-oxo-2',3'-dihydrospiro[morpholine-2,1'-pyrrolo[2,3-c]quinolin]-8'-yl)butanenitrile This compound was prepared using similar procedures as described for Example 23a and 23b, with tert-butyl 7'-bromo-8'-(3-cyanopropyl)-4'-(3-(dimethylamino)azetidin-1-yl)-6'-fluoro-2'-oxo-2',3'-dihydrospiro[morpholine-2,1'-pyrrolo[2,3-c]quinoline]-4-carboxylate replacing tert-butyl 7'-bromo-8'-(3-cyanopropyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate in Step 9. The reaction mixture was purified by prep-HPLC (pH=2, acetonitrile/water+TFA) to give the desired products as TFA salt.

Example 31a. Diastereomer 1. Peak 1. LC-MS calculated for $C_{33}H_{34}FN_6O_3$ $(M+H)^+$: m/z=581.3; found 581.4.

Example 31b. Diastereomer 2. Peak 2. LC-MS calculated for $C_{33}H_{34}FN_6O_3$ $(M+H)^+$: m/z=581.3; found 581.3.

Example 32a, Example 32b and Example 32c. 4-(6'-fluoro-7'-(3-hydroxynaphthalen-1-yl)-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile

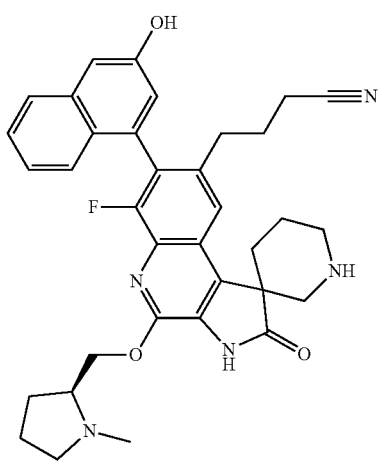 [SMILES: CN1CCC[C@H]1COc1nc2c(F)c(-c3cc(O)cc4ccccc34)c(CCCC#N)cc2c2c1NC(=O)C21CCCNC1]

Step 1. 1-(tert-butyl) 3-methyl 3-(7-bromo-8-fluoro-6-iodo-2-(((S)-1-methylpyrrolidin-2-yl)methoxy)-3-nitroquinolin-4-yl)piperidine-1,3-dicarboxylate

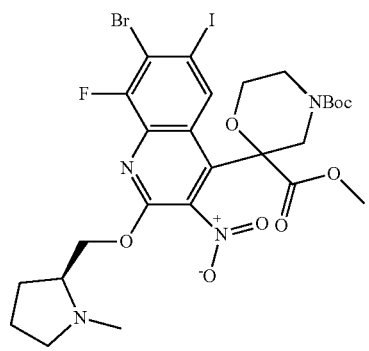

This compound was prepared using similar procedures as described for Example 10, with 1-(tert-butyl) 3-methyl 3-(7-bromo-2-chloro-8-fluoro-6-iodo-3-nitroquinolin-4-yl)piperidine-1,3-dicarboxylate (Example 23a and 23b, Step 5) replacing 1-(tert-butyl) 4-methyl 4-((7-bromo-2,6-dichloro-8-fluoro-3-nitroquinolin-4-yl)amino)piperidine-1,4-dicarboxylate in Step 6. LC-MS calculated for $C_{27}H_{34}BrFIN_4O_7$ $(M+H)^+$: m/z=751.1, 753.1; found 751.0, 753.0.

Step 2. tert-butyl 7'-bromo-6'-fluoro-8'-iodo-4'-(((S)-1-methylpyrrolidin-2-yl)methoxy)-2'-oxo-2',3'-dihydrospiro[piperidine-3,1'-pyrrolo[2,3-c]quinoline]-1-carboxylate

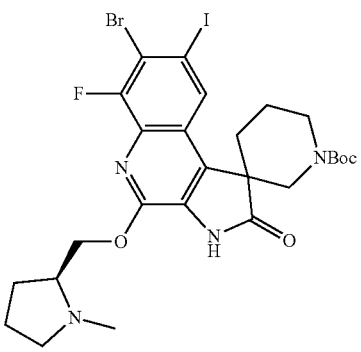 [SMILES: CN1CCC[C@H]1COc1nc2c(F)c(Br)c(I)cc2c2c1NC(=O)C21CCCN(C(=O)OC(C)(C)C)C1]

This compound was prepared using similar procedures as described for Example 23a and 23b, with 1-(tert-butyl) 3-methyl 3-(7-bromo-8-fluoro-6-iodo-2-(((S)-1-methylpyrrolidin-2-yl)methoxy)-3-nitroquinolin-4-yl)piperidine-1,3-dicarboxylate replacing 1-(tert-butyl) 3-methyl 3-(7-bromo-2-(3-(dimethylamino)azetidin-1-yl)-8-fluoro-6-iodo-3-nitroquinolin-4-yl)piperidine-1,3-dicarboxylate in Step 6. LC-MS calculated for $C_{26}H_{32}BrFIN_4O_4$ $(M+H)^+$: m/z=689.1, 691.1; found 689.0, 691.1.

Step 3. tert-butyl 7'-bromo-8'-(3-cyanopropyl)-6'-fluoro-4'-(((S)-1-methylpyrrolidin-2-yl)methoxy)-2'-oxo-2',3'-dihydrospiro[piperidine-3,1'-pyrrolo[2,3-c]quinoline]-1-carboxylate

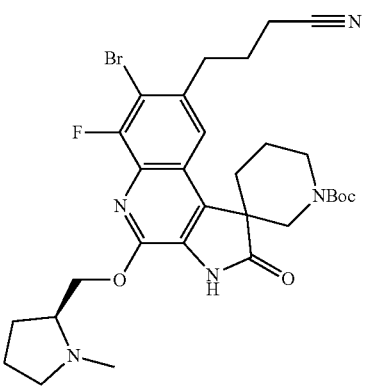 [SMILES: CN1CCC[C@H]1COc1nc2c(F)c(Br)c(CCCC#N)cc2c2c1NC(=O)C21CCCN(C(=O)OC(C)(C)C)C1]

This compound was prepared using similar procedures as described for Example 23a and 23b, with tert-butyl 7'-bromo-6'-fluoro-8'-iodo-4'-(((S)-1-methylpyrrolidin-2-yl)methoxy)-2'-oxo-2',3'-dihydrospiro[piperidine-3,1'-pyrrolo[2,3-c]quinoline]-1-carboxylate replacing tert-butyl 7'-bromo-4'-(3-(dimethylamino)azetidin-1-yl)-6'-fluoro-8'-iodo-2'-oxo-2',3'-dihydrospiro[piperidine-3,1'-pyrrolo[2,3-c]quinoline]-1-carboxylate in Step 8. LC-MS calculated for $C_{30}H_{38}BrFN_5O_4$ $(M+H)^+$: m/z=630.2, 633.2; found 630.2, 633.2.

Step 4. 4-(6'-fluoro-7'-(3-hydroxynaphthalen-1-yl)-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile This compound was prepared using similar procedures as described for Example 23a and 23b, with tert-butyl 7'-bromo-8'-(3-cyanopropyl)-6'-fluoro-4'-(((S)-1-methylpyrrolidin-2-yl)methoxy)-2'-oxo-2',3'-dihydrospiro[piperidine-3,1'-pyrrolo[2,3-c]quinoline]-1-carboxylate replacing tert-butyl 7'-bromo-8'-(3-cyanopropyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate in Step 9. The reaction mixture was purified by prep-HPLC (pH=2, acetonitrile/water+TFA) to give the desired products as TFA salt.

Example 32a. Peak 1. LC-MS calculated for $C_{35}H_{37}FN_5O_3$ (M+H)$^+$: m/z=594.3; found 594.5.

Example 32b. Peak 2. LC-MS calculated for $C_{35}H_{37}FN_5O_3$ (M+H)$^+$: m/z=594.3; found 594.5.

Example 32c. Peak 3. LC-MS calculated for $C_{35}H_{37}FN_5O_3$ (M+H)$^+$: m/z=594.3; found 594.5.

Example 33a, Example 33b and Example 33c. 4-(6'-fluoro-7'-(3-hydroxynaphthalen-1-yl)-3'-methyl-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile

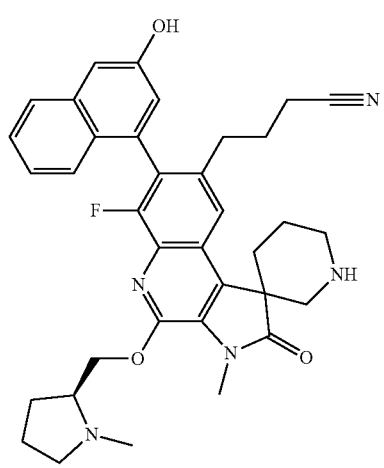 [SMILES: CN1C(=O)C2(CCCNC2)c2c1c(OC[C@@H]1CCCN1C)nc1c(F)c(-c3cc(O)cc4ccccc34)c(CCCC#N)cc21]

Step 1. tert-butyl 8'-(3-cyanopropyl)-6'-fluoro-7'-(3-(methoxymethoxy)naphthalen-1-yl)-4'-(((S)-1-methylpyrrolidin-2-yl)methoxy)-2'-oxo-2',3'-dihydrospiro[piperidine-3,1'-pyrrolo[2,3-c]quinoline]-1-carboxylate

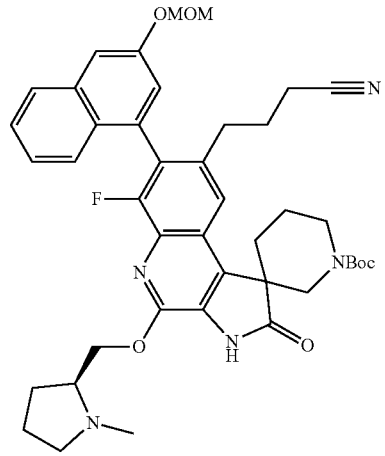

This compound was prepared using similar procedures as described for Example 28a and 28b, with tert-butyl 7'-bromo-8'-(3-cyanopropyl)-6'-fluoro-4'-(((S)-1-methylpyrrolidin-2-yl)methoxy)-2'-oxo-2',3'-dihydrospiro[piperidine-3,1'-pyrrolo[2,3-c]quinoline]-1-carboxylate (Example 32a, 32b, 32c, Step 3) replacing tert-butyl 7'-bromo-8'-(3-cyanopropyl)-4'-(3-(dimethylamino)azetidin-1-yl)-6'-fluoro-2'-oxo-2',3'-dihydrospiro[piperidine-3,1'-pyrrolo[2,3-c]quinoline]-1-carboxylate in Step 1. LC-MS calculated for $C_{42}H_{49}FN_5O_6$ (M+H)$^+$: m/z=738.4; found 738.6.

Step 2. 4-(6'-fluoro-7'-(3-hydroxynaphthalen-1-yl)-3'-methyl-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile To a MeCN solution containing tert-butyl 8'-(3-cyanopropyl)-6'-fluoro-7'-(3-(methoxymethoxy)naphthalen-1-yl)-4'-(((S)-1-methylpyrrolidin-2-yl)methoxy)-2'-oxo-2',3'-dihydrospiro[piperidine-3,1'-pyrrolo[2,3-c]quinoline]-1-carboxylate (0.050 g, 0.068 mmol) was added cesium carbonate (0.044 g, 0.136 mmol) and 2.0 M tert-butyl methyl ether solution of iodomethane (0.041 ml, 0.082 mmol). The reaction was stirred at 60° C. for 1 h. Then the reaction mixture was filtered through a pad of Celite, diluted with water and DCM and separated. The organic layer was dried over $Na_2SO_4$, filtered and evaporated. To the residue, DCM (1.0 ml) and TFA (1.2 ml, 15.5 mmol) were added. After stirring for 30 min at room temperature, water (0.2 ml) was added and the reaction stirred for another 10 min. Then the volatiles were removed under reduced pressure. The residue was dissolved in MeCN, filtered and purified by prep-HPLC (pH=2, acetonitrile/water+TFA) to give the desired products as TFA salt.

Example 33a. Peak 1. LC-MS calculated for $C_{3-6}H_{39}FN_5O_3$ (M+H)$^+$: m/z=608.3; found 608.4.

Example 33b. Peak 2. LC-MS calculated for $C_{3-6}H_{39}FN_5O_3$ (M+H)$^+$: m/z=608.3; found 608.4.

Example 33c. Peak 3. LC-MS calculated for $C_{3-6}H_{39}FN_5O_3$ (M+H)$^+$: m/z=608.3; found 608.4.

Example 34a, Example 34b and Example 34c.
4-(6'-fluoro-3'-(2-hydroxyethyl)-7'-(3-hydroxynaphthalen-1-yl)-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile

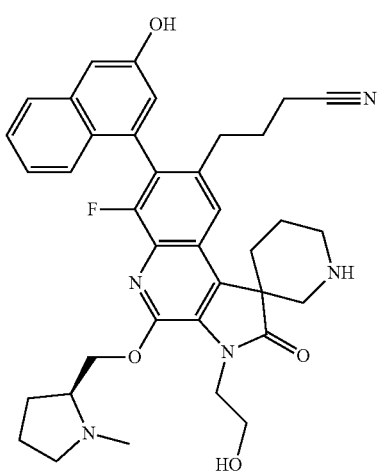 [SMILES: CN1CCC[C@H]1COc1nc2c(F)c(-c3cc(O)cc4ccccc34)c(CCCC#N)cc2c2c1N(CCO)C(=O)C21CCCNC1]

To a MeCN solution containing tert-butyl 8'-(3-cyanopropyl)-6'-fluoro-7'-(3-(methoxymethoxy)naphthalen-1-yl)-4'-(((S)-1-methylpyrrolidin-2-yl)methoxy)-2'-oxo-2',3'-dihydrospiro[piperidine-3,1'-pyrrolo[2,3-c]quinoline]-1-carboxylate (Example 33a, 33b and 33c, Step 1, 0.050 g, 0.068 mmol) was added cesium carbonate (0.044 g, 0.136 mmol) and (2-bromoethoxy)(tert-butyl)dimethylsilane (0.029 ml, 0.136 mmol). The reaction was stirred at 60° C. for 1 h. Then the reaction mixture was filtered through a pad of Celite, diluted with water and DCM and separated. The organic layer was dried over $Na_2SO_4$, filtered and evaporated. The residue was dissolved in anhydrous THF and added 1.0 M THF solution of tetrabutylammonium fluoride (0.10 ml, 0.102 mmol). After stirring for 30 min, the reaction mixture was filtered through a pad of Celite, diluted with water and EtOAc and separated. The organic layer was dried over $Na_2SO_4$, filtered and evaporated. To the residue, DCM (1.0 ml) and TFA (1.2 ml, 15.5 mmol) were added. After stirring for 30 min at room temperature, water (0.2 ml) was added and the reaction stirred for another 10 min. Then the volatiles were removed under reduced pressure. The residue was dissolved in MeCN, filtered and purified by prep-HPLC (pH=2, acetonitrile/water+TFA) to give the desired products as TFA salt.

Example 34a. Peak 1. LC-MS calculated for $C_{37}H_{41}FN_5O_4$ (M+H)$^+$: m/z=638.3; found 638.5.
Example 34b. Peak 2. LC-MS calculated for $C_{37}H_{41}FN_5O_4$ (M+H)$^+$: m/z=638.3; found 638.5.
Example 34c. Peak 3. LC-MS calculated for $C_{37}H_{41}FN_5O_4$ (M+H)$^+$: m/z=638.3; found 638.5.

Example 35a, Example 35b and Example 35c.
4-(6'-fluoro-7'-(3-hydroxynaphthalen-1-yl)-3'-isopentyl-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile

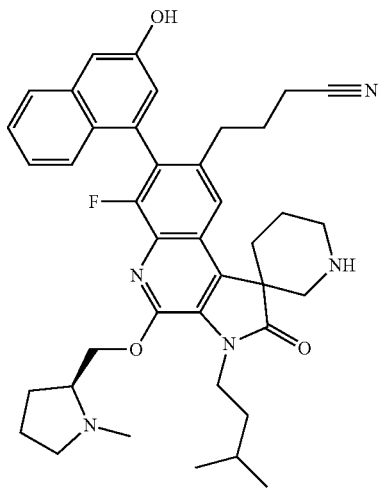 [SMILES: CC(C)CCN1C(=O)C2(CCCNC2)c2c1c(OC[C@@H]1CCCN1C)nc1c(F)c(-c3cc(O)cc4ccccc34)c(CCCC#N)cc21]

This compound was prepared using similar procedures as described for Example 33a, 33b and 33c, with 1-bromo-3-methylbutane replacing iodomethane in Step 2. The reaction mixture was purified by prep-HPLC (pH=2, acetonitrile/water+TFA) to give the desired products as TFA salt.

Example 35a. Peak 1. LC-MS calculated for $C_{40}H_{47}FN_5O_3$ (M+H)$^+$: m/z=664.4; found 664.6.
Example 35b. Peak 2. LC-MS calculated for $C_{40}H_{47}FN_6O_3$ (M+H)$^+$: m/z=664.4; found 664.6.
Example 35c. Peak 3. LC-MS calculated for $C_{40}H_{47}FN_5O_3$ (M+H)$^+$: m/z=664.4; found 664.6.

Example 36a, Example 36b and Example 36c.
4-(3'-(cyanomethyl)-6'-fluoro-7'-(3-hydroxynaphthalen-1-yl)-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile

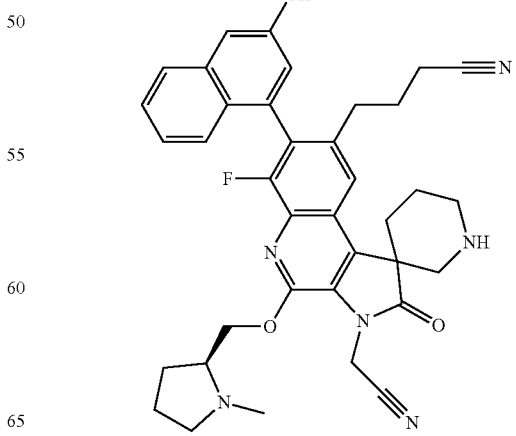

This compound was prepared using similar procedures as described for Example 33a, 33b and 33c, with 2-bromoacetonitrile replacing iodomethane in Step 2. The reaction mixture was purified by prep-HPLC (pH=2, acetonitrile/water+TFA) to give the desired products as TFA salt.

Example 36a. Peak 1. LC-MS calculated for $C_{37}H_{38}FN_6O_3$ $(M+H)^+$: m/z=633.3; found 633.3.
Example 36b. Peak 2. LC-MS calculated for $C_{37}H_{38}FN_6O_3$ $(M+H)^+$: m/z=633.3; found 633.3.
Example 36c. Peak 3. LC-MS calculated for $C_{37}H_{38}FN_6O_3$ $(M+H)^+$: m/z=633.3; found 633.3.

Example 37a, Example 37b and Example 37c.
2-(8'-(3-cyanopropyl)-6'-fluoro-7'-(3-hydroxynaphthalen-1-yl)-4'-(((S)-1-methylpyrrolidin-2-yl)methoxy)-2'-oxospiro[piperidine-3,1'-pyrrolo[2,3-c]quinolin]-3'(2'H)-yl)acetamide

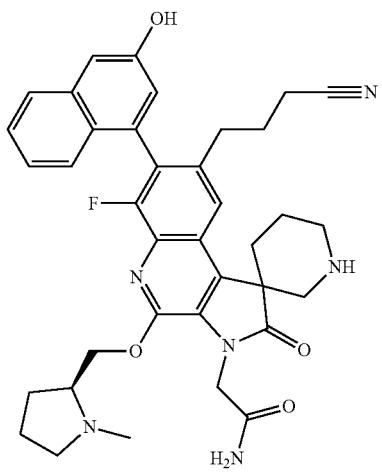 [SMILES: CN1CCC[C@H]1COc1nc2c(F)c(-c3cc(O)cc4ccccc34)c(CCCC#N)cc2c2c1N(CC(N)=O)C(=O)C21CCCNC1]

This compound was prepared using similar procedures as described for Example 33a, 33b and 33c, with 2-bromoacetamide replacing iodomethane in Step 2. The reaction mixture was purified by prep-HPLC (pH=2, acetonitrile/water+TFA) to give the desired products as TFA salt.

Example 37a. Peak 1. LC-MS calculated for $C_{37}H_{40}FN_6O_4$ $(M+H)^+$: m/z=651.3; found 651.5.
Example 37b. Peak 2. LC-MS calculated for $C_{37}H_{40}FN_6O_4$ $(M+H)^+$: m/z=651.3; found 651.5.
Example 37c. Peak 3. LC-MS calculated for $C_{37}H_{40}FN_6O_4$ $(M+H)^+$: m/z=651.3; found 651.5.

Example A. GDP-GTP Exchange Assay

The inhibitor potency of the exemplified compounds was determined in a fluorescence based guanine nucleotide exchange assay, which measures the exchange of bodipy-GDP (fluorescently labeled GDP) for GppNHp (Non-hydrolyzable GTP analog) to generate the active state of KRAS in the presence of SOS1 (guanine nucleotide exchange factor). Inhibitors were serially diluted in DMSO and a volume of 0.1 μL was transferred to the wells of a black low volume 384-well plate. 5 μL/well volume of bodipy-loaded KRAS G12C diluted to 5 nM in assay buffer (25 mM Hepes pH 7.5, 50 mM NaCl, 10 mM $MgCl_2$ and 0.01% Brij-35) was added to the plate and pre-incubated with inhibitor for 2 hours at ambient temperature. Appropriate controls (enzyme with no inhibitor or with a G12C inhibitor (AMG-510)) were included on the plate. The exchange was initiated by the addition of a 5 μL/well volume containing 1 mM GppNHp and 300 nM SOS1 in assay buffer. The 10 μL/well reaction concentration of the bodipy-loaded KRAS G12C, GppNHp, and SOS1 were 2.5 nM, 500 uM, and 150 nM, respectively. The reaction plates were incubated at ambient temperature for 2 hours, a time estimated for complete GDP-GTP exchange in the absence of inhibitor. For the KRAS G12D and G12V mutants, similar guanine nucleotide exchange assays were used with 2.5 nM as final concentration for the bodipy loaded KRAS proteins and with 4 hours and 3 hours incubation after adding GppNHp-SOS1 mixture for G12D and G12V respectively. A cyclic peptide described to selectively bind G12D mutant (Sakamoto et al., BBRC 484.3 (2017), 605-611) or internal compounds with confirmed binding were used as positive controls in the assay plates. Fluorescence intensities were measured on a PheraStar plate reader instrument (BMG Labtech) with excitation at 485 nm and emission at 520 nm.

Either GraphPad prism or XLfit was used to analyze the data. The $IC_{50}$ values were derived by fitting the data to a four parameter logistic equation producing a sigmoidal dose-response curve with a variable Hill coefficient. Prism equation: Y=Bottom+(Top−Bottom)/(1+10^((Log $IC_{50}$−X) *Hill slope)); XLfit equation: Y=(A+((B−A)/(1+((X/C)^D)))) where X is the logarithm of inhibitor concentration and Y is the response.

The KRAS_G12C exchange assay $IC_{50}$ data and KRAS_G12C pERK assay $IC_{50}$ data are provided in Table 1 below. The symbol "†" indicates $IC_{50}$≤100 nM, "†\" indicates $IC_{50}$>100 nM but ≤1 μM; and "†††" indicates $IC_{50}$ is >1 μM but ≤5 μM, "††††" indicates $IC_{50}$ is >5 μM but ≤10 μM. "NA" indicates $IC_{50}$ not available.

TABLE 1

| Ex. No. | G12C_exchange | G12C_pERK |
|---|---|---|
| 1 | †† | ††† |
| 2 | †† | ††† |
| 3 | ††† | NA |
| 4 | †† | NA |
| 5 | ††† | NA |
| 6 | †† | ††† |
| 7 | †† | ††† |
| 8 | †† | ††† |
| 9 | ††† | NA |
| 10 | † | ††† |
| 11 | † | †† |
| 12 | †† | ††† |
| 13 | † | †† |
| 14 | †† | †† |
| 15 | ††† | NA |
| 16a | †† | †† |
| 17 | ††† | NA |
| 18 | †† | ††† |

The KRAS_G12D exchange assay $IC_{50}$ data and KRAS_G12D pERK assay $IC_{50}$ data are provided in Table 2 below. The symbol "†" indicates $IC_{50}$≤100 nM, "††" indicates $IC_{50}$>100 nM but ≤1 μM; "†††" indicates $IC_{50}$ is >1 μM but ≤5 μM; and "††††" indicates $IC_{50}$ is >5 μM but ≤50 μM, "NA" indicates $IC_{50}$ not available.

TABLE 2

| Ex. No. | G12D_exchange | G12D_pERK |
|---|---|---|
| 19b | ††† | NA |
| 20b | ††† | NA |
| 21b | ††† | NA |

TABLE 2-continued

| Ex. No. | G12D_exchange | G12D_pERK |
|---------|---------------|-----------|
| 22      | ††††          | NA        |
| 23b     | ††            | NA        |
| 24a     | †††           | NA        |
| 25b     | †††           | NA        |
| 26b     | †††           | NA        |
| 27b     | †††           | NA        |
| 28b     | †††           | NA        |
| 29      | †††           | NA        |
| 30b     | †††           | NA        |
| 31b     | ††††          | NA        |
| 32b     | †††           | NA        |
| 33b     | †††           | NA        |
| 34b     | †††           | NA        |
| 35a     | †             | ††††      |
| 36a     | †††           | NA        |
| 37b     | †††           | NA        |

Example B: Luminescent Viability Assay

MIA PaCa-2 (KRAS G12C; ATCC® CRL-1420), A427 (KRAS G12D; ATCC® HTB53) and NCI-H838 (KRAS WT; ATCC® CRL-5844) cells are cultured in RPMI 1640 media supplemented with 10% FBS (Gibco/Life Technologies). The cells are seeded ($5 \times 10^3$ cells/well/in 50 uL) into black, clear bottomed 96-well Greiner tissue culture plates and cultured overnight at 37° C., 5% $CO_2$. After overnight culture, 50 uL per well of serially diluted test compounds (2× final concentration) are added to the plates and incubated for 3 days. At the end of the assay, 100 ul/well of CellTiter-Glo reagent (Promega) is added. Luminescence is read after 15 minutes with a TopCount (PerkinElmer). $IC_{50}$ determination is performed by fitting the curve of percent inhibition versus the log of the inhibitor concentration using the GraphPad Prism 7 software.

Example C: Cellular pERK HTRF Assay

MIA PaCa-2 (KRAS G12C; ATCC® CRL-1420), A427 (KRAS G12D; ATCC® HTB53), HPAF-II (KRAS G12D; ATCC® CRL-1997) and NCI-H838 (KRAS WT; ATCC® CRL-5844) cells are purchased from ATCC and maintained in RPMI 1640 media supplemented with 10% FBS (Gibco/Life Technologies). The cells are plated at 5000 cells per well (8 uL) into Greiner 384-well low volume, flat-bottom, tissue culture treated white plates and incubated overnight at 37° C., 5% $CO_2$. The next morning, test compound stock solutions are diluted in media at 3x the final concentration, and 4 uL are added to the cells. The plate is mixed by gentle rotation for 30 seconds (250 rpm) at room temperature. The cells are incubated with the KRAS G12C and G12D compounds for 4 hours or 2 hours respectively at 37° C., 5% $CO_2$.

4 uL of 4× lysis buffer with blocking reagent (1:25) (Cisbio) are added to each well and plates are rotated gently (300 rpm) for 30 minutes at room temperature. 4 uL per well of Cisbio anti Phospho-ERK 1/2 d2 is mixed with anti Phospho-ERK 1/2 Cryptate (1:1) are added to each well, mixed by rotation and incubated overnight in the dark at room temperature. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 7 software.

Example D: Whole Blood pERK1/2 HTRF Assay

MIA PaCa-2 cells (KRAS G12C; ATCC® CRL-1420) and HPAF-II (KRAS G12D; ATCC® CRL-1997) are maintained in RPMI 1640 with 10% FBS (Gibco/Life Technologies).

The cells are seeded into 96 well tissue culture plates (Corning #3596) at 25000 cells per well in 100 uL media and cultured for 2 days at 37° C., 5% $CO_2$ so that they are approximately 80% confluent at the start of the assay. Whole Blood are added to the 1 uL dots of compounds (prepared in DMSO) in 96 well plates and mixed gently by pipetting up and down so that the concentration of the compound in blood is 1x of desired concentration. The media is aspirated from the cells and 50 uL per well of whole blood with G12C or G12D compound is added and incubated for 4 or 2 hours respectively at 37° C., 5% $CO_2$. After dumping the blood, the plates are gently washed twice by adding PBS to the side of the wells and dumping the PBS from the plate onto a paper towel, tapping the plate to drain well. 50 ul/well of 1× lysis buffer #1 (Cisbio) with blocking reagent (1:25) (Cisbio) is then added and incubated at room temperature for 30 minutes with shaking (250 rpm). Following lysis, 16 uL of lysate is transferred into 384-well Greiner small volume white plate using an Assist Plus (Integra Biosciences, NH). 4 uL of 1:1 mixture of anti Phospho-ERK 1/2 d2 and anti Phospho-ERK 1/2 Cryptate (Cisbio) is added to the wells using the Assist Plus and incubated at room temperature overnight in the dark. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 7 software.

Example E: Ras Activation Elisa

The 96-Well Ras Activation ELISA Kit (Cell Biolabs Inc; #STA441) uses the Raf1 RBD (Rho binding domain) bound to a 96-well plate to selectively pull down the active form of Ras from cell lysates. The captured GTP-Ras is then detected by a pan-Ras antibody and HRP-conjugated secondary antibody.

MIA PaCa-2 cells (KRAS G12C; ATCC® CRL-1420) and HPAF-II (KRAS G12D; ATCC® CRL-1997) are maintained in RPMI 1640 with 10% FBS (Gibco/Life Technologies). The cells are seeded into 96 well tissue culture plates (Corning #3596) at 25000 cells per well in 100 uL media and cultured for 2 days at 37° C., 5% $CO_2$ so that they are approximately 80% confluent at the start of the assay. The cells are treated with compounds for either 2 hours or overnight at 37° C., 5% $CO_2$. At the time of harvesting, the cells are washed with PBS, drained well and then lysed with 50 uL of the 1× Lysis buffer (provided by the kit) plus added Halt Protease and Phosphatase inhibitors (1:100) for 1 hour on ice.

The Raf-1 RBD is diluted 1:500 in Assay Diluent (provided in kit) and 100 μL of the diluted Raf-1 RBD is added to each well of the Raf-1 RBD Capture Plate. The plate is covered with a plate sealing film and incubated at room temperature for 1 hour on an orbital shaker. The plate is washed 3 times with 250 μL 1× Wash Buffer per well with thorough aspiration between each wash. 50 μL of Ras lysate sample (10-100 μg) is added per well in duplicate. A "no cell lysate" control is added in a couple of wells for background determination. 50 μL of Assay Diluent is added to all wells immediately to each well and the plate is incubated at room temperature for 1 hour on an orbital shaker. The plate is washed 5 times with 250 µL 1× Wash Buffer per well with thorough aspiration between each wash. 100 µL of the diluted Anti-pan-Ras Antibody is added to each well and the plate is incubated at room temperature for 1 hour on an orbital shaker. The plate is washed 5 times as previously. 100 µL of the diluted Secondary Antibody, HRP Conjugate is added to each well and the plate is incubated at room temperature for 1 hour on an orbital shaker. The plate is washed 5 times as previously and drained well. 100 µL of Chemiluminescent Reagent (provided in the kit) is added to each well, including the blank wells. The plate is incubated at room temperature for 5 minutes on an orbital shaker before the luminescence of each microwell is read on a plate luminometer. The % inhibition is calculated relative to the DMSO control wells after a background level of the "no lysate control" is subtracted from all the values. $IC_{50}$ determination is performed by fitting the curve of inhibitor percent inhibition versus the log of the inhibitor concentration using the GraphPad Prism 7 software.

Example F: Inhibition of RAS-RAF and PI3K-AKT Pathways

The cellular potency of compounds was determined by measuring phosphorylation of KRAS downstream effectors extracellular-signal-regulated kinase (ERK), ribosomal S6 kinase (RSK), AKT (also known as protein kinase B, PKB) and downstream substrate S6 ribosomal protein.

To measure phosphorylated extracellular-signal-regulated kinase (ERK), ribosomal S6 kinase (RSK), AKT and S6 ribosomal protein, cells (details regarding the cell lines and types of data produced are further detailed in Table 4) were seeded overnight in Corning 96-well tissue culture treated plates in RPMI medium with 10% FBS at $4\times10^4$ cells/well. The following day, cells were incubated in the presence or absence of a concentration range of test compounds for 4 hours at 37° C., 5% $CO_2$. Cells were washed with PBS and lysed with 1× lysis buffer (Cisbio) with protease and phosphatase inhibitors. 10 µg of total protein lysates was subjected to SDS-PAGE and immunoblot analysis using following antibodies: phospho-ERK1/2-Thr202/Tyr204 (#9101L), total-ERK1/2 (#9102L), phosphor-AKT-Ser473 (#4060L), phospho-p90RSK-Ser380 (#11989S) and phospho-S6 ribosomal protein-Ser235/Ser236 (#2211S) are from Cell Signaling Technologies (Danvers, Mass.).

TABLE 3

| Cell Line | Histology | KRAS alteration | Readout |
|---|---|---|---|
| H358 | Lung | G12C | pERK, pAKT |
| MIA PaCa-2 | Pancreas | G12C | pERK, pAKT |
| HPAF II | Pancreas | G12D | pERK, pAKT |
| SU.86.86 | Pancreas | G12D | pERK, pAKT |
| PaTu 8988s | Pancreas | G12V | pERK, pAKT |
| H441 | Lung | G12V | pERK, pAKT |

Example G: In Vivo Efficacy Studies

Mia-Paca-2 human pancreatic cancer cells were obtained from the American Type Culture Collection and maintained in RPMI media supplemented with 10% FBS. For efficacy studies experiments, $5\times10^6$ Mia-Paca-2 cells were inoculated subcutaneously into the right hind flank of 6- to 8-week-old BALB/c nude mice (Charles River Laboratories, Wilmington, Mass., USA). When tumor volumes were approximately 150-250 mm3, mice were randomized by tumor volume and compounds were orally administered. Tumor volume was calculated using the formula $(L\times W^2)/2$, where L and W refer to the length and width dimensions, respectively. Tumor growth inhibition was calculated using the formula $(1-(V_T/V_C))\times 100$, where $V_T$ is the tumor volume of the treatment group on the last day of treatment, and VC is the tumor volume of the control group on the last day of treatment. Two-way analysis of variance with Dunnett's multiple comparisons test was used to determine statistical differences between treatment groups (GraphPad Prism). Mice were housed at 10-12 animals per cage, and were provided enrichment and exposed to 12-hour light/dark cycles. Mice whose tumor volumes exceeded limits (10% of body weight) were humanely euthanized by $CO_2$ inhalation. Animals were maintained in a barrier facility fully accredited by the Association for Assessment and Accreditation of Laboratory Animal Care, International. All of the procedures were conducted in accordance with the US Public Service Policy on Human Care and Use of Laboratory Animals and with Incyte Animal Care and Use Committee Guidelines.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:
1. A compound of Formula II:

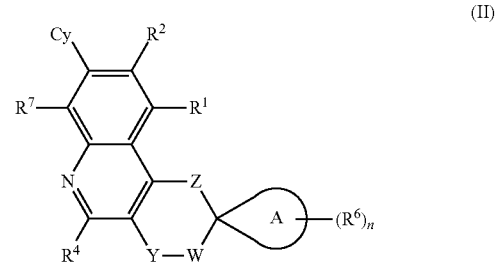

or a pharmaceutically acceptable salt thereof, wherein:
Y is $NR^{5N}$ or C=O;
W is C=O, or $C(R^8)_2$;
Z is O, $NR^{9N}$, or a bond;
$R^1$ is selected from H, D, $C_{1-6}$ alkyl, halo, and CN;
$R^2$ is selected from H, $C_{1-6}$ alkyl, $C_{1-6}$ haloalkyl, and halo; wherein said $C_{1-6}$ alkyl is optionally substituted with 1, 2, or 3 substituents independently selected from $R^{20}$;
Cy is selected from $C_{6-10}$ aryl and 5-10 membered heteroaryl; wherein the 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, or 3 substituents independently selected from $R^{10}$;
$R^4$ is selected from H, $C_{3-10}$ cycloalkyl, 4-10 membered heterocycloalkyl, and $OR^{a3}$; wherein said $C_{3-10}$ cycloalkyl and 4-10 membered heterocycloalkyl are each optionally substituted with 1, 2, or 3 substituents independently selected from $R^{30}$;

$R^{5N}$ is selected from H and $C_{1-6}$ alkyl; wherein said $C_{1-6}$ alkyl is optionally substituted with 1, 2, or 3 substituents independently selected from $R^{50}$;

$R^8$ is H;

ring A is selected from $C_{3-6}$ cycloalkyl and 4-7 membered heterocycloalkyl;

wherein the 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-7 membered heterocycloalkyl is optionally substituted by oxo to form a carbonyl group;

n is 0, 1 or 2;

each $R^6$ is independently selected from $C(O)R^{b6}$ and $C(O)OR^{a6}$;

$R^7$ is halo;

$R^{9N}$ is H;

each $R^{10}$ is independently selected from $C_{1-6}$ alkyl, halo, and $OR^{a10}$;

each $R^{20}$ is independently selected from $C_{1-6}$ alkyl, $C_{3-10}$ cycloalkyl, 4-10 membered heterocycloalkyl, $C_{6-10}$ aryl, 5-10 membered heteroaryl, halo, D, and CN; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, or 3 substituents independently selected from $R^{21}$;

each $R^{21}$ is independently selected from $C_{1-6}$ alkyl, $C_{1-6}$ haloalkyl, halo, D, and CN;

each $R^{30}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a30}$, and $NR^{c30}R^{d30}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, or 3 substituents independently selected from $R^{31}$;

each $R^{31}$ is $C_{1-6}$ alkyl;

each $R^{50}$ is independently selected from $C_{1-6}$ alkyl, $C_{1-6}$ haloalkyl, halo, D, CN, $OR^{a50}$, $C(O)R^{b50}$, $C(O)NR^{c50}R^{d50}$, $C(O)OR^{a50}$, $NR^{c50}R^{d50}$, and $NR^{c50}C(O)R^{b50}$;

$R^{a3}$ is $C_{1-6}$ alkyl optionally substituted with 1, 2, or 3 substituents independently selected from $R^{30}$;

each $R^{a6}$ and $R^{b6}$ is independently selected from H, $C_{1-6}$ alkyl, $C_{2-6}$ alkenyl, $C_{2-6}$ alkynyl, and $C_{1-6}$ haloalkyl;

$R^{a10}$ is selected from H, $C_{1-6}$ alkyl, and $C_{1-6}$ haloalkyl;

each $R^{a30}$, $R^{c30}$ and $R^{d30}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, or 3 substituents independently selected from $R^{31}$;

or any $R^{c30}$ and $R^{d30}$ attached to the same N atom, together with the N atom to which they are attached, form a 4-, 5-, or 6-membered heterocycloalkyl group optionally substituted with 1, 2, or 3 substituents independently selected from $R^{31}$;

and each $R^{a50}$, $R^{b50}$, $R^{c50}$ and $R^{d50}$, is independently selected from H, $C_{1-6}$ alkyl, and $C_{1-6}$ haloalkyl.

2. The compound of claim 1, or a pharmaceutically acceptable salt thereof, wherein Y is $NR^{5N}$, or C=O;

W is C=O, or $C(R^8)_2$;

Z is O, $NR^{9N}$, or a bond;

$R^1$ is selected from H, D, $C_{1-3}$ alkyl, and halo;

$R^2$ is selected from H, $C_{1-6}$ alkyl, $C_{1-6}$ haloalkyl, and halo; wherein said $C_{1-6}$ alkyl is optionally substituted with 1 or 2 substituents independently selected from $R^{20}$;

Cy is selected from $C_{6-10}$ aryl and 5-10 membered heteroaryl; wherein the 5-10 membered heteroaryl each has at least one ring-forming carbon atom and 1, 2, or 3 ring-forming heteroatoms independently selected from N and O; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1 or 2 substituents independently selected from $R^{10}$;

$R^4$ is selected from H, $C_{3-6}$ cycloalkyl, 4-6 membered heterocycloalkyl, and $OR^{a3}$; wherein said $C_{3-6}$ cycloalkyl and 4-6 membered heterocycloalkyl are each optionally substituted with 1, 2, or 3 substituents independently selected from $R^{30}$;

$R^{5N}$ is selected from H and $C_{1-6}$ alkyl; wherein said $C_{1-6}$ alkyl is optionally substituted with 1, 2, or 3 substituents independently selected from $R^{50}$;

$R^8$ is H;

ring A is selected from $C_{3-6}$ cycloalkyl and 4-6 membered heterocycloalkyl; wherein the 4-6 membered heterocycloalkyl has at least one ring-forming carbon atom and 1 or 2 ring-forming heteroatoms independently selected from N and O; wherein a ring-forming carbon atom of 4-6 membered heterocycloalkyl is optionally substituted by oxo to form a carbonyl group;

n is 1;

$R^6$ is $C(O)R^{b6}$;

$R^7$ is halo;

$R^{9N}$ is H;

each $R^{10}$ is independently selected from $C_{1-6}$ alkyl, halo, and $OR^{a10}$;

each $R^{20}$ is independently selected from $C_{1-6}$ alkyl, phenyl, 5-6 membered heteroaryl, halo, D, and CN; wherein said $C_{1-6}$ alkyl, phenyl, and 5-6 membered heteroaryl, are each optionally substituted with 1 or 2 substituents independently selected from $R^{21}$;

each $R^{21}$ is independently selected from $C_{1-6}$ alkyl, $C_{1-6}$ haloalkyl, halo, D, and CN;

each $R^{30}$ is independently selected from $C_{1-6}$ alkyl, $C_{1-6}$ haloalkyl, $C_{3-6}$ cycloalkyl, 4-6 membered heterocycloalkyl, phenyl, 5-6 membered heteroaryl, halo, D, CN, $OR^{a30}$, and $NR^{c30}R^{d30}$; wherein said $C_{1-6}$ alkyl, $C_{3-6}$ cycloalkyl, 4-6 membered heterocycloalkyl, phenyl, and 5-6 membered heteroaryl, are each optionally substituted with 1 or 2 substituents independently selected from $R^{31}$;

each $R^{31}$ is $C_{1-6}$;

each $R^{50}$ is independently selected from $C_{1-6}$ alkyl, $C_{1-6}$ haloalkyl, halo, D, CN, $OR^{a50}$, $C(O)NR^{c50}R^{d50}$, $NR^{c50}R^{d50}$, and $NR^{c50}C(O)R^{b50}$;

$R^{a3}$ is $C_{1-6}$ alkyl optionally substituted with 1, 2, or 3 substituents independently selected from $R^{30}$;

$R^{b6}$ is selected from H, $C_{1-6}$ alkyl, $C_{2-6}$ alkenyl, $C_{2-6}$ alkynyl, and $C_{1-6}$ haloalkyl;

each $R^{a30}$, $R^{c30}$ and $R^{d30}$ is independently selected from H, $C_{1-6}$ alkyl, $C_{1-6}$ haloalkyl, $C_{3-6}$ cycloalkyl, 4-6 membered heterocycloalkyl, phenyl and 5-6 membered heteroaryl; wherein said $C_{1-6}$ alkyl, $C_{3-6}$ cycloalkyl, 4-6 membered heterocycloalkyl, phenyl and 5-6 membered heteroaryl, are each optionally substituted with 1 or 2 substituents independently selected from $R^{31}$;

or any $R^{c30}$ and $R^{d30}$ attached to the same N atom, together with the N atom to which they are attached, form a 4-, 5-, or 6-membered heterocycloalkyl group optionally substituted with 1 or 2 substituents independently selected from $R^{31}$;

and each $R^{a50}$, $R^{c50}$ and $R^{d50}$, is independently selected from H, $C_{1-6}$ alkyl, and $C_{1-6}$ haloalkyl.

3. The compound of claim 1, wherein
Y is $NR^{5N}$ or C=O;
W is C=O, or $C(R^8)_2$;
Z is O, $NR^{9N}$, or a bond;
$R^1$ is selected from H, $C_{1-6}$ alkyl, halo, and CN;
$R^2$ is selected from H, $C_{1-6}$ alkyl, $C_{1-6}$ haloalkyl, and halo;
Cy is $C_{6-10}$ aryl or 5-10 membered heteroaryl, both of which are optionally substituted with 1, 2, or 3 substituents independently selected from $R^{10}$;
$R^4$ is selected from H and $OR^{a3}$;
$R^{5N}$ is H or $C_{1-6}$ alkyl;
each $R^8$ is H;
ring A is 4-7 membered heterocycloalkyl;
n is 1 or 2;
$R^6$ is $C(O)R^{b6}$;
$R^7$ is halo;
$R^{9N}$ is H;
each $R^{10}$ is independently selected from $C_{1-6}$ alkyl, halo, and $OR^{a10}$;
each $R^{30}$ is 4-10 membered heterocycloalkyl optionally substituted with 1, 2, or 3 substituents independently selected from $R^{31}$;
each $R^{31}$ is $C_{1-6}$ alkyl;
$R^{a3}$ is $C_{1-6}$ alkyl optionally substituted one or two times with $R^{30}$;
each $R^{b6}$ is independently selected from H, $C_{1-6}$ alkyl, and $C_{2-6}$ alkenyl; and
$R^{a10}$ is H or $C_{1-6}$ alkyl.

4. The compound of claim 1, wherein
Y is $NR^{5N}$ or C=O;
W is C=O, or $C(R^8)_2$;
Z is O, $NR^{9N}$, or a bond;
$R^1$ and $R^2$ are each independently H or halo;
Cy is $C_{6-10}$ aryl or 5-10 membered heteroaryl, both of which are optionally substituted with 1, 2, or 3 substituents independently selected from $R^{10}$;
$R^4$ is selected from H and $OR^{a3}$;
$R^{5N}$ is H or $C_{1-6}$ alkyl;
$R^8$ is H;
ring A is 4-6 membered heterocycloalkyl;
n is 1;
$R^6$ is $C(O)R^{b6}$;
$R^7$ is halo;
$R^{9N}$ is H;
each $R^{10}$ is independently selected from $C_{1-6}$ alkyl, halo, and $OR^{a10}$;
each $R^{30}$ is 4-10 membered heterocycloalkyl optionally substituted with 1, 2, or 3 substituents independently selected from $R^{31}$;
each $R^{31}$ is $C_{1-6}$ alkyl;
$R^{a3}$ is $C_{1-6}$ alkyl optionally substituted one or two times with $R^{30}$;
each $R^{b6}$ is independently $C_{2-6}$ alkenyl; and
$R^{a10}$ is H or $C_{1-6}$ alkyl.

5. The compound of claim 1, wherein the compound of Formula II is a compound of Formula IIa:

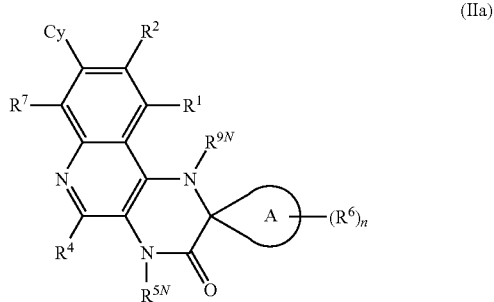

(IIa)

or a pharmaceutically acceptable salt thereof.

6. The compound of claim 1, wherein the compound of Formula II is a compound of Formula IIb:

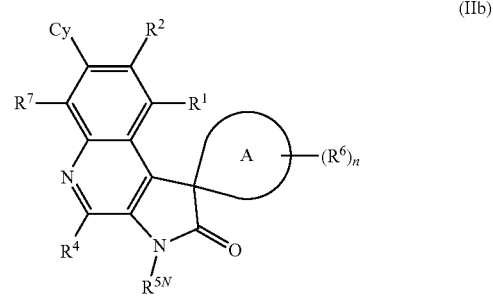

(IIb)

or a pharmaceutically acceptable salt thereof.

7. The compound of claim 1, wherein the compound of Formula II is a compound of Formula IIc:

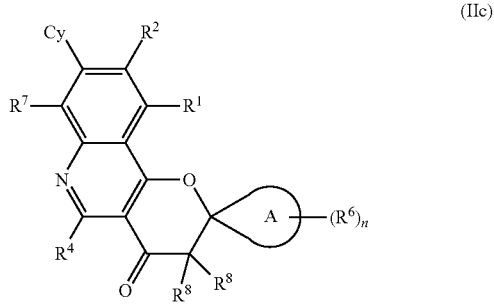

(IIc)

or a pharmaceutically acceptable salt thereof.

8. The compound of claim 1, wherein Y is C=O.
9. The compound of claim 1, wherein Y is $NR^{5N}$.
10. The compound of claim 1, wherein W is C=O.
11. The compound of claim 1, wherein W is $C(R^8)_2$.
12. The compound of claim 1, wherein Z is O.
13. The compound of claim 1, wherein Z is $NR^{9N}$.
14. The compound of claim 1, wherein Z is a bond.
15. The compound of claim 1, wherein $R^1$ is selected from H, D, and $C_{1-3}$ alkyl.
16. The compound of claim 15, wherein $R^1$ is H.
17. The compound of claim 1, wherein $R^2$ is selected from $C_{1-6}$ alkyl and halo.
18. The compound of claim 1, wherein Cy is selected from $C_{6-10}$ aryl and 5-10 membered heteroaryl; wherein the 5-10 membered heteroaryl each has at least one ring-forming carbon atom and 1, 2, or 3 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 6-10 membered heteroaryl are each optionally substituted with 1, 2, or 3 substituents independently selected from $R^{10}$.

19. The compound of claim 18, wherein Cy is selected from phenyl, naphthalenyl and indazolyl; wherein the phenyl, naphthalenyl and indazolyl are each optionally substituted with 1, 2, or 3 substituents independently selected from $R^{10}$.

20. The compound of claim 18, wherein each $R^{10}$ is independently selected from $C_{1-6}$ alkyl, halo, $OR^{a10}$.

21. The compound of claim 20, wherein $R^{a10}$ is H or $C_{1-6}$ alkyl.

22. The compound of claim 18, wherein Cy is selected from 2-fluoro-6-hydroxyphenyl, 2-chloro-5-hydroxy-phenyl, 5-methyl-1H-indazol-4-yl, 3-methyl-1H-indazol-4-yl, and 2-fluoro-6-methoxyphenyl.

23. The compound of claim 1, wherein $R^4$ is selected from H, 4-6 membered heterocycloalkyl, and $OR^{a3}$; wherein said 4-6 membered heterocycloalkyl is optionally substituted with 1 or 2 substituents independently selected from $R^{30}$.

24. The compound of claim 1, wherein $R^4$ is selected from H, 1-(methyl-pyrrolidin-2-yl)methoxy, and 1-(ethoxy)piperidine.

25. The compound of claim 1, wherein $R^4$ is 3-(dimethylamino)-azetidin-1-yl.

26. The compound of claim 1, wherein $R^{5N}$ is $C_{1-6}$ alkyl.

27. The compound of claim 1, wherein $R^{5N}$ is H.

28. The compound of claim 1, wherein $R^{5N}$ is methyl.

29. The compound of claim 1, wherein ring A is $C_{3-6}$ cycloalkyl or 4-6 membered heterocycloalkyl; wherein the 4-6 membered heterocycloalkyl has at least one ring-forming carbon atom and 1 or 2 ring-forming heteroatoms independently selected from N and 0.

30. The compound of claim 1, wherein ring A is 4-6 membered heterocycloalkyl.

31. The compound of claim 1, wherein n is 1.

32. The compound of claim 1, wherein $R^6$ is $C(O)R^{b6}$, and $R^{b6}$ is $C_{2-6}$ alkenyl.

33. The compound of claim 1, wherein ring A-$R^6$ is selected from:

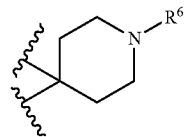

A-1a

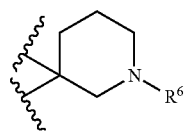

A-2a

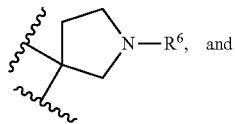

A-3a

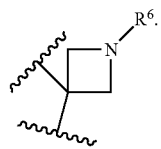

A-4a

34. The compound of claim 33, wherein ring A-$R^6$ is A-1a.

35. The compound of claim 33, wherein ring A-$R^6$ is A-2a.

36. The compound of claim 33, wherein ring A-$R^6$ is A-3a.

37. The compound of claim 33, wherein ring A-$R^6$ is A-4a.

38. The compound of claim 1, wherein $R^7$ is fluoro.

39. The compound of claim 1, wherein the compound of Formula I is selected from:
 1-acryloyl-9'-chloro-7'-fluoro-8'-(2-fluoro-6-hydroxyphenyl)-1',4'-dihydro-3'H-spiro-[piperidine-4,2'-pyrazino[2,3-c]quinolin]-3'-one;
 1-acryloyl-9'-chloro-8'-(2-chloro-5-hydroxyphenyl)-7'-fluoro-1',4'-dihydro-3'H-spiro-[piperidine-4,2'-pyrazino[2,3-c]quinolin]-3'-one;
 1-acryloyl-9'-chloro-7'-fluoro-8'-(3-methyl-1H-indazol-4-yl)-1',4'-dihydro-3'H-spiro-[piperidine-4,2'-pyrazino[2,3-c]quinolin]-3'-one;
 1-acryloyl-9'-chloro-7'-fluoro-8'-(5-methyl-1H-indazol-4-yl)-1',4'-dihydro-3'H-spiro-[piperidine-4,2'-pyrazino[2,3-c]quinolin]-3'-one;
 1-acryloyl-9'-chloro-7'-fluoro-8'-(2-fluoro-6-methoxyphenyl)-1',4'-dihydro-3'H-spiro-[piperidine-4,2'-pyrazino[2,3-c]quinolin]-3'-one;
 1-acryloyl-9'-chloro-7'-fluoro-8'-(2-fluoro-6-hydroxyphenyl)-1',4'-dihydro-3'H-spiro-[azetidine-3,2'-pyrazino[2,3-c]quinolin]-3'-one;
 1-acryloyl-9'-chloro-7'-fluoro-8'-(5-methyl-1H-indazol-4-yl)-1',4'-dihydro-3'H-spiro-[azetidine-3,2'-pyrazino[2,3-c]quinolin]-3'-one;
 t-acryloyl-9-chloro-7-fluoro-8-(2-fluoro-6-hydroxyphenyl)-1,4-dihydro-3H-spiro-[pyrazino[2,3-c]quinoline-2,3'-pyrrolidin]-3-one;
 1'-acryloyl-9-chloro-7-fluoro-8-(5-methyl-1H-indazol-4-yl)-1,4-dihydro-3H-spiro-[pyrazino[2,3-c]quinoline-2,3'-pyrrolidin]-3-one;
 1-acryloyl-9'-chloro-7'-fluoro-8'-(2-fluoro-6-hydroxyphenyl)-5'-((1-methylpyrrolidin-2-yl)-methoxy)-1',4'-dihydro-3'H-spiro[piperidine-4,2'-pyrazino[2,3-c]quinolin]-3'-one;
 1-acryloyl-9'-chloro-7'-fluoro-8'-(3-hydroxynaphthalen-1-yl)-5'-((1-methylpyrrolidin-2-yl)-methoxy)-1',4'-dihydro-3'H-spiro[piperidine-4,2'-pyrazino[2,3-c]quinolin]-3'-one;
 1-acryloyl-9'-chloro-7'-fluoro-8'-(2-fluoro-6-hydroxyphenyl)-5'-(2-(piperidin-1-yl)ethoxy)-1',4'-dihydro-3'H-spiro[piperidine-4,2'-pyrazino[2,3-c]quinolin]-3'-one;
 1-acryloyl-8'-chloro-6'-fluoro-7'-(3-hydroxynaphthalen-1-yl)-4'-((1-methylpyrrolidin-2-yl)-methoxy)spiro[piperidine-4,1'-pyrrolo[2,3-c]quinolin]-2'(3'H)-one;
 1-acryloyl-8'-chloro-6'-fluoro-7'-(3-hydroxynaphthalen-1-yl)-4'-((1-methylpyrrolidin-2-yl)-methoxy)spiro[pyrrolidine-3,1'-pyrrolo[2,3-c]quinolin]-2'(3'H)-one;

1-acryloyl-8'-chloro-6'-fluoro-7'-(3-hydroxynaphthalen-1-yl)-3'-methyl-4'-((1-methyl-pyrrolidin-2-yl)methoxy)spiro[piperidine-4,1'-pyrrolo[2,3-c]quinolin]-2'(3'H)-one;

1-acryloyl-9'-chloro-7'-fluoro-8'-(3-hydroxynaphthalen-1-yl)spiro[piperidine-4,2'-pyrano-[3,2-c]quinolin]-4'(3'H)-one;

1-acryloyl-9'-chloro-7'-fluoro-8'-(2-fluoro-6-hydroxyphenyl)-5'-(((S)-1-methylpyrrolidin-2-yl)methoxy)-1',4'-dihydro-3'H-spiro[azetidine-3,2'-pyrazino[2,3-c]quinolin]-3'-one; and 1-acryloyl-9'-chloro-7'-fluoro-8'-(2-fluoro-6-hydroxyphenyl)-5'-((1-methylpyrrolidin-2-yl)-methoxy)-1',4'-dihydro-3'H-spiro[azetidine-3,2'-pyrazino[2,3-c]quinolin]-3'-one;

or a pharmaceutically acceptable salt thereof.

40. The compound of claim 1, wherein the compound of Formula I is selected from:

4'-(3-(dimethylamino)azetidin-1-yl)-6'-fluoro-7'-(3-hydroxynaphthalen-1-yl)-8'-methylspiro[piperidine-3,1'-pyrrolo[2,3-c]quinolin]-2'(3'H)-one;

8'-chloro-7'-(7-chloro-3-hydroxynaphthalen-1-yl)-4'-(3-(dimethylamino)azetidin-1-yl)-6'-fluorospiro[piperidine-3,1'-pyrrolo[2,3-c]quinolin]-2'(3'H)-one;

8'-chloro-4'-(3-(dimethylamino)azetidin-1-yl)-6'-fluoro-7'-(3-hydroxynaphthalen-1-yl)-5-azaspiro[bicyclo[2.2.1]heptane-2,1'-pyrrolo[2,3-c]quinolin]-2'(3'H)-one;

4-(4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)butanenitrile;

2-(4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)acetonitrile;

3-(4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)propanenitrile;

8'-(2-chlorobenzyl)-4'-(3-(dimethylamino)azetidin-1-yl)-6'-fluoro-7'-(3-hydroxynaphthalen-1-yl)spiro[piperidine-3,1'-pyrrolo[2,3-c]quinolin]-2'(3'H)-one;

2-((4'-(3-(dimethylamino)azetidin-1-yl)-6'-fluoro-7'-(3-hydroxynaphthalen-1-yl)-2'-oxo-2',3'-dihydrospiro[piperidine-3,1'-pyrrolo[2,3-c]quinolin]-8'-yl)methyl)benzonitrile;

4-(4'-(3-(dimethylamino)azetidin-1-yl)-6'-fluoro-7'-(3-hydroxynaphthalen-1-yl)-2',3'-dihydrospiro[piperidine-3,1'-pyrrolo[2,3-c]quinolin]-8'-yl)butanenitrile;

3-(4'-(3-(dimethylamino)azetidin-1-yl)-6'-fluoro-7'-(3-hydroxynaphthalen-1-yl)-2'-oxo-2',3'-dihydrospiro[azetidine-3,1'-pyrrolo[2,3-c]quinolin]-8'-yl)propanenitrile;

4-(4'-(3-(dimethylamino)azetidin-1-yl)-6'-fluoro-7'-(3-hydroxynaphthalen-1-yl)-2'-oxo-2',3'-dihydrospiro[pyrrolidine-3,1'-pyrrolo[2,3-c]quinolin]-8'-yl)butanenitrile;

4-(4'-(3-(dimethylamino)azetidin-1-yl)-6'-fluoro-7'-(3-hydroxynaphthalen-1-yl)-2'-oxo-2',3'-dihydrospiro[morpholine-2,1'-pyrrolo[2,3-c]quinolin]-8'-yl)butanenitrile;

4-(6'-fluoro-7'-(3-hydroxynaphthalen-1-yl)-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile;

4-(6'-fluoro-7'-(3-hydroxynaphthalen-1-yl)-3'-methyl-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile;

4-(6'-fluoro-3'-(2-hydroxyethyl)-7'-(3-hydroxynaphthalen-1-yl)-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile;

4-(6'-fluoro-7'-(3-hydroxynaphthalen-1-yl)-3'-isopentyl-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile;

4-(3'-(cyanomethyl)-6'-fluoro-7'-(3-hydroxynaphthalen-1-yl)-4'-(((S)-1-methylpyrrolidin-2-yl)methoxy)-2'-oxo-2',3'-dihydrospiro[piperidine-3,1'-pyrrolo[2,3-c]quinolin]-8'-yl)butanenitrile; and 2-(8'-(3-cyanopropyl)-6'-fluoro-7'-(3-hydroxynaphthalen-1-yl)-4'-(((S)-1-methylpyrrolidin-2-yl)methoxy)-2'-oxospiro[piperidine-3,1'-pyrrolo[2,3-c]quinolin]-3'(2'H)-yl)acetamide;

or a pharmaceutically acceptable salt thereof.

41. A pharmaceutical composition comprising the compound of claim 1, or a pharmaceutically acceptable salt thereof, and a pharmaceutically acceptable carrier.

42. The compound of claim 1, wherein the compound of Formula (I) is 1-acryloyl-9'-chloro-7'-fluoro-8'-(3-hydroxynaphthalen-1-yl)-5'-(((S)-1-methylpyrrolidin-2-yl)methoxy)-1',4'-dihydro-3'H-spiro[piperidine-4,2'-pyrazino[2,3-c]quinolin]-3'-one, or a pharmaceutically acceptable salt thereof.

\* \* \* \* \*